United States Patent
Siegel et al.

(10) Patent No.: US 11,802,159 B2
(45) Date of Patent: Oct. 31, 2023

(54) HUMANIZED ANTI-GDNF FAMILY ALPHA-RECEPTOR 4 (GRF-ALPHA-4) ANTIBODIES AND CHIMERIC ANTIGEN RECEPTORS (CARS)

(71) Applicants: The Trustees of the University of Pennsylvania, Philadelphia, PA (US); The Scripps Research Institute, La Jolla, CA (US)

(72) Inventors: Donald L. Siegel, Lansdale, PA (US); Vijay Bhoj, Philadelphia, PA (US); Christoph Rader, Jupiter, FL (US); Rebecca Goydel, La Jolla, CA (US)

(73) Assignees: The Trustees of the University of Pennsylvania, Philadelphia, PA (US); The Scripps Research Institute, La Jolla, CA (US)

( * ) Notice: Subject to any disclaimer, the term of this patent is extended or adjusted under 35 U.S.C. 154(b) by 248 days.

(21) Appl. No.: 17/037,203

(22) Filed: Sep. 29, 2020

(65) Prior Publication Data

US 2021/0095036 A1    Apr. 1, 2021

Related U.S. Application Data

(60) Provisional application No. 62/907,909, filed on Sep. 30, 2019.

(51) Int. Cl.
  C07K 16/28    (2006.01)
  C07K 14/725   (2006.01)
  C07K 14/705   (2006.01)
  A61K 35/17    (2015.01)
  A61P 35/00    (2006.01)
  A61K 39/00    (2006.01)

(52) U.S. Cl.
  CPC .......... *C07K 16/2863* (2013.01); *A61K 35/17* (2013.01); *A61P 35/00* (2018.01);
  (Continued)

(58) Field of Classification Search
  CPC ............ C07K 16/2863; C07K 14/7051; C07K 14/70517; C07K 14/70578;
  (Continued)

(56) References Cited

U.S. PATENT DOCUMENTS

2017/0096488 A1   4/2017   Croll
2017/0334967 A1   11/2017  Siegel

FOREIGN PATENT DOCUMENTS

WO   2001062795        8/2001
WO   WO-2016025880 A1 * 2/2016 .............. A61P 35/00
  (Continued)

OTHER PUBLICATIONS

Dekosky et al., "Large-scale sequence and strucural comparisons of human naive and antigen-experienced antibody repertoires." (2016) Proc Natl Acad Sci 113:E2636-E2645.
(Continued)

*Primary Examiner* — Scarlett Y Goon
*Assistant Examiner* — Audrey L Buttice
(74) *Attorney, Agent, or Firm* — Saul Ewing LLP; Kathryn Doyle

(57) ABSTRACT

The present invention relates to compositions and methods for treating diseases, disorders or conditions associated with the expression of the glycosyl-phosphatidylinositol (GPI)-linked GDNF family protein α-receptor 4 (GFRα4).

29 Claims, 31 Drawing Sheets

Specification includes a Sequence Listing.

(52) U.S. Cl.
CPC .... *C07K 14/7051* (2013.01); *C07K 14/70517* (2013.01); *C07K 14/70578* (2013.01); *A61K 2039/505* (2013.01); *C07K 2317/24* (2013.01); *C07K 2317/622* (2013.01); *C07K 2319/02* (2013.01); *C07K 2319/03* (2013.01)

(58) Field of Classification Search
CPC .......... C07K 2317/24; C07K 2317/622; C07K 2317/73; C07K 2319/02; C07K 2319/03; A61K 35/17; A61K 2039/505; A61K 2039/5156; A61K 38/00; A61K 39/001112; A61K 39/00113; A61P 35/00
See application file for complete search history.

(56) References Cited

FOREIGN PATENT DOCUMENTS

WO    WO-2016025884 A1 *   2/2016  ............. A61K 35/17
WO    WO-2019165156 A1 *   8/2019  ............. A61K 35/17

OTHER PUBLICATIONS

Zhang and Ho, "Humanization of rabbit monoclonal antibodies via grafting combined Kabat/IMGT/Paratome complementarity-determining regions: Rationale and examples." (2017) MABS, 9:419-429).

* cited by examiner

Figure 1A. Top row: Rabbit P4-10 HC (Kabat CDRs); Bottom row: Rabbit P4-10 HC (IMGT CDRs)

Figure 1B. Top row: Rabbit P4-10 LC (Kabat CDRs); Bottom row: Rabbit P4-10 LC (IMGT CDRs)

CDR1 / CDR2

```
                                                                                                                                                                    SEQ ID NO: 127
-QSVKESEGGLEKPTDTLTLTCTVSGFSLSRHALT-WVRQAPGNGLEWIGAIDNAGTTYYASWAKSRSTIERNTDLHTVELRMTSLTASDTATYFCAR
-QSVKESEGGLFKPTDTLTLTCTVSGFSLSRHALT-WVRQAPGNGLEWIGAIDNAGTTYYASWAKSRSTIERNTDLHTVTLRMTSLTASDTATYFCAR                                                                   SEQ ID NO: 128

QVQLQESGPGLVKPSETLSLTCAVSGYSISSGYYWGWIRQPPGKGLEWIGSIYHSGSTYYNPSLKSRVTISVDTSKNQFSLKLSSVTAADTAVYYCAR
QVQLQESGPGLVKPSEHLSLTCAVSGYSISR-HALTNIRQPPGKGLEWIGAIDNAGTTYYASWAKSRVTISVDTSKNQFSLRLSSVTAADTAVYYCAR                                                                    SEQ ID NO: 136
QVQLQESGPGLVKPSEHLSLTCAVSGYSISR-HALTNIRQPPGKGLEWIGAIDNAGTTYYASWAKSRVTISVDTSKNQFSLKLSSVTAADTAVYYCAR                                                                    SEQ ID NO: 137
QSVQESGPGLVKPSETLSLTCAVSGFSISR-HALTNIRQPPGKGLEWIGAIDNAGTTYYASWAKSRVTISVDTSKMQFSLKLSSVTAADTAVYYCAR                                                                     SEQ ID NO: 138
QSVQESGPGLVKPSETLSLTCAVSGYSISR-HALTNIRQPPGKGLEWIGAIDNAGTTYYASWAKSRVTISRDDSKLSLKLSSVTAADTAVYGCAR                                                                       SEQ ID NO: 139

EVQLVESGGGLVQPGGSLRLSCAASGFTFSSYEMNWVRQAPGKGLEWVSYISSSGSTIYYADSVKGRFTISRDNAKNSLYLQMNSLRAEDTAVYYCAR                                                                    SEQ ID NO: 140

EVQLVESGGGLVQPGGSLRLSCAASGFTFSSRHALTWVRQAPGKGLEWVSAIDNAGTTYYASWAKS-RFTISRDNAKNSLYLQMNSLRAEDTAVYYCAR                                                                  SEQ ID NO: 141
EVQLVESGGGLVQPGGSLRLSCAASGFTISRHALTWVRQAPGKGLEWVSICAIDNAGTTYYASWAKS-RFTISRDDSKLVYLQMNSLRAEDTAVYGCAR                                                                  SEQ ID NO: 142
```

Rows:

Rabbit P4-10 HC (Rabbit CDRs)
Rabbit P4-10 HC (IMGT CDRs)

(1) IGHV4-38-2*02 54%

H1     85%
H1m3   83%
H1m2   79%
H1m1   69%

(2) IGHV3-48*03 51%

|  | CDR1 | CDR2 | CDR3 | |
|---|---|---|---|---|
| | QFVLTQSPSYVSAALGASARLRCTLSSAHKTYTIDWYQDQQGEAPRYLIIPSVQADEAGYVCGADDNGGY | | | SEQ ID NO: 130 |
| | QFVLTQSPSVVSAALGASAKLRCTLSSAHKTYTIDWYQQQQGEAPRYLIIPSVQADEAGYVCGADDNGGYV | | | SEQ ID NO: 131 |
| | QLVLTQSPSASASLGASVKLRCTLSGHSSYAIAWHQQPEKGPRYLMKINSDGSHSKGDGIPDRFSGSSSGAERYLTISSLQSEDEADYCQTWGTGI | | | SEQ ID NO: 132 |
| | QLVLTQSPSASASLGASVKLRCTLSSAHKTYTIAWHQQPEKGPRYLMKVKSDGSYSKGDGIPDRFSGSSSGAERYLTISSLQSEDEADYCGADDNGGYV | | | SEQ ID NO: 143 |
| | QFVLTQSPSASASLGASVKLRCTLSSAHKTYTIAWHQQPEKGPRYLMKVKSDGSYKGIPDRFSGSSSGAERYLTISSLQSEDEADYCGADDNGGYV | | | SEQ ID NO: 144 |
| | QLVLTQSPSASASLGASVKLRCTLSSAHKTYTIAWHQQPEKGPRYLMKVKSDGSYGIPDRFSGSSSGARYLTISSLQSEDEADYCGADDNGGYV | | | SEQ ID NO: 145 |
| | QLVLTQSPSASASLGASVKLRCTLSSAHKTYTIAWHQQPEKGPRYLMKVKSDGSYGIPDRFSGSSSGARYLTISSLQSEDEADYCGADDNGGYV | | | SEQ ID NO: 146 |
| | QLVLTQSPSASASLGASVKLRCTLSSAHKTYTIAWHQQPEKGPRYLMKVKSDGSYGIPDRFSGSSSGARYLTISSLQSEDEADYCGADDNGGYV | | | SEQ ID NO: 147 |

Rows:

Rabbit P4-10 LC (Kabat CDRs)
Rabbit P4-10 LC (IMGT CDRs)

(1) Human IGLV4-69*01 (69%)

```
          QSVLTQPPSASGTPGQRVTISCSGSSSNIGSNTVNWYQQLPGTAPKLLIYSN----NQRPSGVPDRFSGSKSGTSASLAISGLQSEDEADYCAAWDDSLNG    SEQ ID NO: 133
          QSVLTQPPSASGTPGQRVTISCSGSSAHK-TYTVNWYQQLPGTAPKLLIYVKSDGSYQRPSGVPDRFSGSKSGTSASLAISGLQSEDEADYYCGADDNGGYV    SEQ ID NO: 148
          QSVLTQPPSASGTPGQRVTISCSGSSAHK-TYTVNWYQQLPGTAPKLLIYVKSDGSYNKGSVPDRFSGSKSGTSASLAISGLQSEDEADYYCGADDNGGYV    SEQ ID NO: 149
          QSVLTQPPSASGTPGQRVTISCSGSSAHK-TYTVNWYQQLPGTAPKLLIYVKSDGSYNKGSVPDRFSGSSGTSASLAISGLQSEDEADYYCGADDNGGYV    SEQ ID NO: 150
          QSVLTQPPSASGTPGQRVTISCSGSSAHK-TYTVNWYQQLPGTAPKLLIYVKSDGSYNKGSVPDRFSGSSGDRVLAISGLQSEDEADYYCGADDNGGYV    SEQ ID NO: 151
```

Rows:

(2) Human IGLV1-44*01 (43%)

QSALTQPASVSGGSPGQSITISCTGTSSDVGGINIVSWYQQHPGKAPKLMIYEV----SNRPSGVSNRFSGSKSGNTASLTISGLQAEDEADYYCSSYTSSSTL SEQ ID NO: 134

QSALTQPASVSGGSPGQSITISCTGTSAH-K-TYTVSWYQQHPGKAPKLMIYVKSDGSYNRPSGVSNRFSGSKSGNTASLTISGLQAEDEADYYCGADDNGGYV SEQ ID NO: 152
QSALTQPASVSGGSPGQSITISCTGTSAH-K-TYIIDWYQQHPGKAPKLMIYVKSDGSYNRPSGVSNRFSGSKSGNTASLTISGLQAEDEADYYCGADDNGGYV SEQ ID NO: 153

QSALTQPASVSGGSPGQSITISCTGTSAH-K-TYTVSWYQQHPGKAPKLMIYTLGVKSDGSYNRPSGVSNRFSGSIKGNTASLTISGLQAEDEADYYCGADDNGGYV SEQ ID NO: 154
QSALTQPASVSGGSPGQSITISCTGTSAH-K-TYIIDWYQQHPGKAPKLMIYTLGVKSDGSYNRPSGVSNRFSGSIKGNADRYTISGLQAEDEADYYCGADDNGGYV SEQ ID NO: 155

QSVLTQPASVSGSPGQSITISCTISSAH-K-TYTVSWYQQHPGKAPKLMIYTLGVKSDGSYIKGVSNRFSGSIKGNADRYTISGLQAEDEADYYCGADDNGGYV SEQ ID NO: 156
QSVLTQPASVSGSPGQSITISCTISSAH-K-TYIIDWYQQHPGKAPKLMIYTLGVKSDGSYIKGVSNRFSGSIKGNADRYTISGLQAEDEADYYCVGADDNGGYV SEQ ID NO: 157

Rows:

(3) Human IGLV2-14*01  (42%)

Results of IMGT/DomainGapAlign

Your selection

Domain type: V
Species: (All species)
SW score above: 0
Displayed alignments: 5

Sequence name: H1

● Move your mouse over the amino acids below the alignment for the characterization of AA changes ● Closest reference gene and allele(s) from the IMGT V domain directory: (All species)

| Species | Gene and allele | Domain | Domain label | Smith-Waterman score | % Identity | Overlap | Show alignment |
|---|---|---|---|---|---|---|---|
| Homo sapiens | IGHV4-38-2*01 | 1 | VH | 519 | 84.7 | 98 | ◉ |
| Homo sapiens | IGHV4-38-2*02 | 1 | VH | 514 | 83.7 | 98 | ○ |
| Macaca fascicularis | IGHV4S5*01 | 1 | VH | 502 | 82.7 | 98 | ○ |
| Macaca fascicularis | IGHV4S16*01 | 1 | VH | 496 | 82.7 | 98 | ○ |
| Homo sapiens | IGHV4-4*08 | 1 | VH | 505 | 82.5 | 97 | ○ |

FIG. 12

Results of IMGT/DomainGapAlign

Your selection

Domain type: V
Species: (All species)
SW score above: 0
Displayed alignments: 5

Sequence name: H2

● Move your mouse over the amino acids below the alignment for the characterization of AA changes ● Closest reference gene and allele(s) from the IMGT V domain directory: (All species)

| Species | Gene and allele | Domain | Domain label | Smith-Waterman score | % identity | Overlap | Show alignment |
|---|---|---|---|---|---|---|---|
| Homo sapiens | IGHV3-48*03 | 1 | VH | 542 | 84.7 | 98 | ● |
| Homo sapiens | IGHV3-23*04 | 1 | VH | 545 | 83.7 | 98 | ○ |
| Homo sapiens | IGHV3-48*01 | 1 | VH | 536 | 83.7 | 98 | ○ |
| Homo sapiens | IGHV3-48*04 | 1 | VH | 536 | 83.7 | 98 | ○ |
| Homo sapiens | IGHV3-13*01 | 1 | VH | 525 | 83.5 | 97 | ○ |

FIG. 13

Results of IMGT/DomainGapAlign

Your selection

Domain type: V
Species: (All species)
SW score above: 0
Displayed alignments: 5

Sequence name: L1m3

⦿ Move your mouse over the amino acids below the alignment for the characterization of AA changes ● Closest reference gene and allele(s) from the IMGT V domain directory: (All species)

| Species | Gene and allele | Domain | Domain label | Smith-Waterman score | % identity | Overlap | Show alignment |
|---|---|---|---|---|---|---|---|
| Homo sapiens | IGLV4-69*01 | 1 | V-LAMBDA | 532 | 84.8 | 92 | ● |
| Homo sapiens | IGLV4-69*02 | 1 | V-LAMBDA | 532 | 84.8 | 92 | ○ |
| Oryctolagus cuniculus | IGLV4S4*01 | 1 | V-LAMBDA | 520 | 84.8 | 92 | ○ |
| Oryctolagus cuniculus | IGLV4S3*01 | 1 | V-LAMBDA | 509 | 83.7 | 92 | ○ |
| Macaca mulatta | IGLV4S2*01 | 1 | V-LAMBDA | 499 | 81.5 | 92 | ○ |

FIG. 14

Results of IMGT/DomainGapAlign

Your selection

Domain type: V
Species: (All species)
SW score above: 0
Displayed alignments: 5

Sequence name: L1m1

● Move your mouse over the amino acids below the alignment for the characterization of AA changes ● Closest reference gene and allele(s) from the IMGT V domain directory: (All species)

| Species | Gene and allele | Domain | Domain label | Smith-Waterman score | % Identity | Overlap | Show alignment |
|---|---|---|---|---|---|---|---|
| Oryctolagus cuniculus | IGLV4S3*01 | 1 | V-LAMBDA | 520 | 84.8 | 92 | ● |
| Homo sapiens | IGLV4-69*01 | 1 | V-LAMBDA | 528 | 83.7 | 92 | ○ |
| Homo sapiens | IGLV4-69*02 | 1 | V-LAMBDA | 528 | 83.7 | 92 | ○ |
| Oryctolagus cuniculus | IGLV4S5*01 | 1 | V-LAMBDA | 509 | 83.7 | 92 | ○ |
| Macaca mulatta | IGLV4S2*01 | 1 | V-LAMBDA | 499 | 81.5 | 92 | ○ |

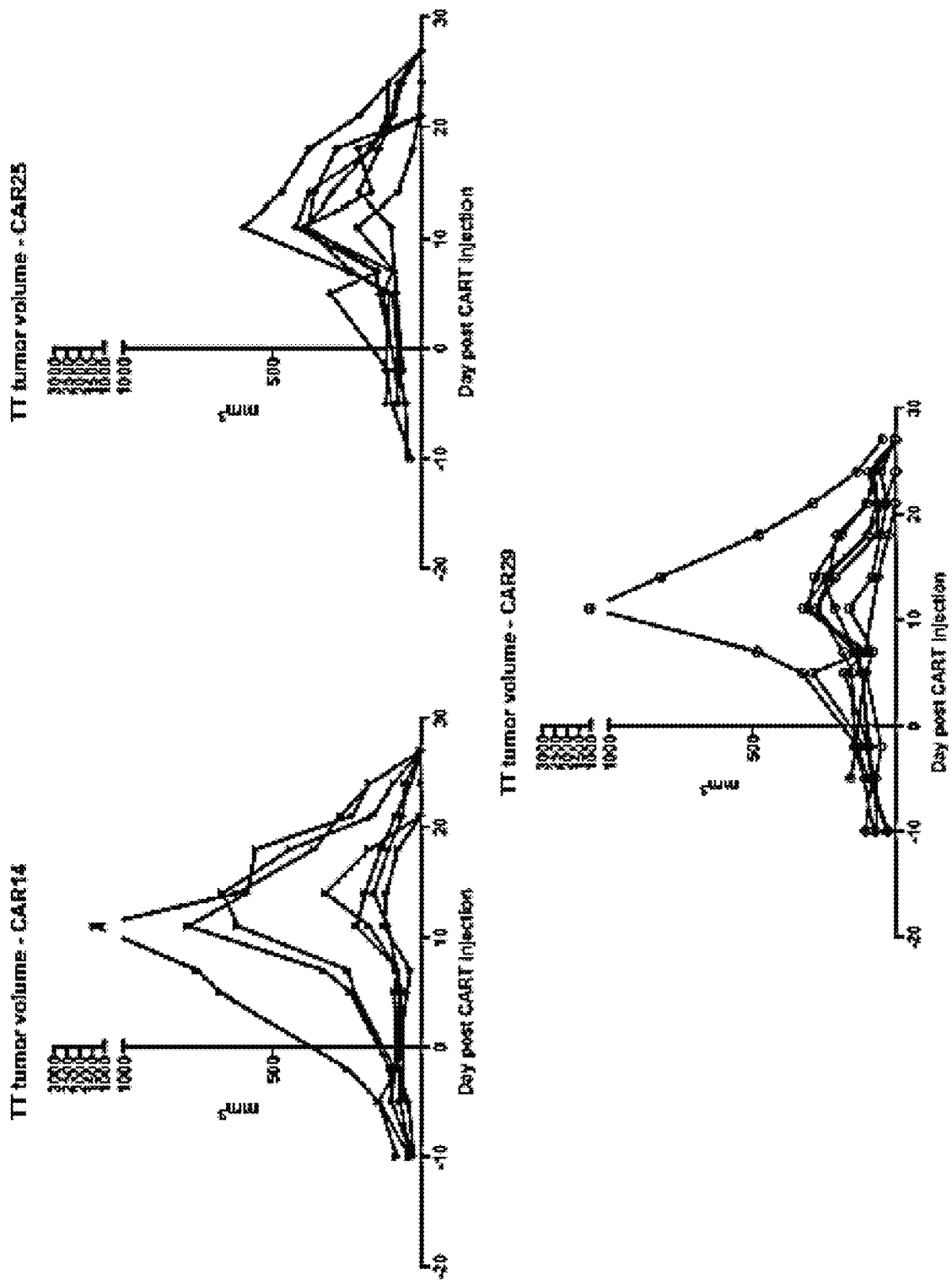
FIG. 26, Continued

SEQUENCE LISTING

<160> NUMBER OF SEQ ID NOS: 169

<210> SEQ ID NO 1
<211> LENGTH: 369
<212> TYPE: DNA
<213> ORGANISM: Artificial Sequence
<220> FEATURE:
<223> OTHER INFORMATION: Heavy Chain
<220> FEATURE:
<223> OTHER INFORMATION: Rabbit P4-10 heavy chain variable region

<400> SEQUENCE: 1

```
cagtccgtga aggagagcga gggcggcctg ttcaagccca ccgacaccct gaccctgacc      60
tgcacagtga gcggcttcag cctgtccaga cacgccctga catgggtgag acaggcccct     120
ggcaacggcc tggaatggat cggcgccatc gacaacgccg gcaccaccta ctacgccagc     180
tgggccaagt ccaggtccac catcaccagg aacaccgacc tccacaccgt gaccctgaag     240
atgacaagcc tgaccgcctc cgacaccgcc acctacttct gcgccaggga gttctacgac     300
atcaacagcg gctactacct ggatggcatg gacctgtggg gacctggcac actggtgacc     360
gtgagcagc                                                             369
```

<210> SEQ ID NO 2
<211> LENGTH: 372
<212> TYPE: DNA
<213> ORGANISM: Artificial Sequence
<220> FEATURE:
<223> OTHER INFORMATION: Heavy Chain
<220> FEATURE:
<223> OTHER INFORMATION: H1

<400> SEQUENCE: 2

```
caagttcagc tgcaagaaag cggacccggt ttagtcaagc ccagcgagac tttatcttta      60
acatgcgccg tgagcggcta ctccatctct cgtcacgctt taacatggat taggcagccc     120
cccggtaagg gtttagaatg gatcggcgcc atcgacaacg ctggcaccac ctactacgcc     180
tcttgggcta agtctcgtgt gacaatcagc gtggacacct ccaagaacca gttttcttta     240
aagctgagca gcgtgaccgc tgccgacacc gctgtgtact attgcgctcg tgtcttctac     300
gacatcaaca gcggctacta tttagatggc atggatttat ggggacccgg tactttagtg     360
accgtgagct cc                                                         372
```

<210> SEQ ID NO 3
<211> LENGTH: 372
<212> TYPE: DNA
<213> ORGANISM: Artificial Sequence
<220> FEATURE:
<223> OTHER INFORMATION: Heavy Chain
<220> FEATURE:
<223> OTHER INFORMATION: H1m1

<400> SEQUENCE: 3

```
cagcagagcg tgaaggagag cggcccccggt ctggtgaagc ccagcgagac tttatcttta     60
acatgcgccg tgagcggctt ctctttatct cgtcacgctt taacttgggt gagacagcct     120
cccggtaaag gtttagagtg gatcggcgcc atcgacaacg ccggcacaac ctactacgcc     180
agctgggcca agtctcgtgt gaccatctct cgtaacaccc atttcacac cgtgtctttta     240 aagctgagct ccgtgaccgc tgccgatacc gccgtgtact tctgcgctag ggtgttctac     300
gacatcaaca gcggctacta tttagatggc atggatctgt ggggcccggg cacactggtc     360
acagtgtcca gc                                                         372
```

<210> SEQ ID NO 4
<211> LENGTH: 372
<212> TYPE: DNA
<213> ORGANISM: Artificial Sequence
<220> FEATURE:
<223> OTHER INFORMATION: Heavy Chain
<220> FEATURE:
<223> OTHER INFORMATION: H2

<400> SEQUENCE: 4

```
gaggtgcagc tggtggaaag cggcggagga ctggtgcagc ccggtggctc tttaagactg    60
agctgtgctg ccagcggctt cacattctct cgtcacgctt taacttgggt gagacaagct   120
cccggaaagg gtttagaatg ggtgagcgcc atcgacaacg ccggaaccac ctactacgcc   180
agctgggcca agtctcgttt caccatctct cgtgataacg ccaagaacag cctctattta   240
cagatgaact ctttaagggc cgaggacacc gccgtgtact actgcgctag ggtgttctac   300
gacatcaaca gcggctacta tctggacggc atggatttat ggggcccgg tacactggtc    360
accgtgagca gc                                                      372
```

<210> SEQ ID NO 5
<211> LENGTH: 369
<212> TYPE: DNA
<213> ORGANISM: Artificial Sequence
<220> FEATURE:
<223> OTHER INFORMATION: Heavy Chain
<220> FEATURE:
<223> OTHER INFORMATION: H2m1

<400> SEQUENCE: 5

```
cagagcgtca aggagtccgg aggaggactg gtgcagcccg gtggctcttt aaggctgagc    60
tgtgccgcct ctggctttac tttatctcgt cacgctttaa catgggtgag acaagctccc   120
ggtaagggac tggagtggat cggcgccatc gacaacgccg gcaccaccta ctacgcctct   180
tgggccaagt ctcgtttcac catctctcgt aacaccgatt acacaccgt gtatttacag    240
atgaactctt taagggccga ggacacagcc gtctatttct gcgctcgtgt gttctacgac   300
atcaatagcg gctactacct cgacggaatg gatctgtggg gccccggtac tttagtgaca   360
gtcagcagc                                                          369
```

<210> SEQ ID NO 6
<211> LENGTH: 123
<212> TYPE: PRT
<213> ORGANISM: Artificial Sequence
<220> FEATURE:
<223> OTHER INFORMATION: Heavy Chain
<220> FEATURE:
<223> OTHER INFORMATION: Rabbit P4-10 heavy chain variable region

<400> SEQUENCE: 6

```
Gln Ser Val Lys Glu Ser Glu Gly Gly Leu Phe Lys Pro Thr Asp Thr
 1               5                  10                  15

Leu Thr Leu Thr Cys Thr Val Ser Gly Phe Ser Leu Ser Arg His Ala
            20                  25                  30

Leu Thr Trp Val Arg Gln Ala Pro Gly Asn Gly Leu Glu Trp Ile Gly
        35                  40                  45

Ala Ile Asp Asn Ala Gly Thr Thr Tyr Tyr Ala Ser Trp Ala Lys Ser
    50                  55                  60

Arg Ser Thr Ile Thr Arg Asn Asp Leu His Thr Val Thr Leu Lys
65                  70                  75                  80
```

```
Met Thr Ser Leu Thr Ala Ser Asp Thr Ala Thr Tyr Phe Cys Ala Arg
                85                  90                  95

Val Phe Tyr Asp Ile Asn Ser Gly Tyr Tyr Leu Asp Gly Met Asp Leu
            100                 105                 110

Trp Gly Pro Gly Thr Leu Val Thr Val Ser Ser
        115                 120

<210> SEQ ID NO 7
<211> LENGTH: 124
<212> TYPE: PRT
<213> ORGANISM: Artificial Sequence
<220> FEATURE:
<223> OTHER INFORMATION: Heavy Chain
<220> FEATURE:
<223> OTHER INFORMATION: H1

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Arg His
            20                  25                  30

Ala Leu Thr Trp Ile Arg Gln Pro Pro Gly Lys Gly Leu Glu Trp Ile
        35                  40                  45

Gly Ala Ile Asp Asn Ala Gly Thr Thr Tyr Tyr Ala Ser Trp Ala Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Phe Tyr Asp Ile Asn Ser Gly Tyr Tyr Leu Asp Gly Met Asp
            100                 105                 110

Leu Trp Gly Pro Gly Thr Leu Val Thr Val Ser Ser
        115                 120

<210> SEQ ID NO 8
<211> LENGTH: 124
<212> TYPE: PRT
<213> ORGANISM: Artificial Sequence
<220> FEATURE:
<223> OTHER INFORMATION: Heavy Chain
<220> FEATURE:
<223> OTHER INFORMATION: H1m1

<400> SEQUENCE: 8

Gln Gln Ser Val Lys Glu Ser Gly Pro Gly Leu Val Lys Pro Ser Glu
1               5                   10                  15

Thr Leu Ser Leu Thr Cys Ala Val Ser Gly Phe Ser Leu Ser Arg His
            20                  25                  30

Ala Leu Thr Trp Val Arg Gln Pro Pro Gly Lys Gly Leu Glu Trp Ile
        35                  40                  45

Gly Ala Ile Asp Asn Ala Gly Thr Thr Tyr Tyr Ala Ser Trp Ala Lys
    50                  55                  60

Ser Arg Val Thr Ile Ser Arg Asn Thr Asp Leu His Thr Val Ser Leu
65                  70                  75                  80

Lys Leu Ser Ser Val Thr Ala Ala Asp Thr Ala Val Tyr Phe Cys Ala
                85                  90                  95

Arg Val Phe Tyr Asp Ile Asn Ser Gly Tyr Tyr Leu Asp Gly Met Asp
            100                 105                 110
```

Leu Trp Gly Pro Gly Thr Leu Val Thr Val Ser Ser
        115                 120

<210> SEQ ID NO 9
<211> LENGTH: 124
<212> TYPE: PRT
<213> ORGANISM: Artificial Sequence
<220> FEATURE:
<223> OTHER INFORMATION: Heavy Chain
<220> FEATURE:
<223> OTHER INFORMATION: H2

<400> SEQUENCE: 9

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Leu Thr Trp Val Arg Gln Ala Pro Gly Lys Gly Leu Glu Trp Val
        35                  40                  45

Ser Ala Ile Asp Asn Ala Gly Thr Thr Tyr Tyr Ala Ser Trp Ala Lys
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Val Phe Tyr Asp Ile Asn Ser Gly Tyr Tyr Leu Asp Gly Met Asp
            100                 105                 110

Leu Trp Gly Pro Gly Thr Leu Val Thr Val Ser Ser
        115                 120

<210> SEQ ID NO 10
<211> LENGTH: 123
<212> TYPE: PRT
<213> ORGANISM: Artificial Sequence
<220> FEATURE:
<223> OTHER INFORMATION: Heavy Chain
<220> FEATURE:
<223> OTHER INFORMATION: H2m1

<400> SEQUENCE: 10

Gln Ser Val Lys Glu Ser Gly Gly Leu Val Gln Pro Gly Gly Ser
1               5                   10                  15

Leu Arg Leu Ser Cys Ala Ala Ser Gly Phe Thr Leu Ser Arg His Ala
            20                  25                  30

Leu Thr Trp Val Arg Gln Ala Pro Gly Lys Gly Leu Glu Trp Ile Gly
        35                  40                  45

Ala Ile Asp Asn Ala Gly Thr Thr Tyr Tyr Ala Ser Trp Ala Lys Ser
    50                  55                  60

Arg Phe Thr Ile Ser Arg Asn Thr Asp Leu His Thr Val Tyr Leu Gln
65                  70                  75                  80

Met Asn Ser Leu Arg Ala Glu Asp Thr Ala Val Tyr Phe Cys Ala Arg
                85                  90                  95

Val Phe Tyr Asp Ile Asn Ser Gly Tyr Tyr Leu Asp Gly Met Asp Leu
            100                 105                 110

Trp Gly Pro Gly Thr Leu Val Thr Val Ser Ser
        115                 120

<210> SEQ ID NO 11
<211> LENGTH: 333
<212> TYPE: DNA

-continued

```
<213> ORGANISM: Artificial Sequence
<220> FEATURE:
<223> OTHER INFORMATION: Light Chain
<220> FEATURE:
<223> OTHER INFORMATION: Rabbit P4-10 light chain variable region

<400> SEQUENCE: 11
cagttcgtgc tgacacagag ccctagcgtg agcgccgccc tgggagcctc cgctaaactg      60
acctgcaccc tgagcagcgc ccacaagacc tacaccatcg actggtacca acagcagcag     120
ggcgaggccc ccaggtatct gatgcaggtg aagtccgacg gcagctacac caaaggcacc     180
ggcgtgcctg acaggttcag cggcagctcc agcggagccg acaggtacct gatcatcccc     240
tccgtgcagg ccgacgacga ggctggctac gtgtgtggcg ccgacgacaa tggcggctac     300
gtgttcggag gcggcaccca gctgaccgtg aca                                  333

<210> SEQ ID NO 12
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L1

<400> SEQUENCE: 12
cagctggtgc tgacccagag ccccagcgct tccgcctctt taggagccag cgtgaagctg      60
acttgtactt taagcagcgc ccacaagacc tacacaatcg cttggcacca gcagcagccc     120
gaaaagggcc ccagatatct gatgaaggtc aagtccgacg gcagctactc caagggcgac     180
ggcatccccg atcgtttcag cggttcttcc agcggcgccg agaggtattt aaccatcagc     240
tctttacaga gcgaggacga ggccgactac tactgcggcg ctgacgacaa cggcggctac     300
gtctttggcg gcggcacaaa actgaccgtg ctg                                  333

<210> SEQ ID NO 13
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L1m1

<400> SEQUENCE: 13
cagtttgtgc tgacccagag ccctagcgct tccgcctctt taggagccag cgtgaagctg      60
acttgtactt tatcctccgc ccacaagacc tacaccatcg actggtacca gcagcagccc     120
gaaaagggcc ctcgttatct gatgcaagtt aagtccgacg gcagctacac caagggaacc     180
ggcgtgcccg acagattctc cggtagcagc agcggcgccg acagatattt aaccatcagc     240
tctttacagt ccgaggacga ggccgactac tactgcggcg ccgacgacaa tggcggctac     300
gtcttcggag gcggcacaca gctgaccgtg act                                  333

<210> SEQ ID NO 14
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L1m2

<400> SEQUENCE: 14
```

```
cagtttgtgc tgacccagag ccctagcgct tccgcctctt taggagccag cgtgaagctg    60
acttgtactt tatcctccgc ccacaagacc tacaccatcg actggcacca gcagcagccc   120
gaaaagggcc ctcgttatct gatgcaagtt aagtccgacg gcagctacac caagggaacc   180 ggcatcccccg acagattctc cggtagcagc agcggcgccg agagatattt aaccatcagc   240
tctttacagt ccgaggacga ggccgactac tactgcggcg ccgacgacaa tggcggctac   300
gtcttcggag gcggcacaca gctgaccgtg ctg                                 333
```

<210> SEQ ID NO 15
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L1m3

<400> SEQUENCE: 15

```
cagctggtgc tcacccaaag ccctagcgcc tctgcctctt taggcgcttc cgtgaagctg    60
acttgtactt taagctccgc ccataagacc tacaccatcg actggtacca gcagcagccc   120
gagaagggcc ctcgttattt aatgcaagtt aagtccgatg gcagctatac caagggcacc   180
ggcgtgcccg acagattcag cggcagctcc agcggagccg atcgttattt aaccatcagc   240
tctttacaga gcgaggacga ggctgactac tactgcggcg ccgacgataa cggcggctac   300
gtgttcggcg gcggcacccca actgacagtg ctg                                333
```

<210> SEQ ID NO 16
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L1m4

<400> SEQUENCE: 16

```
cagttggtgc tcacccaaag ccctagcgcc tctgcctctt taggcgcttc cgtgaagctg    60
acttgtactt taagctccgc ccataagacc tacaccatcg cctggcatca gcagcagccc   120
gagaagggcc ctcgttattt aatgcaagtt aagtccgatg gcagctatac caagggcacc   180
ggcgtgcccg acagattcag cggcagctcc agcggagccg atcgttattt aaccatcagc   240
tctttacaga gcgaggacga ggctgactac tactgcggcg ccgacgataa cggcggctac   300
gtgttcggcg gcggcacccca actgacagtg ctc                                333
```

<210> SEQ ID NO 17
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L2

<400> SEQUENCE: 17

```
cagagcgtgc tgacacagcc tcctagcgcc agcggcacac ccggtcagag agtgaccatc    60
agctgctccg gcagcagcgc ccacaagacc tacaccgtga actggtacca gcagctgccc   120
ggcacagccc ctaagctgct gatctacgtg aaatccgacg gcagctacca gaggcctagc   180
```

```
ggagtgcccg atcgtttcag cggcagcaaa agcggcacaa gcgcctcttt agctatcagc    240
ggtttacaga gcgaggacga ggccgactat tactgcggcg ccgacgataa cggcggctac    300
gtgttcggcg gcggaaccaa gctgacagtg ctg                                 333

<210> SEQ ID NO 18
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L2m1

<400> SEQUENCE: 18
cagttcgtgc tgacacagcc tcccagcgcc tctggcacac ccggtcagag ggtgaccatc    60
tcttgtactt tatcctccgc ccacaagacc tacaccattg actggtacca gcagctgccc    120
ggtaccgccc ctaagctgct gatttacgtg aaatccgacg gcagctacac caagggaacc    180
ggcgtgcccg atcgttttc cggcagctcc agcggcgccg ataggtattt agccatcagc    240
ggtttacagt ccgaggatga ggccgactac tactgcggcg ccgatgacaa cggcggctac    300
gtgttcggcg gaggaacccca gctcaccgtg acc                                333

<210> SEQ ID NO 19
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L2m2

<400> SEQUENCE: 19
cagttcgtgc tgacacagcc tcccagcgcc tctggcacac ccggtcagag ggtgaccatc    60
tcttgtactt tatcctccgc ccacaagacc tacaccattg actggtacca gcagctgccc    120
ggtaccgccc ctaagctgct gatttacgtg aaatccgacg gcagctacac caagggaacc    180
ggcgtgcccg atcgttttc cggcagctcc agcggcgccg atgccagctt agccatcagc    240
ggtttacagt ccgaggatga ggccgactac tactgcggcg ccgatgacaa cggcggctac    300
gtgttcggcg gaggaacccca gctcaccgtg ctg                                333

<210> SEQ ID NO 20
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L2m3

<400> SEQUENCE: 20
cagagcgtgc tgacacagcc tcccagcgcc tctggcacac ccggtcagag ggtgaccatc    60
tcttgtactt tatcctccgc ccacaagacc tacaccattg actggtacca gcagctgccc    120
ggtaccgccc ctaagctgct gatttacgtg aaatccgacg gcagctacac caagggaacc    180
ggcgtgcccg atcgttttc cggcagcaag agcggcacca gcgccagctt agccatcagc    240
ggtttacagt ccgaggatga ggccgactac tactgcggcg ccgatgacaa cggcggctac    300
gtgttcggcg gaggaacccca gctcaccgtg ctg                                333
```

```
<210> SEQ ID NO 21
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L3

<400> SEQUENCE: 21
cagtccgctt taacacagcc cgcttctgtg tccggaagcc ccggtcagag catcaccatc    60
agctgcaccg gcaccagcgc tcacaagacc tacaccgtga gctggtacca gcagcacccc   120
ggtaaggccc ccaaactgat gatctacgtg aagagcgacg gcagctacaa cagacccagc   180
ggcgtgagca atcgtttcag cggcagcaag agcggcaaca ccgcttcttt aaccatcagc   240
ggtttacaag ctgaagacga ggctgactac tactgcggcg ccgacgataa cggcggctac   300
gtgtttggcg gcggcaccaa actgaccgtg ctg                                333

<210> SEQ ID NO 22
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L3m1

<400> SEQUENCE: 22
cagttcgtgc tgacccagcc cgcttctgtg agcggttctc ccggtcagag catcaccatc    60
agctgcactt taagcagcgc ccacaagacc tacaccatcg actggtacca gcagcacccc   120
ggcaaggccc ccaagtattt aatgcaagtt aagtccgacg gcagctacac caagggcacc   180
ggcgtgccca acagattctc cggcagcagc tccggcgccg acagatactt aaccatcagc   240
ggtttacaag ctgaggatga ggccgactat gtgtgcggcg ccgacgacaa tggcggctac   300
gtgttcggcg gcggcacaca gctgaccgtg act                                333

<210> SEQ ID NO 23
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L3m2

<400> SEQUENCE: 23
cagttcgtgc tgacccagcc cgcttctgtg agcggttctc ccggtcagag catcaccatc    60
agctgcactt taagcagcgc ccacaagacc tacaccatcg actggtacca gcagcacccc   120
ggcaaggccc ccaagctgat gatccaagtt aagtccgacg gcagctacac caagggcacc   180
ggcgtgagca acagattctc cggcagcagc tccggcgccg acagatactt aaccatcagc   240
ggtttacaag ctgaggatga ggccgactat tactgcggcg ccgacgacaa tggcggctac   300
gtgttcggcg gcggcacaca gctgaccgtg ctg                                333

<210> SEQ ID NO 24
<211> LENGTH: 333
<212> TYPE: DNA
<213> ORGANISM: Artificial Sequence
<220> FEATURE:
<223> OTHER INFORMATION: Light Chain
<220> FEATURE:
```

<223> OTHER INFORMATION: L3m3

<400> SEQUENCE: 24

| cagagcgccc | tgacccagcc | cgcttctgtg | agcggttctc | ccggtcagag | catcaccatc | 60 |
| agctgcactg | gcaccagcgc | ccacaagacc | tacaccatcg | actggtacca | gcagcacccc | 120 |
| ggcaaggccc | ccaagctgat | gatctatgtt | aagtccgacg | gcagctacac | caagggcacc | 180 |
| ggcgtgagca | acagattctc | cggcagcaag | tccggcaaca | ccgccagctt | aaccatcagc | 240 |
| ggtttacaag | ctgaggatga | ggccgactat | tactgcggcg | ccgacgacaa | tggcggctac | 300 |
| gtgttcggcg | gcggcacaca | gctgaccgtg | ctg | | | 333 |

<210> SEQ ID NO 25
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L3m4

<400> SEQUENCE: 25

| cagagcgctc | tgacccagcc | cgcttctgtg | agcggttctc | ccggtcagag | catcaccatc | 60 |
| agctgcactg | gcacaagcgc | ccacaagacc | tacaccgtga | gctggtacca | gcagcacccc | 120 |
| ggcaaggccc | ccaagtattt | aatgcaagtt | aagtccgacg | gcagctacac | caagggcacc | 180 |
| ggcgtgccca | acagattctc | cggcagcagc | tccggcgccg | acagatactt | aaccatcagc | 240 |
| ggtttacaag | ctgaggatga | ggccgactat | tactgcggcg | ccgacgacaa | tggcggctac | 300 |
| gtgttcggcg | gcggcaccca | actgacagtg | ctg | | | 333 |

<210> SEQ ID NO 26
<211> LENGTH: 333
<212> TYPE: DNA
<213> ORGANISM: Artificial Sequence
<220> FEATURE:
<223> OTHER INFORMATION: Light Chain
<220> FEATURE:
<223> OTHER INFORMATION: L3m5

<400> SEQUENCE: 26

| cagtctgctc | tgacccagcc | cgcttctgtg | agcggttctc | ccggtcagag | catcaccatc | 60 |
| agctgcactg | gcacaagcgc | ccacaagacc | tacaccgtga | gttggtacca | gcagcacccc | 120 |
| ggcaaggccc | ccaagttgat | gatctacgtt | aagtccgacg | gcagctacac | caagggcacc | 180 |
| ggcgtgccca | acagattctc | cggcagcagc | tccggcgccg | acagatactt | aaccatcagc | 240 |
| ggtttacaag | ctgaggatga | ggccgactat | tattgcggcg | ccgacgacaa | tggcggctac | 300 |
| gtgttcggcg | gcggcaccca | actgacagtg | ctc | | | 333 |

<210> SEQ ID NO 27
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: Rabbit P4-10 light chain variable region

<400> SEQUENCE: 27

Gln Phe Val Leu Thr Gln Ser Pro Ser Val Ser Ala Ala Leu Gly Ala
1               5                   10                  15

-continued

Ser Ala Lys Leu Thr Cys Thr Leu Ser Ser Ala His Lys Thr Tyr Thr
            20                  25                  30

Ile Asp Trp Tyr Gln Gln Gln Gly Glu Ala Pro Arg Tyr Leu Met
            35                  40                  45

Gln Val Lys Ser Asp Gly Ser Tyr Thr Lys Gly Thr Gly Val Pro Asp
        50                  55                  60

Arg Phe Ser Gly Ser Ser Gly Ala Asp Arg Tyr Leu Ile Ile Pro
65                  70                  75                  80

Ser Val Gln Ala Asp Asp Glu Ala Gly Tyr Val Cys Gly Ala Asp Asp
                85                  90                  95

Asn Gly Gly Tyr Val Phe Gly Gly Thr Gln Leu Thr Val Thr
            100                 105                 110

<210> SEQ ID NO 28
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L1

<400> SEQUENCE: 28

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Ala Trp His Gln Gln Gln Pro Glu Lys Gly Pro Arg Tyr Leu Met
            35                  40                  45

Lys Val Lys Ser Asp Gly Ser Tyr Ser Lys Gly Asp Gly Ile Pro Asp
        50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Lys Leu Thr Val Leu
            100                 105                 110

<210> SEQ ID NO 29
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L1m1

<400> SEQUENCE: 29

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Asp Trp Tyr Gln Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
        50                  55                  60

Arg Phe Ser Gly Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp 85                  90                  95

Asn Gly Gly Tyr Val Phe Gly Gly Gly Thr Gln Leu Thr Val Thr
                100                 105                 110

<210> SEQ ID NO 30
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L1m2

<400> SEQUENCE: 30

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Asp Trp His Gln Gln Pro Glu Lys Gly Pro Arg Tyr Leu Met
            35                  40                  45

Gln Val Lys Ser Asp Gly Ser Tyr Thr Lys Gly Thr Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu
                100                 105                 110

<210> SEQ ID NO 31
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L1m3

<400> SEQUENCE: 31

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Asp Trp Tyr Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
        50                  55                  60

Arg Phe Ser Gly Ser Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu
                100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Light Chain
<220> FEATURE:

<223> OTHER INFORMATION: L1m4

<400> SEQUENCE: 32

Gln Leu Val Leu Thr Gln Ser Pro Ser Ala Ser Leu Gly Ala
1               5                   10                  15

Ser Val Lys Leu Thr Cys Thr Leu Ser Ser Ala His Lys Thr Tyr Thr
            20                  25                  30

Ile Ala Trp His Gln Gln Pro Glu Lys Gly Pro Arg Tyr Leu Met
        35                  40                  45

Gln Val Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L2

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ala His Lys Thr Tyr Thr
            20                  25                  30

Val Asn Trp Tyr Gln Gln Leu Pro Gly Thr Ala Pro Lys Leu Leu Ile
        35                  40                  45

Tyr Val Lys Ser Asp Gly Ser Tyr Gln Arg Pro Ser Gly Val Pro Asp
    50                  55                  60

Arg Phe Ser Gly Ser Lys Ser Gly Thr Ser Ala Ser Leu Ala Ile Ser
65                  70                  75                  80

Gly Leu Gln Ser Glu Asp Glu Ala Asp Tyr Tyr Cys Gly Ala Asp Asp
                85                  90                  95

Asn Gly Gly Tyr Val Phe Gly Gly Gly Thr Lys Leu Thr Val Leu
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L2m1

<400> SEQUENCE: 34

Gln Phe Val Leu Thr Gln Pro Pro Ser Ala Ser Gly Thr Pro Gly Gln
1               5                   10                  15

Arg Val Thr Ile Ser Cys Thr Leu Ser Ser Ala His Lys Thr Tyr Thr
            20                  25                  30

Ile Asp Trp Tyr Gln Gln Leu Pro Gly Thr Ala Pro Lys Leu Leu Ile
        35                  40                  45

Tyr Val Lys Ser Asp Gly Ser Tyr Thr Lys Gly Thr Gly Val Pro Asp
                50                  55                  60

Arg Phe Ser Gly Ser Ser Ser Gly Ala Asp Arg Tyr Leu Ala Ile Ser
 65                  70                  75                  80

Gly Leu Gln Ser Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Thr
                100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L2m2

<400> SEQUENCE: 35

Gln Phe Val Leu Thr Gln Pro Pro Ser Ala Ser Gly Thr Pro Gly Gln
 1               5                  10                  15

Arg Val Thr Ile Ser Cys Thr Leu Ser Ser Ala His Lys Thr Tyr Thr
                20                  25                  30

Ile Asp Trp Tyr Gln Gln Leu Pro Gly Thr Ala Pro Lys Leu Leu Ile
             35                  40                  45

Tyr Val Lys Ser Asp Gly Ser Tyr Thr Lys Gly Thr Gly Val Pro Asp
         50                  55                  60

Arg Phe Ser Gly Ser Ser Ser Gly Ala Asp Ala Ser Leu Ala Ile Ser
 65                  70                  75                  80

Gly Leu Gln Ser Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Leu
                100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L2m3

<400> SEQUENCE: 36

Gln Ser Val Leu Thr Gln Pro Pro Ser Ala Ser Gly Thr Pro Gly Gln
 1               5                  10                  15

Arg Val Thr Ile Ser Cys Thr Leu Ser Ser Ala His Lys Thr Tyr Thr
                20                  25                  30

Ile Asp Trp Tyr Gln Gln Leu Pro Gly Thr Ala Pro Lys Leu Leu Ile
             35                  40                  45

Tyr Val Lys Ser Asp Gly Ser Tyr Thr Lys Gly Thr Gly Val Pro Asp
         50                  55                  60

Arg Phe Ser Gly Ser Lys Ser Gly Thr Ser Ala Ser Leu Ala Ile Ser
 65                  70                  75                  80

Gly Leu Gln Ser Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Leu
                100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L3

<400> SEQUENCE: 37

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
                20                  25                  30

Val Ser Trp Tyr Gln Gln His Pro Gly Lys Ala Pro Lys Leu Met Ile
            35                  40                  45

Tyr Val Lys Ser Asp Gly Ser Tyr Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Gly Ala Asp Asp
                85                  90                  95

Asn Gly Gly Tyr Val Phe Gly Gly Gly Thr Lys Leu Thr Val Leu
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L3m1

<400> SEQUENCE: 38

Gln Phe Val Leu Thr Gln Pro Ala Ser Val Ser Gly Ser Pro Gly Gln
1               5                   10                  15

Ser Ile Thr Ile Ser Cys Thr Leu Ser Ser Ala His Lys Thr Tyr Thr
                20                  25                  30

Ile Asp Trp Tyr Gln Gln His Pro Gly Lys Ala Pro Lys Tyr Leu Met
            35                  40                  45

Gln Val Lys Ser Asp Gly Ser Tyr Thr Lys Gly Thr Gly Val Pro Asn
    50                  55                  60

Arg Phe Ser Gly Ser Ser Gly Ala Asp Arg Tyr Leu Thr Ile Ser
65                  70                  75                  80

Gly Leu Gln Ala Glu Asp Glu Ala Asp Tyr Val Cys Gly Ala Asp Asp
                85                  90                  95

Asn Gly Gly Tyr Val Phe Gly Gly Gly Thr Gln Leu Thr Val Thr
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L3m2

<400> SEQUENCE: 39

Gln Phe Val Leu Thr Gln Pro Ala Ser Val Ser Gly Ser Pro Gly Gln
1               5                   10                  15

```
Ser Ile Thr Ile Ser Cys Thr Leu Ser Ser Ala His Lys Thr Tyr Thr
            20                  25                  30

Ile Asp Trp Tyr Gln Gln His Pro Gly Lys Ala Pro Lys Leu Met Ile
        35                  40                  45

Gln Val Lys Ser Asp Gly Ser Tyr Thr Lys Gly Thr Gly Val Ser Asn
 50                  55                  60

Arg Phe Ser Gly Ser Ser Ser Gly Ala Asp Arg Tyr Leu Thr Ile Ser
 65                  70                  75                  80

Gly Leu Gln Ala Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Leu
            100                 105                 110
```

<210> SEQ ID NO 40
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L3m3

<400> SEQUENCE: 40

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ala His Lys Thr Tyr Thr
            20                  25                  30

Ile Asp Trp Tyr Gln Gln His Pro Gly Lys Ala Pro Lys Leu Met Ile
        35                  40                  45

Tyr Val Lys Ser Asp Gly Ser Tyr Thr Lys Gly Thr Gly Val Ser Asn
 50                  55                  60

Arg Phe Ser Gly Ser Lys Ser Gly Asn Thr Ala Ser Leu Thr Ile Ser
 65                  70                  75                  80

Gly Leu Gln Ala Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Leu
            100                 105                 110
```

<210> SEQ ID NO 41
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L3m4

<400> SEQUENCE: 41

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ala His Lys Thr Tyr Thr
            20                  25                  30

Val Ser Trp Tyr Gln Gln His Pro Gly Lys Ala Pro Lys Tyr Leu Met
        35                  40                  45

Gln Val Lys Ser Asp Gly Ser Tyr Thr Lys Gly Thr Gly Val Pro Asn
 50                  55                  60

Arg Phe Ser Gly Ser Ser Ser Gly Ala Asp Arg Tyr Leu Thr Ile Ser
 65                  70                  75                  80
```

Gly Leu Gln Ala Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Light Chain
<220> FEATURE:
<223> OTHER INFORMATION: L3m5

<400> SEQUENCE: 42

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
            20                  25                  30

Val Ser Trp Tyr Gln Gln His Pro Gly Lys Ala Pro Lys Leu Met Ile
        35                  40                  45

Tyr Val Lys Ser Asp Gly Ser Tyr Thr Lys Gly Thr Gly Val Pro Asn
50                  55                  60

Arg Phe Ser Gly Ser Ser Ser Gly Ala Asp Arg Tyr Leu Thr Ile Ser
65                  70                  75                  80

Gly Leu Gln Ala Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu
            100                 105                 110

<210> SEQ ID NO 43
<211> LENGTH: 759
<212> TYPE: DNA
<213> ORGANISM: Artificial Sequence
<220> FEATURE:
<223> OTHER INFORMATION: scFv
<220> FEATURE:
<223> OTHER INFORMATION: 0.410HC.410LC

<400> SEQUENCE: 43
cagttcgtgc tgacccagag ccctagcgtg agcgctgctc tgggagccag cgccaagctc        60
acttgtactt taagctccgc ccacaaaacc tacaccatcg actggtacca gcagcagcaa       120
ggtgaggccc ccagatattt aatgcaagtt aagtccgatg gcagctacac caagggcacc       180
ggagtgcccg ataggttcag cggcagctcc agcggcgccg ataggtattt aatcatcccc       240
agcgtgcaag ctgatgatga ggccggctac gtgtgtggcg ccgacgacaa cggcggctac       300
gtgttcggag gcgaacccca gctgacagtg accggaggcg gaagctccag aagctccagc       360
agcggaggag gaggaagcgg aggaggcgga cagtccgtca aggagagcga gggcggttta       420
tttaagccca ccgacacttt aactttaact tgtacagtga gcggcttctc tttatcagat       480
cacgctttaa catgggtgag gcaagctccc ggtaatggtt tagagtggat cggcgccatc       540
gacaacgccg gcaccaccta ctacgccagc tgggccaagt ctcgttccac catcacaaga       600
aacaccgatt tacacaccgt gactttaaag atgacctctt taaccgcctc cgacaccgcc       660
acatacttct gcgctcgtgt gttctacgac atcaattccg gctactattt agacggcatg       720
gatttatggg gccccggtac tttagtgacc gtctccagc                              759

<210> SEQ ID NO 44

<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 1.H1.L3

<400> SEQUENCE: 44

| | | | | | |
|---|---|---|---|---|---|
| cagtccgctt | taacacagcc | cgcttctgtg | tccggaagcc | ccggtcagag | catcaccatc | 60 |
| agctgcaccg | gcaccagcgc | tcacaagacc | tacaccgtga | gctggtacca | gcagcacccc | 120 |
| ggtaaggccc | ccaaactgat | gatctacgtg | aagagcgacg | gcagctacaa | cagacccagc | 180 |
| ggcgtgagca | atcgtttcag | cggcagcaag | agcggcaaca | ccgcttcttt | aaccatcagc | 240 |
| ggtttacaag | ctgaagacga | ggctgactac | tactgcggcg | ccgacgataa | cggcggctac | 300 |
| gtgtttggcg | gcggcaccaa | actgaccgtg | ctgggaggcg | gctccagcag | aagctcctcc | 360 |
| agcggaggag | gaggaagcgg | aggcggagga | caagttcagc | tgcaagaaag | cggacccggt | 420 |
| ttagtcaagc | ccagcgagac | tttatcttta | acatgcgccg | tgagcggcta | ctccatctct | 480 |
| cgtcacgctt | taacatggat | taggcagccc | cccgtaagg | gtttagaatg | gatcggcgcc | 540 |
| atcgacaacc | tggcaccac | ctactacgcc | tcttgggcta | agtctcgtgt | gacaatcagc | 600 |
| gtggacacct | ccaagaacca | gttttcttta | aagctgagca | gcgtgaccgc | tgccgacacc | 660 |
| gctgtgtact | attgcgctcg | tgtcttctac | gacatcaaca | gcggctacta | tttagatggc | 720 |
| atggatttat | ggggacccgg | tactttagtg | accgtgagct | cc | | 762 |

<210> SEQ ID NO 45
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 2.H1.L3m1

<400> SEQUENCE: 45

| | | | | | |
|---|---|---|---|---|---|
| cagttcgtgc | tgacccagcc | cgcttctgtg | agcggttctc | ccggtcagag | catcaccatc | 60 |
| agctgcactt | taagcagcgc | ccacaagacc | tacaccatcg | actggtacca | gcagcacccc | 120 |
| ggcaaggccc | ccaagtattt | aatgcaagtt | aagtccgacg | gcagctacac | caagggcacc | 180 |
| ggcgtgccca | acagattctc | cggcagcagc | tccggcgccg | acagatactt | aaccatcagc | 240 |
| ggtttacaag | ctgaggatga | ggccgactat | gtgtgcggcg | ccgacgacaa | tggcggctac | 300 |
| gtgttcggcg | gcggcacaca | gctgaccgtg | actggtggag | gctccagcag | atccagctcc | 360 |
| agcggcggag | gaggcagcgg | aggcggagga | caagtcagc | tccaagaatc | cggcccggt | 420 |
| ctcgtgaagc | ccagcgagac | tttatcttta | acttgtgccg | tgagcggcta | cagcatctct | 480 |
| cgtcacgctc | tgacttggat | tcgtcaacct | cccggaaagg | gtttagagtg | gatcggcgcc | 540 |
| atcgacaacg | ccggcaccac | ctactacgcc | agctgggcca | aatctcgtgt | gaccattagc | 600 |
| gtggacacca | gcaagaacca | gttctctta | aaactgagca | gcgtgacagc | tgccgacacc | 660 |
| gccgtgtact | actgcgctcg | tgtgttctac | gacatcaaca | gcggctacta | tttagacggc | 720 |
| atggatttat | ggggcccgg | tactttagtg | accgtcagct | cc | | 762 |

<210> SEQ ID NO 46
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 3.H1m1.L3

<400> SEQUENCE: 46

| | | | | | |
|---|---|---|---|---|---|
| cagtccgctt | taacccagcc | cgcctctgtg | tccggaagcc | cggccagag | catcaccatc | 60 |
| agctgcaccg | gcacctccgc | ccacaagacc | tacaccgtga | gctggtatca | gcagcacccc | 120 |
| ggcaaggccc | ccaagctcat | gatctacgtg | aagagcgacg | gctcctacaa | tcgtcccagc | 180 |
| ggagtgagca | atcgtttcag | cggctccaag | tccggcaaca | ccgcctcttt | aaccattagc | 240 |
| ggtttacaag | ctgaggacga | ggctgattac | tactgcggcg | ccgacgataa | cggaggctac | 300 |
| gtgttcggcg | gcggaacaaa | gctgaccgtg | ctgggcggag | gctccagcag | aagcagctcc | 360 |
| agcggaggcg | gaggaagcgg | aggaggagga | cagcagagcg | tgaaggagag | cggcccggt | 420 |
| ctggtgaagc | ccagcgagac | tttatcttta | acatgcgccg | tgagcggctt | ctctttatct | 480 |
| cgtcacgctt | taacttgggt | gagacagcct | cccggtaaag | gtttagagtg | gatcggcgcc | 540 |
| atcgacaacg | ccggcacaac | ctactacgcc | agctgggcca | agtctcgtgt | gaccatctct | 600 |
| cgtaacaccg | atttacacac | cgtgtcttta | aagctgagct | ccgtgaccgc | tgccgatacc | 660 |
| gccgtgtact | tctgcgctag | ggtgttctac | gacatcaaca | gcggctacta | tttagatggc | 720 |
| atggatctgt | ggggccccgg | cacactggtc | acagtgtcca | gc | | 762 |

<210> SEQ ID NO 47
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 4.H1m1.L3m1

<400> SEQUENCE: 47

| | | | | | |
|---|---|---|---|---|---|
| cagttcgtgc | tgacccagcc | cgcttccgtg | agcggttctc | ccggacagag | catcaccatt | 60 |
| agctgcactt | taagcagcgc | ccacaagacc | tacaccatcg | actggtacca | gcagcatccc | 120 |
| ggcaaggccc | ccaagtacct | catgcaagtt | aagagcgacg | gaagctatac | caagggcacc | 180 |
| ggagtgccca | acagattcag | cggcagcagc | tccggagccg | atcgttattt | aacaatcagc | 240 |
| ggactgcaag | ctgaggacga | ggccgactac | gtgtgtggcg | ccgacgacaa | tggcggctac | 300 |
| gtgtttggag | gcggaaccca | gctgaccgtg | actggaggcg | gcagcagcag | aagcagcagc | 360 |
| agcggaggag | tggcagcgg | cggaggcgga | cagcagagcg | tgaaggagag | cggacccggt | 420 |
| ttagtgaagc | ctagcgagac | tttatcttta | acatgcgccg | tgtccggctt | ctctttaagc | 480 |
| agacacgctc | tgacttgggt | gaggcagcct | cccggtaagg | gtttagagtg | gatcggcgcc | 540 |
| atcgacaacg | ccggcaccac | ctactacgcc | agctgggcca | agtccagagt | gaccatctcc | 600 |
| agaaacaccg | acctccacac | agtgtcttta | aagctgtcct | ccgtcacagc | tgccgacacc | 660 |
| gccgtgtact | tctgcgctcg | tgtgttctac | gacatcaaca | gcggctatta | tttagacggc | 720 |
| atggatttat | ggggccccgg | tactttagtg | accgtgagca | gc | | 762 |

<210> SEQ ID NO 48
<211> LENGTH: 762
<212> TYPE: DNA
<213> ORGANISM: Artificial Sequence
<220> FEATURE:
<223> OTHER INFORMATION: scFv
<220> FEATURE:

<223> OTHER INFORMATION: 5.H2.L2

<400> SEQUENCE: 48

| | | | | | |
|---|---|---|---|---|---|
| cagagcgtgc | tgacacagcc | tcctagcgcc | agcggcacac | ccggtcagag | agtgaccatc | 60 |
| agctgctccg | gcagcagcgc | ccacaagacc | tacaccgtga | actggtacca | gcagctgccc | 120 |
| ggcacagccc | ctaagctgct | gatctacgtg | aaatccgacg | gcagctacca | gaggcctagc | 180 |
| ggagtgcccg | atcgtttcag | cggcagcaaa | agcggcacaa | cgcctctttt | agctatcagc | 240 |
| ggtttacaga | gcgaggacga | ggccgactat | tactgcggcg | ccgacgataa | cggcggctac | 300 |
| gtgttcggcg | gcggaaccaa | gctgacagtg | ctgggcggcg | gaagcagcag | aagcagcagc | 360 |
| tctggaggag | gaggaagcgg | aggtggaggc | gaggtgcagc | tggtggaaag | cggcggagga | 420 |
| ctggtgcagc | ccggtggctc | tttaagactg | agctgtgctg | ccagcggctt | cacattctct | 480 |
| cgtcacgctt | taacttgggt | gagacaagct | cccggaaagg | gtttagaatg | ggtgagcgcc | 540 |
| atcgacaacg | ccggaaccac | ctactacgcc | agctgggcca | gtctcgtttc | accatctct | 600 |
| cgtgataacg | ccaagaacag | cctctattta | cagatgaact | ctttaagggc | cgaggacacc | 660 |
| gccgtgtact | actgcgctag | ggtgttctac | gacatcaaca | gcggctacta | tctggacggc | 720 |
| atggattat | ggggccccgg | tacactggtc | accgtgagca | gc | | 762 |

<210> SEQ ID NO 49
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 6.H2.L2m1

<400> SEQUENCE: 49

| | | | | | |
|---|---|---|---|---|---|
| cagttcgtgc | tgacacagcc | tcccagcgcc | tctggcacac | ccggtcagag | ggtgaccatc | 60 |
| tcttgtactt | tatcctccgc | ccacaagacc | tacaccattg | actggtacca | gcagctgccc | 120 |
| ggtaccgccc | ctaagctgct | gatttacgtg | aaatccgacg | gcagctacac | caagggaacc | 180 |
| ggcgtgcccg | atcgttttc | cggcagctcc | agcggcgccg | ataggtattt | agccatcagc | 240 |
| ggtttacagt | ccgaggatga | ggccgactac | tactgcggcg | ccgatgacaa | cggcggctac | 300 |
| gtgttcggcg | gaggaaccca | gctcaccgtg | accggaggag | gctcctctcg | tagctccagc | 360 |
| tccggaggag | gaggaagcgg | aggcggcgga | gaagtgcaac | tggtggagtc | cggcggcgga | 420 |
| ctggtgcagc | ccggtggctc | tttaagactg | agctgtgccg | cctccggctt | caccttagc | 480 |
| agacacgccc | tcacttgggt | cagacaagct | cccggtaagg | gtttagagtg | ggtgagcgcc | 540 |
| atcgacaacg | ccggcacaac | ctactacgcc | tcttgggcca | gtctcgtttc | accatcagc | 600 |
| agagacaacg | ccaagaactc | tttatattta | cagatgaact | ctttaagggc | cgaggacacc | 660 |
| gccgtgtact | actgcgctcg | tgtgttctac | gacatcaaca | gcggctatta | tttagatggc | 720 |
| atggattat | ggggccccgg | tactttagtg | acagtgtcct | cc | | 762 |

<210> SEQ ID NO 50
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 7.H2m1.L2

<400> SEQUENCE: 50

```
cagagcgtgc tgacccagcc tcctagcgcc tctggcacac ccggtcagag ggtgaccatc    60
agctgctccg gctcctccgc ccacaagacc tacaccgtga actggtacca gcagctgccc   120
ggtaccgctc ccaagctgct gatttacgtg aaaagcgacg gcagctacca gagacctagc   180
ggcgtgcccg atcgtttctc cggttctaag agcggcacca gcgcctcttt agccattagc   240
ggcctccaga gcgaggacga ggccgattac tactgcggag ccgacgacaa tggcggctac   300
gtgttcggcg gcggaaacaa agctgaccgt ttaggtggcg aagcagcag aagcagcagc    360 tctggcggcg gcggtagcgg cggtggcgga gagcagagcg tcaaggagtc cggaggagga   420
ctggtgcagc ccgtggctc tttaaggctg agctgtgccg cctctggctt tactttatct    480
cgtcacgctt aacatgggt gagacaagct cccggtaagg gactggagtg gatcggcgcc    540
atcgacaacg ccggcaccac ctactacgcc tcttgggcca agtctcgttt caccatctct   600
cgtaacaccg atttacacac cgtgtattta cagatgaact ctttaagggc cgaggacaca   660
gccgtctatt tctgcgctcg tgtgttctac gacatcaata gcggctacta cctcgacgga   720
atggatctgt ggggccccgg tactttagtg acagtcagca gc                      762

<210> SEQ ID NO 51
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 8.H2m1.L2m1

<400> SEQUENCE: 51
cagtttgttt taacccagcc tcctagcgcc tctggaacac ccggccaaag ggtcaccatc    60
agctgcactt tatcctccgc ccacaagacc tacaccatcg actggtacca gcagctgccc   120
ggaaccgccc ctaagctgct gatctacgtg aagagcgacg gcagctacac caagggcacc   180
ggcgtgcccg ataggttcag cggcagcagc agcggcgccg atagatattt agccatttcc   240
ggtttacaga gcgaggacga ggccgattac tactgtggcg ctgacgacaa cggaggctac   300
gtgttcggag gcggcaccca gctgaccgtg actggtggcg gttctagcag aagcagcagc   360
tccggaggcg gaggctctgg cggcggtggc gagcagtccg tgaaggaaag cggcggcgga   420
ctggtgcagc ccgtggatc tttaagactg agctgcgccg cctctggctt cactttatcc   480
agacatgctt aacatgggt gagacaagct cccggcaagg gactggagtg gatcggcgcc    540
atcgacaacg ccggcaccac ctactacgcc agctgggcca atctcgtttt caccatctct   600
cgtaacaccg atttacacac cgtgtattta cagatgaatt ctttaagggc cgaggacacc   660
gccgtgtact tctgcgctcg tgtgttctac gacatcaaca gcggctacta tttagacggc   720
atggatttat ggggacccgg tacactcgtg accgtgtcca gc                      762

<210> SEQ ID NO 52
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 9.H2.L1

<400> SEQUENCE: 52
cagctggtgc tgacccagag ccccagcgct tccgcctctt taggagccag cgtgaagctg    60
```

-continued

| | |
|---|---|
| acttgtactt taagcagcgc ccacaagacc tacacaatcg cttggcacca gcagcagccc | 120 |
| gaaaagggcc ccagatatct gatgaaggtc aagtccgacg gcagctactc caagggcgac | 180 |
| ggcatccccg atcgtttcag cggttcttcc agcggcgccg agaggtattt aaccatcagc | 240 |
| tctttacaga gcgaggacga ggccgactac tactgcggcg ctgacgacaa cggcggctac | 300 |
| gtctttggcg gcggcacaaa actgaccgtg ctgggcggcg gaagcagcag aagctccagc | 360 |
| tctggaggag gaggttctgg aggtggagga gaggtgcagc tggtggagag cggcggagga | 420 |
| ctggtgcagc ccgtggatc tttaagactg agctgtgccg ccagcggctt caccttctct | 480 |
| cgtcacgctc tgacatgggt gaggcaagcc cccgtaagg gtttagaatg ggtgagcgcc | 540 |
| atcgacaatg ccggaaccac ctattacgcc tcttgggcca agtctcgttt caccatctct | 600 |
| cgtgacaatg ccaagaactc tttatattta cagatgaact cttaagagc tgaggacacc | 660 |
| gccgtctact actgcgccag agtgttctac gacatcaaca gcggctacta cctcgacggc | 720 |
| atggatttat ggggccccgg tactttagtg accgtgagca gc | 762 |

<210> SEQ ID NO 53
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 10.H2.L1m1

<400> SEQUENCE: 53

| | |
|---|---|
| cagtttgtgc tgacccagag ccctagcgct tccgcctctt taggagccag cgtgaagctg | 60 |
| acttgtactt tatcctccgc ccacaagacc tacaccatcg actggtacca gcagcagccc | 120 |
| gaaaagggcc ctcgttatct gatgcaagtt aagtccgacg gcagctacac caagggaacc | 180 |
| ggcgtgcccg acagattctc cggtagcagc agcggcgccg acagatattt aaccatcagc | 240 |
| tctttacagt ccgaggacga ggccgactac tactgcggcg ccgacgacaa tggcggctac | 300 |
| gtcttcggag gcggcacaca gctgaccgtg actggtggag gctcctccag aagcagctct | 360 |
| agcggaggag gaggaagcgg cggaggaggc gaagtgcagc tggtggagtc cggaggagga | 420 |
| ctggtgcagc ccggaggttc tttaagactg agctgcgccg cctccggctt cacctttttct | 480 |
| cgtcacgctt taacatgggt gagacaagct cccggcaagg gactgaatg ggtcagcgcc | 540 |
| atcgataacg ccggcaccac ctattacgcc agctgggcta agtctcgttt caccatcagc | 600 |
| agagacaacg ccaagaactc tttatattta cagatgaatt cttaagagc cgaggacacc | 660 |
| gccgtgtatt actgcgctcg tgtcttctac gacatcaact ccggctacta tttagacggc | 720 |
| atggatttat ggggccccgg tactttagtc accgtgagct cc | 762 |

<210> SEQ ID NO 54
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 11.H2m1.L1

<400> SEQUENCE: 54

| | |
|---|---|
| cagctggtgc tgacacagag cccctccgcc tccgcctctt taggcgcttc cgtgaagctg | 60 |
| acttgtactt tatccagcgc ccacaagacc tacaccatcg cttggcacca gcagcagccc | 120 |
| gagaaaggcc ctcgttacct catgaaagtg aagtccgacg gcagctactc caagggcgac | 180 |

```
ggcatcccg atcgttttag cggcagcagc tccggcgccg agaggtattt aaccatcagc    240
tctttacaga gcgaagacga ggccgactat tactgcggcg ccgatgacaa cggaggctac    300
gtgttcggcg gaggcaccaa actgaccgtg ctgggcggcg aagcagcag  aagctccagc    360 agcggaggag gaggttctgg aggaggcgga gagcagagcg tgaaagagtc cggcggaggt    420
ttagtgcagc ccggtggttc tttaagactg agctgcgccg ccagcggctt cacactgtcc    480
agacacgctt taacatgggt gagacaagct cccggtaagg gactggagtg gatcggcgcc    540
atcgacaatg ccggcaccac ctactacgcc agctgggcca agtctcgttt caccatctct    600
cgtaacaccg atttacacac cgtctattta cagatgaact cttttaagggc cgaggacaca    660 gccgtgtact tttgcgctcg tgtgttctac gacatcaaca gcggctacta tttagacggc    720
atggatctgt ggggccccgg aacactggtg accgtgagca gc                       762

<210> SEQ ID NO 55
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 12.H2m1.L1m1

<400> SEQUENCE: 55
cagtttgtgc tgacccagtc ccctagcgcc tctgcctctt taggagcctc tgtgaaactg    60
acttgtactt taagcagcgc ccacaagaca tacaccatcg actggtacca gcagcagccc    120
gaaaagggcc ctaggtattt aatgcaagtt aagagcgacg gcagctacac aaagggcact    180
ggtgtgcccg acagattcag cggcagcagc agcggcgccg acagatacct caccatcagc    240
tctttacagt ccgaggacga ggccgactac tattgcggcg ccgacgacaa cggcggctac    300
gtgttcggcg gaggaaccca gctgaccgtg actggtggcg aagcagcag  aagcagctcc    360 tccggaggcg gaggttctgg cggaggtgga gaacagagcg tgaaggagag cggaggtgga    420
ctggtgcagc ccggtggttc tttaagactg agctgcgctg cctccggctt caccttatct    480
cgtcacgctt aacatgggt  gagacaagct cccggtaagg gtttagagtg gatcggcgcc    540
atcgacaatg ctggcaccac ctactacgcc agctgggcca agtctcgttt cacaatctct    600
cgtaacaccg atctgcacac cgtgtattta cagatgaact cttttaagagc cgaggacacc    660 gccgtgtatt tctgcgctcg tgtgttctac gacatcaaca gcggctacta tttagacggc    720
atggatttat ggggccccgg tactttagtg accgtgagct cc                       762

<210> SEQ ID NO 56
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 13.H1.L1

<400> SEQUENCE: 56
cagctcgtgc tgacccagtc ccccagcgcc tctgcctctt taggcgccag cgtgaagctg    60
acttgtactt tatccagcgc ccacaagaca tacaccatcg cttggcacca gcagcagccc    120
gaaaagggcc ctcgttattt aatgaaggtc aagtccgacg ctcctactc  caagggcgac    180 ggcatcccg  atagattcag cggtagcagc agcggcgccg agagatattt aacaatcagc    240
```

| | |
|---|---|
| tctttacaga gcgaggacga ggccgactac tactgcggcg ccgacgacaa tggcggctac | 300 |
| gtcttcggcg gcggaaccaa gctcacagtg ctgggtggag gctccagcag aagcagctct | 360 |
| agcggaggcg gaggttccgg cggcggaggc caagttcagc tgcaagaatc cggccccgga | 420 |
| ctggtgaagc cctccgaaac actgtcttta acatgcgccg tgagcggcta cagcatttct | 480 |
| cgtcacgctt taacttggat cagacagccc cccggcaagg gtttagaatg gatcggagcc | 540 |
| atcgataacg ccggcaccac atactacgcc agctgggcca agagcagagt gaccatctcc | 600 |
| gtggacacca gcaagaacca gttttcttta aagctcagct ccgtgaccgc cgccgataca | 660 |
| gccgtgtact actgcgccag agtgttctac gacatcaaca cggctacta tttagacgga | 720 |
| atggatttat ggggccccgg tactttagtg accgtgagca gc | 762 |

<210> SEQ ID NO 57
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 14.H1.L1m1

<400> SEQUENCE: 57

| | |
|---|---|
| cagtttgtgc tcacccaaag ccctagcgcc tctgcctctt taggcgcttc cgtgaagctg | 60 |
| acttgtactt taagctccgc ccataagacc tacaccatcg actggtacca gcagcagccc | 120 |
| gagaagggcc ctcgttattt aatgcaagtt aagtccgatg gcagctatac caagggcacc | 180 |
| ggcgtgcccg acagattcag cggcagctcc agcggagccg atcgttattt aaccatcagc | 240 |
| tctttacaga gcgaggacga ggctgactac tactgcggcg ccgacgataa cggcggctac | 300 |
| gtgttcggcg gcggcacccca actgacagtg accggaggcg gttcttctcg tagcagcagc | 360 |
| agcggaggcg gcggctccgg cggcggaggc caagttcagc tgcaagaatc cggccccggt | 420 |
| ctggtgaaac ccagcgagac tttatcttta acatgcgccg tgagcggcta ctccatctcc | 480 |
| agacacgctt taacttggat cagacagcct cccggcaagg gactggagtg gatcggcgct | 540 |
| atcgacaacg ccggcaccac ctactacgcc tcttgggcca agtctcgtgt caccatcagc | 600 |
| gtggacacat ccaagaacca gttctcttta aagctgtcca gcgtgaccgc cgccgataca | 660 |
| gccgtgtact actgcgctcg tgtgttctac gacatcaact ccggctacta tttagacggc | 720 |
| atggatttat ggggacccgg tactttagtg accgtgtcca gc | 762 |

<210> SEQ ID NO 58
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 15.H1m1.L1

<400> SEQUENCE: 58

| | |
|---|---|
| cagctggtgc tgacacaaag ccccagcgcc agcgcctctt taggcgccag cgtcaaactg | 60 |
| acatgcactt taagcagcgc ccacaagacc tacaccatcg cttggcacca gcagcagccc | 120 |
| gagaagggcc ccagatattt aatgaaggtg aagtccgatg gcagctacag caagggagat | 180 |
| ggcattcccg atcgttttag cggctcctcc agcggcgccg agagatactt aaccatctcc | 240 |
| tctttacaga gcgaggacga ggccgactac tactgcggcg ccgatgacaa cggcggctac | 300 |
| gtgttcggcg gcggaaccaa gctgaccgtg ctgggcggag gcagctccag atccagcagc | 360 |

```
agcggcggag gaggaagcgg aggaggagga cagcagtccg tgaaagagag cggccccggt      420
ttagtgaaac ccagcgagac tttatcttta acttgtgccg tgagcggctt cagcctctct      480
cgtcacgctt taacttgggt gagacagcct cccggcaaag gtttagagtg gattggcgcc      540
atcgacaacg ccggcaccac ctactacgcc agctgggcca aatctcgtgt gaccatttcc      600
agaaacaccg atttacacac cgtgtcttta aagctgtcca gcgtgaccgc cgctgacacc      660
gctgtctact tctgcgctcg tgtgttctac gacatcaact ccggctacta tttagacggc      720
atggatttat ggggccccgg tactttagtg accgtgagct cc                         762
```

<210> SEQ ID NO 59
<211> LENGTH: 763
<212> TYPE: DNA
<213> ORGANISM: Artificial Sequence
<220> FEATURE:
<223> OTHER INFORMATION: scFv
<220> FEATURE:
<223> OTHER INFORMATION: 16.H1m1.L1m1

<400> SEQUENCE: 59

```
cagttcgtgc tcacacagag ccctagcgct tccgcctctt taggagccag cgtgaaactg      60
acatgtactt taagcagcgc ccacaaaacc tacaccatcg actggtacca gcagcaaccc      120
gagaagggcc ctagatattt aatgcaagtt aagagcgacg gctcctacac caaaggcacc      180
ggcgtgcccg ataggttcag cggctcctcc tccggagccg atcgttattt aacaatcagc      240
tctttacaga gcgaagacga ggccgattac tactgcggag ccgatgacaa cggcggctac      300
gtcttcggag gcggaaccca gctgacagtg accgagggcg gcagcagcag atccagcagc      360
tccggaggcg gaggaagcgg aggaggcggc agcaaagcg tgaaggagag cggccccgga      420
ctcgtgaaac cctccgagac tttatcttta acttgtgccg tgagcggctt ctctttatct      480
cgtcacgctt taacatgggt gaggcagcct cccggtaagg gtttagagtg gatcggcgcc      540
atcgacaacg ccggcacaac ctactacgcc agctgggcca agagcagagt gaccatctct      600
cgtaacaccg atttacacac cgtgtcttta aagctgagct ccgtgaccgc cgccgatacc      660
gctgtgtact tctgcgctcg tgtcttctac gacatcaact ccggctatta cctcgacggc      720
atggatctgt ggggccccgg aacactggtg accgtgagca gcg                       763
```

<210> SEQ ID NO 60
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 17.H1.L3m2

<400> SEQUENCE: 60

```
cagttcgtgc tgacccagcc cgcttctgtg agcggttctc ccggtcagag catcaccatc      60
agctgcactt taagcagcgc ccacaagacc tacaccatcg actggtacca gcagcacccc      120
ggcaaggccc ccaagctgat gatccaagtt aagtccgacg gcagctacac caagggcacc      180
ggcgtgagca acagattctc cggcagcagc tccggcgccg acagatactt aaccatcagc      240
ggtttacaag ctgaggatga ggccgactat tactgcggcg ccgacgacaa tggcggctac      300
gtgttcggcg gcggcacaca gctgaccgtg ctggtggag ctccagcag atccagctcc      360 agcggcggag gaggcagcgg aggcggagga caagtgcagc tccaagaatc cggccccgt      420
```

```
ctcgtgaagc ccagcgagac tttatcttta acttgtgccg tgagcggcta cagcatctct    480
cgtcacgctc tgacttggat tcgtcaacct cccggaaagg gtttagagtg gatcggcgcc    540
atcgacaacg ccggcaccac ctactacgcc agctgggcca atctcgtgt gaccattagc    600 gtggacacca gcaagaacca gttctcttta aaactgagca gcgtgacagc tgccgacacc    660
gccgtgtact actgcgctcg tgtgttctac gacatcaaca gcggctacta tttagacggc    720
atggatttat ggggccccgg tactttagtg accgtcagct cc                      762
```

<210> SEQ ID NO 61
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 18.H1.L3m3

<400> SEQUENCE: 61

```
cagagcgccc tgacccagcc cgcttctgtg agcggttctc ccggtcagag catcaccatc     60
agctgcactg gcaccagcgc ccacaagacc tacaccatcg actggtacca gcagcacccc    120
ggcaaggccc ccaagctgat gatctatgtt aagtccgacg gcagctacac caagggcacc    180
ggcgtgagca acagattctc cggcagcaag tccggcaaca ccgccagctt aaccatcagc    240
ggtttacaag ctgaggatga ggccgactat tactgcggcg ccgacgacaa tggcggctac    300
gtgttcggcg gcggcacaca gctgaccgtg ctgggtggag gctccagcag atccagctcc    360
agcggcggag gaggcagcgg aggcggagga caagtgcagc tccaagaatc cggcccggt    420 ctcgtgaagc ccagcgagac tttatcttta acttgtgccg tgagcggcta cagcatctct    480
cgtcacgctc tgacttggat tcgtcaacct cccggaaagg gtttagagtg gatcggcgcc    540
atcgacaacg ccggcaccac ctactacgcc agctgggcca atctcgtgt gaccattagc    600 gtggacacca gcaagaacca gttctcttta aaactgagca gcgtgacagc tgccgacacc    660
gccgtgtact actgcgctcg tgtgttctac gacatcaaca gcggctacta tttagacggc    720
atggatttat ggggccccgg tactttagtg accgtcagct cc                      762
```

<210> SEQ ID NO 62
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 19.H2.L2m2

<400> SEQUENCE: 62

```
cagttcgtgc tgacacagcc tcccagcgcc tctggcacac ccggtcagag ggtgaccatc     60
tcttgtactt tatcctccgc ccacaagacc tacaccattg actggtacca gcagctgccc    120
ggtaccgccc ctaagctgct gatttacgtg aaatccgacg gcagctacac caagggaacc    180
ggcgtgcccg atcgtttttc cggcagctcc agcggcgccg atgccagctt agccatcagc    240
ggtttacagt ccgaggatga ggccgactac tactgcggcg ccgatgacaa cggcggctac    300
gtgttcggcg gaggaaccca gctcaccgtg ctgggaggag gctcctctcg tagctccagc    360
tccggaggag gaggaagcgg aggcggcgga gaagtgcaac tggtggagtc cggcggcgga    420
ctggtgcagc ccggtggctc tttaagactg agctgtgccg cctccggctt cacctttagc    480
agacacgccc tcacttgggt cagacaagct cccggtaagg gtttagagtg ggtgagcgcc    540
```

```
atcgacaacg ccggcacaac ctactacgcc tcttgggcca agtctcgttt caccatcagc    600
agagacaacg ccaagaactc tttatattta cagatgaact ctttaagggc cgaggacacc    660
gccgtgtact actgcgctcg tgtgttctac gacatcaaca gcggctatta tttagatggc    720
atggatttat ggggccccgg tactttagtg acagtgtcct cc                       762
```

<210> SEQ ID NO 63
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 20.H2.L2m3

<400> SEQUENCE: 63

```
cagagcgtgc tgacacagcc tcccagcgcc tctggcacac ccggtcagag ggtgaccatc     60
tcttgtactt tatcctccgc ccacaagacc tacaccattg actggtacca gcagctgccc    120
ggtaccgccc ctaagctgct gatttacgtg aaatccgacg gcagctacac caagggaacc    180
ggcgtgcccg atcgtttttc cggcagcaag agcggcacca cgccagcttt agccatcagc    240
ggtttacagt ccgaggatga ggccgactac tactgcggcg ccgatgacaa cggcggctac    300
gtgttcggcg gaggaaccca gctcaccgtg ctgggaggag gctcctctcg tagctccagc    360
tccggaggag gaggaagcgg aggcggcgga gaagtgcaac tggtggagtc cggcggcgga    420
ctggtgcagc ccgtggcctc tttaagactg agctgtgccg cctccggctt caccttttagc    480 agacacgccc tcacttgggt cagacaagct cccggtaagg gtttagagtg ggtgagcgcc    540
atcgacaacg ccggcacaac ctactacgcc tcttgggcca agtctcgttt caccatcagc    600
agagacaacg ccaagaactc tttatattta cagatgaact ctttaagggc cgaggacacc    660
gccgtgtact actgcgctcg tgtgttctac gacatcaaca gcggctatta tttagatggc    720
atggatttat ggggccccgg tactttagtg acagtgtcct cc                       762
```

<210> SEQ ID NO 64
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 21.H2.L1m2

<400> SEQUENCE: 64

```
cagtttgtgc tgacccagag ccctagcgct tccgcctctt taggagccag cgtgaagctg     60
acttgtactt tatcctccgc ccacaagacc tacaccatcg actggcacca gcagcagccc    120
gaaaagggcc ctcgttatct gatgcaagtt aagtccgacg gcagctacac caagggaacc    180
ggcatccccg acagattctc cggtagcagc agcggcgccg agagatattt aaccatcagc    240
tctttacagt ccgaggacga ggccgactac tactgcggcg ccgacgacaa tggcggctac    300
gtcttcggag gcggcacaca gctgaccgtg ctgggtggag gctcctccag aagcagctct    360
agcggaggag gaggaagcgg cggaggaggc gaagtgcagc tggtggagtc cggaggagga    420
ctggtgcagc ccggaggttc tttaagactg agctgcgccg cctccggctt caccttttct    480
cgtcacgctt taacatgggt gagacaagct cccggcaagg gactgaatg ggtcagcgcc    540 atcgataacg ccggcaccac ctattacgcc agctgggcta agtctcgttt caccatcagc    600
```

| | |
|---|---|
| agagacaacg ccaagaactc tttatattta cagatgaatt ctttaagagc cgaggacacc | 660 |
| gccgtgtatt actgcgctcg tgtcttctac gacatcaact ccggctacta tttagacggc | 720 |
| atggatttat ggggcccegg tactttagtc accgtgagct cc | 762 |

<210> SEQ ID NO 65
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 22.H1.L1m2

<400> SEQUENCE: 65

| | |
|---|---|
| cagtttgtgc tcacccaaag ccctagcgcc tctgcctctt taggcgcttc cgtgaagctg | 60 |
| acttgtactt taagctccgc ccataagacc tacaccatcg actggcacca gcagcagccc | 120 |
| gagaagggcc ctcgttattt aatgcaagtt aagtccgatg gcagctatac caagggcacc | 180 |
| ggcatccccg acagattcag cggcagctcc agcggagccg agcgttattt aaccatcagc | 240 |
| tctttacaga gcgaggacga ggctgactac tactgcggcg ccgacgataa cggcggctac | 300 |
| gtgttcggcg gcggcaccca actgacagtg ctgggaggcg gttcttctcg tagcagcagc | 360 |
| agcggaggcg gcggctccgg cggcggaggc caagttcagc tgcaagaatc cggccccggt | 420 |
| ctggtgaaac ccagcgagac tttatcttta acatgcgccg tgagcggcta ctccatctcc | 480 |
| agacacgctt taacttggat cagacagcct cccggcaagg gactggagtg gatcggcgct | 540 |
| atcgacaacg ccggcaccac ctactacgcc tcttgggcca gtctcgtgt caccatcagc | 600 |
| gtggacacat ccaagaacca gttctcttta aagctgtcca gcgtgaccgc cgccgataca | 660 |
| gccgtgtact actgcgctcg tgtgttctac gacatcaact ccggctacta tttagacggc | 720 |
| atggatttat ggggacccgg tactttagtg accgtgtcca gc | 762 |

<210> SEQ ID NO 66
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 23.H1.L2m1

<400> SEQUENCE: 66

| | |
|---|---|
| cagttcgtgc tgacccagcc tcctagcgct agcggaacac ccggccagag ggtgaccatc | 60 |
| agctgcactt taagcagcgc ccacaagacc tacaccatcg actggtacca gcagctgccc | 120 |
| ggtaccgctc ccaagctgct gatctacgtg aagagcgacg gcagctacac caagggcacc | 180 |
| ggcgtgcccg atagattcag cggcagcagc agcggcgccg acagatattt agccatcagc | 240 |
| ggtttacaga gcgaggacga ggccgactac tactgcggcg ccgacgacaa cggaggctac | 300 |
| gtgttcggcg gcggcacaca gctgaccgtg accgtggag gctccagcag atccagctcc | 360 |
| agcggcggag gaggcagcgg aggcggagga caagtgcagc tccaagaatc cggccccggt | 420 |
| ctcgtgaagc ccagcgagac tttatcttta acttgtgccg tgagcggcta cagcatctct | 480 |
| cgtcacgctc tgacttggat tcgtcaacct cccggaaagg gtttagagtg gatcggcgcc | 540 |
| atcgacaacg ccggcaccac ctactacgcc agctgggcca atctcgtgt gaccattagc | 600 |
| gtggacacca gcaagaacca gttctcttta aaactgagca gcgtgacagc tgccgacacc | 660 |
| gccgtgtact actgcgctcg tgtgttctac gacatcaaca gcggctacta tttagacggc | 720 |

```
atggatttat ggggccccgg tactttagtg accgtcagct cc                    762
```

<210> SEQ ID NO 67
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 24.H2.L3m1

<400> SEQUENCE: 67

```
cagttcgtgc tgacccagcc cgcttctgtg agcggttctc ccggtcagag catcaccatc    60
agctgcactt taagcagcgc ccacaagacc tacaccatcg actggtacca gcagcacccc   120
ggcaaggccc ccaagtattt aatgcaagtt aagtccgacg gcagctacac caagggcacc   180
ggcgtgccca acagattctc cggcagcagc tccggcgccg acagatactt aaccatcagc   240
ggtttacaag ctgaggatga ggccgactat gtgtgcggcg ccgacgacaa tggcggctac   300
gtgttcggcg gcggcacaca gctgaccgtg actggcggtg gttcctctag atcttcctcc   360
tctggtggcg gtggctcggg cggtggtggg gaggtgcagc tggtggagag cggaggaggt   420
ttagtgcagc ccggtggatc tttaagactg agctgcgccg ccagcggctt caccttctct   480
cgtcacgctt aacatgggt gagacaagct cccggtaaag gtttagagtg ggtgagcgcc   540
atcgacaacg ccggcaccac ctactacgcc agctgggcca agtctcgttt caccatctct   600
cgtgacaacg ccaagaactc tttatattta cagatgaact cttttaagggc tgaggacacc   660
gccgtgtact actgcgctcg tgtgttctac gacatcaaca gcggctacta tttagacgga   720
atggatttat ggggccccgg taccctcgtg acagtgagca gc                    762
```

<210> SEQ ID NO 68
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 25.H1.L1m3

<400> SEQUENCE: 68

```
cagctggtgc tcacccaaag ccctagcgcc tctgcctctt taggcgcttc cgtgaagctg    60
acttgtactt taagctccgc ccataagacc tacaccatcg actggtacca gcagcagccc   120
gagaagggcc ctcgttattt aatgcaagtt aagtccgatg gcagctatac caagggcacc   180
ggcgtgcccg acagattcag cggcagctcc agcggagccg atcgttattt aaccatcagc   240
tctttacaga gcgaggacga ggctgactac tactgcggcg ccgacgataa cggcggctac   300
gtgttcggcg gcggcaccca actgacagtg ctgggaggcg gttcttctcg tagcagcagc   360
agcggaggcg gcggctccgg cggcggaggc caagtgcagc tccaagaatc cggcccggt   420
ctcgtgaagc ccagcgagac tttatcttta acttgtgccg tgagcggcta cagcatctct   480
cgtcacgctc tgacttggat tcgtcaacct cccggaaagg gtttagagtg gatcggcgcc   540
atcgacaacg ccggcaccac ctactacgcc agctgggcca aatctcgtgt gaccattagc   600
gtggacacca gcaagaacca gttctcttta aaactgagca gcgtgacagc tgccgacacc   660
gccgtgtact actgcgctcg tgtgttctac gacatcaaca gcggctacta tttagacggc   720
atggatttat ggggccccgg tactttagtg accgtcagct cc                    762
```

<210> SEQ ID NO 69
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 26.H1.L1m4

<400> SEQUENCE: 69

```
cagttggtgc tcacccaaag ccctagcgcc tctgcctctt taggcgcttc cgtgaagctg      60
acttgtactt taagctccgc ccataagacc tacaccatcg cctggcatca gcagcagccc     120
gagaagggcc ctcgttattt aatgcaagtt aagtccgatg gcagctatac caagggcacc     180
ggcgtgcccg acagattcag cggcagctcc agcggagccg atcgttattt aaccatcagc     240
tctttacaga gcgaggacga ggctgactac tactgcggcg ccgacgataa cggcggctac     300
gtgttcggcg gcggcaccca actgacagtg ctcggaggcg gttcttctcg tagcagcagc     360
agcggaggcg gcggctccgg cggcggaggc caagtgcagc tccaagaatc cggccccggt     420
ctcgtgaagc ccagcgagac tttatcttta acttgtgccg tgagcggcta cagcatctct     480
cgtcacgctc tgacttggat tcgtcaacct cccggaaagg gtttagagtg atcggcgcc     540
atcgacaacg ccggcaccac ctactacgcc agctgggcca aatctcgtgt gaccattagc     600
gtggacacca gcaagaacca gttctcttta aaactgagca gcgtgacagc tgccgacacc     660
gccgtgtact actgcgctcg tgtgttctac gacatcaaca gcggctacta tttagacggc     720
atggatttat ggggccccgg tactttagtg accgtcagct cc                       762
```

<210> SEQ ID NO 70
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 27.H1.L3m4

<400> SEQUENCE: 70

```
cagagcgctc tgacccagcc cgcttctgtg agcggttctc ccggtcagag catcaccatc      60
agctgcactg gcacaagcgc ccacaagacc tacaccgtga gctggtacca gcagcacccc     120
ggcaaggccc ccaagtattt aatgcaagtt aagtccgacg gcagctacac caagggcacc     180
ggcgtgccca cagattctc cggcagcagc tccggcgccg acagatactt aaccatcagc     240
ggtttacaag ctgaggatga ggccgactat tactgcggcg ccgacgacaa tggcggctac     300
gtgttcggcg gcggcaccca actgacagtg ctgggtggag ctccagcag atccagctcc     360
agcggcggag gaggcagcgg aggcggagga caagtgcagc tccaagaatc cggccccggt     420
ctcgtgaagc ccagcgagac tttatcttta acttgtgccg tgagcggcta cagcatctct     480
cgtcacgctc tgacttggat tcgtcaacct cccggaaagg gtttagagtg atcggcgcc     540
atcgacaacg ccggcaccac ctactacgcc agctgggcca aatctcgtgt gaccattagc     600
gtggacacca gcaagaacca gttctcttta aaactgagca gcgtgacagc tgccgacacc     660
gccgtgtact actgcgctcg tgtgttctac gacatcaaca gcggctacta tttagacggc     720
atggatttat ggggccccgg tactttagtg accgtcagct cc                       762
```

<210> SEQ ID NO 71
<211> LENGTH: 762

<212> TYPE: DNA
<213> ORGANISM: Artificial Sequence
<220> FEATURE:
<223> OTHER INFORMATION: scFv
<220> FEATURE:
<223> OTHER INFORMATION: 28.H1.L3m5

<400> SEQUENCE: 71

```
cagtctgctc tgacccagcc cgcttctgtg agcggttctc ccggtcagag catcaccatc    60
agctgcactg gcacaagcgc ccacaagacc tacaccgtga gttggtacca gcagcacccc   120
ggcaaggccc ccaagttgat gatctacgtt aagtccgacg gcagctacac caagggcacc   180
ggcgtgccca acagattctc cggcagcagc tccggcgccg acagatactt aaccatcagc   240
ggtttacaag ctgaggatga ggccgactat tattgcggcg ccgacgacaa tggcggctac   300
gtgttcggcg gcggcacccca actgacagtg ctcggtggag gctccagcag atccagctcc   360
agcggcggag gaggcagcgg aggcggagga caagtgcagc tccaagaatc cggccccggt   420
ctcgtgaagc ccagcgagac tttatcttta acttgtgccg tgagcggcta cagcatctct   480
cgtcacgctc tgacttggat tcgtcaacct cccggaaagg gtttagagtg gatcggcgcc   540
atcgacaacg ccggcaccac ctactacgcc agctgggcca atctcgtgt gaccattagc   600
gtggacacca gcaagaacca gttctcttta aaactgagca gcgtgacagc tgccgacacc   660
gccgtgtact actgcgctcg tgtgttctac gacatcaaca gcggctacta tttagacggc   720
atggatttat ggggccccgg tactttagtg accgtcagct cc                      762
```

<210> SEQ ID NO 72
<211> LENGTH: 762
<212> TYPE: DNA
<213> ORGANISM: Artificial Sequence
<220> FEATURE:
<223> OTHER INFORMATION: scFv
<220> FEATURE:
<223> OTHER INFORMATION: 29.H2.L1m3

<400> SEQUENCE: 72

```
cagctggtgc tgacccagag ccctagcgct tccgcctctt taggagccag cgtgaagctg    60
acttgtactt tatcctccgc ccacaagacc tacaccatcg actggtacca gcagcagccc   120
gaaaagggcc ctcgttatct gatgcaagtt aagtccgacg gcagctacac caagggaacc   180
ggcgtgcccg acagattctc cggtagcagc agcggcgccg acagatattt aaccatcagc   240
tctttacagt ccgaggacga ggccgactac tactgcggcg ccgacgacaa tggcggctac   300
gtcttcggag gcggcacaca gctgaccgtg actggtggag gctcctccag aagcagctct   360
agcggaggag gaggaagcgg cggaggaggc gaagtgcagc tggtggagtc cggaggagga   420
ctggtgcagc ccgaggttc tttaagactg agctcgccg cctccggctt caccttttct   480
cgtcacgctt taacatgggt gagacaagct cccggcaagg gactggaatg ggtcagcgcc   540
atcgataacg ccggcaccac ctattacgcc agctgggcta agtctcgttt caccatcagc   600
agagacaacg ccaagaactc tttatattta cagatgaatt cttaagagc cgaggacacc   660
gccgtgtatt actgcgctcg tgtcttctac gacatcaact ccggctacta tttagacggc   720
atggatttat ggggccccgg tactttagtc accgtgagct cc                      762
```

<210> SEQ ID NO 73
<211> LENGTH: 253
<212> TYPE: PRT
<213> ORGANISM: Artificial Sequence
<220> FEATURE:

<223> OTHER INFORMATION: scFv
<220> FEATURE:
<223> OTHER INFORMATION: 0.410HC.410LC

<400> SEQUENCE: 73

```
Gln Phe Val Leu Thr Gln Ser Pro Val Ser Ala Ala Leu Gly Ala
1               5                  10                  15

Ser Ala Lys Leu Thr Cys Thr Leu Ser Ser Ala His Lys Thr Tyr Thr
            20                  25                  30

Ile Asp Trp Tyr Gln Gln Gln Gly Glu Ala Pro Arg Tyr Leu Met
            35                  40                  45

Gln Val Lys Ser Asp Gly Ser Tyr Thr Lys Gly Thr Gly Val Pro Asp
50                  55                  60

Arg Phe Ser Gly Ser Ser Gly Ala Asp Arg Tyr Leu Ile Ile Pro
65                  70                  75                  80

Ser Val Gln Ala Asp Asp Glu Ala Gly Tyr Val Cys Gly Ala Asp Asp
                85                  90                  95

Asn Gly Gly Tyr Val Phe Gly Gly Gly Thr Gln Leu Thr Val Thr Gly
                100                 105                 110

Gly Gly Ser Ser Arg Ser Ser Ser Gly Gly Gly Ser Gly Gly
            115                 120                 125

Gly Gly Gln Ser Val Lys Glu Ser Glu Gly Gly Leu Phe Lys Pro Thr
130                 135                 140

Asp Thr Leu Thr Leu Thr Cys Thr Val Ser Gly Phe Ser Leu Ser Arg
145                 150                 155                 160

His Ala Leu Thr Trp Val Arg Gln Ala Pro Gly Asn Gly Leu Glu Trp
                165                 170                 175

Ile Gly Ala Ile Asp Asn Ala Gly Thr Thr Tyr Tyr Ala Ser Trp Ala
                180                 185                 190

Lys Ser Arg Ser Thr Ile Thr Arg Asn Thr Asp Leu His Thr Val Thr
                195                 200                 205

Leu Lys Met Thr Ser Leu Thr Ala Ser Asp Thr Ala Tyr Phe Cys
                210                 215                 220

Ala Arg Val Phe Tyr Asp Ile Asn Ser Gly Tyr Tyr Leu Asp Gly Met
225                 230                 235                 240

Asp Leu Trp Gly Pro Gly Thr Leu Val Thr Val Ser Ser
                245                 250
```

<210> SEQ ID NO 74
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 1.H1.L3

<400> SEQUENCE: 74

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Tyr Thr
            20                  25                  30

Val Ser Trp Tyr Gln Gln His Pro Gly Lys Ala Pro Lys Leu Met Ile
            35                  40                  45

Tyr Val Lys Ser Asp Gly Ser Tyr Asn Arg Pro Ser Gly Val Ser Asn
50                  55                  60

Arg Phe Ser Gly Ser Lys Ser Gly Asn Thr Ala Ser Leu Thr Ile Ser
```

-continued

```
                65                  70                  75                  80
Gly Leu Gln Ala Glu Asp Glu Ala Asp Tyr Tyr Cys Gly Ala Asp Asp
                    85                  90                  95

Asn Gly Gly Tyr Val Phe Gly Gly Thr Lys Leu Thr Val Leu Gly
                100                 105                 110

Gly Gly Ser Ser Arg Ser Ser Ser Gly Gly Gly Ser Gly Gly
            115                 120                 125

Gly Gly Gln Val Gln Leu Gln Glu Ser Gly Pro Gly Leu Val Lys Pro
        130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 75
<211> LENGTH: 264
<212> TYPE: PRT
<213> ORGANISM: Artificial Sequence
<220> FEATURE:
<223> OTHER INFORMATION: scFv
<220> FEATURE:
<223> OTHER INFORMATION: 2.H1.L3m1

<400> SEQUENCE: 75

Gln Phe Val Leu Thr Gln Pro Ala Ser Val Ser Gly Ser Pro Gly Gln
1               5                   10                  15

Ser Ile Thr Ile Ser Cys Thr Leu Ser Ser Ala His Lys Thr Tyr Thr
                20                  25                  30

Ile Asp Trp Tyr Gln Gln His Pro Gly Lys Ala Pro Lys Tyr Leu Met
            35                  40                  45

Gln Val Lys Ser Asp Gly Ser Tyr Thr Lys Gly Thr Gly Val Pro Asn
        50                  55                  60

Arg Phe Ser Gly Ser Ser Ser Gly Ala Asp Arg Tyr Leu Thr Ile Ser
65                  70                  75                  80

Gly Leu Gln Ala Glu Asp Glu Ala Asp Tyr Val Cys Gly Ala Asp Asp
                85                  90                  95

Asn Gly Gly Tyr Val Phe Gly Gly Gly Thr Gln Leu Thr Val Thr Gly
                100                 105                 110

Gly Gly Ser Ser Arg Ser Ser Ser Gly Gly Gly Ser Gly Gly
            115                 120                 125

Gly Gly Gln Val Gln Leu Gln Glu Ser Gly Pro Gly Leu Val Lys Pro
        130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175
```

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
            195                 200                 205

Ser Leu Lys Leu Ser Ser Val Thr Ala Ala Asp Thr Ala Val Tyr Tyr
210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser Ala Ser
            245                 250                 255

Thr Lys Gly Pro Ser Val Thr Ser
            260

<210> SEQ ID NO 76
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 3.H1m1.L3

<400> SEQUENCE: 76

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
            20                  25                  30

Val Ser Trp Tyr Gln Gln His Pro Gly Lys Ala Pro Lys Leu Met Ile
            35                  40                  45

Tyr Val Lys Ser Asp Gly Ser Tyr Asn Arg Pro Ser Gly Val Ser Asn
50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Gly Ala Asp Asp
            85                  90                  95

Asn Gly Gly Tyr Val Phe Gly Gly Gly Thr Lys Leu Thr Val Leu Gly
            100                 105                 110

Gly Gly Ser Ser Arg Ser Ser Ser Gly Gly Gly Ser Gly Gly
            115                 120                 125

Gly Gly Gln Gln Ser Val Lys Glu Ser Gly Pro Gly Leu Val Lys Pro
            130                 135                 140

Ser Glu Thr Leu Ser Leu Thr Cys Ala Val Ser Gly Phe Ser Leu Ser
145                 150                 155                 160

Arg His Ala Leu Thr Trp Val Arg Gln Pro Pro Gly Lys Gly Leu Glu
            165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Arg Asn Thr Asp Leu His Thr Val
            195                 200                 205

Ser Leu Lys Leu Ser Ser Val Thr Ala Ala Asp Thr Ala Val Tyr Phe
210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
            245                 250

```
<210> SEQ ID NO 77
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 4.H1m1.L3m1

<400> SEQUENCE: 77

Gln Phe Val Leu Thr Gln Pro Ala Ser Val Ser Gly Ser Pro Gly Gln
1               5                   10                  15

Ser Ile Thr Ile Ser Cys Thr Leu Ser Ser Ala His Lys Thr Tyr Thr
            20                  25                  30

Ile Asp Trp Tyr Gln Gln His Pro Gly Lys Ala Pro Lys Tyr Leu Met
        35                  40                  45

Gln Val Lys Ser Asp Gly Ser Tyr Thr Lys Gly Thr Gly Val Pro Asn
    50                  55                  60

Arg Phe Ser Gly Ser Ser Ser Gly Ala Asp Arg Tyr Leu Thr Ile Ser
65                  70                  75                  80

Gly Leu Gln Ala Glu Asp Glu Ala Asp Tyr Val Cys Gly Ala Asp Asp
                85                  90                  95

Asn Gly Gly Tyr Val Phe Gly Gly Gly Thr Gln Leu Thr Val Thr Gly
            100                 105                 110

Gly Gly Ser Ser Arg Ser Ser Ser Gly Gly Gly Gly Ser Gly Gly
        115                 120                 125

Gly Gly Gln Gln Ser Val Lys Glu Ser Gly Pro Gly Leu Val Lys Pro
    130                 135                 140

Ser Glu Thr Leu Ser Leu Thr Cys Ala Val Ser Gly Phe Ser Leu Ser
145                 150                 155                 160

Arg His Ala Leu Thr Trp Val Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Arg Asn Thr Asp Leu His Thr Val
        195                 200                 205

Ser Leu Lys Leu Ser Ser Val Thr Ala Ala Asp Thr Ala Val Tyr Phe
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 78
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 5.H2.L2

<400> SEQUENCE: 78

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ala His Lys Thr Tyr Thr
            20                  25                  30

Val Asn Trp Tyr Gln Gln Leu Pro Gly Thr Ala Pro Lys Leu Leu Ile
```

```
            35                  40                  45
Tyr Val Lys Ser Asp Gly Ser Tyr Gln Arg Pro Ser Gly Val Pro Asp
 50                  55                  60

Arg Phe Ser Gly Ser Lys Ser Gly Thr Ser Ala Ser Leu Ala Ile Ser
 65                  70                  75                  80

Gly Leu Gln Ser Glu Asp Glu Ala Asp Tyr Tyr Cys Gly Ala Asp Asp
                 85                  90                  95

Asn Gly Gly Tyr Val Phe Gly Gly Gly Thr Lys Leu Thr Val Leu Gly
            100                 105                 110

Gly Gly Ser Ser Arg Ser Ser Ser Gly Gly Gly Ser Gly Gly
        115                 120                 125

Gly Gly Glu Val Gln Leu Val Glu Ser Gly Gly Leu Val Gln Pro
    130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
                165                 170                 175

Trp Val Ser Ala Ile Asp Asn Ala Gly Thr Thr Tyr Tyr Ala Ser Trp
            180                 185                 190

Ala Lys Ser Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 79
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 6.H2.L2m1

<400> SEQUENCE: 79

Gln Phe Val Leu Thr Gln Pro Pro Ser Ala Ser Gly Thr Pro Gly Gln
  1               5                  10                  15

Arg Val Thr Ile Ser Cys Thr Leu Ser Ser Ala His Lys Thr Tyr Thr
             20                  25                  30

Ile Asp Trp Tyr Gln Gln Leu Pro Gly Thr Ala Pro Lys Leu Leu Ile
         35                  40                  45

Tyr Val Lys Ser Asp Gly Ser Tyr Thr Lys Gly Thr Gly Val Pro Asp
 50                  55                  60

Arg Phe Ser Gly Ser Ser Ser Gly Ala Asp Arg Tyr Leu Ala Ile Ser
 65                  70                  75                  80

Gly Leu Gln Ser Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Thr Gly
            100                 105                 110

Gly Gly Ser Ser Arg Ser Ser Ser Gly Gly Gly Ser Gly Gly
        115                 120                 125

Gly Gly Glu Val Gln Leu Val Glu Ser Gly Gly Gly Leu Val Gln Pro
    130                 135                 140
```

```
Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
                165                 170                 175

Trp Val Ser Ala Ile Asp Asn Ala Gly Thr Thr Tyr Tyr Ala Ser Trp
            180                 185                 190

Ala Lys Ser Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250
```

<210> SEQ ID NO 80
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 7.H2m1.L2

<400> SEQUENCE: 80

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ala His Lys Thr Tyr Thr
                20                  25                  30

Val Asn Trp Tyr Gln Gln Leu Pro Gly Thr Ala Pro Lys Leu Leu Ile
            35                  40                  45

Tyr Val Lys Ser Asp Gly Ser Tyr Gln Arg Pro Ser Gly Val Pro Asp
        50                  55                  60

Arg Phe Ser Gly Ser Lys Ser Gly Thr Ser Ala Ser Leu Ala Ile Ser
65                  70                  75                  80

Gly Leu Gln Ser Glu Asp Glu Ala Asp Tyr Tyr Cys Gly Ala Asp Asp
                85                  90                  95

Asn Gly Gly Tyr Val Phe Gly Gly Gly Thr Lys Leu Thr Val Leu Gly
                100                 105                 110

Gly Gly Ser Ser Arg Ser Ser Ser Gly Gly Gly Ser Gly Gly
            115                 120                 125

Gly Gly Glu Gln Ser Val Lys Glu Ser Gly Gly Leu Val Gln Pro
        130                 135                 140

Gly Gly Ser Leu Arg Leu Ser Cys Ala Ala Ser Gly Phe Thr Leu Ser
145                 150                 155                 160

Arg His Ala Leu Thr Trp Val Arg Gln Ala Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Phe Thr Ile Ser Arg Asn Thr Asp Leu His Thr Val
        195                 200                 205

Tyr Leu Gln Met Asn Ser Leu Arg Ala Glu Asp Thr Ala Val Tyr Phe
    210                 215                 220

Cys Ala Arg Val Phe Tyr Asp Ile Asn Ser Gly Tyr Tyr Leu Asp Gly
225                 230                 235                 240
```

Met Asp Leu Trp Gly Pro Gly Thr Leu Val Thr Val Ser Ser
               245                 250

<210> SEQ ID NO 81
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 8.H2m1.L2m1

<400> SEQUENCE: 81

Gln Phe Val Leu Thr Gln Pro Pro Ser Ala Ser Gly Thr Pro Gly Gln
1               5                   10                  15

Arg Val Thr Ile Ser Cys Thr Leu Ser Ser Ala His Lys Thr Tyr Thr
            20                  25                  30

Ile Asp Trp Tyr Gln Gln Leu Pro Gly Thr Ala Pro Lys Leu Leu Ile
        35                  40                  45

Tyr Val Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Ala Ile Ser
65                  70                  75                  80

Gly Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Thr Gly
            100                 105                 110

Gly Gly Ser Ser Arg Ser Ser Ser Gly Gly Gly Ser Gly Gly
        115                 120                 125

Gly Gly Glu Gln Ser Val Lys Glu Ser Gly Gly Gly Leu Val Gln Pro
    130                 135                 140

Gly Gly Ser Leu Arg Leu Ser Cys Ala Ala Ser Gly Phe Thr Leu Ser
145                 150                 155                 160

Arg His Ala Leu Thr Trp Val Arg Gln Ala Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Phe Thr Ile Ser Arg Asn Thr Asp Leu His Thr Val
        195                 200                 205

Tyr Leu Gln Met Asn Ser Leu Arg Ala Glu Asp Thr Ala Val Tyr Phe
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 82
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 9.H2.L1

<400> SEQUENCE: 82

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr

```
                 20                  25                  30

Ile Ala Trp His Gln Gln Pro Glu Lys Gly Pro Arg Tyr Leu Met
             35                  40                  45

Lys Val Lys Ser Asp Gly Ser Tyr Ser Lys Gly Asp Gly Ile Pro Asp
         50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Ala Asp Asp
                 85                  90                  95

Asn Gly Gly Tyr Val Phe Gly Gly Thr Lys Leu Thr Val Leu Gly
                100                 105                 110

Gly Gly Ser Ser Arg Ser Ser Ser Gly Gly Gly Ser Gly Gly
             115                 120                 125

Gly Gly Glu Val Gln Leu Val Glu Ser Gly Gly Leu Val Gln Pro
         130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
                165                 170                 175

Trp Val Ser Ala Ile Asp Asn Ala Gly Thr Thr Tyr Tyr Ala Ser Trp
                180                 185                 190

Ala Lys Ser Arg Phe Thr Ile Ser Arg Asp Asn Ala Lys Asn Ser Leu
                195                 200                 205

Tyr Leu Gln Met Asn Ser Leu Arg Ala Glu Asp Thr Ala Val Tyr Tyr
             210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 83
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 10.H2.L1m1

<400> SEQUENCE: 83

Gln Phe Val Leu Thr Gln Ser Pro Ser Ala Ser Ala Ser Leu Gly Ala
 1               5                  10                  15

Ser Val Lys Leu Thr Cys Thr Leu Ser Ser Ala His Lys Thr Tyr Thr
                 20                  25                  30

Ile Asp Trp Tyr Gln Gln Pro Glu Lys Gly Pro Arg Tyr Leu Met
             35                  40                  45

Gln Val Lys Ser Asp Gly Ser Tyr Thr Lys Gly Thr Gly Val Pro Asp
         50                  55                  60

Arg Phe Ser Gly Ser Ser Ser Gly Ala Asp Arg Tyr Leu Thr Ile Ser
 65                  70                  75                  80

Ser Leu Gln Ser Glu Asp Glu Ala Asp Tyr Tyr Cys Gly Ala Asp Asp
                 85                  90                  95

Asn Gly Gly Tyr Val Phe Gly Gly Thr Gln Leu Thr Val Thr Gly
                100                 105                 110

Gly Gly Ser Ser Arg Ser Ser Ser Gly Gly Gly Gly Ser Gly Gly
             115                 120                 125
```

Gly Gly Glu Val Gln Leu Val Glu Ser Gly Gly Leu Val Gln Pro
    130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
                165                 170                 175

Trp Val Ser Ala Ile Asp Asn Ala Gly Thr Thr Tyr Tyr Ala Ser Trp
            180                 185                 190

Ala Lys Ser Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
            245                 250

<210> SEQ ID NO 84
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 11.H2m1.L1

<400> SEQUENCE: 84

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Ala Trp His Gln Gln Gln Pro Glu Lys Gly Pro Arg Tyr Leu Met
        35                  40                  45

Lys Val Lys Ser Asp Gly Ser Tyr Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Lys Leu Thr Val Leu Gly
            100                 105                 110

Gly Gly Ser Ser Arg Ser Ser Ser Gly Gly Gly Gly Ser Gly Gly
        115                 120                 125

Gly Gly Glu Gln Ser Val Lys Glu Ser Gly Gly Leu Val Gln Pro
    130                 135                 140

Gly Gly Ser Leu Arg Leu Ser Cys Ala Ala Ser Gly Phe Thr Leu Ser
145                 150                 155                 160

Arg His Ala Leu Thr Trp Val Arg Gln Ala Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Phe Thr Ile Ser Arg Asn Thr Asp Leu His Thr Val
        195                 200                 205

Tyr Leu Gln Met Asn Ser Leu Arg Ala Glu Asp Thr Ala Val Tyr Phe
    210                 215                 220

```
Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 85
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 12.H2m1.L1m1

<400> SEQUENCE: 85

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Asp Trp Tyr Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
50                  55                  60

Arg Phe Ser Gly Ser Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Thr Gly
            100                 105                 110

Gly Gly Ser Ser Arg Ser Ser Ser Gly Gly Gly Ser Gly Gly
            115                 120                 125

Gly Gly Glu Gln Ser Val Lys Glu Ser Gly Gly Leu Val Gln Pro
130                 135                 140

Gly Gly Ser Leu Arg Leu Ser Cys Ala Ala Ser Gly Phe Thr Leu Ser
145                 150                 155                 160

Arg His Ala Leu Thr Trp Val Arg Gln Ala Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Phe Thr Ile Ser Arg Asn Thr Asp Leu His Thr Val
        195                 200                 205

Tyr Leu Gln Met Asn Ser Leu Arg Ala Glu Asp Thr Ala Val Tyr Phe
210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 86
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 13.H1.L1

<400> SEQUENCE: 86

Gln Leu Val Leu Thr Gln Ser Pro Ser Ala Ser Ala Ser Leu Gly Ala
```

```
            1               5                  10                 15
Ser Val Lys Leu Thr Cys Thr Leu Ser Ser Ala His Lys Thr Tyr Thr
                20                  25                 30

Ile Ala Trp His Gln Gln Pro Glu Lys Gly Pro Arg Tyr Leu Met
            35                  40                  45

Lys Val Lys Ser Asp Gly Ser Tyr Ser Lys Gly Asp Gly Ile Pro Asp
        50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Lys Leu Thr Val Leu Gly
            100                 105                 110

Gly Gly Ser Ser Arg Ser Ser Ser Gly Gly Gly Ser Gly Gly
            115                 120                 125

Gly Gly Gln Val Gln Leu Gln Glu Ser Gly Pro Gly Leu Val Lys Pro
        130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 87
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 14.H1.L1m1

<400> SEQUENCE: 87

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Asp Trp Tyr Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
        50                  55                  60

Arg Phe Ser Gly Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Thr Gly
            100                 105                 110
```

```
Gly Gly Ser Ser Arg Ser Ser Ser Gly Gly Gly Ser Gly Gly
            115                 120                 125

Gly Gly Gln Val Gln Leu Gln Glu Ser Gly Pro Gly Leu Val Lys Pro
        130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 88
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 15.H1m1.L1

<400> SEQUENCE: 88

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Ala Trp His Gln Gln Gln Pro Glu Lys Gly Pro Arg Tyr Leu Met
        35                  40                  45

Lys Val Lys Ser Asp Gly Ser Tyr Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Lys Leu Thr Val Leu Gly
            100                 105                 110

Gly Gly Ser Ser Arg Ser Ser Ser Gly Gly Gly Ser Gly Gly
        115                 120                 125

Gly Gly Gln Gln Ser Val Lys Glu Ser Gly Pro Gly Leu Val Lys Pro
    130                 135                 140

Ser Glu Thr Leu Ser Leu Thr Cys Ala Val Ser Gly Phe Ser Leu Ser
145                 150                 155                 160

Arg His Ala Leu Thr Trp Val Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Arg Asn Thr Asp Leu His Thr Val
        195                 200                 205
```

-continued

```
Ser Leu Lys Leu Ser Ser Val Thr Ala Ala Asp Thr Ala Val Tyr Phe
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 89
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 16.H1m1.L1m1

<400> SEQUENCE: 89

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Asp Trp Tyr Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
 50                  55                  60

Arg Phe Ser Gly Ser Ser Gly Ala Asp Arg Tyr Leu Thr Ile Ser
 65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Thr Gly
                100                 105                 110

Gly Gly Ser Ser Arg Ser Ser Ser Gly Gly Gly Ser Gly Gly
                115                 120                 125

Gly Gly Gln Gln Ser Val Lys Glu Ser Gly Pro Gly Leu Val Lys Pro
            130                 135                 140

Ser Glu Thr Leu Ser Leu Thr Cys Ala Val Ser Gly Phe Ser Leu Ser
145                 150                 155                 160

Arg His Ala Leu Thr Trp Val Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Arg Asn Thr Asp Leu His Thr Val
        195                 200                 205

Ser Leu Lys Leu Ser Ser Val Thr Ala Ala Asp Thr Ala Val Tyr Phe
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 90
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 17.H1.L3m2
```

```
<400> SEQUENCE: 90

Gln Phe Val Leu Thr Gln Pro Ala Ser Val Ser Gly Ser Pro Gly Gln
1               5                   10                  15

Ser Ile Thr Ile Ser Cys Thr Leu Ser Ser Ala His Lys Thr Tyr Thr
            20                  25                  30

Ile Asp Trp Tyr Gln Gln His Pro Gly Lys Ala Pro Lys Leu Met Ile
        35                  40                  45

Gln Val Lys Ser Asp Gly Ser Tyr Thr Lys Gly Thr Gly Val Ser Asn
50                  55                  60

Arg Phe Ser Gly Ser Ser Gly Ala Asp Arg Tyr Leu Thr Ile Ser
65                  70                  75                  80

Gly Leu Gln Ala Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu Gly
            100                 105                 110

Gly Gly Ser Ser Arg Ser Ser Ser Gly Gly Gly Ser Gly Gly
        115                 120                 125

Gly Gly Gln Val Gln Leu Gln Glu Ser Gly Pro Gly Leu Val Lys Pro
130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
            245                 250

<210> SEQ ID NO 91
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 18.H1.L3m3

<400> SEQUENCE: 91

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
            20                  25                  30

Ile Asp Trp Tyr Gln Gln His Pro Gly Lys Ala Pro Lys Leu Met Ile
        35                  40                  45

Tyr Val Lys Ser Asp Gly Ser Tyr Thr Lys Gly Thr Gly Val Ser Asn
50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Gly Ala Asp Asp
                85                  90                  95
```

Asn Gly Gly Tyr Val Phe Gly Gly Gly Thr Gln Leu Thr Val Leu Gly
                100                 105                 110

Gly Gly Ser Ser Arg Ser Ser Ser Gly Gly Gly Ser Gly Gly
            115                 120                 125

Gly Gly Gln Val Gln Leu Gln Glu Ser Gly Pro Gly Leu Val Lys Pro
        130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 92
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 19.H2.L2m2

<400> SEQUENCE: 92

Gln Phe Val Leu Thr Gln Pro Pro Ser Ala Ser Gly Thr Pro Gly Gln
1               5                   10                  15

Arg Val Thr Ile Ser Cys Thr Leu Ser Ser Ala His Lys Thr Tyr Thr
            20                  25                  30

Ile Asp Trp Tyr Gln Gln Leu Pro Gly Thr Ala Pro Lys Leu Leu Ile
        35                  40                  45

Tyr Val Lys Ser Asp Gly Ser Tyr Thr Lys Gly Thr Gly Val Pro Asp
    50                  55                  60

Arg Phe Ser Gly Ser Ser Ser Gly Ala Asp Ala Ser Leu Ala Ile Ser
65                  70                  75                  80

Gly Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu Gly
                100                 105                 110

Gly Gly Ser Ser Arg Ser Ser Ser Gly Gly Gly Ser Gly Gly
            115                 120                 125

Gly Gly Glu Val Gln Leu Val Glu Ser Gly Gly Gly Leu Val Gln Pro
        130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
                165                 170                 175

Trp Val Ser Ala Ile Asp Asn Ala Gly Thr Thr Tyr Tyr Ala Ser Trp
            180                 185                 190

```
Ala Lys Ser Arg Phe Thr Ile Ser Arg Asp Asn Ala Lys Asn Ser Leu
            195                 200                 205

Tyr Leu Gln Met Asn Ser Leu Arg Ala Glu Asp Thr Ala Val Tyr Tyr
        210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 93
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 20.H2.L2m3

<400> SEQUENCE: 93

Gln Ser Val Leu Thr Gln Pro Pro Ser Ala Ser Gly Thr Pro Gly Gln
1               5                   10                  15

Arg Val Thr Ile Ser Cys Thr Leu Ser Ser Ala His Lys Thr Tyr Thr
            20                  25                  30

Ile Asp Trp Tyr Gln Gln Leu Pro Gly Thr Ala Pro Lys Leu Leu Ile
        35                  40                  45

Tyr Val Lys Ser Asp Gly Ser Tyr Thr Lys Gly Thr Gly Val Pro Asp
    50                  55                  60

Arg Phe Ser Gly Ser Lys Ser Gly Thr Ser Ala Ser Leu Ala Ile Ser
65                  70                  75                  80

Gly Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu Gly
            100                 105                 110

Gly Gly Ser Ser Arg Ser Ser Ser Gly Gly Gly Ser Gly Gly
        115                 120                 125

Gly Gly Glu Val Gln Leu Val Glu Ser Gly Gly Leu Val Gln Pro
130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
            165                 170                 175

Trp Val Ser Ala Ile Asp Asn Ala Gly Thr Thr Tyr Tyr Ala Ser Trp
        180                 185                 190

Ala Lys Ser Arg Phe Thr Ile Ser Arg Asp Asn Ala Lys Asn Ser Leu
            195                 200                 205

Tyr Leu Gln Met Asn Ser Leu Arg Ala Glu Asp Thr Ala Val Tyr Tyr
        210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 94
<211> LENGTH: 254
<212> TYPE: PRT
<213> ORGANISM: Artificial Sequence
<220> FEATURE:
<223> OTHER INFORMATION: scFv
```

```
<220> FEATURE:
<223> OTHER INFORMATION: 21.H2.L1m2

<400> SEQUENCE: 94

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Asp Trp His Gln Gln Pro Glu Lys Gly Pro Arg Tyr Leu Met
            35                  40                  45

Gln Val Lys Ser Asp Gly Ser Tyr Thr Lys Gly Thr Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu Gly
                100                 105                 110

Gly Gly Ser Ser Arg Ser Ser Ser Gly Gly Gly Ser Gly Gly
            115                 120                 125

Gly Gly Glu Val Gln Leu Val Glu Ser Gly Gly Gly Leu Val Gln Pro
        130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
                165                 170                 175

Trp Val Ser Ala Ile Asp Asn Ala Gly Thr Thr Tyr Tyr Ala Ser Trp
                180                 185                 190

Ala Lys Ser Arg Phe Thr Ile Ser Arg Asp Asn Ala Lys Asn Ser Leu
            195                 200                 205

Tyr Leu Gln Met Asn Ser Leu Arg Ala Glu Asp Thr Ala Val Tyr Tyr
        210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 95
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 22.H1.L1m2

<400> SEQUENCE: 95

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Asp Trp His Gln Gln Pro Glu Lys Gly Pro Arg Tyr Leu Met
            35                  40                  45

Gln Val Lys Ser Asp Gly Ser Tyr Thr Lys Gly Thr Gly Ile Pro Asp
        50                  55                  60

Arg Phe Ser Gly Ser Ser Ser Gly Ala Glu Arg Tyr Leu Thr Ile Ser
65                  70                  75                  80
```

-continued

Ser Leu Gln Ser Glu Asp Glu Ala Asp Tyr Tyr Cys Gly Ala Asp Asp
              85                  90                  95

Asn Gly Gly Tyr Val Phe Gly Gly Thr Gln Leu Thr Val Leu Gly
             100                 105                 110

Gly Gly Ser Ser Arg Ser Ser Ser Gly Gly Gly Ser Gly Gly
        115                 120                 125

Gly Gly Gln Val Gln Leu Gln Glu Ser Gly Pro Gly Leu Val Lys Pro
    130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
                180                 185                 190

Ala Lys Ser Arg Val Thr Ile Ser Val Asp Thr Ser Lys Asn Gln Phe
            195                 200                 205

Ser Leu Lys Leu Ser Ser Val Thr Ala Ala Asp Thr Ala Val Tyr Tyr
        210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 96
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 23.H1.L2m1

<400> SEQUENCE: 96

Gln Phe Val Leu Thr Gln Pro Pro Ser Ala Ser Gly Thr Pro Gly Gln
1               5                  10                  15

Arg Val Thr Ile Ser Cys Thr Leu Ser Ser Ala His Lys Thr Tyr Thr
            20                  25                  30

Ile Asp Trp Tyr Gln Gln Leu Pro Gly Thr Ala Pro Lys Leu Leu Ile
        35                  40                  45

Tyr Val Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Ala Ile Ser
65                  70                  75                  80

Gly Leu Gln Ser Glu Asp Glu Ala Asp Tyr Tyr Cys Gly Ala Asp Asp
                85                  90                  95

Asn Gly Gly Tyr Val Phe Gly Gly Thr Gln Leu Thr Val Thr Gly
             100                 105                 110

Gly Gly Ser Ser Arg Ser Ser Ser Gly Gly Gly Ser Gly Gly
        115                 120                 125

Gly Gly Gln Val Gln Leu Gln Glu Ser Gly Pro Gly Leu Val Lys Pro
    130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
            195                 200                 205

Ser Leu Lys Leu Ser Ser Val Thr Ala Ala Asp Thr Ala Val Tyr Tyr
            210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
            245                 250

<210> SEQ ID NO 97
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 24.H2.L3m1

<400> SEQUENCE: 97

Gln Phe Val Leu Thr Gln Pro Ala Ser Val Ser Gly Ser Pro Gly Gln
1               5                   10                  15

Ser Ile Thr Ile Ser Cys Thr Leu Ser Ser Ala His Lys Thr Tyr Thr
            20                  25                  30

Ile Asp Trp Tyr Gln Gln His Pro Gly Lys Ala Pro Lys Tyr Leu Met
            35                  40                  45

Gln Val Lys Ser Asp Gly Ser Tyr Thr Lys Gly Thr Gly Val Pro Asn
50                  55                  60

Arg Phe Ser Gly Ser Ser Ser Gly Ala Asp Arg Tyr Leu Thr Ile Ser
65                  70                  75                  80

Gly Leu Gln Ala Glu Asp Glu Ala Asp Tyr Val Cys Gly Ala Asp Asp
            85                  90                  95

Asn Gly Gly Tyr Val Phe Gly Gly Gly Thr Gln Leu Thr Val Thr Gly
            100                 105                 110

Gly Gly Ser Ser Arg Ser Ser Ser Gly Gly Gly Gly Ser Gly Gly
            115                 120                 125

Gly Gly Glu Val Gln Leu Val Glu Ser Gly Gly Gly Leu Val Gln Pro
130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
            165                 170                 175

Trp Val Ser Ala Ile Asp Asn Ala Gly Thr Thr Tyr Tyr Ala Ser Trp
            180                 185                 190

Ala Lys Ser Arg Phe Thr Ile Ser Arg Asp Asn Ala Lys Asn Ser Leu
            195                 200                 205

Tyr Leu Gln Met Asn Ser Leu Arg Ala Glu Asp Thr Ala Val Tyr Tyr
            210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
            245                 250

<210> SEQ ID NO 98
<211> LENGTH: 254
<212> TYPE: PRT

<213> ORGANISM: Artificial Sequence
<220> FEATURE:
<223> OTHER INFORMATION: scFv
<220> FEATURE:
<223> OTHER INFORMATION: 25.H1.L1m3

<400> SEQUENCE: 98

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Asp Trp Tyr Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
    50                  55                  60

Arg Phe Ser Gly Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Thr Gln Leu Thr Val Leu Gly
            100                 105                 110

Gly Gly Ser Ser Arg Ser Ser Ser Gly Gly Gly Ser Gly Gly
        115                 120                 125

Gly Gly Gln Val Gln Leu Gln Glu Ser Gly Pro Gly Leu Val Lys Pro
    130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250
```

<210> SEQ ID NO 99
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 26.H1.L1m4

<400> SEQUENCE: 99

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Ala Trp His Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
    50                  55                  60
```

```
Arg Phe Ser Gly Ser Ser Ser Gly Ala Asp Arg Tyr Leu Thr Ile Ser
 65                  70                  75                  80

Ser Leu Gln Ser Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Leu Gly
            100                 105                 110

Gly Gly Ser Ser Arg Ser Ser Ser Gly Gly Gly Ser Gly Gly
            115                 120                 125

Gly Gly Gln Val Gln Leu Gln Glu Ser Gly Pro Gly Leu Val Lys Pro
        130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 100
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 27.H1.L3m4

<400> SEQUENCE: 100

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ala His Lys Thr Tyr Thr
                20                  25                  30

Val Ser Trp Tyr Gln Gln His Pro Gly Lys Ala Pro Lys Tyr Leu Met
             35                  40                  45

Gln Val Lys Ser Asp Gly Ser Tyr Thr Lys Gly Thr Gly Val Pro Asn
        50                  55                  60

Arg Phe Ser Gly Ser Ser Ser Gly Ala Asp Arg Tyr Leu Thr Ile Ser
 65                  70                  75                  80

Gly Leu Gln Ala Glu Asp Glu Ala Asp Tyr Tyr Cys Gly Ala Asp Asp
                 85                  90                  95

Asn Gly Gly Tyr Val Phe Gly Gly Gly Thr Gln Leu Thr Val Leu Gly
            100                 105                 110

Gly Gly Ser Ser Arg Ser Ser Ser Gly Gly Gly Ser Gly Gly
            115                 120                 125

Gly Gly Gln Val Gln Leu Gln Glu Ser Gly Pro Gly Leu Val Lys Pro
        130                 135                 140

Ser Glu Thr Leu Ser Leu Thr Cys Ala Val Ser Gly Tyr Ser Ile Ser
145                 150                 155                 160
```

```
Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 101
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 28.H1.L3m5

<400> SEQUENCE: 101

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
                20                  25                  30

Val Ser Trp Tyr Gln Gln His Pro Gly Lys Ala Pro Lys Leu Met Ile
            35                  40                  45

Tyr Val Lys Ser Asp Gly Ser Tyr Thr Lys Gly Thr Gly Val Pro Asn
        50                  55                  60

Arg Phe Ser Gly Ser Ser Ser Gly Ala Asp Arg Tyr Leu Thr Ile Ser
65                  70                  75                  80

Gly Leu Gln Ala Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Leu Gly
                100                 105                 110

Gly Gly Ser Ser Arg Ser Ser Ser Gly Gly Gly Ser Gly Gly
        115                 120                 125

Gly Gly Gln Val Gln Leu Gln Glu Ser Gly Pro Gly Leu Val Lys Pro
    130                 135                 140

Ser Glu Thr Leu Ser Leu Thr Cys Ala Val Ser Gly Tyr Ser Ile Ser
145                 150                 155                 160

Arg His Ala Leu Thr Trp Ile Arg Gln Pro Pro Gly Lys Gly Leu Glu
                165                 170                 175

Trp Ile Gly Ala Ile Asp Asn Ala Gly Thr Thr Tyr Tyr Ala Ser Trp
            180                 185                 190

Ala Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250
```

<210> SEQ ID NO 102
<211> LENGTH: 254
<212> TYPE: PRT
<213> ORGANISM: Artificial Sequence
<220> FEATURE:
<223> OTHER INFORMATION: scFv
<220> FEATURE:
<223> OTHER INFORMATION: 29.H2.L1m3

<400> SEQUENCE: 102

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Asp Trp Tyr Gln Gln Pro Glu Lys Gly Pro Arg Tyr Leu Met
        35                  40                  45

Gln Val Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val Phe Gly Gly Gly Thr Gln Leu Thr Val Thr Gly
            100                 105                 110

Gly Gly Ser Ser Arg Ser Ser Ser Gly Gly Gly Ser Gly Gly
        115                 120                 125

Gly Gly Glu Val Gln Leu Val Glu Ser Gly Gly Leu Val Gln Pro
    130                 135                 140

Gly Gly Ser Leu Arg Leu Ser Cys Ala Ala Ser Gly Phe Thr Phe Ser
145                 150                 155                 160

Arg His Ala Leu Thr Trp Val Arg Gln Ala Pro Gly Lys Gly Leu Glu
                165                 170                 175

Trp Val Ser Ala Ile Asp Asn Ala Gly Thr Thr Tyr Tyr Ala Ser Trp
            180                 185                 190

Ala Lys Ser Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Arg Val Phe Tyr Asp Ile Asn Ser Gly Tyr Tyr Leu Asp Gly
225                 230                 235                 240

Met Asp Leu Trp Gly Pro Gly Thr Leu Val Thr Val Ser Ser
                245                 250

<210> SEQ ID NO 103
<211> LENGTH: 750
<212> TYPE: DNA
<213> ORGANISM: Artificial Sequence
<220> FEATURE:
<223> OTHER INFORMATION: scFv
<220> FEATURE:
<223> OTHER INFORMATION: CAR10

<400> SEQUENCE: 103
gaggtgcagc tggtggagtc tggaggagga ctggtgcaac ccggtggctc tttaagactg      60
agctgcgccg cctctggctt cacctttct cgtcacgctt taacatgggt gagacaagct     120
cccggaaagg gactggagtg gtgtccgcc atcgacaacg ccggcaccac ctactacgcc     180
agctgggcca agagcagatt caccatctct cgtgacaacg ccaagaactc tttatattta     240

| | |
|---|---|
| cagatgaact ctttaagggc cgaggacacc gccgtgtact actgcgctcg tgtgttctac | 300 |
| gacatcaact ccggctacta tttagacggc atggatttat ggggacccgg tacactggtc | 360 |
| acagtgagct ctggaggcgg aggtagcgga ggcggaggaa gcagcggtgg aggcagccag | 420 |
| tttgtgctga cacagtcccc ttccgcttcc gcctctttag gagcctccgt gaagctgact | 480 |
| tgtactttaa gcagcgccca caaaacctac accatcgact ggtaccagca gcagcccgag | 540 |
| aagggcccac gttatttaat gcaagttaag tccgacggct cctacaccaa gggcaccggc | 600 |
| gtgcccgata gattcagcgg ctccagcagc ggcgccgata ggtatttaac catctcctct | 660 |
| ttacagagcg aggacgaggc cgactactac tgtggcgccg acgacaacgg cggctacgtg | 720 |
| tttggaggcg gcacccagct gaccgtgctg | 750 |

<210> SEQ ID NO 104
<211> LENGTH: 750
<212> TYPE: DNA
<213> ORGANISM: Artificial Sequence
<220> FEATURE:
<223> OTHER INFORMATION: scFv
<220> FEATURE:
<223> OTHER INFORMATION: CAR14

<400> SEQUENCE: 104

| | |
|---|---|
| caagttcagc tgcaagaaag cggacccggt ttagtgaaac cctccgagac tttatcttta | 60 |
| acatgcgccg tgagcggcta cagcatctct cgtcatgctt taacttggat tcgtcagcct | 120 |
| cccggaaagg gtttagagtg gatcggcgcc atcgacaacg ccggcaccac ctattacgcc | 180 |
| agctgggcca agtctcgtgt gaccatcagc gtggacacca gcaagaacca gttctcttta | 240 |
| aagctgtcca gcgtgaccgc tgccgacaca gccgtgtact actgcgctcg tgtgttctac | 300 |
| gacatcaaca gcggctacta tttagacgga atggatctgt ggggcccgg aactttagtg | 360 |
| acagtcagca gcggaggcgg aggaagcgga ggaggaggaa gctccggagg cggttctcaa | 420 |
| ttcgtgctga cacagagccc tagcgcctct gcctctttag gagcctccgt gaagctgact | 480 |
| tgtactttaa gcagcgccca agacctac accatcgact ggtaccagca gcagcccgag | 540 |
| aagggcccta gatatttaat gcaagttaag agcgacggca gctacaccaa aggcactggt | 600 |
| gtgcccgatc gttttagcgg cagcagcagc ggcgccgata ggtatttaac catcagctct | 660 |
| ttacagagcg aggacgaggc cgactactac tgtggcgccg acgacaacgg cggctacgtg | 720 |
| tttggcggcg gcacacagct gaccgttttta | 750 |

<210> SEQ ID NO 105
<211> LENGTH: 750
<212> TYPE: DNA
<213> ORGANISM: Artificial Sequence
<220> FEATURE:
<223> OTHER INFORMATION: scFv
<220> FEATURE:
<223> OTHER INFORMATION: CAR25

<400> SEQUENCE: 105

| | |
|---|---|
| caagttcagc tgcaagaaag cggacccggt ttagtgaaac cctccgagac tttatcttta | 60 |
| acatgcgccg tgagcggcta cagcatctct cgtcatgctt taacttggat tcgtcagcct | 120 |
| cccggaaagg gtttagagtg gatcggcgcc atcgacaacg ccggcaccac ctattacgcc | 180 |
| agctgggcca agtctcgtgt gaccatcagc gtggacacca gcaagaacca gttctcttta | 240 |
| aagctgtcca gcgtgaccgc tgccgacaca gccgtgtact actgcgctcg tgtgttctac | 300 |
| gacatcaaca gcggctacta tttagacgga atggatctgt ggggcccgg aactttagtg | 360 |

| | |
|---|---:|
| acagtcagca gcggaggcgg aggaagcgga ggaggaggaa gctccggagg cggttctcaa | 420 |
| ctggtgctga cacagagccc tagcgcctct gcctctttag gagcctccgt gaagctgact | 480 |
| tgtactttaa gcagcgccca caagacctac accatcgact ggtaccagca gcagcccgag | 540 |
| aagggcccta gatatttaat gcaagttaag agcgacggca gctacaccaa aggcactggt | 600 |
| gtgcccgatc gttttagcgg cagcagcagc ggcgccgata ggtatttaac catcagctct | 660 |
| ttacagagcg aggacgaggc cgactactac tgtggcgccg acgacaacgg cggctacgtg | 720 |
| tttggcggcg gcacacagct gaccgtttta | 750 |

<210> SEQ ID NO 106
<211> LENGTH: 750
<212> TYPE: DNA
<213> ORGANISM: Artificial Sequence
<220> FEATURE:
<223> OTHER INFORMATION: scFv
<220> FEATURE:
<223> OTHER INFORMATION: CAR29

<400> SEQUENCE: 106

| | |
|---|---:|
| gaggtgcagc tggtggagtc tggaggagga ctggtgcaac ccggtggctc tttaagactg | 60 |
| agctgcgccg cctctggctt cacctttttct cgtcacgctt taacatgggt gagacaagct | 120 |
| cccggaaagg gactggagtg ggtgtccgcc atcgacaacg ccggcaccac ctactacgcc | 180 |
| agctgggcca agagcagatt caccatctct cgtgacaacg ccaagaactc tttatattta | 240 |
| cagatgaact ctttaagggc cgaggacacc gccgtgtact actgcgctcg tgtgttctac | 300 |
| gacatcaact ccggctacta tttagacggc atggatttat ggggacccgg tacactggtc | 360 |
| acagtgagct ctggaggcgg aggtagcgga ggcggaggaa gcagcggtgg aggcagccag | 420 |
| ctggtgctga cacagtcccc ttccgcttcc gcctctttag gagcctccgt gaagctgact | 480 |
| tgtactttaa gcagcgccca caaaacctac accatcgact ggtaccagca gcagcccgag | 540 |
| aagggcccac gttatttaat gcaagttaag tccgacggcc cctacaccaa gggcaccggc | 600 |
| gtgcccgata gattcagcgg ctccagcagc ggcgccgata ggtatttaac catctcctct | 660 |
| ttacagagcg aggacgaggc cgactactac tgtggcgccg acgacaacgg cggctacgtg | 720 |
| tttggaggcg gcacccagct gaccgtgctg | 750 |

<210> SEQ ID NO 107
<211> LENGTH: 250
<212> TYPE: PRT
<213> ORGANISM: Artificial Sequence
<220> FEATURE:
<223> OTHER INFORMATION: scFv
<220> FEATURE:
<223> OTHER INFORMATION: CAR10

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Leu Thr Trp Val Arg Gln Ala Pro Gly Lys Gly Leu Glu Trp Val
        35                  40                  45

Ser Ala Ile Asp Asn Ala Gly Thr Thr Tyr Tyr Ala Ser Trp Ala Lys
    50                  55                  60

Ser Arg Phe Thr Ile Ser Arg Asp Asn Ala Lys Asn Ser Leu Tyr Leu
65                  70                  75                  80

```
Gln Met Asn Ser Leu Arg Ala Glu Asp Thr Ala Val Tyr Tyr Cys Ala
                85                  90                  95

Arg Val Phe Tyr Asp Ile Asn Ser Gly Tyr Tyr Leu Asp Gly Met Asp
            100                 105                 110

Leu Trp Gly Pro Gly Thr Leu Val Thr Val Ser Ser Gly Gly Gly Gly
        115                 120                 125

Ser Gly Gly Gly Gly Ser Ser Gly Gly Gly Ser Gln Phe Val Leu Thr
130                 135                 140

Gln Ser Pro Ser Ala Ser Ala Ser Leu Gly Ala Ser Val Lys Leu Thr
145                 150                 155                 160

Cys Thr Leu Ser Ser Ala His Lys Thr Tyr Thr Ile Asp Trp Tyr Gln
                165                 170                 175

Gln Gln Pro Glu Lys Gly Pro Arg Tyr Leu Met Gln Val Lys Ser Asp
            180                 185                 190

Gly Ser Tyr Thr Lys Gly Thr Gly Val Pro Asp Arg Phe Ser Gly Ser
        195                 200                 205

Ser Ser Gly Ala Asp Arg Tyr Leu Thr Ile Ser Ser Leu Gln Ser Glu
    210                 215                 220

Asp Glu Ala Asp Tyr Tyr Cys Gly Ala Asp Asn Gly Gly Tyr Val
225                 230                 235                 240

Phe Gly Gly Gly Thr Gln Leu Thr Val Leu
                245                 250

<210> SEQ ID NO 108
<211> LENGTH: 250
<212> TYPE: PRT
<213> ORGANISM: Artificial Sequence
<220> FEATURE:
<223> OTHER INFORMATION: scFv
<220> FEATURE:
<223> OTHER INFORMATION: CAR14

<400> SEQUENCE: 108

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Arg His
                20                  25                  30

Ala Leu Thr Trp Ile Arg Gln Pro Pro Gly Lys Gly Leu Glu Trp Ile
            35                  40                  45

Gly Ala Ile Asp Asn Ala Gly Thr Thr Tyr Tyr Ala Ser Trp Ala Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Phe Tyr Asp Ile Asn Ser Gly Tyr Tyr Leu Asp Gly Met Asp
            100                 105                 110

Leu Trp Gly Pro Gly Thr Leu Val Thr Val Ser Ser Gly Gly Gly Gly
        115                 120                 125

Ser Gly Gly Gly Gly Ser Gly Gly Gly Ser Gln Phe Val Leu Thr
130                 135                 140

Gln Ser Pro Ser Ala Ser Ala Ser Leu Gly Ala Ser Val Lys Leu Thr
145                 150                 155                 160

Cys Thr Leu Ser Ser Ala His Lys Thr Tyr Thr Ile Asp Trp Tyr Gln
                165                 170                 175
```

Gln Gln Pro Glu Lys Gly Pro Arg Tyr Leu Met Gln Val Lys Ser Asp
                180                 185                 190

Gly Ser Tyr Thr Lys Gly Thr Gly Val Pro Asp Arg Phe Ser Gly Ser
            195                 200                 205

Ser Ser Gly Ala Asp Arg Tyr Leu Thr Ile Ser Ser Leu Gln Ser Glu
        210                 215                 220

Asp Glu Ala Asp Tyr Tyr Cys Gly Ala Asp Asp Asn Gly Gly Tyr Val
225                 230                 235                 240

Phe Gly Gly Gly Thr Gln Leu Thr Val Leu
                245                 250

<210> SEQ ID NO 109
<211> LENGTH: 250
<212> TYPE: PRT
<213> ORGANISM: Artificial Sequence
<220> FEATURE:
<223> OTHER INFORMATION: scFv
<220> FEATURE:
<223> OTHER INFORMATION: CAR25

<400> SEQUENCE: 109

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Arg His
            20                  25                  30

Ala Leu Thr Trp Ile Arg Gln Pro Pro Gly Lys Gly Leu Glu Trp Ile
        35                  40                  45

Gly Ala Ile Asp Asn Ala Gly Thr Thr Tyr Tyr Ala Ser Trp Ala Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Phe Tyr Asp Ile Asn Ser Gly Tyr Tyr Leu Asp Gly Met Asp
                100                 105                 110

Leu Trp Gly Pro Gly Thr Leu Val Thr Val Ser Ser Gly Gly Gly Gly
            115                 120                 125

Ser Gly Gly Gly Gly Ser Ser Gly Gly Gly Ser Gln Leu Val Leu Thr
        130                 135                 140

Gln Ser Pro Ser Ala Ser Ala Ser Leu Gly Ala Ser Val Lys Leu Thr
145                 150                 155                 160

Cys Thr Leu Ser Ser Ala His Lys Thr Tyr Thr Ile Asp Trp Tyr Gln
                165                 170                 175

Gln Gln Pro Glu Lys Gly Pro Arg Tyr Leu Met Gln Val Lys Ser Asp
                180                 185                 190

Gly Ser Tyr Thr Lys Gly Thr Gly Val Pro Asp Arg Phe Ser Gly Ser
            195                 200                 205

Ser Ser Gly Ala Asp Arg Tyr Leu Thr Ile Ser Ser Leu Gln Ser Glu
        210                 215                 220

Asp Glu Ala Asp Tyr Tyr Cys Gly Ala Asp Asp Asn Gly Gly Tyr Val
225                 230                 235                 240

Phe Gly Gly Gly Thr Gln Leu Thr Val Leu
                245                 250

<210> SEQ ID NO 110
<211> LENGTH: 250
<212> TYPE: PRT

<213> ORGANISM: Artificial Sequence
<220> FEATURE:
<223> OTHER INFORMATION: scFv
<220> FEATURE:
<223> OTHER INFORMATION: CAR29

<400> SEQUENCE: 110

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Arg His
            20                  25                  30
Ala Leu Thr Trp Val Arg Gln Ala Pro Gly Lys Gly Leu Glu Trp Val
        35                  40                  45
Ser Ala Ile Asp Asn Ala Gly Thr Thr Tyr Tyr Ala Ser Trp Ala Lys
    50                  55                  60
Ser Arg Phe Thr Ile Ser Arg Asp Asn Ala Lys Asn Ser Leu Tyr Leu
65                  70                  75                  80
Gln Met Asn Ser Leu Arg Ala Glu Asp Thr Ala Val Tyr Tyr Cys Ala
                85                  90                  95
Arg Val Phe Tyr Asp Ile Asn Ser Gly Tyr Tyr Leu Asp Gly Met Asp
            100                 105                 110
Leu Trp Gly Pro Gly Thr Leu Val Thr Val Ser Ser Gly Gly Gly Gly
        115                 120                 125
Ser Gly Gly Gly Gly Ser Gly Gly Gly Ser Gln Leu Val Leu Thr
    130                 135                 140
Gln Ser Pro Ser Ala Ser Ala Ser Leu Gly Ala Ser Val Lys Leu Thr
145                 150                 155                 160
Cys Thr Leu Ser Ser Ala His Lys Thr Tyr Thr Ile Asp Trp Tyr Gln
                165                 170                 175
Gln Gln Pro Glu Lys Gly Pro Arg Tyr Leu Met Gln Val Lys Ser Asp
            180                 185                 190
Gly Ser Tyr Thr Lys Gly Thr Gly Val Pro Asp Arg Phe Ser Gly Ser
        195                 200                 205
Ser Ser Gly Ala Asp Arg Tyr Leu Thr Ile Ser Ser Leu Gln Ser Glu
    210                 215                 220
Asp Glu Ala Asp Tyr Tyr Cys Gly Ala Asp Asp Asn Gly Gly Tyr Val
225                 230                 235                 240
Phe Gly Gly Gly Thr Gln Leu Thr Val Leu
                245                 250
```

<210> SEQ ID NO 111
<211> LENGTH: 9088
<212> TYPE: DNA
<213> ORGANISM: Artificial Sequence
<220> FEATURE:
<223> OTHER INFORMATION: CAR
<220> FEATURE:
<223> OTHER INFORMATION: pTRPE-C10-gs-BBz

<400> SEQUENCE: 111

```
gtgcacgagt gggttacatc gaactggatc tcaacagcgg taagatcctt gagagttttc      60
gccccgaaga cgttttccaa tgatgagca cttttaaagt tctgctatgt ggcgcggtat      120
tatcccgtat tgacgccggg caagagcaac tcggtcgccg catacactat tctcagaatg     180
acttggttga gtactcacca gtcacagaaa agcatcttac ggatggcatg acagtaagag     240
aattatgcag tgctgccata accatgagtg ataacactgc ggccaactta cttctgacaa     300
cgatcggagg accgaaggag ctaaccgctt ttttgcacaa catgggggat catgtaactc     360
```

```
gccttgatcg ttgggaaccg gagctgaatg aagccatacc aaacgacgag cgtgacacca      420
cgatgcctgt agcaatggca acaacgttgc gcaaactatt aactggcgaa ctacttactc      480
tagcttcccg gcaacaatta atagactgga tggaggcgga taaagttgca ggaccacttc      540
tgcgctcggc ccttccggct ggctggttta ttgctgataa atctggagcc ggtgagcgtg      600
ggtctcgcgg tatcattgca gcactggggc cagatggtaa gccctcccgt atcgtagtta      660
tctacacgac ggggagtcag gcaactatgg atgaacgaaa tagacagatc gctgagatag      720
gtgcctcact gattaagcat tggtaactgt cagaccaagt ttactcatat atactttaga      780
ttgatttaaa acttcatttt taatttaaaa ggatctaggt gaagatcctt tttgataatc      840
tcatgaccaa aatcccttaa cgtgagtttt cgttccactg agcgtcagac cccgtagaaa      900
agatcaaagg atcttcttga tccttttttt tctgcgcgt aatctgctgc ttgcaaacaa       960
aaaaaccacc gctaccagcg gtggtttgtt tgccggatca agagctacca actctttttc     1020
cgaaggtaac tggcttcagc agagcgcaga taccaaatac tgttcttcta gtgtagccgt     1080
agttaggcca ccacttcaag aactctgtag caccgcctac atacctcgct ctgctaatcc     1140
tgttaccagt ggctgctgcc agtggcgata agtcgtgtct taccggggttg gactcaagac    1200 gatagttacc ggataaggcg cagcggtcgg gctgaacggg gggttcgtgc acacagccca     1260
gcttggagcg aacgacctac accgaactga gatacctaca gcgtgagcta tgagaaagcg     1320
ccacgcttcc cgaagggaga aggcggaca ggtatccggt aagcggcagg gtcggaacag      1380
gagagcgcac gagggagctt ccaggggaa acgcctggta tctttatagt cctgtcgggt      1440
ttcgccacct ctgacttgag cgtcgatttt tgtgatgctc gtcaggggg cggagcctat      1500 ggaaaaacgc cagcaacgcg gccttttac ggttcctggc cttttgctgg ccttttgctc       1560
acatgttctt tcctgcgtta tcccctgatt ctgtggataa ccgtattacc gcctttgagt     1620
gagctgatac cgctcgccgc agccgaacga ccgagcgcag cgagtcagtg agcgaggaag     1680
cggaagagcg cccaatacgc aaaccgcctc tccccgcgcg ttggccgatt cattaatgca     1740
gctggcacga caggtttccc gactggaaag cgggcagtga gcgcaacgca attaatgtga     1800
gttagctcac tcattaggca ccccaggctt tacactttat gcttccggct cgtatgttgt     1860
gtggaattgt gagcggataa caatttcaca caggaaacag ctatgaccat gattacgcca     1920
agcgcgcaat taaccctcac taaagggaac aaaagctgga gctgcaagct taatgtagtc     1980
ttatgcaata ctcttgtagt cttgcaacat ggtaacgatg agttagcaac atgccttaca     2040
aggagagaaa aagcaccgtg catgccgatt ggtggaagta aggtggtacg atcgtgcctt     2100
attaggaagg caacagacgg gtctgacatg gattggacga accactgaat tgccgcattg     2160
cagagatatt gtatttaagt gcctagctcg atacataaac gggtctctct ggttagacca     2220
gatctgagcc tgggagctct ctggctaact agggaaccca ctgcttaagc ctcaataaag     2280
cttgccttga gtgcttcaag tagtgtgtgc ccgtctgttg tgtgactctg gtaactagag     2340
atccctcaga ccctttttagt cagtgtggaa atctctagc agtggcgccc gaacagggac     2400
ttgaaagcga aagggaaacc agaggagctc tctcgacgca ggactcggct tgctgaagcg     2460
cgcacggcaa gaggcgaggg gcggcgactg gtgagtacgc caaaaatttt gactagcgga     2520
ggctagaagg agagagatgg gtgcgagagc gtcagtatta gcggggggag aattagatcg     2580
cgatgggaaa aaattcggtt aaggccaggg ggaaagaaaa aatataaatt aaaacatata     2640
gtatgggcaa gcagggagct agaacgattc gcagttaatc ctggcctgtt agaaacatca     2700
```

-continued

```
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata aagtagtaaa aattgaacca ttaggagtag cacccaccaa    3000
ggcaaagaga agagtggtgc agagagaaaa aagagcagtg gaataggag ctttgttcct     3060 tggggttcttg ggagcagcag gaagcactat gggcgcagcg tcaatgacgc tgacggtaca   3120
ggccagacaa ttattgtctg gtatagtgca gcagcagaac aatttgctga ggctattga    3180 ggcgcaacag catctgttgc aactcacagt ctggggcatc aagcagctcc aggcaagaat    3240
cctggctgtg gaaagatacc taaaggatca acagctcctg gggatttggg gttgctctgg    3300
aaaactcatt tgcaccactg ctgtgccttg gaatgctagt tggagtaata atctctgga    3360 acagatttgg aatcacacga cctggatgga gtgggacaga gaaattaaca attacacaag   3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc     3600 tgtactttct atagtgaata gagttaggca gggatattca ccattatcgt ttcagaccca    3660
cctcccaacc ccgaggggac ccgacaggcc cgaaggaata agaagaag gtggagagag      3720 agacagagac agatccattc gattagtgaa cggatctcga cggtatcgat tagactgtag   3780
cccaggaata tggcagctag attgtacaca tttagaagga aaagttatct tggtagcagt    3840
tcatgtagcc agtggatata tagaagcaga gtaattcca gcagagacag gcaagaaac      3900 agcatacttc ctcttaaaat tagcaggaag atggccagta aaaacagtac atacagacaa    3960
tggcagcaat ttcaccagta ctacagttaa ggccgcctgt tggtgggcgg ggatcaagca    4020
ggaatttggc attccctaca atccccaaag tcaaggagta atagaatcta tgaataaaga   4080
attaaagaaa attataggac aggtaagaga tcaggctgaa catcttaaga cagcagtaca    4140
aatggcagta ttcatccaca atttaaaag aaaaggggg attgggggt acagtgcagg      4200 ggaaagaata gtagacataa tagcaacaga catacaaact aaagaattac aaaaacaaat    4260
tacaaaaatt caaaattttc gggttatta caggacagc agagatccag tttggctgca     4320
tacgcgtcgt gaggctccgg tgcccgtcag tgggcagagc gcacatcgcc cacagtcccc    4380
gagaagttgg ggggaggggt cggcaattga accggtgcct agagaaggtg gcgcggggta    4440
aactgggaaa gtgatgtcgt gtactggctc cgccttttc ccgagggtgg gggagaaccg     4500
tatataagtg cagtagtcgc cgtgaacgtt cttttcgca acgggtttgc cgccagaaca     4560
caggtaagtg ccgtgtgtgg ttcccgcggg cctggcctct ttacgggtta tggcccttgc   4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctggggccgc cgcgtgcgaa tctggtggca ccttcgcgcc    4800
tgtctcgctg ctttcgataa gtctctagcc atttaaaatt tttgatgacc tgctgcgacg    4860
ctttttttct ggcaagatag tcttgtaaat gcgggccaag atctgcacac tggtatttcg    4920 gttttttgggg ccgcgggcgg cgacgggggcc cgtgcgtccc agcgcacatg ttcggcgagg   4980
cggggcctgc gagcgcggcc accgagaatc ggacgggggt agtctcaagc tggccggcct    5040
gctctggtgc ctggcctcgc gccgccgtgt atcgccccgc cctgggcggc aaggctggcc    5100
```

```
cggtcggcac cagttgcgtg agcggaaaga tggccgcttc ccggccctgc tgcagggagc    5160
tcaaaatgga ggacgcggcg ctcgggagag cgggcggtg  agtcacccac acaaaggaaa    5220
agggcctttc cgtcctcagc cgtcgcttca tgtgactcca ctgagtaccg ggcgccgtcc    5280
aggcacctcg attagttctc gtgcttttgg agtacgtcgt ctttaggttg gggggagggg    5340
ttttatgcga tggagtttcc ccacactgag tgggtggaga ctgaagttag ccagcttgg     5400 cacttgatgt aattctcctt ggaatttgcc cttttgagt  ttggatcttg gttcattctc    5460
aagcctcaga cagtggttca aagtttttt  cttccatttc aggtgtcgtg agctagagcc    5520
accatggagt ttgggctgag ctggcttttt cttgtggcta tttaaaagg  tgtccagtgc    5580 ggatccgagg tgcagctggt ggagtctgga ggaggactgg tgcaacccgg tggctcttta    5640
agactgagct cgccgcctc  tggcttcacc ttttctcgtc acgctttaac atgggtgaga    5700
caagctcccg aaagggact  ggagtgggtg tccgccatcg acaacgccgg caccacctac    5760
tacgccagct gggccaagag cagattcacc atctctcgtg acaacgccaa gaactcttta    5820
tatttacaga tgaactcttt aagggccgag acaccgccg  tgtactactg cgctcgtgtg    5880
ttctacgaca tcaactccgg ctactattta cggcatgg   atttatgggg acccggtaca    5940
ctggtcacag tgagctctgg aggcggaggt agcggaggcg gaggaagcag cggtggaggc    6000
agccagtttg tgctgacaca gtccccttcc gcttccgcct ctttaggagc ctccgtgaag    6060
ctgacttgta ctttaagcag cgcccacaaa acctacacca tcgactggta ccagcagcag    6120
cccgagaagg gcccacgtta tttaatgcaa gttaagtccg acggctccta caccaagggc    6180
accggcgtgc ccgatagatt cagcggctcc agcagcggcg ccgataggta tttaaccatc    6240
tcctctttac agagcgagga cgaggccgac tactactgtg gcgccgacga caacggcggc    6300
tacgtgtttg gaggcggcac ccagctgacc gtgctggcta gcggtggcgg aggttctgga    6360
ggtggaggtt cctccggaat ctacatctgg gcgcccttgg ccgggacttg tggggtcctt    6420
ctcctgtcac tggttatcac cctttactgc aaacggggca gaaagaaact cctgtatata    6480
ttcaaacaac catttatgag accagtacaa actactcaag aggaagatgg ctgtagctgc    6540
cgatttccag aagaagaaga aggaggatgt gaactgagag tgaagttcag caggagcgca    6600 gacgccccg  cgtaccagca gggccagaac cagctctata cgagctcaa  tctaggacga    6660 agagaggagt acgatgtttt ggacaagaga cgtggccggg accctgagat ggggggaaag    6720
ccgagaagga agaaccctca ggaaggcctg tacaatgaac tgcagaaaga taagatggcg    6780
gaggcctaca gtgagattgg gatgaaaggc gagcgccgga ggggcaaggg gcacgatggc    6840
ctttaccagg gtctcagtac agccaccaag acacctacg  acgcccttca catgcaggcc    6900
ctgccccctc gctaagtcga caatcaacct ctggattaca aaatttgtga agattgact     6960 ggtattctta actatgttgc tccttttacg ctatgtggat acgctgcttt aatgcctttg    7020
tatcatgcta ttgcttcccg tatggctttc attttctcct ccttgtataa atcctggttg    7080
ctgtctcttt atgaggagtt gtggcccgtt gtcaggcaac gtggcgtggt gtgcactgtg    7140
tttgctgacg caacccccac tggttggggc attgccacca cctgtcagct cctttccggg    7200
actttcgctt tccccctccc tattgccacg gcggaactca tcgccgcctg ccttgcccgc    7260
tgctggacag gggctcggct gttgggcact gacaattccg tggtgttgtc ggggaagctg    7320
acgtcctttc cttggctgct cgcctgtgtt gccacctgga ttctgcgcgg gacgtccttc    7380
tgctacgtcc cttcggccct caatccagcg gaccttcctt cccgcggcct gctgccggct    7440
```

```
ctgcggcctc ttccgcgtct tcgccttcgc cctcagacga gtcggatctc cctttgggcc    7500
gcctccccgc ctggaattcg agctcggtac ctttaagacc aatgacttac aaggcagctg    7560
tagatcttag ccactttta aagaaaagg ggggactgga agggctaatt cactcccaac      7620
gaagacaaga tctgcttttt gcttgtactg ggtctctctg gttagaccag atctgagcct    7680
gggagctctc tggctaacta gggaacccac tgcttaagcc tcaataaagc ttgccttgag    7740
tgcttcaagt agtgtgtgcc cgtctgttgt gtgactctgg taactagaga tccctcagac    7800
cctttagtc agtgtggaaa atctctagca gtagtagttc atgtcatctt attattcagt     7860
atttataact tgcaaagaaa tgaatatcag agagtgagag gaacttgttt attgcagctt    7920
ataatggtta caaataaagc aatagcatca caaatttcac aaataaagca ttttttttcac   7980
tgcattctag ttgtggtttg tccaaactca tcaatgtatc ttatcatgtc tggctctagc    8040
tatcccgccc ctaactccgc ccagttccgc ccattctccg cccatggct gactaatttt     8100
ttttatttat gcagaggccg aggccgcctc ggcctctgag ctattccaga agtagtgagg    8160
aggcttttt ggaggcctag ctaggacgt acccaattcg ccctatagtg agtcgtatta      8220
cgcgcgctca ctggccgtcg ttttacaacg tcgtgactgg gaaaaccctg gcgttaccca    8280
acttaatcgc cttgcagcac atccccctt cgccagctgg cgtaatagcg aagaggcccg     8340
caccgatcgc ccttcccaac agttgcgcag cctgaatggc gaatgggacg cgccctgtag    8400
cggcgcatta agcgcggcgg gtgtggtggt tacgcgcagc gtgaccgcta cacttgccag    8460
cgccctagcg cccgctcctt tcgctttctt cccttccttt ctcgccacgt tcgccggctt    8520
tccccgtcaa gctctaaatc gggggctccc tttagggttc cgatttagtg ctttacggca    8580
cctcgacccc aaaaaacttg attagggtga tggttcacgt agtgggccat cgccctgata    8640
gacggttttt cgccctttga cgttggagtc acgttctttt aatagtggac tcttgttcca    8700
aactggaaca acactcaacc tatctcggt ctattcttt gatttataag ggattttgcc      8760
gatttcggcc tattggttaa aaatgagct gatttaacaa aaatttaacg cgaattttaa     8820
caaaatatta acgcttacaa tttaggtggc acttttcggg gaaatgtgcg cggaacccct    8880
atttgttat ttttctaaat acattcaaat atgtatccgc tcatgagaca ataaccctga     8940
taaatgcttc aataatattg aaaaaggaag agtatgagta ttcaacattt ccgtgtcgcc    9000
cttattccct tttttgcggc attttgcctt cctgttttg ctcacccaga aacgctggtg     9060
aaagtaaaag atgctgaaga tcagttgg                                       9088
```

<210> SEQ ID NO 112
<211> LENGTH: 9088
<212> TYPE: DNA
<213> ORGANISM: Artificial Sequence
<220> FEATURE:
<223> OTHER INFORMATION: CAR
<220> FEATURE:
<223> OTHER INFORMATION: pTRPE-C14-gs-BBz

<400> SEQUENCE: 112

```
gtgcacgagt gggttacatc gaactggatc tcaacagcgg taagatcctt gagagttttc    60
gccccgaaga acgttttcca atgatgagca cttttaaagt tctgctatgt ggcgcggtat    120
tatcccgtat tgacgccggg caagagcaac tcggtcgccg catacactat tctcagaatg    180
acttggttga gtactcacca gtcacagaaa agcatcttac ggatggcatg acagtaagag    240
aattatgcag tgctgccata accatgagtg ataacactgc ggccaactta cttctgacaa    300
cgatcggagg accgaaggag ctaaccgctt ttttgcacaa catgggggat catgtaactc    360
```

```
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taaagttgca ggaccacttc    540
tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
tctacacgac ggggagtcag gcaactatgg atgaacgaaa tagacagatc gctgagatag    720
gtgcctcact gattaagcat tggtaactgt cagaccaagt ttactcatat atactttaga    780
ttgatttaaa acttcatttt taatttaaaa ggatctaggt gaagatcctt tttgataatc    840
tcatgaccaa aatcccttaa cgtgagtttt cgttccactg agcgtcagac cccgtagaaa    900
agatcaaagg atcttcttga gatcctttttt ttctgcgcgt aatctgctgc ttgcaaacaa    960
aaaaaccacc gctaccagcg gtggtttgtt tgccggatca agagctacca actcttttttc   1020 cgaaggtaac tggcttcagc agagcgcaga taccaaatac tgttcttcta gtgtagccgt   1080
agttaggcca ccacttcaag aactctgtag caccgcctac atacctcgct ctgctaatcc   1140
tgttaccagt ggctgctgcc agtggcgata agtcgtgtct taccggttg gactcaagac   1200 gatagttacc ggataaggcg cagcggtcgg gctgaacggg gggttcgtgc acacagccca   1260
gcttggagcg aacgacctac accgaactga gatacctaca gcgtgagcta tgagaaagcg   1320
ccacgcttcc cgaagggaga aggcggaca ggtatccggt aagcggcagg gtcggaacag   1380
gagagcgcac gagggagctt ccaggggaa acgcctggta tctttatagt cctgtcgggt   1440
ttcgccacct ctgacttgag cgtcgatttt tgtgatgctc gtcagggggg cggagcctat   1500
ggaaaaacgc cagcaacgcg gccttttttac ggttcctggc cttttgctgg ccttttgctc   1560
acatgttctt tcctgcgtta tcccctgatt ctgtggataa ccgtattacc gcctttgagt   1620
gagctgatac cgctcgccgc agccgaacga ccgagcgcag cgagtcagtg agcgaggaag   1680
cggaagagcg cccaatacgc aaaccgcctc tccccgcgcg ttggccgatt cattaatgca   1740
gctggcacga caggtttccc gactggaaag cgggcagtga gcgcaacgca attaatgtga   1800
gttagctcac tcattaggca ccccaggctt tacactttat gcttccggct cgtatgttgt   1860
gtggaattgt gagcggataa caatttcaca caggaaacag ctatgaccat gattacgcca   1920
agcgcgcaat taaccctcac taaagggaac aaaagctgga gctgcaagct taatgtagtc   1980
ttatgcaata ctcttgtagt cttgcaacat ggtaacgatg agttagcaac atgccttaca   2040
aggagagaaa aagcaccgtg catgccgatt ggtggaagta aggtggtacg atcgtgcctt   2100
attaggaagg caacagacgg gtctgacatg gattggacga accactgaat tgccgcattg   2160
cagagatatt gtatttaagt gcctagctcg atacataaac gggtctctct ggttagacca   2220
gatctgagcc tgggagctct ctggctaact agggaaccca ctgcttaagc ctcaataaag   2280
cttgccttga gtgcttcaag tagtgtgtgc ccgtctgttg tgtgactctg gtaactagag   2340
atccctcaga ccctttttagt cagtgtggaa aatctctagc agtggcgccc gaacagggac   2400
ttgaaagcga aagggaaacc agaggagctc tctcgacgca ggactcggct tgctgaagcg   2460
cgcacggcaa gaggcgaggg gcggcgactg gtgagtacgc caaaaatttt gactagcgga   2520
ggctagaagg agagagatgg gtgcgagagc gtcagtatta gcgggggag aattagatcg   2580 cgatgggaaa aaattcggtt aaggccaggg ggaaagaaaa aatataaatt aaaacatata   2640
gtatgggcaa gcagggagct agaacgattc gcagttaatc ctggcctgtt agaaacatca   2700
```

-continued

```
gaaggctgta gacaaatact gggacagcta caaccatccc ttcagacagg atcagaagaa      2760
cttagatcat tatataatac agtagcaacc ctctattgtg tgcatcaaag gatagagata      2820
aaagacacca aggaagcttt agacaagata gaggaagagc aaaacaaaag taagaccacc      2880
gcacagcaag cggccgctga tcttcagacc tggaggagga gatatgaggg acaattggag      2940
aagtgaatta tataaatata agtagtaaaa aattgaacca ttaggagtag cacccaccaa      3000
ggcaaagaga agagtggtgc agagagaaaa aagagcagtg gaataggag ctttgttcct       3060 tgggttcttg ggagcagcag gaagcactat gggcgcagcg tcaatgacgc tgacggtaca      3120
ggccagacaa ttattgtctg gtatagtgca gcagcagaac aatttgctga ggctattga       3180 ggcgcaacag catctgttgc aactcacagt ctggggcatc aagcagctcc aggcaagaat      3240
cctggctgtg gaaagatacc taaaggatca acagctcctg gggatttggg gttgctctgg      3300
aaaactcatt tgcaccactg ctgtgccttg gaatgctagt tggagtaata atctctgga       3360 acagatttgg aatcacacga cctggatgga gtgggacaga gaaattaaca attacacaag      3420
cttaatacac tccttaattg aagaatcgca aaaccagcaa gaaaagaatg aacaagaatt      3480
attggaatta gataaatggg caagtttgtg gaattggttt aacataacaa attggctgtg      3540
gtatataaaa ttattcataa tgatagtagg aggcttggta ggtttaagaa tagttttgc       3600 tgtactttct atagtgaata gagttaggca gggatattca ccattatcgt ttcagaccca      3660
cctcccaacc ccgaggggac ccgacaggcc cgaaggaata agaagaag gtggagagag        3720 agacagagac agatccattc gattagtgaa cggatctcga cggtatcgat tagactgtag      3780
cccaggaata tggcagctag attgtacaca tttagaagga aaagttatct tggtagcagt      3840
tcatgtagcc agtggatata tagaagcaga agtaattcca gcagagacag ggcaagaaac      3900
agcatacttc ctcttaaaat tagcaggaag atggccagta aaaacagtac atacagacaa      3960
tggcagcaat ttcaccagta ctacagttaa ggccgcctgt tggtgggcgg ggatcaagca      4020
ggaatttggc attccctaca atccccaaag tcaaggagta atagaatcta tgaataaaga      4080
attaaagaaa attataggac aggtaagaga tcaggctgaa catcttaaga cagcagtaca      4140
aatggcagta ttcatccaca attttaaaag aaaaggggggg attgggggt acagtgcagg      4200 ggaaagaata gtagacataa tagcaacaga catacaaact aaagaattac aaaaacaaat      4260
tacaaaaatt caaaattttc gggtttatta caggacagc agagatccag tttggctgca      4320
tacgcgtcgt gaggctccgg tgcccgtcag tgggcagagc gcacatcgcc cacagtcccc      4380
gagaagttgg ggggaggggt cggcaattga accggtgcct agagaaggtg gcgcggggta      4440
aactgggaaa gtgatgtcgt gtactggctc cgccttttc ccgagggtgg gggagaaccg       4500
tatataagtg cagtagtcgc cgtgaacgtt ctttttcgca acgggtttgc cgccagaaca      4560
caggtaagtg ccgtgtgtgg ttcccgcggg cctggcctct ttacgggtta tggcccttgc      4620
gtgccttgaa ttacttccac ctggctgcag tacgtgattc ttgatcccga gcttcgggtt      4680
ggaagtgggt gggagagttc gaggccttgc gcttaaggag ccccttcgcc tcgtgcttga      4740
gttgaggcct ggcctgggcg ctggggccgc cgcgtgcgaa tctggtggca ccttcgcgcc      4800
tgtctcgctg ctttcgataa gtctctagcc atttaaaatt tttgatgacc tgctgcgacg      4860
ctttttttct ggcaagatag tcttgtaaat gcgggccaag atctgcacac tggtatttcg      4920
gtttttgggg ccgcgggcgg cgacggggcc cgtgcgtccc agcgcacatg ttcggcgagg      4980
cggggcctgc gagcgcggcc accgagaatc ggacgggggt agtctcaagc tggccggcct      5040
gctctggtgc ctggcctcgc gccgccgtgt atcgccccgc cctgggcggc aaggctggcc      5100
```

| | |
|---|---|
| cggtcggcac cagttgcgtg agcggaaaga tggccgcttc ccggccctgc tgcagggagc | 5160 |
| tcaaaatgga ggacgcggcg ctcgggagag cgggcggGtg agtcacccac acaaaggaaa | 5220 |
| agggcctttc cgtcctcagc cgtcgcttca tgtgactcca ctgagtaccg ggcgccgtcc | 5280 |
| aggcacctcg attagttctc gtgcttttgg agtacgtcgt ctttaggttg gggggagggg | 5340 |
| ttttatgcga tggagtttcc ccacactgag tgggtggaga ctgaagttag gccagcttgg | 5400 |
| cacttgatgt aattctcctt ggaatttgcc cttttTgagt ttggatcttg gttcattctc | 5460 |
| aagcctcaga cagtggttca aagttttttt cttccatttc aggtgtcgtg agctagagcc | 5520 |
| accatggagt ttgggctgag ctggcttttt cttgtggcta tttaaaagg tgtccagtgc | 5580 |
| ggatcccaag ttcagctgca agaaagcgga cccggtttag tgaaaccctc cgagacttta | 5640 |
| tctttaacat gcgccgtgag cggctacagc atctctcgtc atgctttaac ttggattcgt | 5700 |
| cagcctcccg gaaagggttt agagtggatc ggcgccatcg acaacgccgg caccacctat | 5760 |
| tacgccagct gggccaagtc tcgtgtgacc atcagcgtgg acaccagcaa gaaccagttc | 5820 |
| tctttaaagc tgtccagcgt gaccgctgcc gacacagccg tgtactactg cgctcgtgtg | 5880 |
| ttctacgaca tcaacagcgg ctactattta gacggaatgg atctgtgggg ccccggaact | 5940 |
| tagtgacag tcagcagcgg aggcggagga agcggaggag gaggaagctc cggaggcggt | 6000 |
| tctcaattcg tgctgacaca gagccctagc gcctctgcct ctttaggagc ctccgtgaag | 6060 |
| ctgacttgta ctttaagcag cgcccacaag acctacacca tcgactggta ccagcagcag | 6120 |
| cccgagaagg gccctagata tttaatgcaa gttaagagcg acggcagcta caccaaaggc | 6180 |
| actggtgtgc ccgatcgttt tagcggcagc agcagcggcg ccgataggta tttaaccatc | 6240 |
| agctctttac agagcgagga cgaggccgac tactactgtg gcgccgacga caacggcggc | 6300 |
| tacgtgtttg gcggcggcac acagctgacc gttttagcta gcggtggcgg aggttctgga | 6360 |
| ggtggaggtt cctccggaat ctacatctgg gcgcccttgg ccgggacttg tggggtcctt | 6420 |
| ctcctgtcac tggttatcac ccttttactgc aaacggggca gaaagaaact cctgtatata | 6480 |
| ttcaaacaac catttatgag accagtacaa actactcaag aggaagatgg ctgtagctgc | 6540 |
| cgatttccag aagaagaaga aggaggatgt gaactgagag tgaagttcag caggagcgca | 6600 |
| gacgccccg cgtaccagca gggccagaac cagctctata cgagctcaa tctaggacga | 6660 |
| agagaggagt acgatgtttt ggacaagaga cgtggccggg accctgagat ggggggaaag | 6720 |
| ccgagaagga agaaccctca ggaaggcctg tacaatgaac tgcagaaaga taagatggcg | 6780 |
| gaggcctaca gtgagattgg gatgaaaggc gagcgccgga ggggcaaggg gcacgatggc | 6840 |
| ctttaccagg gtctcagtac agccaccaag gacacctacg acgcccttca catgcaggcc | 6900 |
| ctgccccctc gctaagtcga caatcaacct ctggattaca aaatttgtga agattgact | 6960 |
| ggtattctta actatgttgc tccttttacg ctatgtggat acgctgcttt aatgcctttg | 7020 |
| tatcatgcta ttgcttcccg tatggctttc attttctcct ccttgtataa atcctggttg | 7080 |
| ctgtctcttt atgaggagtt gtggcccgtt gtcaggcaac gtggcgtggt gtgcactgtg | 7140 |
| tttgctgacg caaccccac tggttggggc attgccacca cctgtcagct cctttccggg | 7200 |
| actttcgctt tccccctccc tattgccacg gcggaactca tcgccgcctg ccttgcccgc | 7260 |
| tgctggacag gggctcggct gttgggcact gacaattccg tggtgttgtc ggggaagctg | 7320 |
| acgtcctttc cttggctgct cgcctgtgtt gccacctgga ttctgcgcgg gacgtccttc | 7380 |
| tgctacgtcc cttcggccct caatccagcg gaccttcctt cccgcggcct gctgccggct | 7440 |

```
ctgcggcctc ttccgcgtct tcgccttcgc cctcagacga gtcggatctc cctttgggcc    7500
gcctccccgc ctggaattcg agctcggtac ctttaagacc aatgacttac aaggcagctg    7560
tagatcttag ccactttta aaagaaaagg ggggactgga agggctaatt cactcccaac     7620
gaagacaaga tctgcttttt gcttgtactg ggtctctctg gttagaccag atctgagcct    7680
gggagctctc tggctaacta gggaacccac tgcttaagcc tcaataaagc ttgccttgag    7740
tgcttcaagt agtgtgtgcc cgtctgttgt gtgactctgg taactagaga tccctcagac    7800
ccttttagtc agtgtggaaa atctctagca gtagtagttc atgtcatctt attattcagt    7860
atttataact tgcaaagaaa tgaatatcag agagtgagag gaacttgttt attgcagctt    7920
ataatggtta caaataaagc aatagcatca caaatttcac aaataaagca tttttttcac    7980
tgcattctag ttgtggtttg tccaaactca tcaatgtatc ttatcatgtc tggctctagc    8040
tatcccgccc ctaactccgc ccagttccgc ccattctccg ccccatggct gactaatttt    8100
ttttatttat gcagaggccg aggccgcctc ggcctctgag ctattccaga agtagtgagg    8160 aggcttttt ggaggcctag ctaggacgt acccaattcg ccctatagtg agtcgtatta     8220
cgcgcgctca ctggccgtcg ttttacaacg tcgtgactgg gaaaaccctg gcgttaccca    8280
acttaatcgc cttgcagcac atccccctt cgccagctgg cgtaatagcg aagaggcccg     8340
caccgatcgc ccttcccaac agttgcgcag cctgaatggc gaatgggacg cgccctgtag    8400
cggcgcatta agcgcggcgg gtgtggtggt tacgcgcagc gtgaccgcta cacttgccag    8460
cgccctagcg cccgctcctt tcgctttctt cccttccttt ctcgccacgt tcgccggctt    8520
tccccgtcaa gctctaaatc gggggctccc tttagggttc cgatttagtg ctttacggca    8580
cctcgacccc aaaaaacttg attagggtga tggttcacgt agtgggccat cgccctgata    8640
gacggttttt cgccctttga cgttggagtc acgttctttt aatagtggac tcttgttcca    8700
aactggaaca acactcaacc ctatctcggt ctattctttt gatttataag ggattttgcc    8760
gatttcggcc tattggttaa aaaatgagct gatttaacaa aaatttaacg cgaattttaa    8820
caaaatatta acgcttacaa tttaggtggc acttttcggg gaaatgtgcg cggaacccct    8880
atttgtttat ttttctaaat acattcaaat atgtatccgc tcatgagaca ataaccctga    8940
taaatgcttc aataatattg aaaaaggaag agtatgagta ttcaacattt ccgtgtcgcc    9000
cttattccct tttttgcggc attttgcctt cctgttttg ctcacccaga aacgctggtg     9060
aaagtaaaag atgctgaaga tcagttgg                                      9088

<210> SEQ ID NO 113
<211> LENGTH: 9088
<212> TYPE: DNA
<213> ORGANISM: Artificial Sequence
<220> FEATURE:
<223> OTHER INFORMATION: CAR
<220> FEATURE:
<223> OTHER INFORMATION: pTRPE-C25-gs-BBz

<400> SEQUENCE: 113
gtgcacgagt gggttacatc gaactggatc tcaacagcgg taagatcctt gagagttttc     60
gccccgaaga cgttttcca atgatgagca cttttaaagt tctgctatgt ggcgcggtat     120
tatcccgtat tgacgccggg caagagcaac tcggtcgccg catacactat tctcagaatg    180
acttggttga gtactcacca gtcacagaaa agcatcttac ggatggcatg acagtaagag    240
aattatgcag tgctgccata accatgagtg ataacactgc ggccaactta cttctgacaa    300
cgatcggagg accgaaggag ctaaccgctt ttttgcacaa catgggggat catgtaactc    360
```

```
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taaagttgca ggaccacttc    540
tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
tctacacgac ggggagtcag gcaactatgg atgaacgaaa tagacagatc gctgagatag    720
gtgcctcact gattaagcat tggtaactgt cagaccaagt ttactcatat atactttaga    780
ttgatttaaa acttcatttt taatttaaaa ggatctaggt gaagatcctt tttgataatc    840
tcatgaccaa aatcccttaa cgtgagtttt cgttccactg agcgtcagac cccgtagaaa    900
agatcaaagg atcttcttga tccttttttt tctgcgcgt aatctgctgc ttgcaaacaa    960 aaaaccacc gctaccagcg gtggtttgtt tgccggatca agagctacca actcttttc    1020 cgaaggtaac tggcttcagc agagcgcaga taccaaatac tgttcttcta gtgtagccgt    1080
agttaggcca ccacttcaag aactctgtag caccgcctac atacctcgct ctgctaatcc    1140
tgttaccagt ggctgctgcc agtggcgata agtcgtgtct taccgggttg gactcaagac    1200
gatagttacc ggataaggcg cagcggtcgg gctgaacggg gggttcgtgc acacagccca    1260
gcttggagcg aacgacctac accgaactga gatacctaca gcgtgagcta tgagaaagcg    1320
ccacgcttcc gaagggaga aggcggaca ggtatccggt aagcggcagg gtcggaacag    1380
gagagcgcac gagggagctt ccaggggaa acgcctggta tctttatagt cctgtcgggt    1440
ttcgccacct ctgacttgag cgtcgatttt tgtgatgctc gtcagggggg cggagcctat    1500
ggaaaaacgc cagcaacgcg gcctttttac ggttcctggc cttttgctgg ccttttgctc    1560
acatgttctt tcctgcgtta tcccctgatt ctgtggataa ccgtattacc gcctttgagt    1620
gagctgatac cgctcgccgc agccgaacga ccgagcgcag cgagtcagtg agcgaggaag    1680
cggaagagcg cccaatacgc aaaccgcctc tccccgcgcg ttggccgatt cattaatgca    1740
gctggcacga caggttcccc gactggaaag cgggcagtga gcgcaacgca attaatgtga    1800
gttagctcac tcattaggca ccccaggctt tacactttat gcttccggct cgtatgttgt    1860
gtggaattgt gagcggataa caatttcaca caggaaacag ctatgaccat gattacgcca    1920
agcgcgcaat taaccctcac taaagggaac aaaagctgga gctgcaagct taatgtagtc    1980
ttatgcaata ctcttgtagt cttgcaacat ggtaacgatg agttagcaac atgccttaca    2040
aggagagaaa aagcaccgtg catgccgatt ggtggaagta aggtggtacg atcgtgcctt    2100
attaggaagg caacagacgg gtctgacatg gattggacga accactgaat gccgcattg    2160 cagagatatt gtatttaagt gcctagctcg atacataaac gggtctctct ggttagacca    2220
gatctgagcc tgggagctct ctggctaact agggaaccca ctgcttaagc ctcaataaag    2280
cttgccttga gtgcttcaag tagtgtgtgc ccgtctgttg tgtgactctg gtaactagag    2340
atccctcaga ccctttagt cagtgtggaa aatctctagc agtggcgccc gaacagggac    2400
ttgaaagcga aagggaaacc agaggagctc tctcgacgca ggactcggct tgctgaagcg    2460
cgcacggcaa gaggcgaggg gcggcgactg gtgagtacgc caaaaatttt gactagcgga    2520
ggctagaagg agagagatgg gtgcgagagc gtcagtatta gcggggag attagatcg    2580 cgatgggaaa aaattcggtt aaggccaggg ggaaagaaaa aatataaatt aaaacatata    2640
gtatgggcaa gcagggagct agaacgattc gcagttaatc ctggcctgtt agaaacatca    2700
```

-continued

```
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata agtagtaaa aattgaacca ttaggagtag cacccaccaa     3000
ggcaaagaga agagtggtgc agagagaaaa aagagcagtg gaataggag ctttgttcct     3060 tggggttcttg ggagcagcag gaagcactat gggcgcagcg tcaatgacgc tgacggtaca   3120
ggccagacaa ttattgtctg gtatagtgca gcagcagaac aatttgctga ggctattga    3180 ggcgcaacag catctgttgc aactcacagt ctggggcatc aagcagctcc aggcaagaat   3240
cctggctgtg gaaagatacc taaaggatca acagctcctg gggatttggg gttgctctgg   3300
aaaactcatt tgcaccactg ctgtgccttg gaatgctagt tggagtaata atctctgga    3360 acagatttgg aatcacacga cctggatgga gtgggacaga gaaattaaca attacacaag   3420
cttaatacac tccttaattg aagaatcgca aaaccagcaa gaaaagaatg aacaagaatt   3480
attggaatta gataaatggg caagtttgtg gaattggttt aacataacaa attggctgtg   3540
gtatataaaa ttattcataa tgatagtagg aggcttggta ggtttaagaa tagttttgc    3600 tgtactttct atagtgaata gagttaggca gggatattca ccattatcgt ttcagaccca   3660
cctcccaacc ccgaggggac ccgacaggcc cgaaggaata agaagaagaag gtggagagag  3720 agacagagac agatccattc gattagtgaa cggatctcga cggtatcgat tagactgtag   3780
cccaggaata tggcagctag attgtacaca tttagaagga aaagttatct tggtagcagt   3840
tcatgtagcc agtggatata tagaagcaga gtaattcca gcagagacag ggcaagaaac    3900
agcatacttc ctcttaaaat tagcaggaag atggccagta aaaacagtac atacagacaa   3960
tggcagcaat ttcaccagta ctacagttaa ggccgcctgt tggtgggcgg ggatcaagca   4020
ggaatttggc attcccctaca atccccaaag tcaaggagta atagaatcta tgaataaaga   4080
attaaagaaa attataggac aggtaagaga tcaggctgaa catcttaaga cagcagtaca   4140
aatggcagta ttcatccaca atttaaaag aaaaggggg attgggggt acagtgcagg     4200 ggaaagaata gtagacataa tagcaacaga catacaaact aaagaattac aaaaacaaat   4260
tacaaaaatt caaaattttc gggtttatta caggacagc agagatccag tttggctgca   4320
tacgcgtcgt gaggctccgg tgcccgtcag tgggcagagc gcacatcgcc cacagtcccc   4380
gagaagttgg ggggaggggt cggcaattga accggtgcct agagaaggtg gcgcggggta   4440
aactgggaaa gtgatgtcgt gtactggctc cgccttttc ccgagggtgg gggagaaccg   4500
tatataagtg cagtagtcgc cgtgaacgtt ctttttcgca acgggtttgc cgccagaaca    4560
caggtaagtg ccgtgtgtgg ttcccgcggg cctggcctct ttacgggtta tggcccttgc   4620
gtgccttgaa ttacttccac ctggctgcag tacgtgattc ttgatcccga gcttcgggtt   4680
ggaagtgggt gggagagttc gaggccttgc gcttaaggag cccttcgcc tcgtgcttga    4740 gttgaggcct ggcctgggcg ctggggccgc cgcgtgcgaa tctggtggca ccttcgcgcc   4800
tgtctcgctg ctttcgataa gtctctagcc atttaaaatt tttgatgacc tgctgcgacg   4860
ctttttttct ggcaagatag tcttgtaaat gcgggccaag atctgcacac tggtatttcg   4920
gtttttgggg ccgcgggcgg cgacgggcc cgtgcgtccc agcgcacatg ttcggcgagg    4980
cggggcctgc gagcgcggcc accgagaatc ggacgggggg agtctcaagc tggccggcct   5040
gctctggtgc ctggcctcgc gccgccgtgt atcgccccgc cctgggcggc aaggctggcc   5100
```

| | |
|---|---|
| cggtcggcac cagttgcgtg agcggaaaga tggccgcttc ccggccctgc tgcagggagc | 5160 |
| tcaaaatgga ggacgcggcg ctcgggagag cgggcggtg agtcacccac acaaaggaaa | 5220 |
| agggcctttc cgtcctcagc cgtcgcttca tgtgactcca ctgagtaccg ggcgccgtcc | 5280 |
| aggcacctcg attagttctc gtgcttttgg agtacgtcgt ctttaggttg gggggagggg | 5340 |
| ttttatgcga tggagtttcc ccacactgag tgggtggaga ctgaagttag gccagcttgg | 5400 |
| cacttgatgt aattctcctt ggaatttgcc cttttgagt ttggatcttg gttcattctc | 5460 |
| aagcctcaga cagtggttca aagtttttt cttccatttc aggtgtcgtg agctagagcc | 5520 |
| accatggagt ttgggctgag ctggcttttt cttgtggcta tttaaaagg tgtccagtgc | 5580 |
| ggatcccaag ttcagctgca agaaagcgga cccggtttag tgaaaccctc cgagacttta | 5640 |
| tctttaacat gcgccgtgag cggctacagc atctctcgtc atgctttaac ttggattcgt | 5700 |
| cagcctcccg gaaagggttt agagtggatc ggcgccatcg acaacgccgg caccacctat | 5760 |
| tacgccagct gggccaagtc tcgtgtgacc atcagcgtgg acaccagcaa gaaccagttc | 5820 |
| tctttaaagc tgtccagcgt gaccgctgcc gacacagccg tgtactactg cgctcgtgtg | 5880 |
| ttctacgaca tcaacagcgg ctactattta gacggaatgg atctgtgggg ccccggaact | 5940 |
| ttagtgacag tcagcagcgg aggcggagga agcggaggag gaggaagctc cggaggcggt | 6000 |
| tctcaactgg tgctgacaca gagccctagc gcctctgcct ctttaggagc tccgtgaag | 6060 |
| ctgacttgta ctttaagcag cgcccacaag acctacacca tcgactggta ccagcagcag | 6120 |
| cccgagaagg gccctagata tttaatgcaa gttaagagcg acggcagcta caccaaaggc | 6180 |
| actggtgtgc ccgatcgttt tagcggcagc agcagcggcg ccgataggta tttaaccatc | 6240 |
| agctctttac agagcgagga cgaggccgac tactactgtg cgccgacga caacggcggc | 6300 |
| tacgtgtttg gcggcggcac acagctgacc gttttagcta gcggtggcgg aggttctgga | 6360 |
| ggtggaggtt cctccggaat ctacatctgg gcgcccttgg ccgggacttg tggggtcctt | 6420 |
| ctcctgtcac tggttatcac cctttactgc aaacggggca gaaagaaact cctgtatata | 6480 |
| ttcaaacaac catttatgag accagtacaa actactcaag aggaagatgg ctgtagctgc | 6540 |
| cgatttccag aagaagaaga aggaggatgt gaactgagag tgaagttcag caggagcgca | 6600 |
| gacgcccccg cgtaccagca gggccagaac cagctctata cgagctcaa tctaggacga | 6660 |
| agagaggagt acgatgtttt ggacaagaga cgtggccggg accctgagat ggggggaaag | 6720 |
| ccgagaagga agaaccctca ggaaggcctg tacaatgaac tgcagaaaga taagatggcg | 6780 |
| gaggcctaca gtgagattgg gatgaaaggc gagcgccgga ggggcaaggg gcacgatggc | 6840 |
| ctttaccagg gtctcagtac agccaccaag gacacctacg acgcccttca catgcaggcc | 6900 |
| ctgccccctc gctaagtcga caatcaacct ctggattaca aaatttgtga agattgact | 6960 |
| ggtattctta actatgttgc tcctttacg ctatgtggat acgctgcttt aatgcctttg | 7020 |
| tatcatgcta ttgcttcccg tatggctttc attttctcct ccttgtataa atcctggttg | 7080 |
| ctgtctcttt atgaggagtt gtggcccgtt gtcaggcaac gtggcgtggt gtgcactgtg | 7140 |
| tttgctgacg caaccccac tggttgggc attgccacca cctgtcagct cctttccggg | 7200 |
| actttcgctt tccccctccc tattgccacg gcggaactca tcgccgcctg ccttgcccgc | 7260 |
| tgctggacag ggctcggct gttgggcact gacaattccg tggtgttgtc ggggaagctg | 7320 |
| acgtcctttc cttggctgct cgcctgtgtt gccacctgga ttctgcgcgg gacgtccttc | 7380 |
| tgctacgtcc cttcggccct caatccagcg gaccttcctt cccgcggcct gctgccggct | 7440 |

```
ctgcggcctc ttccgcgtct tcgccttcgc cctcagacga gtcggatctc cctttgggcc    7500
gcctccccgc ctggaattcg agctcggtac ctttaagacc aatgacttac aaggcagctg    7560
tagatcttag ccactttta aaagaaaagg ggggactgga agggctaatt cactcccaac     7620
gaagacaaga tctgcttttt gcttgtactg ggtctctctg gttagaccag atctgagcct    7680
gggagctctc tggctaacta gggaacccac tgcttaagcc tcaataaagc ttgccttgag    7740
tgcttcaagt agtgtgtgcc cgtctgttgt gtgactctgg taactagaga tccctcagac    7800
ccttttagtc agtgtggaaa atctctagca gtagtagttc atgtcatctt attattcagt    7860
atttataact tgcaaagaaa tgaatatcag agagtgagag gaacttgttt attgcagctt    7920
ataatggtta caaataaagc aatagcatca caaatttcac aaataaagca ttttttttcac   7980
tgcattctag ttgtggtttg tccaaactca tcaatgtatc ttatcatgtc tggctctagc    8040
tatcccgccc ctaactccgc ccagttccgc ccattctccg cccatggct gactaatttt     8100
ttttatttat gcagaggccg aggccgcctc ggcctctgag ctattccaga agtagtgagg    8160
aggcttttt ggaggcctag ctaggacgt acccaattcg ccctatagtg agtcgtatta      8220
cgcgcgctca ctggccgtcg ttttacaacg tcgtgactgg gaaaaccctg gcgttaccca    8280
acttaatcgc cttgcagcac atccccctt cgccagctgg cgtaatagcg aagaggcccg     8340
caccgatcgc ccttcccaac agttgcgcag cctgaatggc gaatgggacg cgccctgtag    8400
cggcgcatta agcgcggcgg gtgtggtggt tacgcgcagc gtgaccgcta cacttgccag    8460
cgccctagcg cccgctcctt tcgctttctt cccttccttt ctcgccacgt tcgccggctt    8520
tccccgtcaa gctctaaatc ggggggctcc ctttagggtt ccgatttagtg ctttacggca   8580
cctcgacccc aaaaaacttg attagggtga tggttcacgt agtgggccat cgccctgata    8640
gacggttttt cgccctttga cgttggagtc acgttctttt aatagtggac tcttgttcca    8700
aactggaaca cactcaacc ctatctcggt ctattctttt gatttataag ggattttgcc     8760
gatttcggcc tattggttaa aaaatgagct gatttaacaa aatttaacg cgaattttaa     8820
caaaatatta acgcttacaa tttaggtggc acttttcggg gaaatgtgcg cggaacccct    8880
atttgtttat ttttctaaat acattcaaat atgtatccgc tcatgagaca ataaccctga    8940
taaatgcttc aataatattg aaaaaggaag agtatgagta ttcaacattt ccgtgtcgcc    9000
cttattccct tttttgcggc attttgcctt cctgttttttg ctcacccaga aacgctggtg    9060
aaagtaaaag atgctgaaga tcagttgg                                      9088
```

<210> SEQ ID NO 114
<211> LENGTH: 9088
<212> TYPE: DNA
<213> ORGANISM: Artificial Sequence
<220> FEATURE:
<223> OTHER INFORMATION: CAR
<220> FEATURE:
<223> OTHER INFORMATION: pTRPE-C29-gs-BBz

<400> SEQUENCE: 114

```
gtgcacgagt gggttacatc gaactggatc tcaacagcgg taagatcctt gagagttttc      60
gccccgaaga cgttttcca atgatgagca cttttaaagt tctgctatgt ggcgcggtat       120
tatcccgtat tgacgccggg caagagcaac tcggtcgccg catacactat tctcagaatg     180
acttggttga gtactcacca gtcacagaaa agcatcttac ggatggcatg acagtaagag     240
aattatgcag tgctgccata accatgagtg ataacactgc ggccaactta cttctgacaa     300
cgatcggagg accgaaggag ctaaccgctt ttttgcacaa catgggggat catgtaactc     360
```

```
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taaagttgca ggaccacttc    540
tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
tctacacgac ggggagtcag gcaactatgg atgaacgaaa tagacagatc gctgagatag    720
gtgcctcact gattaagcat tggtaactgt cagaccaagt ttactcatat atactttaga    780
ttgatttaaa acttcatttt taatttaaaa ggatctaggt gaagatcctt tttgataatc    840
tcatgaccaa aatcccttaa cgtgagtttt cgttccactg agcgtcagac cccgtagaaa    900
agatcaaagg atcttcttga tccttttttt tctgcgcgt  aatctgctgc ttgcaaacaa    960
aaaaaccacc gctaccagcg gtggtttgtt tgccggatca agagctacca actcttttc    1020 cgaaggtaac tggcttcagc agagcgcaga taccaaatac tgttcttcta gtgtagccgt    1080
agttaggcca ccacttcaag aactctgtag caccgcctac atacctcgct ctgctaatcc    1140
tgttaccagt ggctgctgcc agtggcgata agtcgtgtct taccgggttg gactcaagac    1200
gatagttacc ggataaggcg cagcggtcgg gctgaacggg gggttcgtgc acacagccca    1260
gcttggagcg aacgacctac accgaactga gatacctaca gcgtgagcta tgagaaagcg    1320
ccacgcttcc cgaagggaga aggcggaca  ggtatccggt aagcggcagg gtcggaacag    1380
gagagcgcac gagggagctt ccaggggaa  acgcctggta tctttatagt cctgtcgggt    1440
ttcgccacct ctgacttgag cgtcgatttt tgtgatgctc gtcagggggg cggagcctat    1500
ggaaaaacgc cagcaacgcg gccttttac  ggttcctggc cttttgctgg ccttttgctc    1560
acatgttctt tcctgcgtta tcccctgatt ctgtggataa ccgtattacc gcctttgagt    1620
gagctgatac cgctcgccgc agccgaacga ccgagcgcag cgagtcagtg agcgaggaag    1680
cggaagagcg cccaatacgc aaaccgcctc tccccgcgcg ttggccgatt cattaatgca    1740
gctggcacga caggtttccc gactggaaag cgggcagtga gcgcaacgca attaatgtga    1800
gttagctcac tcattaggca ccccaggctt tacactttat gcttccggct cgtatgttgt    1860
gtggaattgt gagcggataa caatttcaca caggaaacag ctatgaccat gattacgcca    1920
agcgcgcaat taaccctcac taaagggaac aaaagctgga gctgcaagct taatgtagtc    1980
ttatgcaata ctcttgtagt cttgcaacat ggtaacgatg agttagcaac atgccttaca    2040
aggagagaaa aagcaccgtg catgccgatt ggtggaagta aggtggtacg atcgtgcctt    2100
attaggaagg caacagacgg gtctgacatg gattggacga accactgaat tgccgcattg    2160
cagagatatt gtatttaagt gcctagctcg atacataaac gggtctctct ggttagacca    2220
gatctgagcc tgggagctct ctggctaact agggaaccca ctgcttaagc ctcaataaag    2280
cttgccttga gtgcttcaag tagtgtgtgc ccgtctgttg tgtgactctg gtaactagag    2340
atccctcaga ccctttagt  cagtgtggaa aatctctagc agtggcgccc gaacagggac    2400
ttgaaagcga aagggaaacc agaggagctc tctcgacgca ggactcggct tgctgaagcg    2460
cgcacggcaa gaggcgaggg gcggcgactg gtgagtacgc caaaaatttt gactagcgga    2520
ggctagaagg agagagatgg gtgcgagagc gtcagtatta gcgggggag  aattagatcg    2580 cgatgggaaa aaattcggtt aaggccaggg ggaaagaaaa aatataaatt aaaacatata    2640
gtatgggcaa gcagggagct agaacgattc gcagttaatc ctggcctgtt agaaacatca    2700
```

```
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata aagtagtaaa aattgaacca ttaggagtag cacccaccaa    3000
ggcaaagaga agagtggtgc agagagaaaa aagagcagtg gaataggag ctttgttcct     3060
tgggttcttg ggagcagcag gaagcactat gggcgcagcg tcaatgacgc tgacggtaca    3120
ggccagacaa ttattgtctg gtatagtgca gcagcagaac aatttgctga ggctattga    3180
ggcgcaacag catctgttgc aactcacagt ctggggcatc aagcagctcc aggcaagaat    3240
cctggctgtg gaaagatacc taaaggatca acagctcctg gggatttggg gttgctctgg    3300
aaaactcatt tgcaccactg ctgtgccttg gaatgctagt tggagtaata atctctgga    3360
acagatttgg aatcacacga cctggatgga gtgggacaga gaaattaaca attacacaag    3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc     3600
tgtactttct atagtgaata gagttaggca gggatattca ccattatcgt ttcagaccca    3660
cctcccaacc ccgaggggac ccgacaggcc cgaaggaata aagaagaag gtggagagag    3720
agacagagac agatccattc gattagtgaa cggatctcga cggtatcgat tagactgtag    3780
cccaggaata tggcagctag attgtacaca tttagaagga aaagttatct tggtagcagt    3840
tcatgtagcc agtggatata tagaagcaga gtaattcca gcagagacag gcaagaaac     3900
agcatacttc ctcttaaaat tagcaggaag atggccagta aaaacagtac atacagacaa    3960
tggcagcaat ttcaccagta ctacagttaa ggccgcctgt tggtgggcgg ggatcaagca    4020
ggaatttggc attccctaca atccccaaag tcaaggagta atagaatcta tgaataaaga    4080
attaaagaaa attataggac aggtaagaga tcaggctgaa catcttaaga cagcagtaca    4140
aatggcagta ttcatccaca attttaaaag aaaaggggg attggggggt acagtgcagg    4200
ggaaagaata gtagacataa tagcaacaga catacaaact aaagaattac aaaaacaaat    4260
tacaaaaatt caaaattttc gggtttatta caggacagc agagatccag tttggctgca    4320
tacgcgtcgt gaggctccgg tgcccgtcag tgggcagagc gcacatcgcc cacagtcccc    4380
gagaagttgg ggggagggt cggcaattga accggtgcct agagaaggtg gcgcggggta    4440
aactgggaaa gtgatgtcgt gtactggctc cgccttttc ccgagggtgg gggagaaccg    4500
tatataagtg cagtagtcgc cgtgaacgtt ctttttcgca acgggtttgc cgccagaaca    4560
caggtaagtg ccgtgtgtgg ttcccgcggg cctggcctct ttacgggtta tggcccttgc    4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctggggccgc cgcgtgcgaa tctggtggca ccttcgcgcc    4800
tgtctcgctg ctttcgataa gtctctagcc atttaaaatt tttgatgacc tgctgcgacg    4860
cttttttttct ggcaagatag tcttgtaaat gcgggccaag atctgcacac tggtatttcg    4920
gttttttgggg ccgcgggcgg cgacggggcc cgtgcgtccc agcgcacatg ttcggcgagg    4980
cggggcctgc gagcgcggcc accgagaatc ggacgggggt agtctcaagc tggccggcct    5040
gctctggtgc ctggcctcgc gccgccgtgt atcgccccgc cctgggcggc aaggctggcc    5100
```

```
cggtcggcac cagttgcgtg agcggaaaga tggccgcttc ccggccctgc tgcagggagc    5160
tcaaaatgga ggacgcggcg ctcgggagag cgggcggtg agtcacccac acaaaggaaa    5220
agggcctttc cgtcctcagc cgtcgcttca tgtgactcca ctgagtaccg ggcgccgtcc    5280
aggcacctcg attagttctc gtgcttttgg agtacgtcgt ctttaggttg ggggagggg    5340 ttttatgcga tggagtttcc ccacactgag tgggtggaga ctgaagttag gccagcttgg    5400
cacttgatgt aattctcctt ggaatttgcc cttttgagt ttggatcttg gttcattctc    5460
aagcctcaga cagtggttca aagtttttt cttccatttc aggtgtcgtg agctagagcc    5520
accatggagt ttgggctgag ctggcttttt cttgtggcta tttaaaagg tgtccagtgc    5580 ggatccgagg tgcagctggt ggagtctgga ggaggactgg tgcaacccgg tggctcttta    5640
agactgagct cgccgcctc tggcttcacc ttttctcgtc acgctttaac atgggtgaga    5700
caagctcccg gaagggact ggagtgggtg tccgccatcg acaacgccgg caccacctac    5760
tacgccagct gggccaagag cagattcacc atctctcgtg acaacgccaa gaactcttta    5820
tatttacaga tgaactcttt aagggccgag gacaccgccg tgtactactg cgctcgtgtg    5880
ttctacgaca tcaactccgg ctactattta gacggcatgg atttatgggg acccggtaca    5940
ctggtcacag tgagctctgg aggcggaggt agcggaggcg gaggaagcag cggtggaggc    6000
agccagctgg tgctgacaca gtccccttcc gcttccgcct cttaggagc ctccgtgaag    6060 ctgacttgta ctttaagcag cgcccacaaa acctacacca tcgactggta ccagcagcag    6120
cccgagaagg gcccacgtta tttaatgcaa gttaagtccg acggctccta caccaagggc    6180
accggcgtgc ccgatagatt cagcggctcc agcagcggcg ccgataggta tttaaccatc    6240
tcctctttac agagcgagga cgaggccgac tactactgtg gcgccgacga caacggcggc    6300
tacgtgtttg gaggcggcac ccagctgacc gtgctggcta gcggtggcgg aggttctgga    6360
ggtggaggtt cctccggaat ctacatctgg gcgcccttgg ccgggacttg tgggtccttt    6420
ctcctgtcac tggttatcac cctttactgc aaacggggca gaaagaaact cctgtatata    6480
ttcaaacaac catttatgag accagtacaa actactcaag aggaagatgg ctgtagctgc    6540
cgatttccag aagaagaaga aggaggatgt gaactgagag tgaagttcag caggagcgca    6600
gacgcccccg cgtaccagca gggccagaac cagctctata cgagctcaa tctaggacga    6660 agagaggagt acgatgtttt ggacaagaga cgtggccggg accctgagat ggggggaaag    6720
ccgagaagga agaaccctca ggaaggcctg tacaatgaac tgcagaaaga taagatggcg    6780
gaggcctaca gtgagattgg gatgaaaggc gagcgccgga ggggcaaggg gcacgatggc    6840
ctttaccagg gtctcagtac agccaccaag acacctacg acgcccttca catgcaggcc    6900
ctgccccctc gctaagtcga caatcaacct ctggattaca aaatttgtga aagattgact    6960
ggtattctta actatgttgc tccttttacg ctatgtggat acgctgcttt aatgcctttg    7020
tatcatgcta ttgcttcccg tatggctttc attttctcct ccttgtataa atcctggttg    7080
ctgtctcttt atgaggagtt gtggcccgtt gtcaggcaac gtggcgtggt gtgcactgtg    7140
tttgctgacg caaccccac tggttgggc attgccacca cctgtcagct cctttccggg    7200
actttcgctt tccccctccc tattgccacg gcggaactca tcgccgcctg ccttgcccgc    7260
tgctggacag ggctcggct gttgggcact gacaattccg tggtgttgtc ggggaagctg    7320
acgtcctttc cttggctgct cgcctgtgtt gccacctgga ttctgcgcgg gacgtccttc    7380
tgctacgtcc cttcggccct caatccagcg gaccttcctt cccgcggcct gctgccggct    7440
```

```
ctgcggcctc ttccgcgtct tcgccttcgc cctcagacga gtcggatctc cctttgggcc    7500
gcctccccgc ctggaattcg agctcggtac ctttaagacc aatgacttac aaggcagctg    7560
tagatcttag ccactttta aaagaaaagg ggggactgga agggctaatt cactcccaac     7620
gaagacaaga tctgcttttt gcttgtactg ggtctctctg gttagaccag atctgagcct   7680
gggagctctc tggctaacta gggaacccac tgcttaagcc tcaataaagc ttgccttgag    7740
tgcttcaagt agtgtgtgcc cgtctgttgt gtgactctgg taactagaga tccctcagac    7800
ccttttagtc agtgtggaaa atctctagca gtagtagttc atgtcatctt attattcagt    7860
atttataact tgcaaagaaa tgaatatcag agagtgagag gaacttgttt attgcagctt    7920
ataatggtta caaataaagc aatagcatca caaatttcac aaataaagca ttttttttcac   7980
tgcattctag ttgtggtttg tccaaactca tcaatgtatc ttatcatgtc tggctctagc    8040
tatcccgccc ctaactccgc ccagttccgc ccattctccg ccccatggct gactaatttt    8100
ttttatttat gcagaggccg aggccgcctc ggcctctgag ctattccaga agtagtgagg    8160
aggcttttt ggaggcctag ctaggacgt acccaattcg ccctatagtg agtcgtatta      8220
cgcgcgctca ctggccgtcg ttttacaacg tcgtgactgg gaaaaccctg gcgttaccca    8280
acttaatcgc cttgcagcac atccccctt cgccagctgg cgtaatagcg aagaggcccg     8340
caccgatcgc ccttcccaac agttgcgcag cctgaatggc gaatgggacg cgccctgtag    8400
cggcgcatta agcgcggcgg gtgtggtggt tacgcgcagc gtgaccgcta cacttgccag    8460
cgccctagcg cccgctcctt tcgctttctt cccttccttt ctcgccacgt tcgccggctt    8520
tccccgtcaa gctctaaatc ggggctccc tttagggttc cgatttagtg ctttacggca    8580
cctcgacccc aaaaaacttg attagggtga tggttcacgt agtgggccat cgccctgata    8640
gacggttttt cgccctttga cgttggagtc cacgttcttt aatagtggac tcttgttcca    8700
aactggaaca acactcaacc ctatctcggt ctattctttt gatttataag ggattttgcc    8760
gatttcggcc tattggttaa aaaatgagct gatttaacaa aaatttaacg cgaattttaa    8820
caaaatatta acgcttacaa tttaggtggc acttttcggg gaaatgtgcg cggaacccct    8880
atttgtttat ttttctaaat acattcaaat atgtatccgc tcatgagaca ataaccctga    8940
taaatgcttc aataatattg aaaaaggaag agtatgagta ttcaacattt ccgtgtcgcc    9000
cttattccct tttttgcggc attttgcctt cctgttttg ctcacccaga aacgctggtg     9060
aaagtaaaag atgctgaaga tcagttgg                                       9088

<210> SEQ ID NO 115
<211> LENGTH: 1398
<212> TYPE: DNA
<213> ORGANISM: Artificial Sequence
<220> FEATURE:
<223> OTHER INFORMATION: Antigen
<220> FEATURE:
<223> OTHER INFORMATION: GFRa1

<400> SEQUENCE: 115
atgttcctgg ccaccctgta cttcgccctg cctctgctgg acctgctgct gagcgccgaa     60
gtgagcggag agacagact ggactgcgtg aaggccagcg accaatgtct gaaggagcaa    120
tcctgctcca ccaagtacag gacactcagg cagtgcgtgg ccggaaagga aaccaacttc   180
agcctggcca gcggcctcga agctaaggac gaatgcagga gcgccatgga ggccctgaaa   240
cagaagagcc tgtacaactg caggtgcaag aggggcatga gaaggagaa aaactgcctg   300
aggatctact ggagcatgta tcagagcctc caggcaacg atctgctgga ggacagcccc    360
```

```
tacgagcctg tcaacagcag gctgtccgat atcttcaggg tggtgccttt cattagcgac    420
gtgttccagc aggtggagca catccccaaa ggcaacaatt gtctggacgc tgccaaagct    480
tgcaacctcg atgacatctg taagaaatac aggagcgcct acatcacccc ctgcaccaca    540
tccgtgagca atgacgtgtg taacaggagg aagtgccaca agctctgag gcagttcttc     600 gacaaggtgc ctgccaagca cagctacgga atgctctttt gcagctgcag agacatcgcc    660
tgtaccgaga ggaggagaca aaccatcgtg cccgtgtgct cctatgaaga gagggagaaa    720
cccaactgcc tgaatctgca ggacagctgc aagaccaact acatctgcag gagcaggctg    780
gccgacttct tcaccaattg tcagcccgaa tccagatccg tgagctcctg cctgaaagag    840
aattatgccg actgcctgct ggcttacagc ggactgatcg gcacagtcat gacacccaac    900
tacatcgaca gctcctccct gtccgtggcc ccttggtgcg attgctccaa ctccggcaac    960
gacctggagg agtgtctgaa gttcctgaac ttcttcaagg acaataccctg cctcaagaac   1020 gccatccagg ctttcggaaa cggcagcgac gtgaccgtgt ggcagcccgc ctttcccgtg   1080
cagaccacca cagctaccac aaccaccgcc ctgagggtga agaataagcc tctgggcccc   1140
gccggcagcg agaatgagat ccccacacac gtgctgcctc cttgtgccaa tctccaggcc   1200
cagaagctga agtccaacgt gagcggcaat acccacctct gcatctccaa tggcaactac   1260
gagaaggagg gactgggagc cagcagccac attaccacca aatccatggc tgcccctccc   1320
agctgtggac tgagccctct cctcgtgctg gtggtcaccg ccctgtccac actgctgtcc   1380
ctcaccgaga ccagctga                                                  1398

<210> SEQ ID NO 116
<211> LENGTH: 1395
<212> TYPE: DNA
<213> ORGANISM: Artificial Sequence
<220> FEATURE:
<223> OTHER INFORMATION: Antigen
<220> FEATURE:
<223> OTHER INFORMATION: GFRa2

<400> SEQUENCE: 116
atgatcctcg ccaacgtgtt ctgcctgttc tttttcctgg acgagaccct gagaagcctg     60
gctagcccct ccagcctcca gggacctgaa ctgcacggct ggaggccccc tgtggattgc    120
gtgagagcca acgagctgtg cgccgccgag agcaactgtt ccagcagata caggaccctc    180
agacagtgcc tggccggcag agacagaaac accatgctgg ccaacaagga gtgtcaggcc    240
gccctggaag tgctgcaaga gtcccctctg tacgattgta ggtgcaagag gggcatgaag    300
aaggaactgc agtgcctgca gatctattgg agcatccatc tgggcctcac cgagggcgaa    360 gaatttatg aggccagccc ctacgagccc gtgacctcca gactcagcga catcttcagg    420
ctcgcttcca tcttcagcgg cacaggcgcc gatcctgtgg tgagcgccaa gagcaaccat    480
tgcctggacg ctgccaaggc ctgcaacctc aacgacaact gcaagaagct caggagctcc    540
tatatcagca tttgcaacag ggagatttcc cccaccgaga ggtgtaacag agaaagtgc    600 cacaaggccc tgagacagtt cttcgacaga gtgccttccg agtacaccta caggatgctc    660
ttctgcagct gccaggacca agcctgcgct gagagaagga ggcagaccat cctgccctcc    720
tgcagctacg aagacaagga gaagcctaac tgcctggatc tcagggcgt ctgcagaacc    780 gaccacctct gtaggtccag actggccgac ttccacgcca attgcagggc cagctaccaa    840
accgtgacca gctgccccgc cgacaactat caggcctgcc tgggcagcta cgccggcatg    900
```

```
attggcttcg acatgacccc caattacgtt gatagctccc ccacaggcat cgtggtgagc    960
ccttggtgca gctgcagggg cagcggcaac atggaggaag agtgcgagaa gttcctgagg   1020
gacttcaccg agaatccctg cctgagaaac gccatccagg ccttcggcaa cggcacagac   1080
gtgaacgtgt cccccaaagg ccccagcttt caggccaccc aagctcccag ggtcgagaaa   1140
accccttccc tgcccgacga cctgagcgat tccacatccc tcggcacctc cgtgatcacc   1200
acctgcacat ccgtgcagga acagggcctg aaggccaata actccaagga gctgagcatg   1260
tgcttcacag agctgaccac caacattatc cccggcagca caaggtgat caagcccaat   1320 tccggaccta gcagagccag acccagcgcc gctctgacag tgctgtccgt gctgatgctg   1380
aaactggccc tgtga                                                    1395

<210> SEQ ID NO 117
<211> LENGTH: 1203
<212> TYPE: DNA
<213> ORGANISM: Artificial Sequence
<220> FEATURE:
<223> OTHER INFORMATION: Antigen
<220> FEATURE:
<223> OTHER INFORMATION: GFRa3

<400> SEQUENCE: 117
atggtgaggc ctctgaatcc cagacccctg cctcccgtgg tgctgatgct gctgctgctg     60
ctccctccct cccctctgcc cctggccgct ggagatcctc tgcccacaga gagcagactc    120
atgaacagct gcctccaggc caggagaaag tgccaggccg accctacctg ttccgccgcc    180
taccaccacc tggactcctg caccagcagc atcagcaccc ctctgcccag cgaagaaccc    240
tccgtccccg ctgattgcct ggaagccgcc cagcagctga aaatagcag cctgatcggc    300 tgcatgtgcc acagaaggat gaagaaccag gtggcctgcc tggatattta ctggaccgtc    360
cacagggcca aagcctggga aaattacgaa ctggacgtgt cccctacga ggacacagtg    420 acaagcaagc cctggaagat gaacctcagc aagctgaaca tgctcaagcc cgacagcgac    480
ctgtgcctca aattcgccat gctgtgcacc ctgaacgaca agtgcgacag gctgaggaaa    540
gcctacggag aagcctgtag cggcccccat tgccagaggc acgtgtgcct gagacagctg    600
ctgaccttct tcgagaaggc cgctgagcct cacgcccaag gactgctcct gtgcccttgc    660
gcccccaatg atagggctg cggcgagagg agaagaaaca ccatcgctcc caactgcgcc    720
ctgccccctg tgcccctaa ttgcctcgag ctgagaagac tgtgcttctc cgaccctctg    780
tgcaggagca gactggtgga tttccagacc cactgtcacc ccatggacat cctcggaacc    840
tgcgccaccg agcagagcag gtgtctcaga gcctacctgg gcctgatcgg caccgccatg    900
acccccaatt ttgtgagcaa cgtgaacacc tccgtggccc tgtcctgtac ctgcaggga    960 agcggcaacc tccaggagga gtgcgagatg ctcgagggct tcttctccca caatccctgc   1020
ctgaccgagg ccatcgccgc caagatgagg ttccacagcc agctgttctc ccaggattgg   1080
ccccacccca ccttcgctgt gatggcccac cagaacgaaa accccgctgt gagaccccag   1140
ccttgggtgc cctccctgtt cagctgcacc ctgcctctca tcctgctgct gagcctgtgg   1200
tga                                                                 1203

<210> SEQ ID NO 118
<211> LENGTH: 465
<212> TYPE: PRT
<213> ORGANISM: Artificial Sequence
<220> FEATURE:
<223> OTHER INFORMATION: Antigen
```

<220> FEATURE:
<223> OTHER INFORMATION: GFRa4 isoform a

<400> SEQUENCE: 118

```
Asn Arg Cys Val Asp Ala Ala Glu Ala Cys Thr Ala Asp Ala Arg Cys
1               5                   10                  15

Gln Arg Leu Arg Ser Glu Tyr Val Ala Gln Cys Leu Gly Arg Ala Ala
            20                  25                  30

Gln Gly Gly Cys Pro Arg Ala Arg Cys Arg Arg Ala Leu Arg Arg Phe
        35                  40                  45

Phe Ala Arg Gly Pro Pro Ala Leu Thr His Ala Leu Leu Phe Cys Pro
    50                  55                  60

Cys Ala Gly Pro Ala Cys Ala Glu Arg Arg Gln Thr Phe Val Pro
65                  70                  75                  80

Ser Cys Ala Phe Ser Gly Pro Gly Pro Ala Pro Pro Ser Cys Leu Glu
                85                  90                  95

Pro Leu Asn Phe Cys Glu Arg Ser Arg Val Cys Arg Pro Arg Leu Leu
            100                 105                 110

Ala Phe Gln Val Ser Cys Thr Pro Ala Pro Ser Ala Pro Asp Gly Cys
        115                 120                 125

Leu Leu Asp Gln Gly Ala Arg Cys Leu Arg Ala Tyr Ala Gly Leu Val
130                 135                 140

Gly Thr Ala Val Thr Pro Asn Tyr Val Asp Asn Val Ser Ala Arg Val
145                 150                 155                 160

Ala Pro Trp Cys Asp Cys Gly Ala Ser Gly Asn Arg Arg Glu Asp Cys
                165                 170                 175

Glu Ala Phe Arg Gly Leu Phe Thr Arg Asn Arg Cys Leu Asp Gly Ala
            180                 185                 190

Ile Gln Ala Phe Ala Ser Gly Trp Pro Pro Val Leu Leu Asp Gln Leu
        195                 200                 205

Asn Pro Gln Gly Asp Pro Glu His Ser Leu Leu Gln Val Ser Ile Glu
210                 215                 220

Gly Arg Met Asp Pro Lys Ser Cys Asp Lys Thr His Thr Cys Pro Pro
225                 230                 235                 240

Cys Pro Ala Pro Glu Ala Glu Gly Ala Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400
```

```
Asn Asn Tyr Lys Ala Thr Pro Pro Val Leu Asp Ser Asp Gly Ser Phe
            405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys His His His His
    450                 455                 460

His
465

<210> SEQ ID NO 119
<211> LENGTH: 497
<212> TYPE: PRT
<213> ORGANISM: Artificial Sequence
<220> FEATURE:
<223> OTHER INFORMATION: Antigen
<220> FEATURE:
<223> OTHER INFORMATION: GFRa4 isoform b

<400> SEQUENCE: 119

Asn Arg Cys Val Asp Ala Ala Glu Ala Cys Thr Ala Asp Ala Arg Cys
1               5                   10                  15

Gln Arg Leu Arg Ser Glu Tyr Val Ala Gln Cys Leu Gly Arg Ala Ala
            20                  25                  30

Gln Gly Gly Cys Pro Arg Ala Arg Cys Arg Arg Ala Leu Arg Arg Phe
        35                  40                  45

Phe Ala Arg Gly Pro Pro Ala Leu Thr His Ala Leu Leu Phe Cys Pro
    50                  55                  60

Cys Ala Gly Pro Ala Cys Ala Glu Arg Arg Gln Thr Phe Val Pro
65                  70                  75                  80

Ser Cys Ala Phe Ser Gly Pro Gly Pro Ala Pro Ser Cys Leu Glu
                85                  90                  95

Pro Leu Asn Phe Cys Glu Arg Ser Arg Val Cys Arg Cys Ala Arg Ala
            100                 105                 110

Ala Ala Gly Pro Trp Arg Gly Trp Gly Arg Gly Leu Ser Pro Ala His
            115                 120                 125

Arg Pro Pro Ala Ala Gln Ala Ser Pro Gly Leu Ser Gly Leu Val
130                 135                 140

His Pro Ser Ala Gln Arg Pro Arg Leu Pro Ala Gly Pro Gly Arg
145                 150                 155                 160

Pro Leu Pro Ala Arg Leu Arg Gly Pro Arg Gly Val Pro Ala Gly Thr
            165                 170                 175

Ala Val Thr Pro Asn Tyr Val Asp Asn Val Ser Ala Arg Val Ala Pro
            180                 185                 190

Trp Cys Asp Cys Gly Ala Ser Gly Asn Arg Arg Glu Asp Cys Glu Ala
        195                 200                 205

Phe Arg Gly Leu Phe Thr Arg Asn Arg Cys Leu Asp Gly Ala Ile Gln
    210                 215                 220

Ala Phe Ala Ser Gly Trp Pro Pro Val Leu Leu Asp Gln Leu Asn Pro
225                 230                 235                 240

Gln Gly Asp Pro Glu His Ser Leu Leu Gln Val Gly Gly Glu Asn
                245                 250                 255

Leu Tyr Phe Gln Gly Gly Gly Gly Ala Gly Gly Gly Asp Lys
            260                 265                 270
```

```
Thr His Thr Cys Pro Pro Cys Pro Ala Pro Glu Leu Leu Gly Gly Pro
            275                 280                 285

Ser Val Phe Leu Phe Pro Lys Pro Lys Asp Thr Leu Met Ile Ser
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
435                 440                 445

Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 120
<211> LENGTH: 94
<212> TYPE: PRT
<213> ORGANISM: Artificial Sequence
<220> FEATURE:
<223> OTHER INFORMATION: Heavy Chain
<220> FEATURE:
<223> OTHER INFORMATION: Fig2A

<400> SEQUENCE: 120

Val Lys Glu Ser Glu Gly Gly Leu Phe Lys Pro Thr Asp Thr Leu Thr
1               5                   10                  15

Leu Thr Cys Thr Val Ser Gly Phe Ser Leu Ser Arg His Ala Leu Thr
            20                  25                  30

Trp Val Arg Gln Ala Pro Gly Asn Gly Leu Glu Trp Ile Gly Ala Ile
        35                  40                  45

Asp Asn Ala Gly Thr Thr Tyr Tyr Ala Ser Trp Ala Lys Ser Arg Ser
    50                  55                  60

Thr Ile Thr Arg Asn Thr Asp Leu His Thr Val Thr Leu Lys Met Thr
65                  70                  75                  80

Ser Leu Thr Ala Ser Asp Thr Ala Thr Tyr Phe Cys Ala Arg
            85                  90

<210> SEQ ID NO 121
<211> LENGTH: 94
<212> TYPE: PRT
<213> ORGANISM: Artificial Sequence
```

<220> FEATURE:
<223> OTHER INFORMATION: Heavy Chain
<220> FEATURE:
<223> OTHER INFORMATION: IGHV4-38-2*02

<400> SEQUENCE: 121

Leu Gln Glu Ser Gly Pro Gly Leu Val Lys Pro Ser Glu Thr Leu Ser
1               5                   10                  15

Leu Thr Cys Thr Val Ser Gly Tyr Ser Ile Ser Ser Gly Tyr Tyr Trp
                20                  25                  30

Gly Val Ile Gln Ala Pro Gly Asn Lys Leu Glu Trp Ile Gly Ser Ile
            35                  40                  45

Tyr His Ser Gly Ser Thr Tyr Tyr Asn Pro Ser Leu Lys Ser Arg Val
50                  55                  60

Thr Ile Ser Val Asp Thr Ser Lys Asn Gln Phe Ser Leu Lys Leu Ser
65                  70                  75                  80

Ser Val Thr Ala Ala Asp Thr Ala Val Tyr Tyr Cys Ala Arg
                85                  90

<210> SEQ ID NO 122
<211> LENGTH: 92
<212> TYPE: PRT
<213> ORGANISM: Artificial Sequence
<220> FEATURE:
<223> OTHER INFORMATION: Heavy Chain
<220> FEATURE:
<223> OTHER INFORMATION: IGHV4-59*05

<400> SEQUENCE: 122

Leu Gln Glu Ser Gly Pro Gly Leu Val Lys Pro Ser Glu Thr Leu Ser
1               5                   10                  15

Leu Thr Cys Thr Val Ser Gly Gly Ser Ile Ser Ser Tyr Tyr Trp Ser
                20                  25                  30

Val Ile Gln Ala Pro Gly Asn Lys Leu Glu Trp Ile Gly Arg Ile Tyr
            35                  40                  45

Tyr Ser Gly Ser Thr Tyr Tyr Asn Pro Ser Leu Lys Ser Arg Val Thr
50                  55                  60

Ile Ser Val Asp Thr Ser Lys Asn Gln Phe Ser Leu Lys Leu Ser Ser
65                  70                  75                  80

Val Thr Ala Ala Asp Thr Ala Val Tyr Tyr Cys Ala
                85                  90

<210> SEQ ID NO 123
<211> LENGTH: 93
<212> TYPE: PRT
<213> ORGANISM: Artificial Sequence
<220> FEATURE:
<223> OTHER INFORMATION: Heavy Chain
<220> FEATURE:
<223> OTHER INFORMATION: IGHV4-59*07

<400> SEQUENCE: 123

Leu Gln Glu Ser Gly Pro Gly Leu Val Lys Pro Ser Asp Thr Leu Ser
1               5                   10                  15

Leu Thr Cys Thr Val Ser Gly Gly Ser Ile Ser Ser Tyr Tyr Trp Ser
                20                  25                  30

Val Ile Gln Ala Pro Gly Asn Lys Leu Glu Trp Ile Gly Tyr Ile Tyr
            35                  40                  45

Tyr Ser Gly Ser Thr Ser Tyr Asn Pro Ala Leu Lys Ser Arg Val Thr
50                  55                  60

Ile Ser Val Asp Thr Ser Lys Asn Gln Phe Ser Leu Lys Leu Ser Ser
65                  70                  75                  80

Val Thr Ala Ala Asp Thr Ala Val Tyr Tyr Cys Ala Arg
                85                  90

<210> SEQ ID NO 124
<211> LENGTH: 92
<212> TYPE: PRT
<213> ORGANISM: Artificial Sequence
<220> FEATURE:
<223> OTHER INFORMATION: Light Chain
<220> FEATURE:
<223> OTHER INFORMATION: Fig2B

<400> SEQUENCE: 124

Gln Phe Val Leu Thr Gln Ser Pro Ser Val Ala Ala Leu Gly Ala
1               5                   10                  15

Ser Ala Lys Leu Thr Cys Thr Leu Ser Ser Ala His Lys Thr Tyr Thr
                20                  25                  30

Ile Asp Trp Tyr Gln Gln Gln Gly Glu Ala Pro Arg Tyr Leu Met
                35                  40                  45

Gln Val Lys Ser Asp Gly Ser Tyr Thr Lys Gly Thr Gly Val Pro Asp
50                  55                  60

Arg Phe Ser Gly Ser Ser Gly Ala Asp Arg Tyr Leu Ile Ile Pro
65                  70                  75                  80

Ser Val Gln Ala Asp Asp Glu Ala Gly Tyr Val Cys
                85                  90

<210> SEQ ID NO 125
<211> LENGTH: 90
<212> TYPE: PRT
<213> ORGANISM: Artificial Sequence
<220> FEATURE:
<223> OTHER INFORMATION: Light Chain
<220> FEATURE:
<223> OTHER INFORMATION: IGLV4-3*01

<400> SEQUENCE: 125

Val Leu Thr Gln Ser Pro Ser Ala Ser Ala Leu Leu Gly Ala Ser Ile
1               5                   10                  15

Lys Leu Thr Cys Thr Leu Ser Ser Glu His Ser Thr Tyr Thr Ile Glu
                20                  25                  30

Trp Tyr Gln Gln Arg Pro Gly Arg Ser Pro Gln Tyr Thr Met Lys Val
                35                  40                  45

Lys Ser Asp Gly Ser His Ser Lys Gly Asp Gly Ile Pro Asp Arg Phe
50                  55                  60

Met Gly Ser Ser Gly Ala Asp Arg Tyr Leu Thr Phe Ser Asn Leu
65                  70                  75                  80

Gln Ser Asp Asp Glu Ala Glu Tyr His Cys
                85                  90

<210> SEQ ID NO 126
<211> LENGTH: 92
<212> TYPE: PRT
<213> ORGANISM: Artificial Sequence
<220> FEATURE:
<223> OTHER INFORMATION: Light Chain
<220> FEATURE:
<223> OTHER INFORMATION: IGLV4-69*01 02

<400> SEQUENCE: 126

Gln Leu Val Leu Thr Gln Ser Pro Ser Ala Ser Ala Ser Leu Gly Ala

```
                1               5                   10                  15
Ser Val Lys Leu Thr Cys Thr Leu Ser Ser Gly His Ser Ser Tyr Ala
                20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys
                85                  90
```

<210> SEQ ID NO 127
<211> LENGTH: 96
<212> TYPE: PRT
<213> ORGANISM: Artificial Sequence
<220> FEATURE:
<223> OTHER INFORMATION: Heavy Chain
<220> FEATURE:
<223> OTHER INFORMATION: Fig3A

<400> SEQUENCE: 127

```
Gln Ser Val Lys Glu Ser Gly Gly Leu Phe Lys Pro Thr Asp Thr
1               5                   10                  15

Leu Thr Leu Thr Cys Thr Val Ser Gly Phe Ser Leu Ser Arg His Ala
                20                  25                  30

Leu Thr Trp Val Arg Gln Ala Pro Gly Asn Gly Leu Glu Trp Ile Gly
            35                  40                  45

Ala Ile Asp Asn Ala Gly Thr Thr Tyr Tyr Ala Ser Trp Ala Lys Ser
        50                  55                  60

Arg Ser Thr Ile Thr Arg Asn Thr Asp Leu His Thr Val Thr Leu Lys
65                  70                  75                  80

Met Thr Ser Leu Thr Ala Ser Asp Thr Ala Thr Tyr Phe Cys Ala Arg
                85                  90                  95
```

<210> SEQ ID NO 128
<211> LENGTH: 98
<212> TYPE: PRT
<213> ORGANISM: Artificial Sequence
<220> FEATURE:
<223> OTHER INFORMATION: Heavy Chain
<220> FEATURE:
<223> OTHER INFORMATION: IGHV-38-2*02

<400> SEQUENCE: 128

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg
```

```
<210> SEQ ID NO 129
<211> LENGTH: 98
<212> TYPE: PRT
<213> ORGANISM: Artificial Sequence
<220> FEATURE:
<223> OTHER INFORMATION: Heavy Chain
<220> FEATURE:
<223> OTHER INFORMATION: IGHV-48*03

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Thr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 130
<211> LENGTH: 100
<212> TYPE: PRT
<213> ORGANISM: Artificial Sequence
<220> FEATURE:
<223> OTHER INFORMATION: Light Chain
<220> FEATURE:
<223> OTHER INFORMATION: Fig3B

<400> SEQUENCE: 130

Gln Phe Val Leu Thr Gln Ser Pro Ser Val Ser Ala Ala Leu Gly Ala
1               5                   10                  15

Ser Ala Lys Leu Thr Cys Thr Leu Ser Ser Ala His Lys Thr Tyr Thr
            20                  25                  30

Ile Asp Trp Tyr Gln Gln Gln Gly Glu Ala Pro Arg Tyr Leu Met
        35                  40                  45

Gln Val Lys Ser Asp Gly Ser Tyr Thr Lys Gly Thr Gly Val Pro Asp
    50                  55                  60

Arg Phe Ser Gly Ser Ser Gly Ala Asp Arg Tyr Leu Ile Ile Pro
65                  70                  75                  80

Ser Val Gln Ala Asp Asp Glu Ala Gly Tyr Val Cys Gly Ala Asp Asp
                85                  90                  95

Asn Gly Gly Tyr
            100

<210> SEQ ID NO 131
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: Fig3B

<400> SEQUENCE: 131

Gln Phe Val Leu Thr Gln Ser Pro Ser Val Ser Ala Ala Leu Gly Ala
1               5                   10                  15
```

-continued

Ser Ala Lys Leu Thr Cys Thr Leu Ser Ser Ala His Lys Thr Tyr Thr
            20                  25                  30

Ile Asp Trp Tyr Gln Gln Gln Gly Glu Ala Pro Arg Tyr Leu Met
            35                  40                  45

Gln Val Lys Ser Asp Gly Ser Tyr Thr Lys Gly Thr Gly Val Pro Asp
 50                  55                  60

Arg Phe Ser Gly Ser Ser Gly Ala Asp Arg Tyr Leu Ile Ile Pro
 65                  70                  75                  80

Ser Val Gln Ala Asp Asp Glu Ala Gly Tyr Val Cys Gly Ala Asp Asp
                    85                  90                  95

Asn Gly Gly Tyr Val
            100

<210> SEQ ID NO 132
<211> LENGTH: 99
<212> TYPE: PRT
<213> ORGANISM: Artificial Sequence
<220> FEATURE:
<223> OTHER INFORMATION: Light Chain
<220> FEATURE:
<223> OTHER INFORMATION: IGLV4-69*01

<400> SEQUENCE: 132

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
 50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gln Thr Trp Gly
                    85                  90                  95

Thr Gly Ile

<210> SEQ ID NO 133
<211> LENGTH: 98
<212> TYPE: PRT
<213> ORGANISM: Artificial Sequence
<220> FEATURE:
<223> OTHER INFORMATION: Light Chain
<220> FEATURE:
<223> OTHER INFORMATION: IGLV1-44*01

<400> SEQUENCE: 133

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu

Asn Gly

<210> SEQ ID NO 134
<211> LENGTH: 99
<212> TYPE: PRT
<213> ORGANISM: Artificial Sequence
<220> FEATURE:
<223> OTHER INFORMATION: Light Chain
<220> FEATURE:
<223> OTHER INFORMATION: IGLV2-14*01

<400> SEQUENCE: 134

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 135
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: IGLV4-3*01

<400> SEQUENCE: 135

Val Leu Thr Gln Pro Pro Ser Ala Ser Ala Leu Leu Gly Ala Ser Ile
1               5                   10                  15

Lys Leu Thr Cys Thr Leu Ser Ser Glu His Ser Thr Tyr Thr Ile Glu
            20                  25                  30

Trp Tyr Gln Gln Arg Pro Gly Arg Ser Pro Gln Tyr Ile Met Lys Val
        35                  40                  45

Lys Ser Asp Gly Ser His Ser Lys Gly Asp Gly Ile Pro Asp Arg Phe
    50                  55                  60

Met Gly Ser Ser Ser Gly Ala Asp Arg Tyr Leu Thr Phe Ser Asn Leu
65                  70                  75                  80

Gln Ser Asp Asp Glu Ala Glu Tyr His Cys Gly Glu Ser His Thr Ile
                85                  90                  95

Asp Gly Gln Val Gly
            100

<210> SEQ ID NO 136
<211> LENGTH: 97
<212> TYPE: PRT
<213> ORGANISM: Artificial Sequence
<220> FEATURE:
<223> OTHER INFORMATION: Heavy Chain
<220> FEATURE:
<223> OTHER INFORMATION: H1

-continued

<400> SEQUENCE: 136

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Arg His
            20                  25                  30

Ala Leu Thr Trp Ile Arg Gln Pro Pro Gly Lys Gly Leu Glu Trp Ile
        35                  40                  45

Gly Ala Ile Asp Asn Ala Gly Thr Thr Tyr Tyr Ala Ser Trp Ala Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 137
<211> LENGTH: 97
<212> TYPE: PRT
<213> ORGANISM: Artificial Sequence
<220> FEATURE:
<223> OTHER INFORMATION: Heavy Chain
<220> FEATURE:
<223> OTHER INFORMATION: H1m3

<400> SEQUENCE: 137

Gln Val Gln Leu Gln Glu Ser Gly Pro Gly Leu Val Lys Pro Ser Glu
1               5                   10                  15

Thr Leu Ser Leu Thr Cys Ala Val Ser Gly Phe Ser Leu Ser Arg His
            20                  25                  30

Ala Leu Thr Trp Ile Arg Gln Pro Pro Gly Lys Gly Leu Glu Trp Ile
        35                  40                  45

Gly Ala Ile Asp Asn Ala Gly Thr Thr Tyr Tyr Ala Ser Trp Ala Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 138
<211> LENGTH: 97
<212> TYPE: PRT
<213> ORGANISM: Artificial Sequence
<220> FEATURE:
<223> OTHER INFORMATION: Heavy Chain
<220> FEATURE:
<223> OTHER INFORMATION: H1m2

<400> SEQUENCE: 138

Gln Gln Ser Val Lys Glu Ser Gly Pro Gly Leu Val Lys Pro Ser Glu
1               5                   10                  15

Thr Leu Ser Leu Thr Cys Ala Val Ser Gly Phe Ser Leu Ser Arg His
            20                  25                  30

Ala Leu Thr Trp Ile Arg Gln Pro Pro Gly Lys Gly Leu Glu Trp Ile
        35                  40                  45

Gly Ala Ile Asp Asn Ala Gly Thr Thr Tyr Tyr Ala Ser Trp Ala Lys
    50                  55                  60

Ser Arg Val Thr Ile Ser Val Asp Thr Ser Lys Asn Gln Phe Ser Leu

```
                65                  70                  75                  80
Lys Leu Ser Ser Val Thr Ala Ala Asp Thr Ala Val Tyr Tyr Cys Ala
                    85                  90                  95
Arg

<210> SEQ ID NO 139
<211> LENGTH: 97
<212> TYPE: PRT
<213> ORGANISM: Artificial Sequence
<220> FEATURE:
<223> OTHER INFORMATION: Heavy Chain
<220> FEATURE:
<223> OTHER INFORMATION: H1m1

<400> SEQUENCE: 139

Gln Gln Ser Val Lys Glu Ser Gly Pro Gly Leu Val Lys Pro Ser Glu
1               5                   10                  15

Thr Leu Ser Leu Thr Cys Ala Val Ser Gly Phe Ser Leu Ser Arg His
                20                  25                  30

Ala Leu Thr Trp Val Arg Gln Pro Pro Gly Lys Gly Leu Glu Trp Ile
            35                  40                  45

Gly Ala Ile Asp Asn Ala Gly Thr Thr Tyr Tyr Ala Ser Trp Ala Lys
        50                  55                  60

Ser Arg Val Thr Ile Ser Arg Asn Thr Asp Leu His Thr Val Ser Leu
65                  70                  75                  80

Lys Leu Ser Ser Val Thr Ala Ala Asp Thr Ala Val Tyr Phe Cys Ala
                85                  90                  95

Arg

<210> SEQ ID NO 140
<211> LENGTH: 98
<212> TYPE: PRT
<213> ORGANISM: Artificial Sequence
<220> FEATURE:
<223> OTHER INFORMATION: Heavy Chain
<220> FEATURE:
<223> OTHER INFORMATION: IGHV3-48*03

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 141
<211> LENGTH: 97
<212> TYPE: PRT
<213> ORGANISM: Artificial Sequence
<220> FEATURE:
<223> OTHER INFORMATION: Heavy Chain
<220> FEATURE:
```

<223> OTHER INFORMATION: H2

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Ala Leu Thr Trp Val Arg Gln Ala Pro Gly Lys Gly Leu Glu Trp Val
        35                  40                  45

Ser Ala Ile Asp Asn Ala Gly Thr Thr Tyr Tyr Ala Ser Trp Ala Lys
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 142
<211> LENGTH: 97
<212> TYPE: PRT
<213> ORGANISM: Artificial Sequence
<220> FEATURE:
<223> OTHER INFORMATION: Heavy Chain
<220> FEATURE:
<223> OTHER INFORMATION: H2m1

<400> SEQUENCE: 142

Glu Gln Ser Val Lys Glu Ser Gly Gly Gly Leu Val Gln Pro Gly Gly
1               5                   10                  15

Ser Leu Arg Leu Ser Cys Ala Ala Ser Gly Phe Thr Leu Ser Arg His
            20                  25                  30

Ala Leu Thr Trp Val Arg Gln Ala Pro Gly Lys Gly Leu Glu Trp Ile
        35                  40                  45

Gly Ala Ile Asp Asn Ala Gly Thr Thr Tyr Tyr Ala Ser Trp Ala Lys
    50                  55                  60

Ser Arg Phe Thr Ile Ser Arg Asn Thr Asp Leu His Thr Val Tyr Leu
65                  70                  75                  80

Gln Met Asn Ser Leu Arg Ala Glu Asp Thr Ala Val Tyr Phe Cys Ala
                85                  90                  95

Arg

<210> SEQ ID NO 143
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L1

<400> SEQUENCE: 143

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Ala Trp His Gln Gln Gln Pro Glu Lys Gly Pro Arg Tyr Leu Met
        35                  40                  45

Lys Val Lys Ser Asp Gly Ser Tyr Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val
            100

<210> SEQ ID NO 144
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L1m2

<400> SEQUENCE: 144

Gln Phe Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Asp Trp His Gln Gln Pro Glu Lys Gly Pro Arg Tyr Leu Met
            35                  40                  45

Gln Val Lys Ser Asp Gly Ser Tyr Thr Lys Gly Thr Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val
            100

<210> SEQ ID NO 145
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L1m4

<400> SEQUENCE: 145

Gln Leu Val Leu Thr Gln Ser Pro Ser Ala Ser Ala Ser Leu Gly Ala
1               5                   10                  15

Ser Val Lys Leu Thr Cys Thr Leu Ser Ser Ala His Lys Thr Tyr Thr
                20                  25                  30

Ile Ala Trp His Gln Gln Pro Glu Lys Gly Pro Arg Tyr Leu Met
            35                  40                  45

Gln Val Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val
            100

<210> SEQ ID NO 146
<211> LENGTH: 101

<212> TYPE: PRT
<213> ORGANISM: Artificial Sequence
<220> FEATURE:
<223> OTHER INFORMATION: Light Chain
<220> FEATURE:
<223> OTHER INFORMATION: L1m3

<400> SEQUENCE: 146

```
Gln Leu Val Leu Thr Gln Ser Pro Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Asp Trp Tyr Gln Gln Pro Glu Lys Gly Pro Arg Tyr Leu Met
        35                  40                  45

Gln Val Lys Ser Asp Gly Ser Tyr Thr Lys Gly Thr Gly Val Pro Asp
50                      55                  60

Arg Phe Ser Gly Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val
            100
```

<210> SEQ ID NO 147
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L1m1

<400> SEQUENCE: 147

```
Gln Phe Val Leu Thr Gln Ser Pro Ala Ser Ala Ser Leu Gly Ala
1               5                   10                  15

Ser Val Lys Leu Thr Cys Thr Leu Ser Ser Ala His Lys Thr Tyr Thr
            20                  25                  30

Ile Asp Trp Tyr Gln Gln Pro Glu Lys Gly Pro Arg Tyr Leu Met
        35                  40                  45

Gln Val Lys Ser Asp Gly Ser Tyr Thr Lys Gly Thr Gly Val Pro Asp
50                      55                  60

Arg Phe Ser Gly Ser Ser Gly Ala Asp Arg Tyr Leu Thr Ile Ser
65                  70                  75                  80

Ser Leu Gln Ser Glu Asp Glu Ala Asp Tyr Tyr Cys Gly Ala Asp Asp
                85                  90                  95

Asn Gly Gly Tyr Val
            100
```

<210> SEQ ID NO 148
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L2

<400> SEQUENCE: 148

```
Gln Ser Val Leu Thr Gln Pro Pro Ser Ala Ser Gly Thr Pro Gly Gln
1               5                   10                  15

Arg Val Thr Ile Ser Cys Thr Leu Ser Ser Ala His Lys Thr Tyr Thr
```

```
                20                  25                  30

Ile Asp Trp Tyr Gln Gln Leu Pro Gly Thr Ala Pro Lys Leu Leu Ile
            35                  40                  45

Tyr Val Lys Ser Asp Gly Ser Tyr Thr Lys Gly Thr Gly Val Pro Asp
 50                  55                  60

Arg Phe Ser Gly Ser Lys Ser Gly Thr Ser Ala Ser Leu Ala Ile Ser
 65                  70                  75                  80

Gly Leu Gln Ser Glu Asp Glu Ala Asp Tyr Tyr Cys Gly Ala Asp Asp
                85                  90                  95

Asn Gly Gly Tyr Val
                100

<210> SEQ ID NO 149
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L2m3

<400> SEQUENCE: 149

Gln Ser Val Leu Thr Gln Pro Pro Ser Ala Ser Gly Thr Pro Gly Gln
 1               5                  10                  15

Arg Val Thr Ile Ser Cys Thr Leu Ser Ser Ala His Lys Thr Tyr Thr
                20                  25                  30

Ile Asp Trp Tyr Gln Gln Leu Pro Gly Thr Ala Pro Lys Leu Leu Ile
            35                  40                  45

Tyr Val Lys Ser Asp Gly Ser Tyr Thr Lys Gly Thr Gly Val Pro Asp
 50                  55                  60

Arg Phe Ser Gly Ser Lys Ser Gly Thr Ser Ala Ser Leu Ala Ile Ser
 65                  70                  75                  80

Gly Leu Gln Ser Glu Asp Glu Ala Asp Tyr Tyr Cys Gly Ala Asp Asp
                85                  90                  95

Asn Gly Gly Tyr Val
                100

<210> SEQ ID NO 150
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L2m2

<400> SEQUENCE: 150

Gln Phe Val Leu Thr Gln Pro Pro Ser Ala Ser Gly Thr Pro Gly Gln
 1               5                  10                  15

Arg Val Thr Ile Ser Cys Thr Leu Ser Ser Ala His Lys Thr Tyr Thr
                20                  25                  30

Ile Asp Trp Tyr Gln Gln Leu Pro Gly Thr Ala Pro Lys Leu Leu Ile
            35                  40                  45

Tyr Val Lys Ser Asp Gly Ser Tyr Thr Lys Gly Thr Gly Val Pro Asp
 50                  55                  60

Arg Phe Ser Gly Ser Ser Ser Gly Ala Asp Ala Ser Leu Ala Ile Ser
 65                  70                  75                  80

Gly Leu Gln Ser Glu Asp Glu Ala Asp Tyr Tyr Cys Gly Ala Asp Asp
                85                  90                  95
```

Asn Gly Gly Tyr Val
            100

<210> SEQ ID NO 151
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L2m1

<400> SEQUENCE: 151

Gln Phe Val Leu Thr Gln Pro Pro Ser Ala Ser Gly Thr Pro Gly Gln
1               5                   10                  15

Arg Val Thr Ile Ser Cys Thr Leu Ser Ser Ala His Lys Thr Tyr Thr
            20                  25                  30

Ile Asp Trp Tyr Gln Gln Leu Pro Gly Thr Ala Pro Lys Leu Leu Ile
        35                  40                  45

Tyr Val Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Ala Ile Ser
65                  70                  75                  80

Gly Leu Gln Ser Glu Asp Glu Ala Asp Tyr Tyr Cys Gly Ala Asp Asp
                85                  90                  95

Asn Gly Gly Tyr Val
            100

<210> SEQ ID NO 152
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L3

<400> SEQUENCE: 152

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
            20                  25                  30

Val Ser Trp Tyr Gln Gln His Pro Gly Lys Ala Pro Lys Leu Met Ile
        35                  40                  45

Tyr Val Lys Ser Asp Gly Ser Tyr Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Gly Ala Asp Asp
                85                  90                  95

Asn Gly Gly Tyr Val
            100

<210> SEQ ID NO 153
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L3m3

-continued

```
<400> SEQUENCE: 153

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
            20                  25                  30

Ile Asp Trp Tyr Gln Gln His Pro Gly Lys Ala Pro Lys Leu Met Ile
        35                  40                  45

Tyr Val Lys Ser Asp Gly Ser Tyr Thr Lys Gly Thr Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Gly Ala Asp Asp
                85                  90                  95

Asn Gly Gly Tyr Val
            100

<210> SEQ ID NO 154
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L3m5

<400> SEQUENCE: 154

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
            20                  25                  30

Val Ser Trp Tyr Gln Gln His Pro Gly Lys Ala Pro Lys Leu Met Ile
        35                  40                  45

Tyr Val Lys Ser Asp Gly Ser Tyr Thr Lys Gly Thr Gly Val Pro Asn
    50                  55                  60

Arg Phe Ser Gly Ser Ser Ser Gly Ala Asp Arg Tyr Leu Thr Ile Ser
65                  70                  75                  80

Gly Leu Gln Ala Glu Asp Glu Ala Asp Tyr Tyr Cys Gly Ala Asp Asp
                85                  90                  95

Asn Gly Gly Tyr Val
            100

<210> SEQ ID NO 155
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L3m4

<400> SEQUENCE: 155

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ala His Lys Thr Tyr Thr
            20                  25                  30

Val Ser Trp Tyr Gln Gln His Pro Gly Lys Ala Pro Lys Tyr Leu Met
        35                  40                  45

Gln Val Lys Ser Asp Gly Ser Tyr Thr Lys Gly Thr Gly Val Pro Asn
```

```
                 50                  55                  60
Arg Phe Ser Gly Ser Ser Gly Ala Asp Arg Tyr Leu Thr Ile Ser
 65                  70                  75                  80

Gly Leu Gln Ala Glu Asp Glu Ala Asp Tyr Tyr Cys Gly Ala Asp Asp
                 85                  90                  95

Asn Gly Gly Tyr Val
            100

<210> SEQ ID NO 156
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L3m2

<400> SEQUENCE: 156

Gln Phe Val Leu Thr Gln Pro Ala Ser Val Ser Gly Ser Pro Gly Gln
  1               5                  10                  15

Ser Ile Thr Ile Ser Cys Thr Leu Ser Ser Ala His Lys Thr Tyr Thr
                 20                  25                  30

Ile Asp Trp Tyr Gln Gln His Pro Gly Lys Ala Pro Lys Leu Met Ile
             35                  40                  45

Gln Val Lys Ser Asp Gly Ser Tyr Thr Lys Gly Thr Gly Val Ser Asn
         50                  55                  60

Arg Phe Ser Gly Ser Ser Gly Ala Asp Arg Tyr Leu Thr Ile Ser
 65                  70                  75                  80

Gly Leu Gln Ala Glu Asp Glu Ala Asp Tyr Tyr Cys Gly Ala Asp Asp
                 85                  90                  95

Asn Gly Gly Tyr Val
            100

<210> SEQ ID NO 157
<211> LENGTH: 101
<212> TYPE: PRT
<213> ORGANISM: Artificial Sequence
<220> FEATURE:
<223> OTHER INFORMATION: Light Chain
<220> FEATURE:
<223> OTHER INFORMATION: L3m1

<400> SEQUENCE: 157

Gln Phe Val Leu Thr Gln Pro Ala Ser Val Ser Gly Ser Pro Gly Gln
  1               5                  10                  15

Ser Ile Thr Ile Ser Cys Thr Leu Ser Ser Ala His Lys Thr Tyr Thr
                 20                  25                  30

Ile Asp Trp Tyr Gln Gln His Pro Gly Lys Ala Pro Lys Tyr Leu Met
             35                  40                  45

Gln Val Lys Ser Asp Gly Ser Tyr Thr Lys Gly Thr Gly Val Pro Asn
         50                  55                  60

Arg Phe Ser Gly Ser Ser Gly Ala Asp Arg Tyr Leu Thr Ile Ser
 65                  70                  75                  80

Gly Leu Gln Ala Glu Asp Glu Ala Asp Tyr Val Cys Gly Ala Asp Asp
                 85                  90                  95

Asn Gly Gly Tyr Val
            100

<210> SEQ ID NO 158
```

```
<211> LENGTH: 254
<212> TYPE: PRT
<213> ORGANISM: Artificial Sequence
<220> FEATURE:
<223> OTHER INFORMATION: CAR
<220> FEATURE:
<223> OTHER INFORMATION: CAR10

<400> SEQUENCE: 158

Gly Ser Glu Val Gln Leu Val Glu Ser Gly Gly Leu Val Gln Pro
1               5                   10                  15

Gly Gly Ser Leu Arg Leu Ser Cys Ala Ala Ser Gly Phe Thr Phe Ser
            20                  25                  30

Arg His Ala Leu Thr Trp Val Arg Gln Ala Pro Gly Lys Gly Leu Glu
        35                  40                  45

Trp Val Ser Ala Ile Asp Asn Ala Gly Thr Thr Tyr Tyr Ala Ser Trp
    50                  55                  60

Ala Lys Ser Arg Phe Thr Ile Ser Arg Asp Asn Ala Lys Asn Ser Leu
65              70                  75                  80

Tyr Leu Gln Met Asn Ser Leu Arg Ala Glu Asp Thr Ala Val Tyr Tyr
                85                  90                  95

Cys Ala Arg Val Phe Tyr Asp Ile Asn Ser Gly Tyr Tyr Leu Asp Gly
            100                 105                 110

Met Asp Leu Trp Gly Pro Gly Thr Leu Val Thr Val Ser Ser Gly Gly
        115                 120                 125

Gly Gly Ser Gly Gly Gly Gly Ser Gly Gly Gly Ser Gln Phe Val
130                 135                 140

Leu Thr Gln Ser Pro Ser Ala Ser Ala Ser Leu Gly Ala Ser Val Lys
145                 150                 155                 160

Leu Thr Cys Thr Leu Ser Ser Ala His Lys Thr Tyr Thr Ile Asp Trp
                165                 170                 175

Tyr Gln Gln Gln Pro Glu Lys Gly Pro Arg Tyr Leu Met Gln Val Lys
            180                 185                 190

Ser Asp Gly Ser Tyr Thr Lys Gly Thr Gly Val Pro Asp Arg Phe Ser
        195                 200                 205

Gly Ser Ser Ser Gly Ala Asp Arg Tyr Leu Thr Ile Ser Ser Leu Gln
    210                 215                 220

Ser Glu Asp Glu Ala Asp Tyr Tyr Cys Gly Ala Asp Asp Asn Gly Gly
225                 230                 235                 240

Tyr Val Phe Gly Gly Gly Thr Gln Leu Thr Val Leu Ala Ser
                245                 250

<210> SEQ ID NO 159
<211> LENGTH: 254
<212> TYPE: PRT
<213> ORGANISM: Artificial Sequence
<220> FEATURE:
<223> OTHER INFORMATION: CAR
<220> FEATURE:
<223> OTHER INFORMATION: CAR14

<400> SEQUENCE: 159

Gly Ser Gln Val Gln Leu Gln Glu Ser Gly Pro Gly Leu Val Lys Pro
1               5                   10                  15

Ser Glu Thr Leu Ser Leu Thr Cys Ala Val Ser Gly Tyr Ser Ile Ser
            20                  25                  30

Arg His Ala Leu Thr Trp Ile Arg Gln Pro Pro Gly Lys Gly Leu Glu
        35                  40                  45
```

Trp Ile Gly Ala Ile Asp Asn Ala Gly Thr Thr Tyr Ala Ser Trp
           50                  55                  60

Ala Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Phe Tyr Asp Ile Asn Ser Gly Tyr Tyr Leu Asp Gly
                100                 105                 110

Met Asp Leu Trp Gly Pro Gly Thr Leu Val Thr Val Ser Ser Gly Gly
            115                 120                 125

Gly Gly Ser Gly Gly Gly Gly Ser Ser Gly Gly Gly Ser Gln Phe Val
    130                 135                 140

Leu Thr Gln Ser Pro Ser Ala Ser Ala Ser Leu Gly Ala Ser Val Lys
145                 150                 155                 160

Leu Thr Cys Thr Leu Ser Ser Ala His Lys Thr Tyr Thr Ile Asp Trp
                165                 170                 175

Tyr Gln Gln Gln Pro Glu Lys Gly Pro Arg Tyr Leu Met Gln Val Lys
            180                 185                 190

Ser Asp Gly Ser Tyr Thr Lys Gly Thr Gly Val Pro Asp Arg Phe Ser
            195                 200                 205

Gly Ser Ser Ser Gly Ala Asp Arg Tyr Leu Thr Ile Ser Ser Leu Gln
    210                 215                 220

Ser Glu Asp Glu Ala Asp Tyr Tyr Cys Gly Ala Asp Asn Gly Gly
225                 230                 235                 240

Tyr Val Phe Gly Gly Gly Thr Gln Leu Thr Val Leu Ala Ser
                245                 250

<210> SEQ ID NO 160
<211> LENGTH: 254
<212> TYPE: PRT
<213> ORGANISM: Artificial Sequence
<220> FEATURE:
<223> OTHER INFORMATION: CAR
<220> FEATURE:
<223> OTHER INFORMATION: CAR25

<400> SEQUENCE: 160

Gly Ser Gln Val Gln Leu Gln Glu Ser Gly Pro Gly Leu Val Lys Pro
 1               5                  10                  15

Ser Glu Thr Leu Ser Leu Thr Cys Ala Val Ser Gly Tyr Ser Ile Ser
                 20                  25                  30

Arg His Ala Leu Thr Trp Ile Arg Gln Pro Pro Gly Lys Gly Leu Glu
             35                  40                  45

Trp Ile Gly Ala Ile Asp Asn Ala Gly Thr Thr Tyr Ala Ser Trp
           50                  55                  60

Ala Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Phe Tyr Asp Ile Asn Ser Gly Tyr Tyr Leu Asp Gly
                100                 105                 110

Met Asp Leu Trp Gly Pro Gly Thr Leu Val Thr Val Ser Ser Gly Gly
            115                 120                 125

Gly Gly Ser Gly Gly Gly Gly Ser Ser Gly Gly Gly Ser Gln Leu Val
    130                 135                 140

Leu Thr Gln Ser Pro Ser Ala Ser Ala Ser Leu Gly Ala Ser Val Lys

```
              145                 150                 155                 160
Leu Thr Cys Thr Leu Ser Ser Ala His Lys Thr Tyr Thr Ile Asp Trp
                165                 170                 175

Tyr Gln Gln Pro Glu Lys Gly Pro Arg Tyr Leu Met Gln Val Lys
            180                 185                 190

Ser Asp Gly Ser Tyr Thr Lys Gly Thr Gly Val Pro Asp Arg Phe Ser
            195                 200                 205

Gly Ser Ser Ser Gly Ala Asp Arg Tyr Leu Thr Ile Ser Ser Leu Gln
            210                 215                 220

Ser Glu Asp Glu Ala Asp Tyr Tyr Cys Gly Ala Asp Asp Asn Gly Gly
225                 230                 235                 240

Tyr Val Phe Gly Gly Gly Thr Gln Leu Thr Val Leu Ala Ser
                245                 250

<210> SEQ ID NO 161
<211> LENGTH: 254
<212> TYPE: PRT
<213> ORGANISM: Artificial Sequence
<220> FEATURE:
<223> OTHER INFORMATION: CAR
<220> FEATURE:
<223> OTHER INFORMATION: CAR29

<400> SEQUENCE: 161

Gly Ser Glu Val Gln Leu Val Glu Ser Gly Gly Leu Val Gln Pro
1               5                   10                  15

Gly Gly Ser Leu Arg Leu Ser Cys Ala Ala Ser Gly Phe Thr Phe Ser
            20                  25                  30

Arg His Ala Leu Thr Trp Val Arg Gln Ala Pro Gly Lys Gly Leu Glu
        35                  40                  45

Trp Val Ser Ala Ile Asp Asn Ala Gly Thr Thr Tyr Tyr Ala Ser Trp
    50                  55                  60

Ala Lys Ser Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Val Phe Tyr Asp Ile Asn Ser Gly Tyr Tyr Leu Asp Gly
                100                 105                 110

Met Asp Leu Trp Gly Pro Gly Thr Leu Val Thr Val Ser Ser Gly Gly
            115                 120                 125

Gly Gly Ser Gly Gly Gly Gly Ser Ser Gly Gly Gly Ser Gln Leu Val
        130                 135                 140

Leu Thr Gln Ser Pro Ser Ala Ser Ala Ser Leu Gly Ala Ser Val Lys
145                 150                 155                 160

Leu Thr Cys Thr Leu Ser Ser Ala His Lys Thr Tyr Thr Ile Asp Trp
                165                 170                 175

Tyr Gln Gln Pro Glu Lys Gly Pro Arg Tyr Leu Met Gln Val Lys
            180                 185                 190

Ser Asp Gly Ser Tyr Thr Lys Gly Thr Gly Val Pro Asp Arg Phe Ser
            195                 200                 205

Gly Ser Ser Ser Gly Ala Asp Arg Tyr Leu Thr Ile Ser Ser Leu Gln
            210                 215                 220

Ser Glu Asp Glu Ala Asp Tyr Tyr Cys Gly Ala Asp Asp Asn Gly Gly
225                 230                 235                 240

Tyr Val Phe Gly Gly Gly Thr Gln Leu Thr Val Leu Ala Ser
                245                 250
```

```
<210> SEQ ID NO 162
<211> LENGTH: 5
<212> TYPE: PRT
<213> ORGANISM: Artificial Sequence
<220> FEATURE:
<223> OTHER INFORMATION: CDR
<220> FEATURE:
<223> OTHER INFORMATION: HCDR1

<400> SEQUENCE: 162

Arg His Ala Leu Thr
1               5

<210> SEQ ID NO 163
<211> LENGTH: 16
<212> TYPE: PRT
<213> ORGANISM: Artificial Sequence
<220> FEATURE:
<223> OTHER INFORMATION: CDR
<220> FEATURE:
<223> OTHER INFORMATION: HCDR2

<400> SEQUENCE: 163

Ala Ile Asp Asn Ala Gly Thr Thr Tyr Tyr Ala Ser Trp Ala Lys Ser
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: CDR
<220> FEATURE:
<223> OTHER INFORMATION: HCDR3

<400> SEQUENCE: 164

Val Phe Tyr Asp Ile Asn Ser Gly Tyr Tyr Leu Asp Gly Met Asp Leu
1               5                   10                  15

<210> SEQ ID NO 165
<211> LENGTH: 7
<212> TYPE: PRT
<213> ORGANISM: Artificial Sequence
<220> FEATURE:
<223> OTHER INFORMATION: CDR
<220> FEATURE:
<223> OTHER INFORMATION: LCDR1

<400> SEQUENCE: 165

Ser Ala His Lys Thr Tyr Thr
1               5

<210> SEQ ID NO 166
<211> LENGTH: 7
<212> TYPE: PRT
<213> ORGANISM: Artificial Sequence
<220> FEATURE:
<223> OTHER INFORMATION: CDR
<220> FEATURE:
<223> OTHER INFORMATION: LCDR2

<400> SEQUENCE: 166

Val Lys Ser Asp Gly Ser Tyr
1               5

<210> SEQ ID NO 167
<211> LENGTH: 9
```

```
<212> TYPE: PRT
<213> ORGANISM: Artificial Sequence
<220> FEATURE:
<223> OTHER INFORMATION: CDR
<220> FEATURE:
<223> OTHER INFORMATION: LCDR3

<400> SEQUENCE: 167

Gly Ala Asp Asp Asn Gly Gly Tyr Val
1               5

<210> SEQ ID NO 168
<211> LENGTH: 10
<212> TYPE: PRT
<213> ORGANISM: Artificial Sequence
<220> FEATURE:
<223> OTHER INFORMATION: Hinge
<220> FEATURE:
<223> OTHER INFORMATION: GS-linker

<400> SEQUENCE: 168

Gly Gly Gly Gly Ser Gly Gly Gly Gly Ser
1               5                   10

<210> SEQ ID NO 169
<211> LENGTH: 18
<212> TYPE: PRT
<213> ORGANISM: Artificial Sequence
<220> FEATURE:
<223> OTHER INFORMATION: Hinge
<220> FEATURE:
<223> OTHER INFORMATION: GS-linker

<400> SEQUENCE: 169

Gly Gly Ser Ser Arg Ser Ser Ser Ser Gly Gly Gly Gly Ser Gly Gly
1               5                   10                  15

Gly Gly
```

HUMANIZED ANTI-GDNF FAMILY ALPHA-RECEPTOR 4 (GRF-ALPHA-4) ANTIBODIES AND CHIMERIC ANTIGEN RECEPTORS (CARS)

CROSS-REFERENCE TO RELATED APPLICATION

The present application is entitled to priority under U.S.C. § 119(e) to U.S. Provisional Patent Application No. 62/907,909 filed Sep. 30, 2019, which is hereby incorporated by reference in its entirety herein.

BACKGROUND OF THE INVENTION

Thyroid cancer is one of the few cancers that has increased in incidence over recent years with the incidence of new cases rising on average 5.5% each year from 2002-2011. It is the most common endocrine cancer with an expected incidence of ~60,000 new cases this year and about 2,000 deaths. Papillary and follicular thyroid carcinomas comprise 80-90% of all thyroid cancers while medullary and anaplastic comprise 5-10% and 1-2% respectively. While thyroid cancer has a good prognosis overall, this is not necessarily the case for the medullary and anaplastic forms if they are not treated early before they spread beyond the thyroid gland.

Medullary Thyroid Cancer (MTC) is a type of thyroid cancer that develops from the parafollicular cells of the thyroid that are not related with the main function of the thyroid gland, i.e. production and secretion of thyroid hormone. Rather, these cells are involved in the production of calcitonin, a calcium-regulatory hormone apparently unimportant to humans for maintaining calcium homeostasis. Approximately 25% of MTC is genetic in nature caused by a mutation in the proto-oncogene receptor tyrosine kinase RET. MTC can also coexist with tumors of the parathyroid gland and adrenal gland (pheochromocytoma) in a syndrome known as multiple endocrine neoplasia type 2 (MEN2). Calcitonin doubling time (CDT) can be used as a prognostic marker; e.g. when the CDT is <6 months, 5-year survival is <25%. Surgery and radiation therapy are used for MTC, though risk of recurrence remains high due to the fact that 50% of patients have metastasis to regional lymph nodes at the time of diagnosis. Tyrosine kinase inhibitors such as vandetanib (Caprelsa) and cabozantinib (Cometriq) were approved by the FDA in April, 2011 and November, 2012, respectively, for treatment of late-stage metastatic MTC, though only 10-30% of patients show clear evidence of response.

The GDNF family of neurotrophic factors includes four members: glial cell line-derived neurotrophic factor (GDNF), neurturin, artemin, and persephin (PSPN). GDNF family ligands signal through receptors consisting of a GPI-linked GFRα subunit and the transmembrane receptor tyrosine kinase RET. In order to activate the transmembrane receptor tyrosine kinase RET, each of the GDNF family neurotrophic factors binds preferentially to one of the glycosyl-phosphatidylinositol (GPI)-linked GDNF family α-receptors (GFRα1-4) (Airaksinen et al., *Mol Cell Neurosci.*; 13(5):313-25, 1999). GDNF signals via GFRα1, neurturin via GFRα2, artemin via GFRα3; however, the mammalian GFRα receptor for persephin (PSPN) and the biological role of GFRα4 has so far remained unclear. In adult humans, GFRα4 is restricted to normal and malignant thyroid medullary cells (Lindahl et al., *J. Biol. Chem.* 276:9344-51, 2001), although it may be expressed elsewhere during fetal development. GFRα1, GFRα2, and GFRα3 appear to be expressed in non-thyroid tissues of the human body that may include brain.

Thus, the relative specific expressions of GFRα4 on the cell surface of malignant parafollicular cells of the thyroid tissues make it an attractive target for MTC tumor diagnosis and therapy. Although generic anti-GFRα4 antibodies were previously identified (WO2001062795A1), humanized GFRα4-specific antibodies and fragments thereof, remain unexplored.

There is a need in the art for the development of therapies to treat medullary thyroid carcinoma. The present invention addresses this need.

SUMMARY OF THE INVENTION

Provided is an isolated binding polypeptide comprising a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds a glial cell derived neurotrophic factor (GDNF) family receptor alpha-4 (GFRα4). In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region comprising an amino acid sequence having at least 95-99% identity to the amino acid sequence of any of the heavy chain variable regions set forth in SEQ ID NOs: 7-10. In some embodiments, the binding polypeptide comprises a heavy chain variable region comprising at least 1, 2, or 3 modifications but not more than 20 modifications of the amino acid sequence of any of the heavy chain variable regions set forth in SEQ ID NOs: 7-10. In further embodiments, the binding polypeptide comprises a heavy chain variable region comprising an amino acid sequence of any of the heavy chain variable regions set forth in SEQ ID NOs: 7-10. In yet further embodiments, the binding polypeptide comprises a heavy chain variable region consisting of an amino acid sequence of any of the heavy chain variable regions set forth in SEQ ID NOs: 7-10.

In some embodiments, the binding polypeptide comprises a light chain variable region comprising an amino acid sequence having at least 95-99% identity to the amino acid sequence of any of the light chain variable regions set forth in SEQ ID NOs: 28-42. In some embodiments, the binding polypeptide comprises a light chain variable region comprising at least 1, 2, or 3 modifications but not more than 20 modifications of the amino acid sequence of any of the light chain variable regions set forth in SEQ ID NOs: 28-42. In further embodiments, the binding polypeptide comprises a light chain variable region comprising an amino acid sequence of any of the light chain variable regions set forth in SEQ ID NOs: 28-42. In yet further embodiments, the binding polypeptide comprises a light chain variable region consisting of an amino acid sequence of any of the light chain variable regions set forth in SEQ ID NOs: 28-42.

Provided is an isolated binding polypeptide comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

Provided is a single-chain variable fragment (scFv) comprising a heavy chain variable region that comprises three heavy chain complementarity determining regions (HCDRs), wherein HCDR1 comprises the amino acid sequence RHALT (SEQ ID NO:162), HCDR2 comprises the amino acid sequence AIDNAGTTYYASWAKS (SEQ ID NO:163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is a single-chain variable fragment (scFv) comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

Also provided is a single chain variable fragment comprising any one of the amino acid sequences set forth in SEQ ID NOs: 74-102. Also provided is a is a single chain variable fragment consisting of any one of the amino acid sequences set forth in SEQ ID NOs: 74-102.

Provided is an isolated nucleic acid encoding the binding polypeptide or scFv of any preceding embodiment.

Provided is an isolated nucleic acid encoding a binding polypeptide comprising a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region encoded by a nucleotide sequence having at least 95-99% identity to the nucleotide sequence of any of the heavy chain variable regions set forth in SEQ ID NOs: 2-5. In further embodiments, the binding polypeptide comprises a heavy chain variable region encoded by a nucleotide sequence comprising any of the heavy chain variable region sequences provided in SEQ ID NOs: 2-5. In yet further embodiments, the binding polypeptide comprises a heavy chain variable region encoded by a nucleotide sequence consisting of any of the heavy chain variable region sequences provided in SEQ ID NOs: 2-5.

In some embodiments, the binding polypeptide comprises a light chain variable region encoded by a nucleotide sequence having at least 95-99% identity to the nucleotide sequence of any of the light chain variable regions provided in SEQ ID NOs: 12-26. In further embodiments, the binding polypeptide comprises a light chain variable region encoded by a nucleotide sequence comprising any of the light chain variable region sequences provided in SEQ ID NOs: 12-26. In yet further embodiments, the binding polypeptide comprises a light chain variable region encoded by a nucleotide sequence consisting of any of the light chain variable region sequences provided in SEQ ID NOs: 12-26.

Provided is an isolated nucleic acid encoding a binding polypeptide comprising: a heavy chain variable region encoded by any of the nucleotide sequences set forth in SEQ ID NO: 2-5; and a light chain variable region encoded by any of the nucleotide sequences set forth in SEQ ID NO: 12-26.

Provided is an isolated nucleic acid encoding a single-chain variable fragment (scFv) comprising a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is isolated nucleic acid encoding a single-chain variable fragment (scFv) comprising: a heavy chain variable region comprising any of the nucleotide sequences set forth in SEQ ID NO: 2-5; and a light chain variable region comprising any of the nucleotide sequences set forth in SEQ ID NO: 12-26. Also provided is an isolated nucleic acid encoding a single-chain variable fragment (scFv) comprising any one of the nucleotide sequences set forth in SEQ ID NOs: 43-72. Also provided is an isolated nucleic acid encoding a single-chain variable fragment (scFv) consisting of any one of the nucleotide sequences set forth in SEQ ID NOs: 43-72.

Provided is a vector comprising the isolated nucleic acid of any one of the preceding embodiments. In further embodiments, the vector is an expression vector. In yet further embodiments, the vector is selected from the group consisting of a DNA vector, an RNA vector, a plasmid, a lentiviral vector, an adenoviral vector, an adeno-associated viral vector, and a retroviral vector.

Provided is a host cell comprising the vector of any one of the preceding embodiments. In further embodiments, the host cell is of eukaryotic or prokaryotic origin. In some embodiments, the host cell is of mammalian origin. In some embodiments, the host cell is of bacterial origin.

Provided is a pharmaceutical composition comprising the binding polypeptide or scFv of any one of the preceding embodiments. Also provided is a pharmaceutical composition comprising the antibody or an antigen-binding fragment of any one of the preceding embodiments.

Provided is a chimeric chimeric antigen receptor (CAR) comprising an antigen binding domain, a transmembrane domain, and an intracellular domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody.

In some embodiments, the antibody or antigen-binding fragment is a humanized antibody or a fragment thereof. In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42. In some embodiments, the antigen binding domain comprises a light chain variable region comprising at least 1, 2, or 3 modifications but not more than 20 modifications of the amino acid sequence of any of the light chain variable regions set forth in SEQ ID NOs: 28-42. In further embodiments, the antigen binding domain comprises a light chain variable region comprising an amino acid sequence of any of the light chain variable regions set forth in SEQ ID NOs: 28-42. In yet further embodiments, the antigen binding domain comprises a light chain variable region consisting of an amino acid sequence of any of the light chain variable regions set forth in SEQ ID NOs: 28-42.

Provided is a chimeric antigen receptor (CAR) comprising an antigen binding domain, a transmembrane domain, and an intracellular domain, wherein the antigen binding domain comprises: a heavy chain variable region comprising any of the amino acid sequences set forth in SEQ ID NO: 7-10; and a light chain variable region comprising any of the amino acid sequences set forth in SEQ ID NO: 28-42.

Provided is a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CDS, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CDS, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3.

Provided is a chimeric antigen receptor (CAR) comprising an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO:

165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

Provided is a chimeric antigen receptor (CAR) comprising an antigen binding domain comprising: a heavy chain variable region comprising any of the amino acid sequences set forth in SEQ ID NO: 7-10; and a light chain variable region comprising any of the amino acid sequences set forth in SEQ ID NO: 28-42; a CD8 transmembrane domain; a 4-1BB costimulatory domain; and a CD3ζ intracellular signaling domain.

Provided is a chimeric antigen receptor (CAR) comprising any one of the amino acid sequences set forth in SEQ ID NOs: 107-110. Also provided is a chimeric antigen receptor (CAR) consisting of any one of the amino acid sequences set forth in SEQ ID NOs: 107-110.

Provided is a nucleic acid encoding for the CAR of any one of the preceding embodiments.

Provided is a nucleic acid encoding a chimeric antigen receptor (CAR) comprising an antigen binding domain, a transmembrane domain, and an intracellular domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region encoded by a nucleotide sequence having at least 95-99% identity to the nucleotide sequence of any of the heavy chain variable regions set forth in SEQ ID NOs: 2-5. In some embodiments, the antigen binding domain comprises a heavy chain variable region encoded by a nucleotide sequence comprising any of the heavy chain variable region sequences set forth in SEQ ID NOs: 2-5. In further embodiments, the antigen binding domain comprises a heavy chain variable region encoded by a nucleotide sequence consisting of any of the heavy chain variable region sequences set forth in SEQ ID NOs: 2-5.

In some embodiments, the antigen binding domain comprises a light chain variable region encoded by a nucleotide sequence having at least 95-99% identity to the nucleotide sequence of any of the light chain variable regions set forth in SEQ ID NOs: 12-26. In some embodiments, the antigen binding domain comprises a light chain variable region encoded by a nucleotide sequence comprising any of the light chain variable region sequences set forth in SEQ ID NOs: 12-26. In further embodiments, the antigen binding domain comprises a light chain variable region encoded by a nucleotide sequence consisting of any of the light chain variable region sequences set forth in SEQ ID NOs: 12-26.

Provided is a nucleic acid encoding a chimeric antigen receptor (CAR) comprising an antigen binding domain, a transmembrane domain, and an intracellular domain, wherein the antigen binding domain comprises a heavy chain variable region encoded by any of the nucleotide sequences set forth in SEQ ID NO: 2-5; and a light chain variable region encoded by any of the nucleotide sequences set forth in SEQ ID NOs: 12-26.

Provided is a nucleic acid encoding a chimeric antigen receptor (CAR) comprising an antigen binding domain, a transmembrane domain, and an intracellular signaling domain, wherein the antigen binding domain is encoded by any one of the nucleotide sequences set forth in SEQ ID NOs: 103-106.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CDS, ICAM-1, LFA-1, Lck, TNFR-I, TNFI-II, Fas, CD30, CD40, ICOS, NKG2C, and B7-H3 (CD276), or a variant thereof. In some embodiments, the costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

Provided is a nucleic acid encoding a chimeric antigen receptor (CAR) comprising an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164);

and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

Provided is a nucleic acid encoding a chimeric antigen receptor (CAR) comprising an antigen binding domain comprising: a heavy chain variable region encoded by any of the nucleotide sequences set forth in SEQ ID NO: 2-5; and a light chain variable region encoded by any of the nucleotide sequences set forth in SEQ ID NO: 12-26; a CD8 transmembrane domain; a 4-1BB costimulatory domain; and a CD3ζ intracellular signaling domain.

Also provided is a nucleic acid encoding a chimeric antigen receptor (CAR) comprising any one of the nucleotide sequences set forth in SEQ ID NOs: 111-114.

Provided is a nucleic acid encoding a chimeric antigen receptor (CAR) consisting of any one of the nucleotide sequences set forth in SEQ ID NOs: 111-114.

Provided is a vector comprising the nucleic acid of any one of the preceding embodiments. In some embodiments, the vector is an expression vector. In some embodiments, the vector is selected from the group consisting of a DNA vector, an RNA vector, a plasmid, a lentiviral vector, an adenoviral vector, an adeno-associated viral vector, and a retroviral vector. In some embodiments, the vector further comprises an EF-1 a promoter. In some embodiments, the vector further comprises a woodchuck hepatitis virus post-transcriptional regulatory element (WPRE). In further embodiments, the vector further comprises a rev response element (RRE). In further embodiments, the vector further comprises a cPPT sequence. In yet further embodiments, the vector is a self-inactivating vector.

Also provided is a cell comprising the CAR of any one of the preceding embodiments, the nucleic acid of any one of the preceding embodiments, or the vector of any one of the preceding embodiments. In some embodiments, the cell is selected from the group consisting of a T cell, a natural killer (NK) cell, a cytotoxic T lymphocyte (CTL), and a regulatory T cell.

Also provided is the CAR of any one of the preceding embodiments, the nucleic acid of any one of the preceding embodiments, the vector of any one of the preceding embodiments, or the cell of any one of the preceding embodiments, for use in the treatment of a disease associated with expression of a thyroid cell antigen.

Provided is a modified immune cell or precursor cell thereof, comprising a chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42.

Provided is the cell of any one of the preceding embodiments, wherein the antigen binding domain comprises a light chain variable region comprising at least 1, 2, or 3 modifications but not more than 20 modifications of the amino acid sequence of any of the light chain variable regions set forth in SEQ ID NOs: 28-42. Provided is the cell of any one of the preceding embodiments, wherein the antigen binding domain comprises a light chain variable region comprising an amino acid sequence of any of the light chain variable regions set forth in SEQ ID NOs: 28-42. In some embodiments, the antigen binding domain comprises a light chain variable region consisting of an amino acid sequence of any of the light chain variable regions set forth in SEQ ID NOs: 28-42.

Provided is a modified immune cell or precursor cell thereof, comprising a chimeric antigen receptor (CAR) comprising an antigen binding domain, a transmembrane domain, and an intracellular domain, wherein the antigen binding domain comprises a heavy chain variable region comprising any of the amino acid sequences set forth in SEQ ID NO: 7-10; and a light chain variable region comprising any of the amino acid sequences set forth in SEQ ID NO: 28-42.

Also provided is a modified immune cell or precursor cell thereof, comprising a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102. In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

Provided is a modified immune cell or precursor cell thereof, comprising a chimeric antigen receptor (CAR) comprising an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO:164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

Provided is a modified immune cell or precursor cell thereof, comprising chimeric antigen receptor (CAR) comprising an antigen binding domain comprising a heavy chain variable region comprising any of the amino acid sequences set forth in SEQ ID NO: 7-10; a light chain variable region comprising any of the amino acid sequences set forth in SEQ ID NO: 28-42; a CD8 transmembrane domain; a 4-1BB costimulatory domain; and a CD3ζ intracellular signaling domain.

Provided is a modified immune cell or precursor cell thereof, comprising a chimeric antigen receptor (CAR) comprising any one of the amino acid sequences set forth in SEQ ID NOs: 107-110.

Provided is a modified immune cell or precursor cell thereof, comprising a chimeric antigen receptor (CAR) consisting of any one of the amino acid sequences set forth in SEQ ID NOs: 107-110.

In some embodiments, the modified cell is a modified immune cell. In some embodiments, the modified cell is a modified T cell. In some embodiments, the modified cell is an autologous cell. In further embodiments, the modified cell is an autologous cell obtained from a human subject.

Provided is a pharmaceutical composition comprising a therapeutically effective amount of the modified cell of any one of the preceding embodiments.

Provided is a method of treating a disease in a subject in need thereof, comprising administering to the subject an effective amount of the cell of any one of the preceding embodiments, or the pharmaceutical composition of any one of the preceding embodiments. In some embodiments, the disease is associated with expression of a thyroid cell antigen. In further embodiments, the disease is associated with expression of GFRα4. In yet further embodiments, the disease is a cancer. In yet further embodiments, the cancer is medullary thyroid carcinoma (MTC) or a metastasis resulting from MTC.

Provided is a method of treating a disease associated with expression of a thyroid cell antigen in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is a method of treating a GFRα4-associated disease in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is a method of treating medullary thyroid cancer (MTC) in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1B are a series of illustrations showing amino acid sequences for rabbit P4-10 anti-GFRα4 antibody variable regions. FIG. 1A shows the heavy chain (SEQ ID NO: 6), and FIG. 1B shows the light chain (SEQ ID NO: 27). Framework regions are indicated by dotted underlines, complementarity-determining regions (CDRs) using either Kabat or IMGT analysis are indicated in bold letters with solid underlines.

FIGS. 2A-2B illustrate the alignments of rabbit P4-10 anti-GFRα4 antibody variable regions with human variable region genes with closest homology. P4-10 heavy chain (FIG. 2A) (SEQ ID NO: 120) or light chain (FIG. 2B) (SEQ ID NO: 124) amino acid sequences ("Query 1") were submitted to IgBlast to identify human VH or VL genes with greatest amino acid identity. The search returned human VH and VL genes that encode proteins with the greatest amino acid identity to the VH (SEQ ID NOs: 121-123) or VL (SEQ ID NOs: 125-126) queries. Percent identity and number of identical amino acids/total amino acids indicated to the left of the name of each human heavy or light chain gene.

FIGS. 3A-3B illustrate an alignment of rabbit P4-10 anti-GFRα4 antibody variable regions with additional human variable region genes selected on the basis of pairing frequency found in vivo. FIG. 3A shows the alignment of the heavy chains. FIG. 3B shows the alignment of the light chains. CDR regions are indicated in underlined bold letters. Percent identity to human germline genes are indicated after the germline gene name.

FIG. 4 illustrates the design of humanized versions of rabbit P4-10 heavy chain variable regions. For each human VH germline gene IGHV4-38-2*02 (1) and IGHV3-48*03 (2), P4-10 CDR1 and CDR2 have replaced the corresponding human CDRs to create humanized versions of P4-10 heavy chain. Amino acid residues in white against a black background represent amino acids back-mutated to those in the original rabbit chain. Percent identity to human germline genes are indicated after the name of each candidate.

FIGS. 5A-5C illustrate the design of humanized versions of rabbit P4-10 light chain variable regions. For each human VL germline gene IGLV4-69*01 (FIG. 5A), IGLV1-44*01 (FIG. 5B), and IGLV2-14*01 (FIG. 5C), P4-10 CDR1, CDR2, and CDR3 have replaced the corresponding human CDRs to create humanized versions of the P4-10 light chain. Amino acid residues in white against a black background represent amino acids back-mutated to those in the original rabbit chain. Percent identity to human germline genes are indicated after the name of each candidate.

FIG. 12 are the results of a search for species, heavy chain germline genes, and percent amino acid identities for "top hits" for P4-10 humanized heavy chain H1.

FIG. 13 are the results of a search for species, heavy chain germline genes, and percent amino acid identities for "top hits" for P4-10 humanized heavy chain H2.

FIG. 14 are the results of a search for species, light chain germline genes, and percent amino acid identities for "top hits" for P4-10 humanized light chain L1m3.

FIG. 15 are the results of a search for species, light chain germline genes, and percent amino acid identities for "top hits" for P4-10 humanized light chain L1m1.

FIGS. 16A-16B illustrate amino acid alignments of top P4-10 humanized heavy chain (FIG. 16A) and light chain (FIG. 16B) variable regions.

FIG. 17 is a sequence alignment illustrating amino acid alignments of scFv gene segments for CARs 10, 14, 25, and 29.

FIG. 24A: Blood samples collected on Day 23 from mice treated as in shown in FIG. 23 were stained with anti-CD19 and anti-GFRα4 P4-10 antibodies to assess expression of CD19 and GFRα4b in residual Nalm6 cells post treatment with CAR-Ts (5 representative mice from each group). FIG. 24B: Control samples of wild-type Nalm6 cells and Nalm6-GFRα4 target cells spiked into mouse blood were stained with also anti-CD19 and anti-GFRα4 P4-10 antibodies (in duplicate).

DETAILED DESCRIPTION

Definitions

Figure 6:
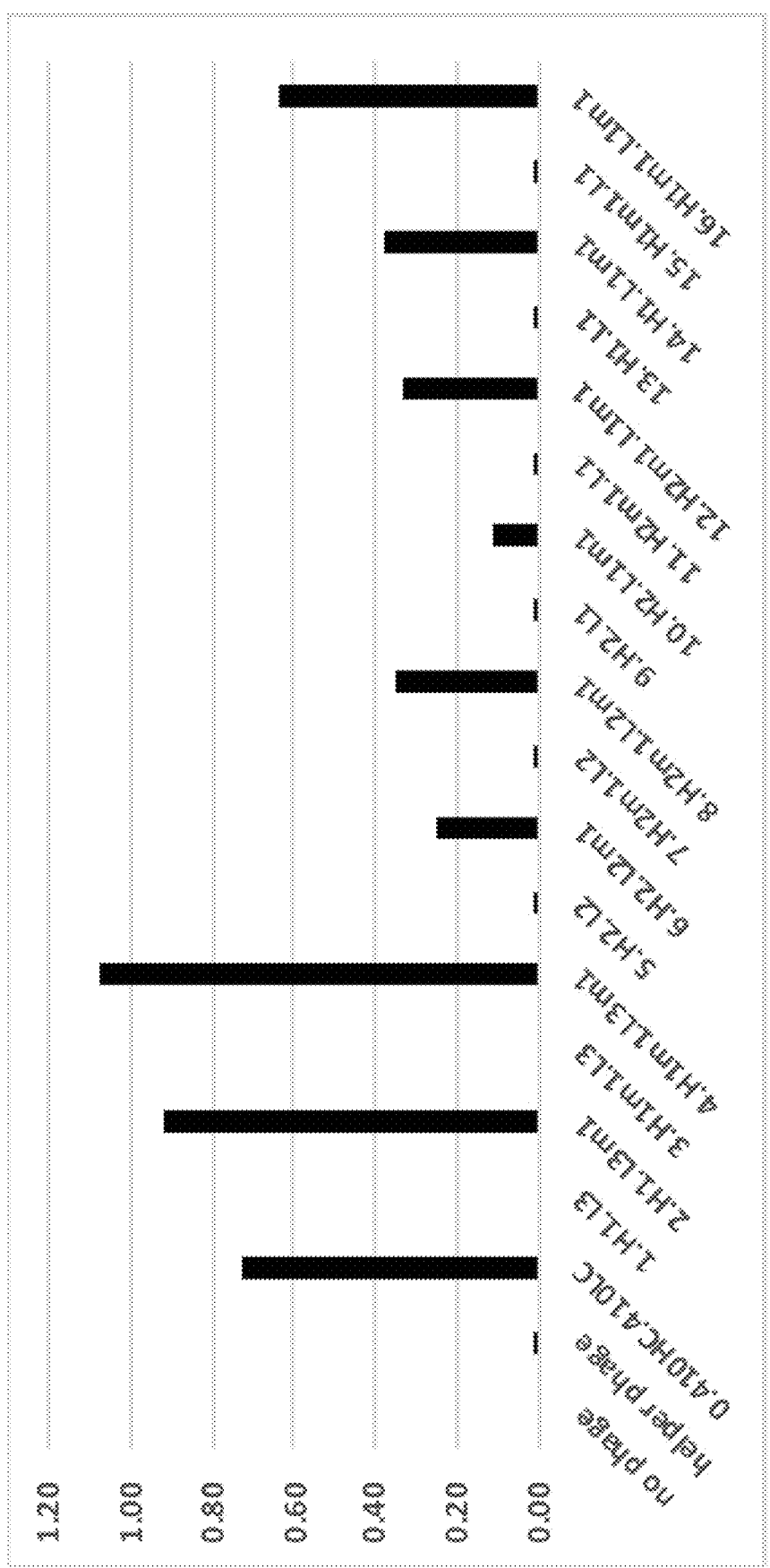
FIG. 6 is a graph illustrating the binding of humanized scFv 1 through 16 to immobilized GFRα4 isoform a (GFR4α4a) as measured by ELISA. "410HC.410LC" is an scFv of the original rabbit antibody for comparison. scFV names include the heavy and light chains of which they are comprised (e.g. "H1.L3" is heavy chain "H1" and light chain "L3").

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab')$_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigen determining variable regions of an intact antibody. Examples of antibody fragments include, but are not limited to, Fab, Fab', F(ab')$_2$, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind GFRα4 using the functional assays described herein.

"Co-stimulatory ligand", as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "dysregulated" when used in the context of the level of expression or activity of GFRα4 refers to the level of expression or activity that is different from the expression level or activity of GFRα4 in an otherwise identical healthy animal, organism, tissue, cell or component thereof. The term "dysregulated" also refers to the altered regulation of the level of expression and activity of GFRα4 compared to the regulation in an otherwise identical healthy animal, organism, tissue, cell or component thereof.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" and "chimeric" forms of non-human (e.g., murine) antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized and chimeric antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized and chimeric antibodies can comprise residues which are found neither in the recipient antibody nor in the imported CDR or framework sequences. These modifications are made to further refine and optimize antibody performance. In general, the humanized and chimeric antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized and chimeric antibody optimally also will comprise at least a portion of an immunoglobulin constant region (Fc), typically that of a human immunoglobulin. The World Health Organization (WHO) International Nonproprietary Name (INN) Expert Group has defined requirements for non-human derived antibodies to be considered "humanized". According to guidelines, comparison of a candidate antibody to human sequences should be done through the International Immunogenetics Information System® (IMGT®) DomainGapAlign tool (www.imgt.org). This tool interrogates the IMGT® database of antibody germline variable region genes where the alignment score is made only against germline sequence variable region exons, thus omitting part of CDR3 and the J region from the analysis. For an antibody to be "humanized", in addition to being "closer to human than to other species", the top "hit" should be human and the identity to human sequences must be at least 85%, otherwise the antibody would be designated as "chimeric". For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

As used herein, the terms "GDNF family receptor alpha 4" and "GFRα4", are used interchangeably, and include variants, isoforms and species homologs of human GFRα4. Isoforms of GFRα4 include GFRα4a and GFRα4b. Accordingly, human antibodies of this disclosure may, in certain cases, cross-react with GFRα4 from species other than human. In certain embodiments, the antibodies may be completely specific for one or more human GFRα4 proteins and may not exhibit species or other types of non-human cross-reactivity. The complete amino acid sequence of an exemplary human GFRα4 has Genbank/NCBI accession number: NM_022139.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human GFRα4.

"Single chain antibodies" refer to antibodies formed by recombinant DNA techniques in which immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell and/or on a tumor cell.

A "stimulatory ligand," as used herein, means a ligand that when present on an antigen presenting cell (e.g., an aAPC, a dendritic cell, a B-cell, and the like) or a tumor cell, can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MEW Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides isolated antibodies that bind specifically to GFRα4. In certain embodiments, the antibodies of the invention comprise particular structural features such as CDR regions comprising particular amino acid sequences. The invention also provides methods of making such antibodies.

In one embodiment, peptides containing amino acids of human GFRα4 isoform "a" and GFRα4 isoform "b" were obtained from R&D Systems (Minneapolis, Minn.) and LakePhama, Inc (Belmont, Calif.), respectively, and used to screen a phage display library in order to isolate single-chain variable fragments (scFv) against GFRα4. In a particular embodiment, the isolated scFv targets GFRα4 isoform "a" (SEQ ID NO: 118). In another embodiment, the isolated scFv targets GFRα4 isoform "b" (SEQ ID NO: 119).

In one embodiment, the scFv antibodies of the invention can be used for diagnosing the presence of GFRα4 in a biological sample. In one embodiment, the scFv antibodies of the invention can be used for diagnosing the presence of GFRα4 in a tumor cell.

In one embodiment, the scFv antibodies of the invention can be used for therapy against a disease, disorder or condition associated with normal or dysregulated expression of GFRα4. The level of expression of GFRα4 on the surface of medullary cancer cells may be considered the same as on normal thyroid C-cells. That said, should a different cell type (e.g. adrenal cells, neuronal cells) exhibit a pathology that is the result of dysregulated GFRα4, the present invention may be useful in targeting these cells to relieve the pathology.

In one embodiment, the scFv antibodies of the invention can be used for cancer therapy against cancers associated with normal or dysregulated expression of GFRα4. In another embodiment, the scFv antibodies of the invention can be used for cancer therapy against thyroid cancers. In yet another embodiment, the scFv antibodies of the invention can be used for cancer therapy against Medullary Thyroid Cancer (MTC).

The present invention relates generally to the treatment of a patient having a cancer associated with the expression of GFRα4, or at risk of having a cancer associated with the expression of GFRα4, using cellular infusion. In one embodiment, lymphocyte infusion, preferably autologous lymphocyte infusion is used in the treatment. In another embodiment, the cancer associated with expression of GFRα4 is a thyroid cancer. In yet another embodiment, the cancer associated with expression of GFRα4 is MTC.

The present invention may also be useful to prevent disease in patients identified as at-risk.

In one embodiment, peripheral blood mononuclear cells (PBMCs) are collected from a patient in need of treatment and T cells therefrom are engineered and expanded using the methods described herein and then infused back into the patient. In another embodiment, autologous or heterologous NK cells or NK cell lines are engineered and expanded using the methods described herein and then infused back into the patient. The invention should not be limited to a particular cell or cell type. Rather, any cell or cell type can be engineered and expanded using the methods described herein and then infused back into the patient.

In one embodiment, the scFv antibodies of the invention can be cloned into vectors that allow expression in cis with cellular cytotoxins. The combination of the scFv antibodies with cellular cytotoxins can be used for transarterial infusion into patients in need thereof.

The antibodies of the invention can be incorporated into an immunoconjugate, a chimeric antigen receptor (CAR), a pharmaceutical composition, and the like. In one embodiment, the immunoconjugates of the invention may be therapeutic agents, for example, cytotoxins or radioactive isotopes. Accordingly, the present invention provides compositions and methods for treating, among other diseases, cancer or any malignancy or autoimmune disease in which expression of GFRα4 is expressed on the cell surface.

The present invention also relates generally to the use of T cells engineered to express a Chimeric Antigen Receptor (CAR). CARs combine an antigen recognition domain of a specific antibody with an intracellular signaling molecule. For example, the intracellular signaling molecule can include but is not limited to CD3-zeta chain, 4-1BB and CD28 signaling modules and combinations thereof. Preferably, the antigen recognition domain binds to GFRα4. In some instances, the antigen recognition domain comprises an anti-GFRα4. Accordingly, the invention provides an anti-GFRα4-CAR engineered into a T cell and methods of their use for adoptive therapy.

In one embodiment, the invention includes autologous cells that are transfected with a vector comprising an anti-GFRα4 CAR transgene. Preferably, the vector is a retroviral vector. More preferably, the vector is a self-inactivating lentiviral vector as described elsewhere herein.

In certain embodiments, the vector further comprises an EF-la promoter. In certain embodiments, the vector further comprises a rev response element (RRE). In certain embodiments, the vector further comprises a woodchuck hepatitis virus posttranscriptional regulatory element (WPRE). In certain embodiments, the vector further comprises a cPPT sequence.

In certain embodiments, the expression construct is a viral vector selected from the group consisting of a retroviral vector, a lentiviral vector, an adenoviral vector, and an adeno-associated viral vector.

In certain embodiments, the expression construct is a lentiviral vector. In certain embodiments, the lentiviral vector is a self-inactivating lentiviral vector.

In one embodiment, the anti-GFRα 4-CAR T cells of the invention can be generated by introducing a lentiviral vector comprising a GFRα4 binding domain, a glycine-serine linker and transmembrane domain, and a CD3zeta signaling domain into the cells. In another embodiment, the anti-GFRα 4-CAR T cells of the invention can be generated by introducing a lentiviral vector comprising a GFRα4 binding domain, CD8a hinge and transmembrane domain, and a CD3zeta signaling domain into the cells. In some instances, the vector further comprises the signaling domain of 4-1BB, CD28, or a combination of both. This is because the present invention is partly based on the discovery that CAR-mediated T-cell responses can be further enhanced with the addition of costimulatory domains. For example, inclusion of the CD28 signaling domain significantly increased anti-tumor activity and in vivo persistence of CAR T cells compared to an otherwise identical CAR T cell not engineered to express CD28.

In one embodiment, the CAR-modified T cells of the invention are expected to replicate in vivo resulting in long-term persistence that can lead to sustained tumor control.

Binding Polypeptides and Antibodies

The binding polypeptides and antibodies of the invention are characterized by particular functional features or properties of the antibodies. For example, the binding polypeptides and antibodies specifically bind to human GFRα4. Preferably, the binding polypeptides and antibodies of the invention bind to GFRα4 with high affinity. Preferably, the binding polypeptides and antibodies of the invention specifically recognize naturally expressed hGFRα4 protein on a cell and do not cross-react to other surface molecules.

Provided is an isolated binding polypeptide comprising:
a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds a glial cell derived neurotrophic factor (GDNF) family receptor alpha-4 (GFRα4). In further embodiments, the binding polypeptide binds GFRα4a and GFRα4b.

In some embodiments, the binding polypeptide comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or an antigen-binding fragment thereof.

In some embodiments, the binding polypeptide comprises a heavy chain variable region comprising an amino acid sequence with 95-99% identity to the amino acid sequence of any of the heavy chain variable regions set forth in SEQ ID NOs: 7-10. In some embodiments, the binding polypeptide comprises a heavy chain variable region comprising at least 1, 2, or 3 modifications but not more than 20 modifications of the amino acid sequence of any of the heavy chain variable regions set forth in SEQ ID NOs: 7-10. In further embodiments, the binding polypeptide comprises a heavy chain variable region comprising an amino acid sequence of any of the heavy chain variable regions set forth in SEQ ID NOs: 7-10. In yet further embodiments, the binding polypeptide comprises a heavy chain variable region consisting of an amino acid sequence of any of the heavy chain variable regions set forth in SEQ ID NOs: 7-10.

In some embodiments, the binding polypeptide comprises a light chain variable region comprising an amino acid sequence with 95-99% identity to the amino acid sequence of any of the light chain variable regions set forth in SEQ ID NOs: 28-42. In some embodiments, the binding polypeptide comprises a light chain variable region comprising at least 1, 2, or 3 modifications but not more than 20 modifications of the amino acid sequence of any of the light chain variable regions set forth in SEQ ID NOs: 28-42. In further embodiments, the binding polypeptide comprises a light chain variable region comprising an amino acid sequence of any of the light chain variable regions set forth in SEQ ID NOs: 28-42. In yet further embodiments, the binding polypeptide comprises a light chain variable region consisting of an amino acid sequence of any of the light chain variable regions set forth in SEQ ID NOs: 28-42.

Given that each of these antibodies binds to GFRα4, the VH and VL sequences can be "mixed and matched" to create other anti-GFRα4 binding molecules of the invention. GFRα4 binding of such "mixed and matched" antibodies can be tested using the binding assays described herein, in the art, for example, in the Examples section (e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. It will be readily apparent to the ordinary skilled artisan that novel VH and VL sequences can be created by substituting one or more VH and/or VL CDR region sequences with structurally similar sequences from the CDR sequences disclosed herein.

In another embodiment, the invention includes antibodies that bind to the same epitope on human GFRα4 as any of the GFRα4 antibodies of the invention (i.e., antibodies that have the ability to cross-compete for binding to GFRα4 with any of the antibodies of the invention). In a preferred embodiment, the reference antibody for cross-competition studies can be one of the antibodies described herein (e.g., P4-10). For example, Biacore analysis, ELISA assays or flow cytometry may be used to demonstrate cross-competition with the antibodies of the current invention. The ability of a test antibody to inhibit the binding of, for example, P4-10, to human GFRα4 demonstrates that the test antibody can compete with P4-10 for binding to human GFRα4 and thus is considered to bind to the same epitope on human GFRα4 as P4-10.

An antibody of the invention is prepared using an antibody having one or more of the VH and/or VL sequences disclosed herein as a starting material to engineer a modified antibody, which modified antibody may have altered properties as compared with the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

Humanized Antibodies

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-GFRα4 antibodies directed against the human GFRα4 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and Duchosal et al., *Nature,* 355:258 (1992).

Human antibodies can also be derived from phage-display libraries (Hoogenboom et al., *J. Mol. Biol.,* 227:381 (1991); Marks et al., *J. Mol. Biol.,* 222:581-597 (1991); Vaughan et al., *Nature Biotech.,* 14:309 (1996)). Phage display technology (McCafferty et al., *Nature,* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., *J. Mol. Biol.,* 222:581-597 (1991), or Griffith et al., *EMBO J.,* 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al., *Methods Enzymol.,* 121:140-167 (1986).

Alternatively, in some embodiments, a non-human antibody is humanized, where specific sequences or regions of the antibody are modified to increase similarity to an antibody naturally produced in a human. For instance, in the present invention, the GFRα4 antibody comprises a rabbit scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, *Protein Engineering,* 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., *J. Immunol.,* 169:1119-25 (2002), Caldas et al., *Protein Eng.,* 13(5):353-60 (2000), Morea et al., *Methods,* 20(3):267-79 (2000), Baca et al., *J. Biol. Chem.,* 272(16):10678-84 (1997), Roguska et al., *Protein Eng.,* 9(10):895-904 (1996), Couto et al., *Cancer Res.,* 55 (23 Supp):5973s-5977s (1995), Couto et al., *Cancer Res.,* 55(8):1717-22 (1995), Sandhu J S, *Gene,* 150(2):409-10 (1994), and Pedersen et al., *J. Mol. Biol.,* 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature,* 332:323, each of which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, *Molecular Immunology*, 28(4/5):489-498; Studnicka et al., *Protein Engineering*, 7(6):805-814 (1994); and Roguska et al., *PNAS*, 91:969-973 (1994)) or chain shuffling (U.S. Pat. No. 5,565,332), the contents of which are incorporated herein by reference herein in their entirety.

In some instances, a human scFv may also be derived from a yeast display library. The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the rabbit scFv of the present invention, the ability to bind human GFRα4. However, using certain methods of humanization, the affinity and/or specificity of binding of the antibody for human GFRα4 may be increased using methods of "directed evolution," as described by Wu et al., *J. Mol. Biol.*, 294:151 (1999), the contents of which are incorporated herein by reference herein in their entirety.

Antigen Binding Moiety

The choice of moiety depends upon the type and number of ligands that define the surface of a target cell. For example, the antigen binding domain may be chosen to recognize a ligand that acts as a cell surface marker on target cells associated with a particular disease state.

In the context of the present invention, "tumor antigen" refers to antigens that are common to specific thyroid disorders. In certain aspects, the thyroid antigens of the present invention are derived from, cancers including but not limited to thyroid cancer, papillary thyroid cancer, follicular thyroid cancer, medullary thyroid cancer, anaplastic thyroid cancer and the like. Preferably, the cancer is a medullary thyroid carcinoma (MTC).

In one embodiment, the tumor antigen of the present invention comprises one or more antigenic cancer epitopes immunologically recognized by tumor infiltrating lymphocytes (TIL) derived from a cancer tumor of a mammal.

The antigen binding domain can be any domain that binds to the antigen including but not limited to monoclonal antibodies, polyclonal antibodies, synthetic antibodies, human antibodies, humanized antibodies, non-human antibodies and fragments thereof. Thus, in one embodiment, the antigen binding domain portion comprises a rabbit antibody or a fragment thereof.

CAR Composition

The present invention encompasses a recombinant DNA construct comprising sequences of the antigen binding domain of the invention that specifically binds to human GFRα4, wherein the sequence of the antigen binding domain is operably linked to the nucleic acid sequence of a transmembrane domain and of an intracellular domain. The intracellular domain or otherwise the intracellular domain comprises a costimulatory signaling region and/or an intracellular signaling domain, e.g., a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

The present invention therefore encompasses a recombinant DNA construct comprising sequences of a fully human CAR, wherein the sequence comprises the nucleic acid sequence of a GFRα4 binding domain operably linked to the nucleic acid sequence of an intracellular domain. An exemplary intracellular domain that can be used in the CAR includes but is not limited to the intracellular domain of CD3-zeta, CD28, 4-1BB, CD27, and the like. In some instances, the CAR can comprise any combination of CD3-zeta, CD28, 4-1BB, CD27, and the like.

Between the extracellular domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the intracellular domain in the polypeptide chain. A spacer domain may comprise up to 300 amino acids, preferably 10 to 100 amino acids and most preferably 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as cloned molecules. In one embodiment, the CAR of the invention comprises a target-specific binding element otherwise referred to as an antigen binding moiety as described elsewhere herein. Examples of cell surface markers that may act as ligands for the antigen moiety domain in the CAR of the invention include those associated with viral, bacterial and parasitic infections, autoimmune disease and cancer cells.

In one embodiment, the CAR-mediated T-cell response can be directed to an antigen of interest by way of engineering a desired antigen into the CAR.

In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof.

In one embodiment, the antigen binding moiety of the CAR includes a nucleic acid sequence encoding an antibody or antibody fragment as described elsewhere herein.

In a preferred embodiment, the antigen binding moiety portion of the CAR targets GFRα4, preferably human GFRα4.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Intracellular Domain

The intracellular domain of the CAR of the invention is responsible for activation of at least one of the normal effector functions of the immune cell in which the CAR has been placed in. In some embodiments, the intracellular domain comprises a costimulatory domain and an intracellular signaling domain. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the intracellular domain of the CAR can be designed to comprise the CD3-zeta signaling domain by itself or combined with any other desired intracellular domain(s) useful in the context of the CAR of the invention. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., Molecular Cloning: A Laboratory Manual, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the EFlalpha promoter. An additional example includes the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., Molecular Cloning: A Laboratory Manual, volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-$CD3^3$/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., *Cell* 66:807-815, 1991; Henderson et al., *Immun.* 73:316-321, 1991; Bierer et al., *Curr. Opin. Immun.* 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately predominantly of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one embodiment, the invention pertains to a method of inhibiting growth of a GFRα4-expressing tumor cell, comprising contacting the tumor cell with at least one antibody or a fragment thereof of the invention such that growth of the tumor cell is inhibited.

Without wishing to be bound by any particular theory, the anti-tumor immunity response elicited by the GFRα4 antibody of this invention may be an active or a passive immune response. The GFRα4 antibody of the invention may be used in some type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

The procedure for ex vivo expansion of hematopoietic stem and progenitor cells is described in U.S. Pat. No. 5,199,942, incorporated herein by reference, can be applied to the cells of the present invention. Other suitable methods are known in the art; therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

The GFRα4 antibody of the present invention may be administered either alone, or as a pharmaceutical composition in combination with diluents and/or with other components such as IL-2 or other cytokines or cell populations.

In one embodiment, the invention pertains to a method of inhibiting growth of a GFRα4-expressing tumor cell, comprising contacting the tumor cell with an anti-GFRα4 CAR T cell of the present invention such that growth of the tumor cell is inhibited.

In another aspect, the invention pertains to a method of treating cancer in a subject. The method comprises administering to the subject an antibody or a fragment of the invention or an anti-GFRα4 CAR T cell of the present invention such that the cancer is treated in the subject. Particularly preferred cancers for treatment are thyroid cancer, papillary thyroid cancer, follicular thyroid cancer, medullary thyroid cancer and anaplastic thyroid cancer. More specifically, the cancer for treatment is a medullary thyroid cancer.

Provided is a chimeric antigen receptor (CAR) comprising an antigen binding domain, a transmembrane domain, and an intracellular domain, wherein the antigen binding domain comprises:
  a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and
  a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

The present invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control (unless using mRNA electroporation introduction of CAR). In various embodiments, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

Without wishing to be bound by any particular theory, the anti-tumor immunity response elicited by the CAR-modified T cells may be an active or a passive immune response. In another embodiment, the CAR transduced T cells exhibit specific proinflammatory cytokine secretion and potent cytolytic activity in response to human cancer cells expressing GFRα4, resist soluble GFRα4 inhibition, mediate bystander killing and mediate regression of an established human tumor. For example, antigen-less tumor cells within a heterogeneous field of GFRα4-expressing tumor may be susceptible to indirect destruction by GFRα4-redirected T cells that has previously reacted against adjacent antigen-positive cancer cells.

The CAR-modified T cells of the invention may be a type of vaccine for ex vivo immunization and/or in vivo therapy in a mammal. Preferably, the mammal is a human.

Ex vivo procedures are well known in the art as discussed more fully above. Briefly, cells are isolated from a mammal (preferably a human) and genetically modified (i.e., transduced or transfected in vitro) with a vector expressing a CAR disclosed elsewhere herein, or by electroporating the CAR mRNA disclosed elsewhere herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with the normal or dysregulated expression of GFRα4. In certain embodiments, the cells of the invention are used in the treatment of patients at risk for developing diseases, disorders and conditions associated with expression of GFRα4. Thus, the present invention provides methods for the treatment or prevention of diseases, disorders and conditions associated with expression of GFRα4 comprising administering to a subject in need thereof, a therapeutically effective amount of the CAR-modified T cells of the invention.

Provided is a method of treating a disease associated with expression of a thyroid cell antigen in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises:
  a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and
  a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

The CAR-modified T cells of the present invention may be administered either alone, or as a pharmaceutical composition in combination with diluents and/or with other components such as IL-2 or other cytokines or cell populations.

Pharmaceutical Compositions

Pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

Rabbit P4-10 Heavy Chain Variable Region and Humanized Heavy Chain Variants that are Used in the Invention

```
Rabbit P4-10 heavy chain variable region
                                          (SEQ ID NO: 1)
CAGTCCGTGAAGGAGAGCGAGGGCGGCCTGTTCAAGCCCACCGACACCCTG

ACCCTGACCTGCACAGTGAGCGGCTTCAGCCTGTCCAGACACGCCCTGACA

TGGGTGAGACAGGCCCCTGGCAACGGCCTGGAATGGATCGGCGCCATCGAC

AACGCCGGCACCACCTACTACGCCAGCTGGGCCAAGTCCAGGTCCACCATC
```

ACCAGGAACACCGACCTCCACACCGTGACCCTGAAGATGACAAGCCTGACC
GCCTCCGACACCGCCACCTACTTCTGCGCCAGGGTGTTCTACGACATCAAC
AGCGGCTACTACCTGGATGGCATGGACCTGTGGGGACCTGGCACACTGGTG
ACCGTGAGCAGC

Rabbit P4-10 heavy chain variable region
(SEQ ID NO: 6)
QSVKESEGGLFKPTDTLTLTCTVSGFSLSRHALTWVRQAPGNGLEWIGAID
NAGTTYYASWAKSRSTITRNTDLHTVTLKMTSLTASDTATYFCARVFYDIN
SGYYLDGMDLWGPGTLVTVSS H1
(SEQ ID NO: 2)
CAAGTTCAGCTGCAAGAAAGCGGACCCGGTTTAGTCAAGCCCAGCGAGACT
TTATCTTTAACATGCGCCGTGAGCGGCTACTCCATCTCTCGTCACGCTTTA
ACATGGATTAGGCAGCCCCCGGTAAGGGTTTAGAATGGATCGGCGCCATC
GACAACGCTGGCACCACCTACTACGCCTCTTGGGCTAAGTCTCGTGTGACA
ATCAGCGTGGACACCTCCAAGAACCAGTTTTCTTTAAAGCTGAGCAGCGTG
ACCGCTGCCGACACCGCTGTGTACTATTGCGCTCGTGTCTTCTACGACATC
AACAGCGGCTACTATTTAGATGGCATGGATTTATGGGGACCCGGTACTTTA
GTGACCGTGAGCTCC H1
(SEQ ID NO: 7)
QVQLQESGPGLVKPSETLSLTCAVSGYSISRHALTWIRQPPGKGLEWIGAI
DNAGTTYYASWAKSRVTISVDTSKNQFSLKLSSVTAADTAVYYCARVFYDI
NSGYYLDGMDLWGPGTLVTVSS H1m1
(SEQ ID NO: 3)
CAGCAGAGCGTGAAGGAGAGCGGCCCCGGTCTGGTGAAGCCCAGCGAGACT
TTATCTTTAACATGCGCCGTGAGCGGCTTCTCTTTATCTCGTCACGCTTTA
ACTTGGGTGAGACAGCCTCCCGGTAAAGGTTTAGAGTGGATCGGCGCCATC
GACAACGCCGGCACAACCTACTACGCCAGCTGGGCCAAGTCTCGTGTGACC
ATCTCTCGTAACACCGATTTACACACCGTGTCTTTAAAGCTGAGCTCCGTG
ACCGCTGCCGATACCGCCGTGTACTTCTGCGCTAGGGTGTTCTACGACATC
AACAGCGGCTACTATTTAGATGGCATGGATCTGTGGGGCCCCGGCACACTG
GTCACAGTGTCCAGC H1m1
(SEQ ID NO: 8)
QQSVKESGPGLVKPSETLSLTCAVSGFSLSRHALTWVRQPPGKGLEWIGAI
DNAGTTYYASWAKSRVTISRNTDLHTVSLKLSSVTAADTAVYFCARVFYDI
NSGYYLDGMDLWGPGTLVTVSS H2
(SEQ ID NO: 4)
GAGGTGCAGCTGGTGGAAAGCGGCGGAGGACTGGTGCAGCCCGGTGGCTCT
TTAAGACTGAGCTGTGCTGCCAGCGGCTTCACATTCTCTCGTCACGCTTTA
ACTTGGGTGAGACAAGCTCCCGGAAAGGGTTTAGAATGGGTGAGCGCCATC
GACAACGCCGGAACCACCTACTACGCCAGCTGGGCCAAGTCTCGTTTCACC
ATCTCTCGTGATAACGCCAAGAACAGCCTCTATTTACAGATGAACTCTTTA
AGGGCCGAGGACACCGCCGTGTACTACTGCGCTAGGGTGTTCTACGACATC
AACAGCGGCTACTATCTGGACGGCATGGATTTATGGGGCCCCGGTACACTG
GTCACCGTGAGCAGC H2
(SEQ ID NO: 9)
EVQLVESGGGLVQPGGSLRLSCAASGFTFSRHALTWVRQAPGKGLEWVSAI
DNAGTTYYASWAKSRFTISRDNAKNSLYLQMNSLRAEDTAVYYCARVFYDI
NSGYYLDGMDLWGPGTLVTVSS H2m1
(SEQ ID NO: 5)
CAGAGCGTCAAGGAGTCCGGAGGAGGACTGGTGCAGCCCGGTGGCTCTTTA
AGGCTGAGCTGTGCCGCCTCTGGCTTTACTTTATCTCGTCACGCTTTAACA
TGGGTGAGACAAGCTCCCGGTAAGGGACTGGAGTGGATCGGCGCCATCGAC
AACGCCGGCACCACCTACTACGCCTCTTGGGCCAAGTCTCGTTTCACCATC
TCTCGTAACACCGATTTACACACCGTGTATTTACAGATGAACTCTTTAAGG
GCCGAGGACACAGCCGTCTATTTCTGCGCTCGTGTGTTCTACGACATCAAT
AGCGGCTACTACCTCGACGGAATGGATCTGTGGGGCCCCGGTACTTTAGTG
ACAGTCAGCAGC H2m1
(SEQ ID NO: 10)
QSVKESGGGLVQPGGSLRLSCAASGFTLSRHALTWVRQAPGKGLEWIGAID
NAGTTYYASWAKSRFTISRNTDLHTVYLQMNSLRAEDTAVYFCARVFYDIN
SGYYLDGMDLWGPGTLVTVSS Rabbit P4-10 Light Chain Variable Region and Humanized Light Chain Variants that are Used in the Invention Rabbit P4-10 light chain variable region
(SEQ ID NO: 11)
CAGTTCGTGCTGACACAGAGCCCTAGCGTGAGCGCCGCCCTGGGAGCCTCC
GCTAAACTGACCTGCACCCTGAGCAGCGCCCACAAGACCTACACCATCGAC
TGGTACCAACAGCAGCAGGGCGAGGCCCCCAGGTATCTGATGCAGGTGAAG
TCCGACGGCAGCTACACCAAAGGCACCGGCGTGCCTGACAGGTTCAGCGGC
AGCTCCAGCGGAGCCGACAGGTACCTGATCATCCCCTCCGTGCAGGCCGAC
GACGAGGCTGGCTACGTGTGGCGCCGACGACAATGGCGGCTACGTGTTC
GGAGGCGGCACCCAGCTGACCGTGACA Rabbit P4-10 light chain variable region
(SEQ ID NO: 27)
QFVLTQSPSVSAALGASAKLTCTLSSAHKTYTIDWYQQQQGEAPRYLMQVK
SDGSYTKGTGVPDRFSGSSSGADRYLIIPSVQADDEAGYVCGADDNGGYVF
GGGTQLTVT L1
(SEQ ID NO: 12)
CAGCTGGTGCTGACCCAGAGCCCCAGCGCTTCCGCCTCTTTAGGAGCAGC
GTGAAGCTGACTTGTACTTTAAGCAGCGCCCACAAGACCTACACAATCGCT
TGGTACCAGCAGCAGCCCGAAAAGGGCCCCAGATATCTGATGAAGGTCAAG
TCCGACGGCAGCTACTCCAAGGGCGACGGCATCCCCGATCGTTTCAGCGGT
TCTTCCAGCGGCGCCGAGAGGTATTTAACCATCAGCTCTTTACAGAGCGAG

GACGAGGCCGACTACTACTGCGGCGCTGACGACAACGGCGGCTACGTCTTT
GGCGGCGGCACAAAACTGACCGTGCTG

L1
(SEQ ID NO: 28)
QLVLTQSPSASASLGASVKLTCTLSSAHKTYTIAWHQQPEKGPRYLMKVK
SDGSYSKGDGIPDRFSGSSSGAERYLTISSLQSEDEADYYCGADDNGGYVF
GGGTKLTVL

L1m1
(SEQ ID NO: 13)
CAGTTTGTGCTGACCCAGAGCCCTAGCGCTTCCGCCTCTTTAGGAGCCAGC
GTGAAGCTGACTTGTACTTTATCCTCCGCCCACAAGACCTACACCATCGAC
TGGTACCAGCAGCAGCCCGAAAAGGGCCCTCGTTATCTGATGCAAGTTAAG
TCCGACGGCAGCTACACCAAGGGAACCGGCGTGCCCGACAGATTCTCCGGT
AGCAGCAGCGGCGCCGACAGATATTTAACCATCAGCTCTTTACAGTCCGAG
GACGAGGCCGACTACTACTGCGGCGCCGACGACAATGGCGGCTACGTCTTC
GGAGGCGGCACACAGCTGACCGTGACT

L1m1
(SEQ ID NO: 29)
QFVLTQSPSASASLGASVKLTCTLSSAHKTYTIDWYQQQPEKGPRYLMQVK
SDGSYTKGTGVPDRFSGSSSGADRYLTISSLQSEDEADYYCGADDNGGYVF
GGGTQLTVT

L1m2
(SEQ ID NO: 14)
CAGTTTGTGCTGACCCAGAGCCCTAGCGCTTCCGCCTCTTTAGGAGCCAGC
GTGAAGCTGACTTGTACTTTATCCTCCGCCCACAAGACCTACACCATCGAC
TGGCACCAGCAGCAGCCCGAAAAGGGCCCTCGTTATCTGATGCAAGTTAAG
TCCGACGGCAGCTACACCAAGGGAACCGGCATCCCCGACAGATTCTCCGGT
AGCAGCAGCGGCGCCGAGAGATATTTAACCATCAGCTCTTTACAGTCCGAG
GACGAGGCCGACTACTACTGCGGCGCCGACGACAATGGCGGCTACGTCTTC
GGAGGCGGCACACAGCTGACCGTGCTG

L1m2
(SEQ ID NO: 30)
QFVLTQSPSASASLGASVKLTCTLSSAHKTYTIDWHQQQPEKGPRYLMQVK
SDGSYTKGTGIPDRFSGSSSGAERYLTISSLQSEDEADYYCGADDNGGYVF
GGGTQLTVL

L1m3
(SEQ ID NO: 15)
CAGCTGGTGCTCACCCAAAGCCCTAGCGCCTCTGCCTCTTTAGGCGCTTCC
GTGAAGCTGACTTGTACTTTAAGCTCCGCCCATAAGACCTACACCATCGAC
TGGTACCAGCAGCAGCCCGAGAAGGGCCCTCGTTATTTAATGCAAGTTAAG
TCCGATGGCAGCTATACCAAGGGCACCGGCGTGCCCGACAGATTCAGCGGC
AGCTCCAGCGGAGCCGATCGTTATTTAACCATCAGCTCTTTACAGAGCGAG
GACGAGGCTGACTACTACTGCGGCGCCGACGATAACGGCGGCTACGTGTTC
GGCGGCGGCACCCAACTGACAGTGCTG

L1m3
(SEQ ID NO: 31)
QLVLTQSPSASASLGASVKLTCTLSSAHKTYTIDWYQQQPEKGPRYLMQVK
SDGSYTKGTGVPDRFSGSSSGADRYLTISSLQSEDEADYYCGADDNGGYVF
GGGTQLTVL

L1m4
(SEQ ID NO: 16)
CAGTTGGTGCTCACCCAAAGCCCTAGCGCCTCTGCCTCTTTAGGCGCTTCC
GTGAAGCTGACTTGTACTTTAAGCTCCGCCCATAAGACCTACACCATCGCC
TGGCATCAGCAGCAGCCCGAGAAGGGCCCTCGTTATTTAATGCAAGTTAAG
TCCGATGGCAGCTATACCAAGGGCACCGGCGTGCCCGACAGATTCAGCGGC
AGCTCCAGCGGAGCCGATCGTTATTTAACCATCAGCTCTTTACAGAGCGAG
GACGAGGCTGACTACTACTGCGGCGCCGACGATAACGGCGGCTACGTGTTC
GGCGGCGGCACCCAACTGACAGTGCTC

L1m4
(SEQ ID NO: 32)
QLVLTQSPSASASLGASVKLTCTLSSAHKTYTIAWHQQQPEKGPRYLMQVK
SDGSYTKGTGVPDRFSGSSSGADRYLTISSLQSEDEADYYCGADDNGGYVF
GGGTQLTVL

L2
(SEQ ID NO: 17)
CAGAGCGTGCTGACACAGCCTCCTAGCGCCAGCGGCACACCCGGTCAGAGA
GTGACCATCAGCTGCTCCGGCAGCAGCGCCCACAAGACCTACACCGTGAAC
TGGTACCAGCAGCTGCCCGGCACAGCCCCTAAGCTGCTGATCTACGTGAAA
TCCGACGGCAGCTACCAGAGGCCTAGCGGAGTGCCCGATCGTTTCAGCGGC
AGCAAAAGCGGCACAAGCGCCTCTTTAGCTATCAGCGGTTTACAGAGCGAG
GACGAGGCCGACTATTACTGCGGCGCCGACGATAACGGCGGCTACGTGTTC
GGCGGCGGAACCAAGCTGACAGTGCTG

L2
(SEQ ID NO: 33)
QSVLTQPPSASGTPGQRVTISCSGSSAHKTYTVNWYQQLPGTAPKLLIYVK
SDGSYQRPSGVPDRFSGSKSGTSASLAISGLQSEDEADYYCGADDNGGYVF
GGGTKLTVL

L2m1
(SEQ ID NO: 18)
CAGTTCGTGCTGACACAGCCTCCCAGCGCCTCTGGCACACCCGGTCAGAGG
GTGACCATCTCTTGTACTTTATCCTCCGCCCACAAGACCTACACCATTGAC
TGGTACCAGCAGCTGCCCGGTACCGCCCCTAAGCTGCTGATTTACGTGAAA
TCCGACGGCAGCTACACCAAGGGAACCGGCGTGCCCGATCGTTTTTCCGGC
AGCTCCAGCGGCGCCGATAGGTATTTAGCCATCAGCGGTTTACAGTCCGAG
GATGAGGCCGACTACTACTGCGGCGCCGATGACAACGGCGGCTACGTGTTC
GGCGGAGGAACCCAGCTCACCGTGACC

L2m1
(SEQ ID NO: 34)
QFVLTQPPSASGTPGQRVTISCTLSSAHKTYTIDWYQQLPGTAPKLLIYVK
SDGSYTKGTGVPDRFSGSSSGADRYLAISGLQSEDEADYYCGADDNGGYVF
GGGTQLTVT

L2m2
(SEQ ID NO: 19)
CAGTTCGTGCTGACACAGCCTCCCAGCGCCTCTGGCACACCCGGTCAGAGG
GTGACCATCTCTTGTACTTTATCCTCCGCCCACAAGACCTACACCATTGAC
TGGTACCAGCAGCTGCCCGGTACCGCCCCTAAGCTGCTGATTTACGTGAAA
TCCGACGGCAGCTACACCAAGGGAACCGGCGTGCCCGATCGTTTTTCCGGC
AGCTCCAGCGGCGCCGATGCCAGCTTAGCCATCAGCGGTTTACAGTCCGAG
GATGAGGCCGACTACTACTGCGGCGCCGATGACAACGGCGGCTACGTGTTC
GGCGGAGGAACCCAGCTCACCGTGCTG

L2m2
(SEQ ID NO: 35)
QFVLTQPPSASGTPGQRVTISCTLSSAHKTYTIDWYQQLPGTAPKLLIYVK
SDGSYTKGTGVPDRFSGSSSGADASLAISGLQSEDEADYYCGADDNGGYVF
GGGTQLTVL

L2m3
(SEQ ID NO: 20)
CAGAGCGTGCTGACACAGCCTCCCAGCGCCTCTGGCACACCCGGTCAGAGG
GTGACCATCTCTTGTACTTTATCCTCCGCCCACAAGACCTACACCATTGAC
TGGTACCAGCAGCTGCCCGGTACCGCCCCTAAGCTGCTGATTTACGTGAAA
TCCGACGGCAGCTACACCAAGGGAACCGGCGTGCCCGATCGTTTTTCCGGC
AGCAAGAGCGGCACCAGCGCCAGCTTAGCCATCAGCGGTTTACAGTCCGAG
GATGAGGCCGACTACTACTGCGGCGCCGATGACAACGGCGGCTACGTGTTC
GGCGGAGGAACCCAGCTCACCGTGCTG

L2m3
(SEQ ID NO: 36)
QSVLTQPPSASGTPGQRVTISCTLSSAHKTYTIDWYQQLPGTAPKLLIYVK
SDGSYTKGTGVPDRFSGSKSGTSASLAISGLQSEDEADYYCGADDNGGYVF
GGGTQLTVL

L3
(SEQ ID NO: 21)
CAGTCCGCTTTAACACAGCCCGCTTCTGTGTCCGGAAGCCCCGGTCAGAGC
ATCACCATCAGCTGCACCGGCACCAGCGCTCACAAGACCTACACCGTGAGC
TGGTACCAGCAGCACCCCGGTAAGGCCCCCAAACTGATGATCTACGTGAAG
AGCGACGGCAGCTACAACAGACCCAGCGGCGTGAGCAATCGTTTCAGCGGC
AGCAAGAGCGGCAACACCGCTTCTTTAACCATCAGCGGTTTACAAGCTGAA
GACGAGGCTGACTACTACTGCGGCGCCGACGATAACGGCGGCTACGTGTTT
GGCGGCGGCACCAAACTGACCGTGCTG

L3
(SEQ ID NO: 37)
QSALTQPASVSGSPGQSITISCTGTSAHKTYTVSWYQQHPGKAPKLMIYVK
SDGSYNRPSGVSNRFSGSKSGNTASLTISGLQAEDEADYYCGADDNGGYVF
GGGTKLTVL

L3m1
(SEQ ID NO: 22)
CAGTTCGTGCTGACCCAGCCCGCTTCTGTGAGCGGTTCTCCCGGTCAGAGC
ATCACCATCAGCTGCACTTTAAGCAGCGCCCACAAGACCTACACCATCGAC
TGGTACCAGCAGCACCCCGGCAAGGCCCCCAAGTATTTAATGCAAGTTAAG
TCCGACGGCAGCTACACCAAGGGCACCGGCGTGCCCAACAGATTCTCCGGC
AGCAGCTCCGGCGCCGACAGATACTTAACCATCAGCGGTTTACAAGCTGAG
GATGAGGCCGACTATGTGTGCGGCGCCGACGACAATGGCGGCTACGTGTTC
GGCGGCGGCACACAGCTGACCGTGACT

L3m1
(SEQ ID NO: 38)
QFVLTQPASVSGSPGQSITISCTLSSAHKTYTIDWYQQHPGKAPKYLMQVK
SDGSYTKGTGVPNRFSGSSSGADRYLTISGLQAEDEADYVCGADDNGGYVF
GGGTQLTVT

L3m2
(SEQ ID NO: 23)
CAGTTCGTGCTGACCCAGCCCGCTTCTGTGAGCGGTTCTCCCGGTCAGAGC
ATCACCATCAGCTGCACTTTAAGCAGCGCCCACAAGACCTACACCATCGAC
TGGTACCAGCAGCACCCCGGCAAGGCCCCCAAGCTGATGATCCAAGTTAAG
TCCGACGGCAGCTACACCAAGGGCACCGGCGTGAGCAACAGATTCTCCGGC
AGCAGCTCCGGCGCCGACAGATACTTAACCATCAGCGGTTTACAAGCTGAG
GATGAGGCCGACTATTACTGCGGCGCCGACGACAATGGCGGCTACGTGTTC
GGCGGCGGCACACAGCTGACCGTGCTG

L3m2
(SEQ ID NO: 39)
QFVLTQPASVSGSPGQSITISCTLSSAHKTYTIDWYQQHPGKAPKLMIQVK
SDGSYTKGTGVSNRFSGSSSGADRYLTISGLQAEDEADYYCGADDNGGYVF
GGGTQLTVL

L3m3
(SEQ ID NO: 24)
CAGAGCGCCCTGACCCAGCCCGCTTCTGTGAGCGGTTCTCCCGGTCAGAGC
ATCACCATCAGCTGCACTGGCACCAGCGCCCACAAGACCTACACCATCGAC
TGGTACCAGCAGCACCCCGGCAAGGCCCCCAAGCTGATGATCTATGTTAAG
TCCGACGGCAGCTACACCAAGGGCACCGGCGTGAGCAACAGATTCTCCGGC
AGCAAGTCCGGCAACACCGCCAGCTTAACCATCAGCGGTTTACAAGCTGAG
GATGAGGCCGACTATTACTGCGGCGCCGACGACAATGGCGGCTACGTGTTC
GGCGGCGGCACACAGCTGACCGTGCTG

L3m3
(SEQ ID NO: 40)
QSALTQPASVSGSPGQSITISCTGTSAHKTYTIDWYQQHPGKAPKLMIYVK
SDGSYTKGTGVSNRFSGSKSGNTASLTISGLQAEDEADYYCGADDNGGYVF
GGGTQLTVL

L3m4
(SEQ ID NO: 25)
CAGAGCGCTCTGACCCAGCCCGCTTCTGTGAGCGGTTCTCCCGGTCAGAGC
ATCACCATCAGCTGCACTGGCACAAGCGCCCACAAGACCTACACCGTGAGC
TGGTACCAGCAGCACCCCGGCAAGGCCCCCAAGTATTAATGCAAGTTAAG
TCCGACGGCAGCTACACCAAGGGCACCGGCGTGCCCAACAGATTCTCCGGC
AGCAGCTCCGGCGCCGACAGATACTTAACCATCAGCGGTTTACAAGCTGAG
GATGAGGCCGACTATTACTGCGGCGCCGACGACAATGGCGGCTACGTGTTC
GGCGGCGGCACCCAACTGACAGTGCTG

L3m4

(SEQ ID NO: 41)
QSALTQPASVSGSPGQSITISCTGTSAHKTYTVSWYQQHPGKAPKYLMQVK

SDGSYTKGTGVPNRFSGSSSGADRYLTISGLQAEDEADYYCGADDNGGYVF

GGGTQLTVL

L3m5

(SEQ ID NO: 26)
CAGTCTGCTCTGACCCAGCCCGCTTCTGTGAGCGGTTCTCCCGGTCAGAGC

ATCACCATCAGCTGCACTGGCACAAGCGCCCACAAGACCTACACCGTGAGT

TGGTACCAGCAGCACCCCGGCAAGGCCCCCAAGTTGATGATCTACGTTAAG

TCCGACGGCAGCTACACCAAGGGCACCGGCGTGCCCAACAGATTCTCCGGC

AGCAGCTCCGGCGCCGACAGATACTTAACCATCAGCGGTTTACAAGCTGAG

GATGAGGCCGACTATTATTGCGGCGCCGACGACAATGGCGGCTACGTGTTC

GGCGGCGGCACCCAACTGACAGTGCTC

L3m5

(SEQ ID NO: 42)
QSALTQPASVSGSPGQSITISCTGTSAHKTYTVSWYQQHPGKAPKLMIYVK

SDGSYTKGTGVPNRFSGSSSGADRYLTISGLQAEDEADYYCGADDNGGYVF

GGGTQLTVL scFv Constructs of Original P4-10 and Humanized Variants for Bacterial Expression 0.410HC.410LC (SEQ ID NO: 43)
CAGTTCGTGCTGACCCAGAGCCCTAGCGTGAGCGCTGCTCTGGGAGCCAGC

GCCAAGCTCACTTGTACTTTAAGCTCCGCCCACAAAACCTACACCATCGAC

TGGTACCAGCAGCAGCAAGGTGAGGCCCCCAGATATTTAATGCAAGTTAAG

TCCGATGGCAGCTACACCAAGGGCACCGGAGTGCCCGATAGGTTCAGCGGC

AGCTCCAGCGGCGCCGATAGGTATTTAATCATCCCCAGCGTGCAAGCTGAT

GATGAGGCCGGCTACGTGTGTGGCGCCGACGACAACGGCGGCTACGTGTTC

GGAGGCGGAACCCAGCTGACAGTGACCGGAGGCGGAAGCTCCAGAAGCTCC

AGCAGCGGAGGAGGAGGAAGCGGAGGAGGCGGACAGTCCGTCAAGGAGAGC

GAGGGCGGTTTATTTAAGCCCACCGACACTTTAACTTTAACTTGTACAGTG

AGCGGCTTCTCTTTATCCAGACACGCTTTAACATGGGTGAGGCAAGCTCCC

GGTAATGGTTTAGAGTGGATCGGCGCCATCGACAACGCCGGCACCACCTAC

TACGCCAGCTGGGCCAAGTCTCGTTCCACCATCACAAGAAACACCGATTTA

CACACCGTGACTTTAAAGATGACCTCTTTAACCGCCTCCGACACCGCCACA

TACTTCTGCGCTCGTGTGTTCTACGACATCAATTCCGGCTACTATTTAGAC

GGCATGGATTTATGGGCCCCGGTACTTTAGTGACCGTCTCCAGC 0.410HC.410LC (SEQ ID NO: 73)
QFVLTQSPSVSAALGASAKLTCTLSSARKTYTIDWYQQQGEAPRYLMQVK

SDGSYTKGTGVPDRFSGSSSGADRYLIIPSVQADDEAGYVCGADDNGGYVF

GGGTQLTVTGGGSSRSSSSGGGGSGGGGQSVKESEGGLFKPTDTLTLTCTV

SGFSLSRHALTWVRQAPGNGLEWIGAIDNAGTTYYASWAKSRSTITRNTDL

HTVTLKMTSLTASDTATYFCARVFYDINSGYYLDGMDLWGPGTLVTVSS

1.H1.L3

(SEQ ID NO: 44)
CAGTCCGCTTTAACACAGCCCGCTTCTGTGTCCGGAAGCCCCGGTCAGAGC

ATCACCATCAGCTGCACCGGCACCAGCGCTCACAAGACCTACACCGTGAGC

TGGTACCAGCAGCACCCCGGTAAGGCCCCCAAACTGATGATCTACGTGAAG

AGCGACGGCAGCTACAACAGACCCAGCGGCGTGAGCAATCGTTTCAGCGGC

AGCAAGAGCGGCAACACCGCTTCTTTAACCATCAGCGGTTTACAAGCTGAA

GACGAGGCTGACTACTACTGCGGCGCCGACGATAACGGCGGCTACGTGTTT

GGCGGCGGCACCAAACTGACCGTGCTGGGAGGCGGCTCCAGCAGAAGCTCC

TCCAGCGGAGGAGGAGGAAGCGGAGGCGGAGGACAAGTTCAGCTGCAAGAA

AGCGGACCCGGTTTAGTCAAGCCCAGCGAGACTTTATCTTTAACATGCGCC

GTGAGCGGCTACTCCATCTCTCGTCACGCTTTAACATGGATTAGGCAGCCC

CCCGGTAAGGGTTTAGAATGGATCGGCGCCATCGACAACGCTGGCACCACC

TACTACGCCTCTTGGGCTAAGTCTCGTGTGACAATCAGCGTGGACACCTCC

AAGAACCAGTTTTCTTTAAAGCTGAGCAGCGTGACCGCTGCCGACACCGCT

GTGTACTATTGCGCTCGTGTCTTCTACGACATCAACAGCGGCTACTATTTA

GATGGCATGGATTTATGGGACCCGGTACTTTAGTGACCGTGAGCTCC

1.H1.L3

(SEQ ID NO: 74)
QSALTQPASVSGSPGQSITISCTGTSAHKTYTVSWYQQHPGKAPKLMIYVK

SDGSYNRPSGVSNRFSGSKSGNTASLTISGLQAEDEADYYCGADDNGGYVF

GGGTKLTVLGGGSSRSSSSGGGGSGGGGQVQLQESGPGLVKPSETLSLTCA

VSGYSISRHALTWIRQPPGKGLEWIGAIDNAGTTYYASWAKSRVTISVDTS

KNQFSLKLSSVTAADTAVYYCARVFYDINSGYYLDGMDLWGPGTLVTVSS

2.H1.L3m1

(SEQ ID NO: 45)
CAGTTCGTGCTGACCCAGCCCGCTTCTGTGAGCGGTTCTCCCGGTCAGAGC

ATCACCATCAGCTGCACTTTAAGCAGCGCCCACAAGACCTACACCATCGAC

TGGTACCAGCAGCACCCCGGCAAGGCCCCCAAGTATTTAATGCAAGTTAAG

TCCGACGGCAGCTACACCAAGGGCACCGGCGTGCCCAACAGATTCTCCGGC

AGCAGCTCCGGCGCCGACAGATACTTAACCATCAGCGGTTTACAAGCTGAG

GATGAGGCCGACTATGTGTGCGGCGCCGACGACAATGGCGGCTACGTGTTC

GGCGGCGGCACACAGCTGACCGTGACTGGTGGAGGCTCCAGCAGATCCAGC

TCCAGCGGCGGAGGAGGCAGCGGAGGCGGAGGACAAGTGCAGCTCCAAGAA

TCCGGCCCCGGTCTCGTGAAGCCCAGCGAGACTTTATCTTTAACTTGTGCC

GTGAGCGGCTACAGCATCTCTCGTCACGCTCTGACTTGGATTCGTCAACCT

CCCGGAAAGGGTTTAGAGTGGATCGGCGCCATCGACAACGCCGGCACCACC

TACTACGCCAGCTGGGCCAAATCTCGTGTGACCATTAGCGTGGACACCAGC

AAGAACCAGTTCTCTTTAAAACTGAGCAGCGTGACAGCTGCCGACACCGCC

GTGTACTACTGCGCTCGTGTGTTCTACGACATCAACAGCGGCTACTATTTA

GACGGCATGGATTTATGGGCCCCGGTACTTTAGTGACCGTCAGCTCC

2.H1.L3m1
(SEQ ID NO: 75)
QFVLTQPASVSGSPGQSITISCTLSSAHKTYTIDWYQQHPGKAPKYLMQVK
SDGSYTKGTVPNRFSGSSSGADRYLTISGLQAEDEADYVCGADDNGGYVF
GGGTQLTVTGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSSA
STKGPSVTS

3.H1m1.L3
(SEQ ID NO: 46)
CAGTCCGCTTTAACCCAGCCCGCCTCTGTGTCCGGAAGCCCCGGCCAGAGC
ATCACCATCAGCTGCACCGGCACCTCCGCCCACAAGACCTACACCGTGAGC
TGGTATCAGCAGCACCCCGGCAAGGCCCCCAAGCTCATGATCTACGTGAAG
AGCGACGGCTCCTACAATCGTCCCAGCGGAGTGAGCAATCGTTTCAGCGGC
TCCAAGTCCGGCAACACCGCCTCTTTAACCATTAGCGGTTTACAAGCTGAG
GACGAGGCTGATTACTACTGCGGCGCCGACGATAACGGAGGCTACGTGTTC
GGCGGCGGAACAAAGCTGACCGTGCTGGGCGGAGGCTCCAGCAGAAGCAGC
TCCAGCGGAGGCGGAGGAAGCGGAGGAGGAGGACAGCAGAGCGTGAAGGAG
AGCGGCCCCGGTCTGGTGAAGCCCAGCGAGACTTTATCTTTAACATGCGCC
GTGAGCGGCTTCTCTTTATCTCGTCACGCTTTAACTTGGGTGAGACAGCCT
CCCGGTAAAGGTTTAGAGTGGATCGGCGCCATCGACAACGCCGGCACAACC
TACTACGCCAGCTGGGCCAAGTCTCGTGTGACCATCTCTCGTAACACCGAT
TTACACACCGTGTCTTTAAAGCTGAGCTCCGTGACCGCTGCCGATACCGCC
GTGTACTTCTGCGCTAGGGTGTTCTACGACATCAACAGCGGCTACTATTTA
GATGGCATGGATCTGTGGGGCCCCGGCACACTGGTCACAGTGTCCAGC

3.H1m1.L3
(SEQ ID NO: 76)
QSALTQPASVSGSPGQSITISCTGTSAHKTYTVSWYQQHPGKAPKLMIYVK
SDGSYNRPSGVSNRFSGSKSGNTASLTISGLQAEDEADYYCGADDNGGYVF
GGGTKLTVLGGGSSRSSSSGGGGSGGGGQQSVKESGPGLVKPSETLSLTCA
VSGFSLSRHALTWVRQPPGKGLEWIGAIDNAGTTYYASWAKSRVTISRNTD
LHTVSLKLSSVTAADTAVYFCARVFYDINSGYYLDGMDLWGPGTLVTVSS

4.H1m1.L3m1
(SEQ ID NO: 47)
CAGTTCGTGCTGACCCAGCCCGCTTCCGTGAGCGGTTCTCCCGGACAGAGC
ATCACCATTAGCTGCACTTTAAGCAGCGCCCACAAGACCTACACCATCGAC
TGGTACCAGCAGCATCCCGGCAAGGCCCCCAAGTACCTCATGCAAGTTAAG
AGCGACGGAAGCTATACCAAGGGCACCGGAGTGCCCAACAGATTCAGCGGC
AGCAGCTCCGGAGCCGATCGTTATTTAACAATCAGCGGACTGCAAGCTGAG
GACGAGGCCGACTACGTGTGTGGCGCCGACGACAATGGCGGCTACGTGTTT
GGAGGCGGAACCCAGCTGACCGTGACTGGAGGCGGCAGCAGCAGAAGCAGC
AGCGGAGGAGGTGGCAGCGGCGGAGGCGGACAGCAGAGCGTGAAGGAG
AGCGGACCCGGTTTAGTGAAGCCTAGCGAGACTTTATCTTTAACATGCGCC
GTGTCCGGCTTCTCTTTAAGCAGACACGCTCTGACTTGGGTGAGGCAGCCT

CCCGGTAAGGGTTTAGAGTGGATCGGCGCCATCGACAACGCCGGCACCACC
TACTACGCCAGCTGGGCCAAGTCCAGAGTGACCATCTCCAGAAACACCGAC
CTCCACACAGTGTCTTTAAAGCTGTCCTCCGTCACAGCTGCCGACACCGCC
GTGTACTTCTGCGCTCGTGTGTTCTACGACATCAACAGCGGCTATTATTTA
GACGGCATGGATTTATGGGGCCCCGGTACTTTAGTGACCGTGAGCAGC

4.H1m1.L3m1
(SEQ ID NO: 77)
QFVLTQPASVSGSPGQSITISCTLSSAHKTYTIDWYQQHPGKAPKYLMQVK
SDGSYTKGTVPNRFSGSSSGADRYLTISGLQAEDEADYVCGADDNGGYVF
GGGTQLTVTGGGSSRSSSSGGGGSGGGGQQSVKESGPGLVKPSETLSLTCA
VSGFSLSRHALTWVRQPPGKGLEWIGAIDNAGTTYYASWAKSRVTISRNTD
LHTVSLKLSSVTAADTAVYFCARVFYDINSGYYLDGMDLWGPGTLVTVSS

5.H2.L2
(SEQ ID NO: 48)
CAGAGCGTGCTGACACAGCCTCCTAGCGCCAGCGGCACACCCGGTCAGAGA
GTGACCATCAGCTGCTCCGGCAGCAGCGCCCACAAGACCTACACCGTGAAC
TGGTACCAGCAGCTGCCCGGCACAGCCCCTAAGCTGCTGATCTACGTGAAA
TCCGACGGCAGCTACCAGAGGCCTAGCGGAGTGCCCGATCGTTTCAGCGGC
AGCAAAAGCGGCACAAGCGCCTCTTTAGCTATCAGCGGTTTACAGAGCGAG
GACGAGGCCGACTATTACTGCGGCGCCGACGATAACGGCGGCTACGTGTTC
GGCGGCGGAACCAAGCTGACAGTGCTGGGCGGCGGAAGCAGCAGAAGCAGC
AGCTCTGGAGGAGGAGGAAGCGGAGGTGGAGGCGAGGTGCAGCTGGTGGAA
AGCGGCGGAGGACTGGTGCAGCCCGGTGGCTCTTTAAGACTGAGCTGTGCT
GCCAGCGGCTTCACATTCTCTCGTCACGCTTTAACTTGGGTGAGACAAGCT
CCCGGAAAGGGTTTAGAATGGGTGAGCGCCATCGACAACGCCGGAACCACC
TACTACGCCAGCTGGGCCAAGTCTCGTTTCACCATCTCTCGTGATAACGCC
AAGAACAGCCTCTATTTACAGATGAACTCTTTAAGGGCCGAGGACACCGCC
GTGTACTACTGCGCTAGGGTGTTCTACGACATCAACAGCGGCTACTATCTG
GACGGCATGGATTTATGGGGCCCCGGTACACTGGTCACCGTGAGCAGC

5.H2.L2
(SEQ ID NO: 78)
QSVLTQPPSASGTPGQRVTISCSGSSAHKTYTVNWYQQLPGTAPKLLIYVK
SDGSYQRPSGVPDRFSGSKSGTSASLAISGLQSEDEADYYCGADDNGGYVF
GGGTKLTVLGGGSRSSSSGGGGSGGGGEVQLVESGGGLVQPGGSLRLSCAA
SGFTFSRHALTWVRQAPGKGLEWVSAIDNAGTTYYASWAKSRFTISRDNAK
NSLYLQMNSLRAEDTAVYYCARVFYDINSGYYLDGMDLWGPGTLVTVSS

6.H2.L2m1
(SEQ ID NO: 49)
CAGTTCGTGCTGACACAGCCTCCCAGCGCCTCTGGCACACCCGGTCAGAGG
GTGACCATCTCTTGTACTTTATCCTCCGCCCACAAGACCTACACCATTGAC
TGGTACCAGCAGCTGCCCGGTACCGCCCCTAAGCTGCTGATTTACGTGAAA
TCCGACGGCAGCTACACCAAGGGAACCGGCGTGCCCGATCGTTTTTCCGGC
AGCTCCAGCGGCGCCGATAGGTATTTAGCCATCAGCGGTTTACAGTCCGAG
GATGAGGCCGACTACTACTGCGGCGCCGATGACAACGGCGGCTACGTGTTC
GGCGGAGGAACCCAGCTCACCGTGACCGGAGGAGGCTCCTCTCGTAGCTCC

```
AGCTCCGGAGGAGGAGGAAGCGGAGGCGGCGGAGAAGTGCAACTGGTGGAG
TCCGGCGGCGGACTGGTGCAGCCCGGTGGCTCTTTAAGACTGAGCTGTGCC
GCCTCCGGCTTCACCTTTAGCAGACACGCCCTCACTTGGGTCAGACAAGCT
CCCGGTAAGGGTTTAGAGTGGGTGAGCGCCATCGACAACGCCGGCACAACC
TACTACGCCTCTTGGGCCAAGTCTCGTTTCACCATCAGCAGAGACAACGCC
AAGAACTCTTTATATTTACAGATGAACTCTTTAAGGGCCGAGGACACCGCC
GTGTACTACTGCGCTCGTGTGTTCTACGACATCAACAGCGGCTATTATTTA
GATGGCATGGATTTATGGGGCCCCGGTACTTTAGTGACAGTGTCCTCC

6.H2.L2m1
                                            (SEQ ID NO: 79)
QFVLTQPPSASGTPGQRVTISCTLSSAHKTYTIDWYQQLPGTAPKLLIYVK
SDGSYTKGTVPDRFSGSSSGADRYLAISGLQSEDEADYYCGADDNGGYVF
GGGTQLTVTGGGSSRSSSSGGGGSGGGGEVQLVESGGGLVQPGGSLRLSCA
ASGFTFSRHALTWVRQAPGKGLEWVSAIDNAGTTYYASWAKSRFTISRDNA
KNSLYLQMNSLRAEDTAVYYCARVFYDINSGYYLDGMDLWGPGTLVTVSS

7.H2m1.L2
                                            (SEQ ID NO: 50)
CAGAGCGTGCTGACCCAGCCTCCTAGCGCCTCTGGCACACCCGGTCAGAGG
GTGACCATCAGCTGCTCCGGCTCCTCCGCCCACAAGACCTACACCGTGAAC
TGGTACCAGCAGCTGCCCGGTACCGCTCCCAAGCTGCTGATTTACGTGAAA
AGCGACGGCAGCTACCAGAGACCTAGCGGCGTGCCCGATCGTTTCTCCGGT
TCTAAGAGCGGCACCAGCGCCTCTTTAGCCATTAGCGGCCTCCAGAGCGAG
GACGAGGCCGATTACTACTGCGGAGCCGACGACAATGGCGGCTACGTGTTC
GGCGGCGGAACAAAGCTGACCGTTTTAGGTGGCGGAAGCAGCAGAAGCAGC
AGCTCTGGCGGCGGCGGTAGCGGCGGTGGCGGAGAGCAGAGCGTCAAGGAG
TCCGGAGGAGGACTGGTGCAGCCCGGTGGCTCTTTAAGGCTGAGCTGTGCC
GCCTCTGGCTTTACTTTATCTCGTCACGCTTTAACATGGGTGAGACAAGCT
CCCGGTAAGGGACTGGAGTGGATCGGCGCCATCGACAACGCCGGCACCACC
TACTACGCCTCTTGGGCCAAGTCTCGTTTCACCATCTCTCGTAACACCGAT
TTACACACCGTGTATTTACAGATGAATCTCTTTAAGGGCCGAGGACACAGCC
GTCTATTTCTGCGCTCGTGTGTTCTACGACATCAATAGCGGCTACTACCTC
GACGGAATGGATCTGTGGGGCCCCGGTACTTTAGTGACAGTCAGCAGC

7.H2m1.L2
                                            (SEQ ID NO: 80)
QSVLTQPPSASGTPGQRVTISCSGSSAHKTYTVNWYQQLPGTAPKLLIYVK
SDGSYQRPSGVPDRFSGSKSGTSASLAISGLQSEDEADYYCGADDNGGYVF
GGGTKLTVLGGGSSRSSSSGGGGSGGGGEQSVKESGGGLVQPGGSLRLSCA
ASGFTLSRHALTWVRQAPGKGLEWIGAIDNAGTTYYASWAKSRFTISRNTD
LHTVYLQMNSLRAEDTAVYFCARVFYDINSGYYLDGMDLWGPGTLVTVSS

8.H2m1.L2m1
                                            (SEQ ID NO: 51)
CAGTTTGTTTTAACCCAGCCTCCTAGCGCCTCTGGAACACCCGGCCAAAGG
GTCACCATCAGCTGCACTTTATCCTCCGCCCACAAGACCTACACCATCGAC
TGGTACCAGCAGCTGCCCGGAACCGCCCCTAAGCTGCTGATCTACGTGAAG
AGCGACGGCAGCTACACCAAGGGCACCGGCGTGCCCGATAGGTTCAGCGGC
AGCAGCAGCGGCGCCGATAGATATTTAGCCATTTCCGGTTTACAGAGCGAG
GACGAGGCCGATTACTACTGTGGCGCTGACGACAACGGAGGCTACGTGTTC
GGAGGCGGCACCCAGCTGACCGTGACTGGTGGCGGTTCTAGCAGAAGCAGC
AGCTCCGGAGGCGGAGGCTCTGGCGGCGGTGGCGAGCAGTCCGTGAAGGAA
AGCGGCGGCGGACTGGTGCAGCCCGGTGGATCTTTAAGACTGAGCTGCGCC
GCCTCTGGCTTCACTTTATCCAGACATGCTTTAACATGGGTGAGACAAGCT
CCCGGCAAGGGACTGGAGTGGATCGGCGCCATCGACAACGCCGGCACCACC
TACTACGCCAGCTGGGCCAAATCTCGTTTCACCATCTCTCGTAACACCGAT
TTACACACCGTGTATTTACAGATGAATTCTTTAAGGGCCGAGGACACCGCC
GTGTACTTCTGCGCTCGTGTGTTCTACGACATCAACAGCGGCTACTATTTA
GACGGCATGGATTTATGGGGACCCGGTACACTCGTGACCGTGTCCAGC

8.H2m1.L2m1
                                            (SEQ ID NO: 81)
QFVLTQPPSASGTPGQRVTISCTLSSAHKTYTIDWYQQLPGTAPKLLIYVK
SDGSYTKGTVPDRFSGSSSGADRYLAISGLQSEDEADYYCGADDNGGYVF
GGGTQLTVTGGGSSRSSSSGGGGSGGGGEQSVKESGGGLVQPGGSLRLSCA
ASGFTLSRHALTWVRQAPGKGLEWIGAIDNAGTTYYASWAKSRFTISRNTD
LHTVYLQMNSLRAEDTAVYFCARVFYDINSGYYLDGMDLWGPGTLVTVSS

9.H2.L1
                                            (SEQ ID NO: 52)
CAGCTGGTGCTGACCCAGAGCCCCAGCGCTTCCGCCTCTTTAGGAGCCAGC
GTGAAGCTGACTTGTACTTTAAGCAGCGCCCACAAGACCTACACAATCGCT
TGGCACCAGCAGCAGCCCGAAAAGGGCCCCAGATATCTGATGAAGGTCAAG
TCCGACGGCAGCTACTCCAAGGGCGACGGCATCCCCGATCGTTTCAGCGGT
TCTTCCAGCGGCGCCGAGAGGTATTTAACCATCAGCTCTTTACAGAGCGAG
GACGAGGCCGACTACTACTGCGGCGCTGACGACAACGGCGGCTACGTCTTT
GGCGGCGGCACAAAACTGACCGTGCTGGGCGGCGGAAGCAGCAGAAGCTCC
AGCTCTGGAGGAGGAGGTTCTGGAGGTGGAGGAGAGGTGCAGCTGGTGGAG
AGCGGCGGAGGACTGGTGCAGCCCGGTGGATCTTTAAGACTGAGCTGTGCC
GCCAGCGGCTTCACCTTCTCTGTCACGCTCTGACATGGGTGAGGCAAGCC
CCCGGTAAGGGTTTAGAATGGGTGAGCGCCATCGACAATGCCGGAACCACC
TATTACGCCTCTTGGGCCAAGTCTCGTTTCACCATCTCTCGTGACAATGCC
AAGAACTCTTTATATTTACAGATGAACTCTTTAAGAGCTGAGGACACCGCC
GTCTACTACTGCGCCAGAGTGTTCTACGACATCAACAGCGGCTACTACCTC
GACGGCATGGATTTATGGGGCCCCGGTACTTTAGTGACCGTGAGCAGC

9.H2.L1
                                            (SEQ ID NO: 82)
QLVLTQSPSASASLGASVKLTCTLSSAHKTYTIAWHQQQPEKGPRYLMKVK
SDGSYSKGDGIPDRFSGSSSGAERYLTISSLQSEDEADYYCGADDNGGYVF
GGGTKLTVLGGGSRSSSSGGGGSGGGGEVQLVESGGGLVQPGGSLRLSCA
ASGFTFSRHALTWVRQAPGKGLEWVSAIDNAGTTYYASWAKSRFTISRDNA
KNSLYLQMNSLRAEDTAVYYCARVFYDINSGYYLDGMDLWGPGTLVTVSS
```

10.H2.L1m1

(SEQ ID NO: 53)
CAGTTTGTGCTGACCCAGAGCCCTAGCGCTTCCGCCTCTTTAGGAGCCAGC

GTGAAGCTGACTTGTACTTTATCCTCCGCCCACAAGACCTACACCATCGAC

TGGTACCAGCAGCAGCCCGAAAAGGGCCCTCGTTATCTGATGCAAGTTAAG

TCCGACGGCAGCTACACCAAGGGAACCGGCGTGCCCGACAGATTCTCCGGT

AGCAGCAGCGGCGCCGACAGATATTTAACCATCAGCTCTTTACAGTCCGAG

GACGAGGCCGACTACTACTGCGGCGCCGACGACAATGGCGGCTACGTCTTC

GGAGGCGGCACACAGCTGACCGTGACTGGTGGAGGCTCCTCCAGAAGCAGC

TCTAGCGGAGGAGGAGGAAGCGGCGGAGGAGGCGAAGTGCAGCTGGTGGAG

TCCGAGGAGGACTGGTGCAGCCCGGAGGTTCTTTAAGACTGAGCTGCGCC

GCCTCCGGCTTCACCTTTTCTCGTCACGCTTTAACATGGGTGAGACAAGCT

CCCGGCAAGGGACTGGAATGGGTCAGCGCCATCGATAACGCCGGCACCACC

TATTACGCCAGCTGGGCTAAGTCTCGTTTCACCATCAGCAGAGACAACGCC

AAGAACTCTTTATATTTACAGATGAATTCTTTAAGAGCCGAGGACACCGCC

GTGTATTACTGCGCTCGTGTCTTCTACGACATCAACTCCGGCTACTATTTA

GACGGCATGGATTTATGGGGCCCCGGTACTTTAGTCACCGTGAGCTCC

10.H2.L1m1

(SEQ ID NO: 83)
QFVLTQSPSASASLGASVKLTCTLSSAHKTYTIDWYQQQPEKGPRYLMQVK

SDGSYTKGTGVPDRFSGSSSGADRYLTISSLQSEDEADYYCGADDNGGYVF

GGGTQLTVTGGGSSRSSSSGGGGSGGGGEVQLVESGGGLVQPGGSLRLSCA

ASGFTFSRHALTWVRQAPGKGLEWVSAIDNAGTTYYASWAKSRFTISRDNA

KNSLYLQMNSLRAEDTAVYYCARVFYDINSGYYLDGMDLWGPGTLVTVSS

11.H2m1.L1

(SEQ ID NO: 54)
CAGCTGGTGCTGACACAGAGCCCCTCCGCCTCCGCCTCTTTAGGCGCTTCC

GTGAAGCTGACTTGTACTTTATCCAGCGCCCACAAGACCTACACCATCGCT

TGGCACCAGCAGCAGCCCGAGAAAGGCCCTCGTTACCTCATGAAAGTGAAG

TCCGACGGCAGCTACTCCAAGGGCGACGGCATCCCCGATCGTTTTAGCGGC

AGCAGCTCCGGCGCCGAGAGGTATTTAACCATCAGCTCTTTACAGAGCGAA

GACGAGGCCGACTATTACTGCGGCGCCGATGACAACGGAGGCTACGTGTTC

GGCGGAGGCACCAAACTGACCGTGCTGGGCGGCGGAAGCAGCAGAAGCTCC

AGCAGCGGAGGAGGAGGTTCTGGAGGAGGCGGAGAGCAGAGCGTGAAAGAG

TCCGGCGGAGGTTTAGTGCAGCCCGGTGGTTCTTTAAGACTGAGCTGCGCC

GCCAGCGGCTTCACACTGTCCAGACACGCTTTAACATGGGTGAGACAAGCT

CCCGGTAAGGGACTGGAGTGGATCGGCGCCATCGACAATGCCGGCACCACC

TACTACGCCAGCTGGGCCAAGTCTCGTTTCACCATCTCTCGTAACACCGAT

TTACACACCGTCTATTTACAGATGAACTCTTTAAGGGCCGAGGACACAGCC

GTGTACTTTTGCGCTCGTGTGTTCTACGACATCAACAGCGGCTACTATTTA

GACGGCATGGATCTGTGGGGCCCCGGAACACTGGTGACCGTGAGCAGC

11.H2m1.L1

(SEQ ID NO: 84)
QLVLTQSPSASASLGASVKLTCTLSSAHKTYTIAWHQQQPEKGPRYLMKVK

SDGSYSKGDGIPDRFSGSSSGAERYLTISSLQSEDEADYYCGADDNGGYVF

GGGTKLTVLGGGSSRSSSSGGGGSGGGGEQSVKESGGGLVQPGGSLRLSCA

ASGFTLSRHALTWVRQAPGKGLEWIGAIDNAGTTYYASWAKSRFTISRNTD

LHTVYLQMNSLRAEDTAVYFCARVFYDINSGYYLDGMDLWGPGTLVTVSS

12.H2m1.L1m1

(SEQ ID NO: 55)
CAGTTTGTGCTGACCCAGTCCCCTAGCGCCTCTGCCTCTTTAGGAGCCTCT

GTGAAACTGACTTGTACTTTAAGCAGCGCCCACAAGACATACACCATCGAC

TGGTACCAGCAGCAGCCCGAAAAGGGCCCTAGGTATTTAATGCAAGTTAAG

AGCGACGGCAGCTACACAAAGGGCACTGGTGTGCCCGACAGATTCAGCGGC

AGCAGCAGCGGCGCCGACAGATACCTCACCATCAGCTCTTTACAGTCCGAG

GACGAGGCCGACTACTATTGCGGCGCCGACGACAACGGCGGCTACGTGTTC

GGCGGAGGAACCCAGCTGACCGTGACTGGTGGCGGAAGCAGCAGAAGCAGC

TCCTCCGGAGGCGGAGGTTCTGGCGGAGGTGGAGAACAGAGCGTGAAGGAG

AGCGGAGGTGGACTGGTGCAGCCCGGTGGTTCTTTAAGACTGAGCTGCGCT

GCCTCCGGCTTCACCTTATCTCGTCACGCTTTAACATGGGTGAGACAAGCT

CCCGGTAAGGGTTTAGAGTGGATCGGCGCCATCGACAATGCTGGCACCACC

TACTACGCCAGCTGGGCCAAGTCTCGTTTCACAATCTCTCGTAACACCGAT

CTGCACACCGTGTATTTACAGATGAACTCTTTAAGAGCCGAGGACACCGCC

GTGTATTTCTGCGCTCGTGTGTTCTACGACATCAACAGCGGCTACTATTTA

GACGGCATGGATTTATGGGGCCCCGGTACTTTAGTGACCGTGAGCTCC

12.H2m1.L1m1

(SEQ ID NO: 85)
QFVLTQSPSASASLGASVKLTCTLSSAHKTYTIDWYQQQPEKGPRYLMQVK

SDGSYTKGTGVPDRFSGSSSGADRYLTISSLQSEDEADYYCGADDNGGYVF

GGGTQLTVTGGGSSRSSSSGGGGSGGGGEQSVKESGGGLVQPGGSLRLSCA

ASGFTLSRHALTWVRQAPGKGLEWIGAIDNAGTTYYASWAKSRFTISRNTD

LHTVYLQMNSLRAEDTAVYFCARVFYDINSGYYLDGMDLWGPGTLVTVSS

13.H1.L1

(SEQ ID NO: 56)
CAGCTCGTGCTGACCCAGTCCCCCAGCGCCTCTGCCTCTTTAGGCGCCAGC

GTGAAGCTGACTTGTACTTTATCCAGCGCCCACAAGACATACACCATCGCT

TGGCACCAGCAGCAGCCCGAAAAGGGCCCTCGTTATTTAATGAAGGTCAAG

TCCGACGGCTCCTACTCCAAGGGCGACGGCATCCCCGATAGATTCAGCGGT

AGCAGCAGCGGCGCCGAGAGATATTTAACAATCAGCTCTTTACAGAGCGAG

GACGAGGCCGACTACTACTGCGGCGCCGACGACAATGGCGGCTACGTCTTC

GGCGGCGGAACCAAGCTCACAGTGCTGGGTGGAGGCTCCAGCAGAAGCAGC

TCTAGCGGAGGCGGAGGTTCCGGCGGCGGAGGCCAAGTTCAGCTGCAAGAA

TCCGGCCCCGGACTGGTGAAGCCCTCCGAAACACTGTCTTTAACATGCGCC

GTGAGCGGCTACAGCATTTCTCGTCACGCTTTAACTTGGATCAGACAGCCC

CCCGGCAAGGGTTTAGAATGGATCGGAGCCATCGATAACGCCGGCACCACA

TACTACGCCAGCTGGGCCAAGAGCAGAGTGACCATCTCCGTGGACACCAGC
AAGAACCAGTTTTCTTTAAAGCTCAGCTCCGTGACCGCCGCCGATACAGCC
GTGTACTACTGCGCCAGAGTGTTCTACGACATCAACAGCGGCTACTATTTA
GACGGAATGGATTTATGGGGCCCCGGTACTTTAGTGACCGTGAGCAGC

13.H1.L1
(SEQ ID NO: 86)
QLVLTQSPSASASLGASVKLTCTLSSAHKTYTIAWHQQQPEKGPRYLMKVK
SDGSYSKGDGIPDRFSGSSSGAERYLTISSLQSEDEADYYCGADDNGGYVF
GGGTKLTVLGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS

14.H1.L1m1
(SEQ ID NO: 57)
CAGTTTGTGCTCACCCAAAGCCCTAGCGCCTCTGCCTCTTTAGGCGCTTCC
GTGAAGCTGACTTGTACTTTAAGCTCCGCCCATAAGACCTACACCATCGAC
TGGTACCAGCAGCAGCCCGAGAAGGGCCCTCGTTATTTAATGCAAGTTAAG
TCCGATGGCAGCTATACCAAGGGCACCGGCGTGCCCGACAGATTCAGCGGC
AGCTCCAGCGGAGCCGATCGTTATTTAACCATCAGCTCTTTACAGAGCGAG
GACGAGGCTGACTACTACTGCGGCGCCGACGATAACGGCGGCTACGTGTTC
GGCGGCGGCACCCAACTGACAGTGACCGGAGGCGGTTCTTCTCGTAGCAGC
AGCAGCGGAGGCGGCGGCTCCGGCGGCGGAGGCCAAGTTCAGCTGCAAGAA
TCCGGCCCCGGTCTGGTGAAACCCAGCGAGACTTTATCTTTAACATGCGCC
GTGAGCGGCTACTCCATCTCCAGACACGCTTTAACTTGGATCAGACAGCCT
CCCGGCAAGGGACTGGAGTGGATCGGCGCTATCGACAACGCCGGCACCACC
TACTACGCCTCTTGGGCCAAGTCTCGTGTCACCATCAGCGTGGACACATCC
AAGAACCAGTTCTCTTTAAAGCTGTCCAGCGTGACCGCCGCCGATACAGCC
GTGTACTACTGCGCTCGTGTGTTCTACGACATCAACTCCGGCTACTATTTA
GACGGCATGGATTTATGGGGACCCGGTACTTTAGTGACCGTGTCCAGC

14.H1.L1m1
(SEQ ID NO: 87)
QFVLTQSPSASASLGASVKLTCTLSSAHKTYTIDWYQQQPEKGPRYLMQVK
SDGSYTKGTGVPDRFSGSSSGADRYLTISSLQSEDEADYYCGADDNGGYVF
GGGTQLTVTGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS

15.H1m1.L1
(SEQ ID NO: 58)
CAGCTGGTGCTGACACAAAGCCCCAGCGCCAGCGCCTCTTTAGGCGCCAGC
GTCAAACTGACATGCACTTTAAGCAGCGCCCACAAGACCTACACCATCGCT
TGGCACCAGCAGCAGCCCGAGAAGGGCCCCAGATATTTAATGAAGGTGAAG
TCCGATGGCAGCTACAGCAAGGGAGATGGCATTCCCGATCGTTTTAGCGGC
TCCTCCAGCGGCGCCGAGAGATACTTAACCATCTCCTCTTTACAGAGCGAG
GACGAGGCCGACTACTACTGCGGCGCCGATGACAACGGCGGCTACGTGTTC
GGCGGCGGAACCAAGCTGACCGTGCTGGGCGGAGGCAGCTCCAGATCCAGC
AGCAGCGGCGGAGGAGGAAGCGGAGGAGGCGGACAGCAGTCCGTGAAAGAG

AGCGGCCCCGGTTTAGTGAAACCCAGCGAGACTTTATCTTTAACTTGTGCC
GTGAGCGGCTTCAGCCTCTCTCGTCACGCTTTAACTTGGGTGAGACAGCCT
CCCGGCAAAGGTTTAGAGTGGATTGGCGCCATCGACAACGCCGGCACCACC
TACTACGCCAGCTGGGCCAAATCTCGTGTGACCATTTCCAGAAACACCGAT
TTACACACCGTGTCTTTAAAGCTGTCCAGCGTGACCGCCGCTGACACCGCT
GTCTACTTCTGCGCTCGTGTGTTCTACGACATCAACTCCGGCTACTATTTA
GACGGCATGGATTTATGGGGCCCCGGTACTTTAGTGACCGTGAGCTCC

15.H1m1.L1
(SEQ ID NO: 88)
QLVLTQSPSASASLGASVKLTCTLSSAHKTYTIAWHQQQPEKGPRYLMKVK
SDGSYSKGDGIPDRFSGSSSGAERYLTISSLQSEDEADYYCGADDNGGYVF
GGGTKLTVLGGGSSRSSSSGGGGSGGGGQQSVKESGPGLVKPSETLSLTCA
VSGFSLSRHALTWVRQPPGKGLEWIGAIDNAGTTYYASWAKSRVTISRNTD
LHTVSLKLSSVTAADTAVYFCARVFYDINSGYYLDGMDLWGPGTLVTVSS

16.H1m1.L1m1
(SEQ ID NO: 59)
CAGTTCGTGCTCACACAGAGCCCTAGCGCTTCCGCCTCTTTAGGAGCCAGC
GTGAAACTGACATGTACTTTAAGCAGCGCCCACAAAACCTACACCATCGAC
TGGTACCAGCAGCAACCCGAGAAGGGCCCTAGATATTTAATGCAAGTTAAG
AGCGACGGCTCCTACACCAAAGGCACCGGCGTGCCCGATAGGTTCAGCGGC
TCCTCCTCCGGAGCCGATCGTTATTTAACAATCAGCTCTTTACAGAGCGAA
GACGAGGCCGATTACTACTGCGGAGCCGATGACAACGGCGGCTACGTCTTC
GGAGGCGGAACCCAGCTGACAGTGACCGGAGGCGGCAGCAGCAGATCCAGC
AGCTCCGGAGGCGGAGGAAGCGGAGGAGGCGGCCAGCAAAGCGTGAAGGAG
AGCGGCCCCGGACTCGTGAAACCCTCCGAGACTTTATCTTTAACTTGTGCC
GTGAGCGGCTTCTCTTTATCTCGTCACGCTTTAACATGGGTGAGGCAGCCT
CCCGGTAAGGGTTTAGAGTGGATCGGCGCCATCGACAACGCCGGCACAACC
TACTACGCCAGCTGGGCCAAGAGCAGAGTGACCATCTCTCGTAACACCGAT
TTACACACCGTGTCTTTAAAGCTGAGCTCCGTGACCGCCGCCGATACCGCT
GTGTACTTCTGCGCTCGTGTCTTCTACGACATCAACTCCGGCTATTACCTC
GACGGCATGGATCTGTGGGGCCCCGGAACACTGGTGACCGTGAGCAGCG

16.H1m1.L1m1
(SEQ ID NO: 89)
QFVLTQSPSASASLGASVKLTCTLSSAHKTYTIDWYQQQPEKGPRYLMQVK
SDGSYTKGTGVPDRFSGSSSGADRYLTISSLQSEDEADYYCGADDNGGYVF
GGGTQLTVTGGGSRSSSSGGGGSGGGGQQSVKESGPGLVKPSETLSLTCA
VSGFSLSRHALTWVRQPPGKGLEWIGAIDNAGTTYYASWAKSRVTISRNTD
LHTVSLKLSSVTAADTAVYFCARVFYDINSGYYLDGMDLWGPGTLVTVSS

17.H1.L3m2
(SEQ ID NO: 60)
CAGTTCGTGCTGACCCAGCCCGCTTCTGTGAGCGGTTCTCCCGGTCAGAGC
ATCACCATCAGCTGCACTTTAAGCAGCGCCCACAAGACCTACACCATCGAC
TGGTACCAGCAGCACCCCGGCAAGGCCCCCAAGCTGATGATCCAAGTTAAG
TCCGACGGCAGCTACACCAAGGGCACCGGCGTGAGCAACAGATTCTCCGGC

```
AGCAGCTCCGGCGCCGACAGATACTTAACCATCAGCGGTTTACAAGCTGAG
GATGAGGCCGACTATTACTGCGGCGCCGACGACAATGGCGGCTACGTGTTC
GGCGGCGGCACACAGCTGACCGTGCTGGGTGGAGGCTCCAGCAGATCCAGC
TCCAGCGGCGGAGGAGGCAGCGGAGGCGGAGGACAAGTGCAGCTCCAAGAA
TCCGGCCCCGGTCTCGTGAAGCCCAGCGAGACTTTATCTTTAACTTGTGCC
GTGAGCGGCTACAGCATCTCTCGTCACGCTCTGACTTGGATTCGTCAACCT
CCCGGAAAGGGTTTAGAGTGGATCGGCGCCATCGACAACGCCGGCACCACC
TACTACGCCAGCTGGGCCAAATCTCGTGTGACCATTAGCGTGGACACCAGC
AAGAACCAGTTCTCTTTAAAACTGAGCAGCGTGACAGCTGCCGACACCGCC
GTGTACTACTGCGCTCGTGTGTTCTACGACATCAACAGCGGCTACTATTTA
GACGGCATGGATTTATGGGGCCCCGGTACTTTAGTGACCGTCAGCTCC
```

17.H1.L3m2
(SEQ ID NO: 90)
```
QFVLTQPASVSGSPGQSITISCTLSSAHKTYTIDWYQQHPGKAPKLMIQVK
SDGSYTKGTGVSNRFSGSSSGADRYLTISGLQAEDEADYYCGADDNGGYVF
GGGTQLTVLGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS
```

18.H1.L3m3
(SEQ ID NO: 61)
```
CAGAGCGCCCTGACCCAGCCCGCTTCTGTGAGCGGTTCTCCCGGTCAGAGC
ATCACCATCAGCTGCACTGGCACCAGCGCCCACAAGACCTACACCATCGAC
TGGTACCAGCAGCACCCCGGCAAGGCCCCCAAGCTGATGATCTATGTTAAG
TCCGACGGCAGCTACACCAAGGGCACCGGCGTGAGCAACAGATTCTCCGGC
AGCAAGTCCGGCAACACCGCCAGCTTAACCATCAGCGGTTTACAAGCTGAG
GATGAGGCCGACTATTACTGCGGCGCCGACGACAATGGCGGCTACGTGTTC
GGCGGCGGCACACAGCTGACCGTGCTGGGTGGAGGCTCCAGCAGATCCAGC
TCCAGCGGCGGAGGAGGCAGCGGAGGCGGAGGACAAGTGCAGCTCCAAGAA
TCCGGCCCCGGTCTCGTGAAGCCCAGCGAGACTTTATCTTTAACTTGTGCC
GTGAGCGGCTACAGCATCTCTCGTCACGCTCTGACTTGGATTCGTCAACCT
CCCGGAAAGGGTTTAGAGTGGATCGGCGCCATCGACAACGCCGGCACCACC
TACTACGCCAGCTGGGCCAAATCTCGTGTGACCATTAGCGTGGACACCAGC
AAGAACCAGTTCTCTTTAAAACTGAGCAGCGTGACAGCTGCCGACACCGCC
GTGTACTACTGCGCTCGTGTGTTCTACGACATCAACAGCGGCTACTATTTA
GACGGCATGGATTTATGGGGCCCCGGTACTTTAGTGACCGTCAGCTCC
```

18.H1.L3m3
(SEQ ID NO: 91)
```
QSALTQPASVSGSPGQSITISCTGTSAHKTYTIDWYQQHPGKAPKLMIYVK
SDGSYTKGTGVSNRFSGSKSGNTASLTISGLQAEDEADYYCGADDNGGYVF
GGGTQLTVLGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS
```

19.H2.L2m2
(SEQ ID NO: 62)
```
CAGTTCGTGCTGACACAGCCTCCCAGCGCCTCTGGCACACCCGGTCAGAGG
GTGACCATCTCTTGTACTTTATCCTCCGCCCACAAGACCTACACCATTGAC
TGGTACCAGCAGCTGCCCGGTACCGCCCCTAAGCTGCTGATTTACGTGAAA
TCCGACGGCAGCTACACCAAGGGAACCGGCGTGCCCGATCGTTTTTCCGGC
AGCTCCAGCGGCGCCGATGCCAGCTTAGCCATCAGCGGTTTACAGTCCGAG
GATGAGGCCGACTACTACTGCGGCGCCGATGACAACGGCGGCTACGTGTTC
GGCGGAGGAACCCAGCTCACCGTGCTGGGAGGAGGCTCCTCTCGTAGCTCC
AGCTCCGGAGGAGGAAGCGGAGGCGGCGGAGAAGTGCAACTGGTGGAG
TCCGGCGGCGGACTGGTGCAGCCCGGTGGCTCTTTAAGACTGAGCTGTGCC
GCCTCCGGCTTCACCTTTAGCAGACACGCCCTCACTTGGGTCAGACAAGCT
CCCGGTAAGGGTTTAGAGTGGGTGAGCGCCATCGACAACGCCGGCACAACC
TACTACGCCCTTGGGCCAAGTCTCGTTTCACCATCAGCAGAGACAACGCC
AAGAACTCTTTATATTTACAGATGAACTCTTTAAGGGCCGAGGACACCGCC
GTGTACTACTGCGCTCGTGTGTTCTACGACATCAACAGCGGCTATTATTTA
GATGGCATGGATTTATGGGGCCCCGGTACTTTAGTGACAGTGTCCTCC
```

19.H2.L2m2
(SEQ ID NO: 92)
```
QFVLTQPPSASGTPGQRVTISCTLSSAHKTYTIDWYQQLPGTAPKLLIYVK
SDGSYTKGTGVPDRFSGSSSGADASLAISGLQEDEADYYCGADDNGGYVFG
GGTQLTVLGGGSSRSSSSGGGGSGGGGEVQLVESGGGLVQPGGSLRLSCAA
SGFTFSRHALTWVRQAPGKGLEWVSAIDNAGTTYYASWAKSRFTISRDNAK
NSLYLQMNSLRAEDTAVYYCARVFYDINSGYYLDGMDLWGPGTLVTVSS
```

20.H2.L2m3
(SEQ ID NO: 63)
```
CAGAGCGTGCTGACACAGCCTCCCAGCGCCTCTGGCACACCCGGTCAGAGG
GTGACCATCTCTTGTACTTTATCCTCCGCCCACAAGACCTACACCATTGAC
TGGTACCAGCAGCTGCCCGGTACCGCCCCTAAGCTGCTGATTTACGTGAAA
TCCGACGGCAGCTACACCAAGGGAACCGGCGTGCCCGATCGTTTTTCCGGC
AGCAAGAGCGGCACCAGCGCCAGCTTAGCCATCAGCGGTTTACAGTCCGAG
GATGAGGCCGACTACTACTGCGGCGCCGATGACAACGGCGGCTACGTGTTC
GGCGGAGGAACCCAGCTCACCGTGCTGGGAGGAGGCTCCTCTCGTAGCTCC
AGCTCCGGAGGAGGAAGCGGAGGCGGCGGAGAAGTGCAACTGGTGGAG
TCCGGCGGCGGACTGGTGCAGCCCGGTGGCTCTTTAAGACTGAGCTGTGCC
GCCTCCGGCTTCACCTTTAGCAGACACGCCCTCACTTGGGTCAGACAAGCT
CCCGGTAAGGGTTTAGAGTGGGTGAGCGCCATCGACAACGCCGGCACAACC
TACTACGCCCTTGGGCCAAGTCTCGTTTCACCATCAGCAGAGACAACGCC
AAGAACTCTTTATATTTACAGATGAACTCTTTAAGGGCCGAGGACACCGCC
GTGTACTACTGCGCTCGTGTGTTCTACGACATCAACAGCGGCTATTATTTA
GATGGCATGGATTTATGGGGCCCCGGTACTTTAGTGACAGTGTCCTCC
```

20.H2.L2m3

(SEQ ID NO: 93)
QSVLTQPPSASGTPGQRVTISCTLSSAHKTYTIDWYQQLPGTAPKLLIYVK
SDGSYTKGTGVPDRFSGSKSGTSASLAISGLQSEDEADYYCGADDNGGYVF
GGGTQLTVLGGGSSRSSSSGGGGSGGGGEVQLVESGGGLVQPGGSLRLSCA
ASGFTFSRHALTWVRQAPGKGLEWVSAIDNAGTTYYASWAKSRFTISRDNA
KNSLYLQMNSLRAEDTAVYYCARVFYDINSGYYLDGMDLWGPGTLVTVSS

21.H2.L1m2

(SEQ ID NO: 64)
CAGTTTGTGCTGACCCAGAGCCCTAGCGCTTCCGCCTCTTTAGGAGCCAGC
GTGAAGCTGACTTGTACTTTATCCTCCGCCCACAAGACCTACACCATCGAC
TGGCACCAGCAGCAGCCCGAAAAGGGCCCTCGTTATCTGATGCAAGTTAAG
TCCGACGGCAGCTACACCAAGGGAACCGGCATCCCCGACAGATTCTCCGGT
AGCAGCAGCGGCGCCGAGAGATATTTAACCATCAGCTCTTTACAGTCCGAG
GACGAGGCCGACTACTACTGCGGCGCCGACGACAATGGCGGCTACGTCTTC
GGAGGCGGCACACAGCTGACCGTGCTGGGTGGAGGCTCCTCCAGAAGCAGC
TCTAGCGGAGGAGGAGGAAGCGGCGGAGGAGGCGAAGTGCAGCTGGTGGAG
TCCGGAGGAGGACTGGTGCAGCCCGGAGGTTCTTTAAGACTGAGCTGCGCC
GCCTCCGGCTTCACCTTTTCTCGTCACGCTTTAACATGGGTGAGACAAGCT
CCCGGCAAGGGACTGGAATGGGTCAGCGCCATCGATAACGCCGGCACCACC
TATTACGCCAGCTGGGCTAAGTCTCGTTTCACCATCAGCAGAGACAACGCC
AAGAACTCTTTATATTTACAGATGAATTCTTTAAGAGCCGAGGACACCGCC
GTGTATTACTGCGCTCGTGTCTTCTACGACATCAACTCCGGCTACTATTTA
GACGGCATGGATTTATGGGGCCCCGGTACTTTAGTCACCGTGAGCTCC

21.H2.L1m2

(SEQ ID NO: 94)
QFVLTQSPSASASLGASVKLTCTLSSAHKTYTIDWHQQQPEKGPRYLMQVK
SDGSYTKGTGIPDRFSGSSSGAERYLTISSLQSEDEADYYCGADDNGGYVF
GGGTQLTVLGGGSSRSSSSGGGGSGGGGEVQLVESGGGLVQPGGSLRLSCA
ASGFTFSRHALTWVRQAPGKGLEWVSAIDNAGTTYYASWAKSRFTISRDNA
KNSLYLQMNSLRAEDTAVYYCARVFYDINSGYYLDGMDLWGPGTLVTVSS

22.H1.L1m2

(SEQ ID NO: 65)
CAGTTTGTGCTCACCCAAAGCCCTAGCGCCTCTGCCTCTTTAGGCGCTTCC
GTGAAGCTGACTTGTACTTTAAGCTCCGCCCATAAGACCTACACCATCGAC
TGGCACCAGCAGCAGCCCGAGAAGGGCCCTCGTTATTTAATGCAAGTTAAG
TCCGATGGCAGCTATACCAAGGGCACCGGCATCCCCGACAGATTCAGCGGC
AGCTCCAGCGGAGCCGAGCGTTATTTAACCATCAGCTCTTTACAGAGCGAG
GACGAGGCTGACTACTACTGCGGCGCCGACGATAACGGCGGCTACGTGTTC
GGCGGCGGCACCCAACTGACAGTGCTGGGAGGCGGTTCTTCTCGTAGCAGC
AGCAGCGGAGGCGGCGGCTCCGGCGGCGGAGGCCAAGTTCAGCTGCAAGAA
TCCGGCCCCGGTCTGGTGAAACCCAGCGAGACTTTATCTTTAACATGCGCC
GTGAGCGGCTACTCCATCTCCAGACACGCTTTAACTTGGATCAGACAGCCT
CCCGGCAAGGGACTGGAGTGGATCGGCGCTATCGACAACGCCGGCACCACC
TACTACGCCTCTTGGGCCAAGTCTCGTGTCACCATCAGCGTGGACACATCC
AAGAACCAGTTCTCTTTAAAAGCTGTCCAGCGTGACCGCCGCCGATACAGCC
GTGTACTACTGCGCTCGTGTGTTCTACGACATCAACTCCGGCTACTATTTA
GACGGCATGGATTTATGGGGACCCGGTACTTTAGTGACCGTGTCCAGC

22.H1.L1m2

(SEQ ID NO: 95)
QFVLTQSPSASASLGASVKLTCTLSSAHKTYTIDWHQQQPEKGPRYLMQVK
SDGSYTKGTGIPDRFSGSSSGAERYLTISSLQSEDEADYYCGADDNGGYVF
GGGTQLTVLGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS

23.H1.L2m1

(SEQ ID NO: 66)
CAGTTCGTGCTGACCCAGCCTCCTAGCGCTAGCGGAACACCCGGCCAGAGG
GTGACCATCAGCTGCACTTTAAGCAGCGCCCACAAGACCTACACCATCGAC
TGGTACCAGCAGCTGCCCGGTACCGCTCCCAAGCTGCTGATCTACGTGAAG
AGCGACGGCAGCTACACCAAGGGCACCGGCGTGCCCGATAGATTCAGCGGC
AGCAGCAGCGGCGCCGACAGATATTTAGCCATCAGCGGTTTACAGAGCGAG
GACGAGGCCGACTACTACTGCGGCGCCGACGACAACGGAGGCTACGTGTTC
GGCGGCGGCACACAGCTGACCGTGACCGGTGGAGGCTCCAGCAGATCCAGC
TCCAGCGGCGGAGGAGGCAGCGGAGGCGGAGGACAAGTGCAGCTCCAAGAA
TCCGGCCCCGGTCTCGTGAAGCCCAGCGAGACTTTATCTTTAACTTGTGCC
GTGAGCGGCTACAGCATCTCTCGTCACGCTCTGACTTGGATTCGTCAACCT
CCCGGAAAGGGTTTAGAGTGGATCGGCGCCATCGACAACGCCGGCACCACC
TACTACGCCAGCTGGGCCAAATCTCGTGTGACCATTAGCGTGGACACCAGC
AAGAACCAGTTCTCTTTAAAAACTGAGCAGCGTGACAGCTGCCGACACCGCC
GTGTACTACTGCGCTCGTGTGTTCTACGACATCAACAGCGGCTACTATTTA
GACGGCATGGATTTATGGGGCCCCGGTACTTTAGTGACCGTCAGCTCC

23.H1.L2m1

(SEQ ID NO: 96)
QFVLTQPPSASGTPGQRVTISCTLSSAHKTYTIDWYQQLPGTAPKLLIYVK
SDGSYTKGTGVPDRFSGSSSGADRYLAISGLQSEDEADYYCGADDNGGYVF
GGGTQLTVTGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS

24.H2.L3m1

(SEQ ID NO: 67)
CAGTTCGTGCTGACCCAGCCCGCTTCTGTGAGCGGTTCTCCCGGTCAGAGC
ATCACCATCAGCTGCACTTTAAGCAGCGCCCACAAGACCTACACCATCGAC
TGGTACCAGCAGCACCCCGGCAAGGCCCCCAAGTATTTAATGCAAGTTAAG
TCCGACGGCAGCTACACCAAGGGCACCGGCGTGCCCAACAGATTCTCCGGC
AGCAGCTCCGGCGCCGACAGATACTTAACCATCAGCGGTTTACAAGCTGAG
GATGAGGCCGACTATGTGTGCGGCGCCGACGACAATGGCGGCTACGTGTTC
GGCGGCGGCACACAGCTGACCGTGACTGGCGGTGGTTCCTCTAGATCTTCC
TCCTCTGGTGGCGGTGGCTCGGGCGGTGGTGGGGAGGTGCAGCTGGTGGAG

-continued

AGCGGAGGAGGTTTAGTGCAGCCCGGTGGATCTTTAAGACTGAGCTGCGCC
GCCAGCGGCTTCACCTTCTCTCGTCACGCTTTAACATGGGTGAGACAAGCT
CCCGGTAAAGGTTTAGAGTGGGTGAGCGCCATCGACAACGCCGGCACCACC
TACTACGCCAGCTGGGCCAAGTCTCGTTTCACCATCTCTCGTGACAACGCC
AAGAACTCTTTATATTTACAGATGAACTCTTTAAGGGCTGAGGACACCGCC
GTGTACTACTGCGCTCGTGTGTTCTACGACATCAACAGCGGCTACTATTTA
GACGGAATGGATTTATGGGGCCCCGGTACCCTCGTGACAGTGAGCAGC

24.H2.L3m1
(SEQ ID NO: 97)
QFVLTQPASVSGSPGQSITISCTLSSAHKTYTIDWYQQHPGKAPKYLMQVK
SDGSYTKGTGVPNRFSGSSSGADRYLTISGLQAEDEADYVCGADDNGGYVF
GGGTQLTVTGGGSSRSSSSGGGGSGGGGEVQLVESGGGLVQPGGSLRLSCA
ASGFTFSRHALTWVRQAPGKGLEWVSAIDNAGTTYYASWAKSRFTISRDNA
KNSLYLQMNSLRAEDTAVYYCARVFYDINSGYYLDGMDLWGPGTLVTVSS

25.H1.L1m3
(SEQ ID NO: 68)
CAGCTGGTGCTCACCCAAAGCCCTAGCGCCTCTGCCTCTTTAGGCGCTTCC
GTGAAGCTGACTTGTACTTTAAGCTCCGCCCATAAGACCTACACCATCGAC
TGGTACCAGCAGCAGCCCGAGAAGGGCCCTCGTTATTTAATGCAAGTTAAG
TCCGATGGCAGCTATACCAAGGGCACCGGCGTGCCCGACAGATTCAGCGGC
AGCTCCAGCGGAGCCGATCGTTATTTAACCATCAGCTCTTTACAGAGCGAG
GACGAGGCTGACTACTACTGCGGCGCCGACGATAACGGCGGCTACGTGTTC
GGCGGCGGCACCCAACTGACAGTGCTGGGAGGCGGTTCTTCTCGTAGCAGC
AGCAGCGGAGGCGGCGGCTCCGGCGGCGGAGGCCAAGTGCAGCTCCAAGAA
TCCGGCCCCGGTCTCGTGAAGCCCAGCGAGACTTTATCTTTAACTTGTGCC
GTGAGCGGCTACAGCATCTCTCGTCACGCTCTGACTTGGATTCGTCAACCT
CCCGGAAAGGGTTTAGAGTGGATCGGCGCCATCGACAACGCCGGCACCACC
TACTACGCCAGCTGGGCCAAATCTCGTGTGACCATTAGCGTGGACACCAGC
AAGAACCAGTTCTCTTTAAAACTGAGCAGCGTGACAGCTGCCGACACCGCC
GTGTACTACTGCGCTCGTGTGTTCTACGACATCAACAGCGGCTACTATTTA
GACGGCATGGATTTATGGGGCCCCGGTACTTTAGTGACCGTCAGCTCC

25.H1.L1m3
(SEQ ID NO: 98)
QLVLTQSPSASASLGASVKLTCTLSSAHKTYTIDWYQQQPEKGPRYLMQVK
SDGSYTKGTGVPDRFSGSSSGADRYLTISSLQSEDEADYYCGADDNGGYVF
GGGTQLTVLGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS

26.H1.L1m4
(SEQ ID NO: 69)
CAGTTGGTGCTCACCCAAAGCCCTAGCGCCTCTGCCTCTTTAGGCGCTTCC
GTGAAGCTGACTTGTACTTTAAGCTCCGCCCATAAGACCTACACCATCGCC
TGGCATCAGCAGCAGCCCGAGAAGGGCCCTCGTTATTTAATGCAAGTTAAG
TCCGATGGCAGCTATACCAAGGGCACCGGCGTGCCCGACAGATTCAGCGGC
AGCTCCAGCGGAGCCGATCGTTATTTAACCATCAGCTCTTTACAGAGCGAG
GACGAGGCTGACTACTACTGCGGCGCCGACGATAACGGCGGCTACGTGTTC
GGCGGCGGCACCCAACTGACAGTGCTCGGAGGCGGTTCTTCTCGTAGCAGC
AGCAGCGGAGGCGGCGGCTCCGGCGGCGGAGGCCAAGTGCAGCTCCAAGAA
TCCGGCCCCGGTCTCGTGAAGCCCAGCGAGACTTTATCTTTAACTTGTGCC
GTGAGCGGCTACAGCATCTCTCGTCACGCTCTGACTTGGATTCGTCAACCT
CCCGGAAAGGGTTTAGAGTGGATCGGCGCCATCGACAACGCCGGCACCACC
TACTACGCCAGCTGGGCCAAATCTCGTGTGACCATTAGCGTGGACACCAGC
AAGAACCAGTTCTCTTTAAAACTGAGCAGCGTGACAGCTGCCGACACCGCC
GTGTACTACTGCGCTCGTGTGTTCTACGACATCAACAGCGGCTACTATTTA
GACGGCATGGATTTATGGGGCCCCGGTACTTTAGTGACCGTCAGCTCC

26.H1.L1m4
(SEQ ID NO: 99)
QLVLTQSPSASASLGASVKLTCTLSSAHKTYTIAWHQQQPEKGPRYLMQVK
SDGSYTKGTGVPDRFSGSSSGADRYLTISSLQSEDEADYYCGADDNGGYVF
GGGTQLTVLGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS

27.H1.L3m4
(SEQ ID NO: 70)
CAGAGCGCTCTGACCCAGCCCGCTTCTGTGAGCGGTTCTCCCGGTCAGAGC
ATCACCATCAGCTGCACTGGCACAAGCGCCCACAAGACCTACACCGTGAGC
TGGTACCAGCAGCACCCCGGCAAGGCCCCCAAGTATTTAATGCAAGTTAAG
TCCGACGGCAGCTACACCAAGGGCACCGGCGTGCCCAACAGATTCTCCGGC
AGCAGCTCCGGCGCCGACAGATACTTAACCATCAGCGGTTTACAAGCTGAG
GATGAGGCCGACTATTACTGCGGCGCCGACGACAATGGCGGCTACGTGTTC
GGCGGCGGCACCCAACTGACAGTGCTGGGTGGAGGCTCCAGCAGATCCAGC
TCCAGCGGCGGAGGAGGCAGCGGAGGCGGAGGACAAGTGCAGCTCCAAGAA
TCCGGCCCCGGTCTCGTGAAGCCCAGCGAGACTTTATCTTTAACTTGTGCC
GTGAGCGGCTACAGCATCTCTCGTCACGCTCTGACTTGGATTCGTCAACCT
CCCGGAAAGGGTTTAGAGTGGATCGGCGCCATCGACAACGCCGGCACCACC
TACTACGCCAGCTGGGCCAAATCTCGTGTGACCATTAGCGTGGACACCAGC
AAGAACCAGTTCTCTTTAAAACTGAGCAGCGTGACAGCTGCCGACACCGCC
GTGTACTACTGCGCTCGTGTGTTCTACGACATCAACAGCGGCTACTATTTA
GACGGCATGGATTTATGGGGCCCCGGTACTTTAGTGACCGTCAGCTCC

27.H1.L3m4
(SEQ ID NO: 100)
QSALTQPASVSGSPGQSITISCTGTSAHKTYTVSWYQQHPGKAPKYLMQVK
SDGSYTKGTGVPNRFSGSSSGADRYLTISGLQAEDEADYYCGADDNGGYVF
GGGTQLTVLGGGSSRSSSSGGGGSGGGGQVQLQESGPGLVKPSETLSLTCA
VSGYSISRHALTWIRQPPGKGLEWIGAIDNAGTTYYASWAKSRVTISVDTS
KNQFSLKLSSVTAADTAVYYCARVFYDINSGYYLDGMDLWGPGTLVTVSS

-continued

28.H1.L3m5

(SEQ ID NO: 71)
CAGTCTGCTCTGACCCAGCCCGCTTCTGTGAGCGGTTCTCCCGGTCAGAGC

ATCACCATCAGCTGCACTGGCACAAGCGCCCACAAGACCTACACCGTGAGT

TGGTACCAGCAGCACCCCGGCAAGGCCCCCAAGTTGATGATCTACGTTAAG

TCCGACGGCAGCTACACCAAGGGCACCGGCGTGCCCAACAGATTCTCCGGC

AGCAGCTCCGGCGCCGACAGATACTTAACCATCAGCGGTTTACAAGCTGAG

GATGAGGCCGACTATTATTGCGGCGCCGACGACAATGGCGGCTACGTGTTC

GGCGGCGGCACCCAACTGACAGTGCTCGGTGGAGGCTCCAGCAGATCCAGC

TCCAGCGGCGGAGGAGGCAGCGGAGGCGGAGGACAAGTGCAGCTCCAAGAA

TCCGGCCCCGGTCTCGTGAAGCCCAGCGAGACTTTATCTTTAACTTGTGCC

GTGAGCGGCTACAGCATCTCTCGTCACGCTCTGACTTGGATTCGTCAACCT

CCCGGAAAGGGTTTAGAGTGGATCGGCGCCATCGACAACGCCGGCACCACC

TACTACGCCAGCTGGGCCAAATCTCGTGTGACCATTAGCGTGGACACCAGC

AAGAACCAGTTCTCTTTAAAACTGAGCAGCGTGACAGCTGCCGACACCGCC

GTGTACTACTGCGCTCGTGTGTTCTACGACATCAACAGCGGCTACTATTTA

GACGGCATGGATTTATGGGGCCCCGGTACTTTAGTGACCGTCAGCTCC

28.H1.L3m5

(SEQ ID NO: 101)
QSALTQPASVSGSPGQSITISCTGTSAHKTYTVSWYQQHPGKAPKLMIYVK

SDGSYTKGTGVPNRFSGSSSGADRYLTISGLQAEDEADYYCGADDNGGYVF

GGGTQLTVLGGGSSRSSSSGGGGSGGGGQVQLQESGPGLVKPSETLSLTCA

VSGYSISRHALTWIRQPPGKGLEWIGAIDNAGTTYYASWAKSRVTISVDTS

KNQFSLKLSSVTAADTAVYYCARVFYDINSGYYLDGMDLWGPGTLVTVSS

29.H2.L1m3

(SEQ ID NO: 72)
CAGCTGGTGCTGACCCAGAGCCCTAGCGCTTCCGCCTCTTTAGGAGCCAGC

GTGAAGCTGACTTGTACTTTATCCTCCGCCCACAAGACCTACACCATCGAC

TGGTACCAGCAGCAGCCCGAAAAGGGCCCTCGTTATCTGATGCAAGTTAAG

TCCGACGGCAGCTACACCAAGGGAACCGGCGTGCCCGACAGATTCTCCGGT

AGCAGCAGCGGCGCCGACAGATATTTAACCATCAGCTCTTTACAGTCCGAG

GACGAGGCCGACTACTACTGCGGCGCCGACGACAATGGCGGCTACGTCTTC

GGAGGCGGCACACAGCTGACCGTGACTGGTGGAGGCTCCTCCAGAAGCAGC

TCTAGCGGAGGAGGAGGAAGCGGCGGAGGAGGCGAAGTGCAGCTGGTGGAG

TCCGGAGGAGGACTGGTGCAGCCCGGAGGTTCTTTAAGACTGAGCTGCGCC

GCCTCCGGCTTCACCTTTTCTCGTCACGCTTTAACATGGGTGAGACAAGCT

CCCGGCAAGGGACTGGAATGGGTCAGCGCCATCGATAACGCCGGCACCACC

TATTACGCCAGCTGGGCTAAGTCTCGTTTCACCATCAGCAGAGACAACGCC

AAGAACTCTTTATATTTACAGATGAATCTTTAAGAGCCGAGGACACCGCC

GTGTATTACTGCGCTCGTGTCTTCTACGACATCAACTCCGGCTACTATTTA

GACGGCATGGATTTATGGGGCCCCGGTACTTTAGTCACCGTGAGCTCC

29.H2.L1m3

(SEQ ID NO: 102)
QLVLTQSPSASASLGASVKLTCTLSSAHKTYTIDWYQQQPEKGPRYLMQVK

SDGSYTKGTGVPDRFSGSSSGADRYLTISSLQSEDEADYYCGADDNGGYVF

GGGTQLTVTGGGSRSSSSGGGGSGGGGEVQLVESGGGLVQPGGSLRLSCA

ASGFTFSRHALTWVRQAPGKGLEWVSAIDNAGTTYYASWAKSRFTISRDNA

KNSLYLQMNSLRAEDTAVYYCARVFYDINSGYYLDGMDLWGPGTLVTVSS scFv Constructs of Humanized Rabbit P4-10 Variants for CARs 10, 14, 25, and 29

CAR10

(SEQ ID NO: 103)
GAGGTGCAGCTGGTGGAGTCTGGAGGAGGACTGGTGCAACCCGGTGGCTCT

TTAAGACTGAGCTGCGCCGCCTCTGGCTTCACCTTTTCTCGTCACGCTTTA

ACATGGGTGAGACAAGCTCCCGGAAAGGGACTGGAGTGGGTGTCCGCCATC

GACAACGCCGGCACCACCTACTACGCCAGCTGGGCCAAGAGCAGATTCACC

ATCTCTCGTGACAACGCCAAGAACTCTTTATATTTACAGATGAACTCTTTA

AGGGCCGAGGACACCGCCGTGTACTACTGCGCTCGTGTGTTCTACGACATC

AACTCCGGCTACTATTTAGACGGCATGGATTTATGGGGACCCGGTACACTG

GTCACAGTGAGCTCTGGAGGCGGAGGTAGCGGAGGCGGAGGAAGCAGCGGT

GGAGGCAGCCAGTTTGTGCTGACACAGTCCCCTTCCGCTTCCGCCTCTTTA

GGAGCCTCCGTGAAGCTGACTTGTACTTTAAGCAGCGCCCACAAAACCTAC

ACCATCGACTGGTACCAGCAGCAGCCCGAGAAGGGCCCACGTTATTTAATG

CAAGTTAAGTCCGACGGCTCCTACACCAAGGGCACCGGCGTGCCCGATAGA

TTCAGCGGCTCCAGCAGCGGCGCCGATAGGTATTTAACCATCTCCTCTTTA

CAGAGCGAGGACGAGGCCGACTACTACTGTGGCGCCGACGACAACGGCGGC

TACGTGTTTGGAGGCGGCACCCAGCTGACCGTGCTG

CAR10

(SEQ ID NO: 107)
EVQLVESGGGLVQPGGSLRLSCAASGFTFSRHALTWVRQAPGKGLEWVSAI

DNAGTTYYASWAKSRFTISRDNAKNSLYLQMNSLRAEDTAVYYCARVFYDI

NSGYYLDGMDLWGPGTLVTVSSGGGGSGGGGSSGGGSQFVLTQSPSASASL

GASVKLTCTLSSAHKTYTIDWYQQQPEKGPRYLMQVKSDGSYTKGTGVPDR

FSGSSSGADRYLTISSLQSEDEADYYCGADDNGGYVFGGGTQLTVL

Figure 17:
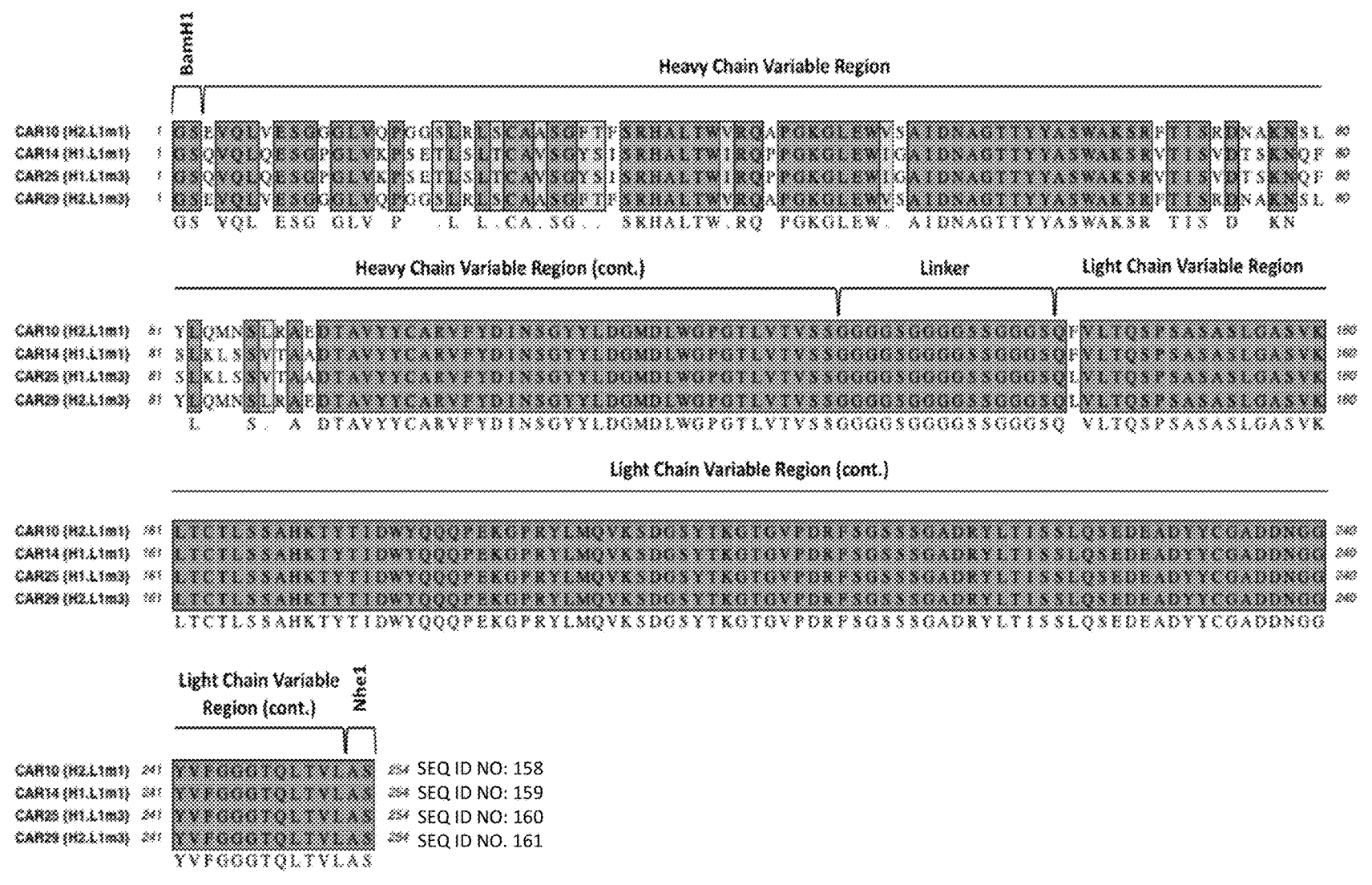

CAR10- From Figure 17

(SEQ ID NO: 158)
GSEVQLVESGGGLVQPGGSLRLSCAASGFTFSRHALTWVRQAPGKGLEWVS

AIDNAGTTYYASWAKSRFTISRDNAKNSLYLQMNSLRAEDTAVYYCARVFY

DINSGYYLDGMDLWGPGTLVTVSSGGGGSGGGGSSGGGSQFVLTQSPSASA

SLGASVKLTCTLSSAHKTYTIDWYQQQPEKGPRYLMQVKSDGSYTKGTGVP

DRFSGSSSGADRYLTISSLQSEDEADYYCGADDNGGYVFGGGTQLTVLAS

CAR14

(SEQ ID NO: 104)
CAAGTTCAGCTGCAAGAAAGCGGACCCGGTTTAGTGAAACCCTCCGAGACT

TTATCTTTAACATGCGCCGTGAGCGGCTACAGCATCTCTCGTCATGCTTTA

ACTTGGATTCGTCAGCCTCCCGGAAAGGGTTTAGAGTGGATCGGCGCCATC

-continued

```
GACAACGCCGGCACCACCTATTACGCCAGCTGGGCCAAGTCTCGTGTGACC
ATCAGCGTGGACACCAGCAAGAACCAGTTCTCTTTAAAGCTGTCCAGCGTG
ACCGCTGCCGACACAGCCGTGTACTACTGCGCTCGTGTGTTCTACGACATC
AACAGCGGCTACTATTTAGACGGAATGGATCTGTGGGGCCCCGGAACTTTA
GTGACAGTCAGCAGCGGAGGCGGAGGAAGCGGAGGAGGAGGAAGCTCCGGA
GGCGGTTCTCAATTCGTGCTGACACAGAGCCCTAGCGCCTCTGCCTCTTTA
GGAGCCTCCGTGAAGCTGACTTGTACTTTAAGCAGCGCCCACAAGACCTAC
ACCATCGACTGGTACCAGCAGCAGCCCGAGAAGGGCCCTAGATATTTAATG
CAAGTTAAGAGCGACGGCAGCTACACCAAAGGCACTGGTGTGCCCGATCGT
TTTAGCGGCAGCAGCAGCGGCGCCGATAGGTATTTAACCATCAGCTCTTTA
CAGAGCGAGGACGAGGCCGACTACTACTGTGGCGCCGACGACAACGGCGGC
TACGTGTTTGGCGGCGGCACACAGCTGACCGTTTTA
```

CAR14
(SEQ ID NO: 108)
QVQLQESGPGLVKPSETLSLTCAVSGYSISRHALTWIRQPPGKGLEWIGAI
DNAGTTYYASWAKSRVTISVDTSKNQFSLKLSSVTAADTAVYYCARVFYDI
NSGYYLDGMDLWGPGTLVTVSSGGGGSGGGGSSGGGSQFVLTQSPSASASL
GASVKLTCTLSSAHKTYTIDWYQQQPEKGPRYLMQVKSDGSYTKGTGVPDR
FSGSSSGADRYLTISSLQSEDEADYYCGADDNGGYVFGGGTQLTVL

CAR15- From FIG. 17
(SEQ ID NO: 159)
GSQVQLQESGPGLVKPSETLSLTCAVSGYSISRHALTWIRQPPGKGLEWIG
AIDNAGTTYYASWAKSRVTISVDTSKNQFSLKLSSVTAADTAVYYCARVFY
DINSGYYLDGMDLWGPGTLVTVSSGGGGSGGGGSSGGGSQFVLTQSPSASA
SLGASVKLTCTLSSAHKTYTIDWYQQQPEKGPRYLMQVKSDGSYTKGTGVP
DRFSGSSSGADRYLTISSLQSEDEADYYCGADDNGGYVFGGGTQLTVLAS CAR25
(SEQ ID NO: 105)
CAAGTTCAGCTGCAAGAAAGCGGACCCGGTTTAGTGAAACCCTCCGAGACT
TTATCTTTAACATGCGCCGTGAGCGGCTACAGCATCTCTCGTCATGCTTTA
ACTTGGATTCGTCAGCCTCCCGGAAAGGGTTTAGAGTGGATCGGCGCCATC
GACAACGCCGGCACCACCTATTACGCCAGCTGGGCCAAGTCTCGTGTGACC
ATCAGCGTGGACACCAGCAAGAACCAGTTCTCTTTAAAGCTGTCCAGCGTG
ACCGCTGCCGACACAGCCGTGTACTACTGCGCTCGTGTGTTCTACGACATC
AACAGCGGCTACTATTTAGACGGAATGGATCTGTGGGGCCCCGGAACTTTA
GTGACAGTCAGCAGCGGAGGCGGAGGAAGCGGAGGAGGAGGAAGCTCCGGA
GGCGGTTCTCAACTGGTGCTGACACAGAGCCCTAGCGCCTCTGCCTCTTTA
GGAGCCTCCGTGAAGCTGACTTGTACTTTAAGCAGCGCCCACAAGACCTAC
ACCATCGACTGGTACCAGCAGCAGCCCGAGAAGGGCCCTAGATATTTAATG
CAAGTTAAGAGCGACGGCAGCTACACCAAAGGCACTGGTGTGCCCGATCGT
TTTAGCGGCAGCAGCAGCGGCGCCGATAGGTATTTAACCATCAGCTCTTTA
CAGAGCGAGGACGAGGCCGACTACTACTGTGGCGCCGACGACAACGGCGGC
TACGTGTTTGGCGGCGGCACACAGCTGACCGTTTTA CAR25
(SEQ ID NO: 109)
QVQLQESGPGLVKPSETLSLTCAVSGYSISRHALTWIRQPPGKGLEWIGAI
DNAGTTYYASWAKSRVTISVDTSKNQFSLKLSSVTAADTAVYYCARVFYDI
NSGYYLDGMDLWGPGTLVTVSSGGGGSGGGGSSGGGSQLVLTQSPSASASL
GASVKLTCTLSSAHKTYTIDWYQQQPEKGPRYLMQVKSDGSYTKGTGVPDR
FSGSSSGADRYLTISSLQSEDEADYYCGADDNGGYVFGGGTQLTVL CAR25- From FIG. 17
(SEQ ID NO: 160)
GSQVQLQESGPGLVKPSETLSLTCAVSGYSISRHALTWIRQPPGKGLEWIG
AIDNAGTTYYASWAKSRVTISVDTSKNQFSLKLSSVTAADTAVYYCARVFY
DINSGYYLDGMDLWGPGTLVTVSSGGGGSGGGGSSGGGSQLVLTQSPSASA
SLGASVKLTCTLSSARKTYTIDWYQQQPEKGPRYLMQVKSDGSYTKGTGVP
DRFSGSSSGADRYLTISSLQSEDEADYYCGADDNGGYVFGGGTQLTVLAS CAR29
(SEQ ID NO: 106)
GAGGTGCAGCTGGTGGAGTCTGGAGGAGGACTGGTGCAACCCGGTGGCTCT
TTAAGACTGAGCTGCGCCGCCTCTGGCTTCACCTTTTCTCGTCACGCTTTA
ACATGGGTGAGACAAGCTCCCGGAAAGGGACTGGAGTGGGTGTCCGCCATC
GACAACGCCGGCACCACCTACTACGCCAGCTGGGCCAAGAGCAGATTCACC
ATCTCTCGTGACAACGCCAAGAACTCTTTATATTTACAGATGAACTCTTTA
AGGGCCGAGGACACCGCCGTGTACTACTGCGCTCGTGTGTTCTACGACATC
AACTCCGGCTACTATTTAGACGGCATGGATTTATGGGGACCCGGTACACTG
GTCACAGTGAGCTCTGGAGGCGGAGGTAGCGGAGGCGGAGGAAGCAGCGGT
GGAGGCAGCCAGCTGGTGCTGACACAGTCCCCTTCCGCTTCCGCCTCTTTA
GGAGCCTCCGTGAAGCTGACTTGTACTTTAAGCAGCGCCCACAAAACCTAC
ACCATCGACTGGTACCAGCAGCAGCCCGAGAAGGGCCCACGTTATTTAATG
CAAGTTAAGTCCGACGGCTCCTACACCAAGGGCACCGGCGTGCCCGATAGA
TTCAGCGGCTCCAGCAGCGGCGCCGATAGGTATTTAACCATCTCCTCTTTA
CAGAGCGAGGACGAGGCCGACTACTACTGTGGCGCCGACGACAACGGCGGC
TACGTGTTTGGAGGCGGCACCCAGCTGACCGTGCTG CAR29
(SEQ ID NO: 110)
EVQLVESGGGLVQPGGSLRLSCAASGFTFSRHALTWVRQAPGKGLEWVSAI
DNAGTTYYASWAKSRFTISRDNAKNSLYLQMNSLRAEDTAVYYCARVFYDI
NSGYYLDGMDLWGPGTLVTVSSGGGGSGGGGSSGGGSQLVLTQSPSASASL
GASVKLTCTLSSAHIKTYTIDWYQQQPEKGPRYLMQVKSDGSYTKGTGVPD
RFSGSSSGADRYLTISSLQSEDEADYYCGADDNGGYVFGGGTQLTVL CAR29- From FIG. 17
(SEQ ID NO: 161)
GSEVQLVESGGGLVQPGGSLRLSCAASGFTFSRHALTWVRQAPGKGLEWVS
AIDNAGTTYYASWAKSRFTISRDNAKNSLYLQMNSLRAEDTAVYYCARVFY
DINSGYYLDGMDLWGPGTLVTVSSGGGGSGGGGSSGGGSQLVLTQSPSASA
SLGASVKLTCTLSSAHKTYTIDWYQQQPEKGPRYLMQVKSDGSYTKGTGVP
DRFSGSSSGADRYLTISSLQSEDEADYYCGADDNGGYVFGGGTQLTVLAS CAR Plasmids for Lentivirus pTRPE-C10-gs-BBz (plasmid for CAR10)

(SEQ ID NO: 111)

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

GAGAGAAAAAGCACCGTGCATGCCGATTGGTGGAAGTAAGGTGGTACGATCGTGCC

TTATTAGGAAGGCAACAGACGGGTCTGACATGGATTGGACGAACCACTGAATTGCC

GCATTGCAGAGATATTGTATTTAAGTGCCTAGCTCGATACATAAACGGGTCTCTCTG

-continued

```
GTTAGACCAGATCTGAGCCTGGGAGCTCTCTGGCTAACTAGGGAACCCACTGCTTAA
GCCTCAATAAAGCTTGCCTTGAGTGCTTCAAGTAGTGTGTGCCCGTCTGTTGTGTGA
CTCTGGTAACTAGAGATCCCTCAGACCCTTTTAGTCAGTGTGGAAAATCTCTAGCAG
TGGCGCCCGAACAGGGACTTGAAAGCGAAAGGGAAACCAGAGGAGCTCTCTCGAC
GCAGGACTCGGCTTGCTGAAGCGCGCACGGCAAGAGGCGAGGGGCGGCGACTGGT
GAGTACGCCAAAAATTTTGACTAGCGGAGGCTAGAAGGAGAGAGATGGGTGCGAG
AGCGTCAGTATTAAGCGGGGGAGAATTAGATCGCGATGGGAAAAAATTCGGTTAAG
GCCAGGGGGAAAGAAAAAATATAAATTAAAACATATAGTATGGGCAAGCAGGGAG
CTAGAACGATTCGCAGTTAATCCTGGCCTGTTAGAAACATCAGAAGGCTGTAGACA
AATACTGGGACAGCTACAACCATCCCTTCAGACAGGATCAGAAGAACTTAGATCAT
TATATAATACAGTAGCAACCCTCTATTGTGTGCATCAAAGGATAGAGATAAAAGAC
ACCAAGGAAGCTTTAGACAAGATAGAGGAAGAGCAAAACAAAAGTAAGACCACCG
CACAGCAAGCGGCCGCTGATCTTCAGACCTGGAGGAGGAGATATGAGGGACAATTG
GAGAAGTGAATTATATAAATATAAAGTAGTAAAAATTGAACCATTAGGAGTAGCAC
CCACCAAGGCAAAGAGAAGAGTGGTGCAGAGAGAAAAAGAGCAGTGGGAATAGG
AGCTTTGTTCCTTGGGTTCTTGGGAGCAGCAGGAAGCACTATGGGCGCAGCGTCAAT
GACGCTGACGGTACAGGCCAGACAATTATTGTCTGGTATAGTGCAGCAGCAGAACA
ATTTGCTGAGGGCTATTGAGGCGCAACAGCATCTGTTGCAACTCACAGTCTGGGCA
TCAAGCAGCTCCAGGCAAGAATCCTGGCTGTGGAAAGATACCTAAAGGATCAACAG
CTCCTGGGGATTTGGGGTTGCTCTGGAAAACTCATTTGCACCACTGCTGTGCCTTGG
AATGCTAGTTGGAGTAATAAATCTCTGGAACAGATTTGGAATCACACGACCTGGATG
GAGTGGGACAGAGAAATTAACAATTACACAAGCTTAATACACTCCTTAATTGAAGA
ATCGCAAAACCAGCAAGAAAAGAATGAACAAGAATTATTGGAATTAGATAAATGGG
CAAGTTTGTGGAATTGGTTTAACATAACAAATTGGCTGTGGTATATAAAATTATTCA
TAATGATAGTAGGAGGCTTGGTAGGTTTAAGAATAGTTTTTGCTGTACTTTCTATAGT
GAATAGAGTTAGGCAGGGATATTCACCATTATCGTTTCAGACCCACCTCCCAACCCC
GAGGGGACCCGACAGGCCCGAAGGAATAGAAGAAGAAGGTGGAGAGAGAGACAG
AGACAGATCCATTCGATTAGTGAACGGATCTCGACGGTATCGATTAGACTGTAGCCC
AGGAATATGGCAGCTAGATTGTACACATTTAGAAGGAAAAGTTATCTTGGTAGCAG
TTCATGTAGCCAGTGGATATATAGAAGCAGAAGTAATTCCAGCAGAGACAGGGCAA
GAAACAGCATACTTCCTCTTAAAATTAGCAGGAAGATGGCCAGTAAAAACAGTACA
TACAGACAATGGCAGCAATTTCACCAGTACTACAGTTAAGGCCGCCTGTTGGTGGGC
GGGGATCAAGCAGGAATTTGGCATTCCCTACAATCCCCAAAGTCAAGGAGTAATAG
AATCTATGAATAAAGAATTAAAGAAAATTATAGGACAGGTAAGAGATCAGGCTGAA
CATCTTAAGACAGCAGTACAAATGGCAGTATTCATCCACAATTTTAAAAGAAAAGG
GGGGATTGGGGGGTACAGTGCAGGGGAAGAATAGTAGACATAATAGCAACAGAC
ATACAAACTAAAGAATTACAAAAACAAATTACAAAAATTCAAAATTTTCGGGTTTAT
TACAGGGACAGCAGAGATCCAGTTTGGCTGCATACGCGTCGTGAGGCTCCGGTGCC
CGTCAGTGGGCAGAGCGCACATCGCCCACAGTCCCCGAGAAGTTGGGGGAGGGGT
CGGCAATTGAACCGGTGCCTAGAGAAGGTGGCGCGGGGTAAACTGGGAAAGTGATG
```

-continued

```
TCGTGTACTGGCTCCGCCTTTTTCCCGAGGGTGGGGGAGAACCGTATATAAGTGCAG
TAGTCGCCGTGAACGTTCTTTTTCGCAACGGGTTTGCCGCCAGAACACAGGTAAGTG
CCGTGTGTGGTTCCCGCGGGCCTGGCCTCTTTACGGGTTATGGCCCTTGCGTGCCTTG
AATTACTTCCACCTGGCTGCAGTACGTGATTCTTGATCCCGAGCTTCGGGTTGGAAG
TGGGTGGGAGAGTTCGAGGCCTTGCGCTTAAGGAGCCCCTTCGCCTCGTGCTTGAGT
TGAGGCCTGGCCTGGGCGCTGGGGCCGCCGCGTGCGAATCTGGTGGCACCTTCGCG
CCTGTCTCGCTGCTTTCGATAAGTCTCTAGCCATTTAAAATTTTTGATGACCTGCTGC
GACGCTTTTTTTCTGGCAAGATAGTCTTGTAAATGCGGGCCAAGATCTGCACACTGG
TATTTCGGTTTTTGGGGCCGCGGGCGGCGACGGGGCCCGTGCGTCCCAGCGCACATG
TTCGGCGAGGCGGGGCCTGCGAGCGCGGCCACCGAGAATCGGACGGGGGTAGTCTC
AAGCTGGCCGGCCTGCTCTGGTGCCTGGCCTCGCGCCGCCGTGTATCGCCCCGCCCT
GGGCGGCAAGGCTGGCCCGGTCGGCACCAGTTGCGTGAGCGGAAAGATGGCCGCTT
CCCGGCCCTGCTGCAGGGAGCTCAAAATGGAGGACGCGGCGCTCGGGAGAGCGGGC
GGGTGAGTCACCCACACAAAGGAAAAGGGCCTTTCCGTCCTCAGCCGTCGCTTCATG
TGACTCCACTGAGTACCGGGCGCCGTCCAGGCACCTCGATTAGTTCTCGTGCTTTTG
GAGTACGTCGTCTTTAGGTTGGGGGAGGGGTTTTATGCGATGGAGTTTCCCCACAC
TGAGTGGGTGGAGACTGAAGTTAGGCCAGCTTGGCACTTGATGTAATTCTCCTTGGA
ATTTGCCCTTTTTGAGTTTGGATCTTGGTTCATTCTCAAGCCTCAGACAGTGGTTCAA
AGTTTTTTTCTTCCATTTCAGGTGTCGTGAGCTAGAGCCACCATGGAGTTTGGGCTGA
GCTGGCTTTTTCTTGTGGCTATTTTAAAAGGTGTCCAGTGCGGATCCGAGGTGCAGC
TGGTGGAGTCTGGAGGAGGACTGGTGCAACCCGGTGGCTCTTTAAGACTGAGCTGC
GCCGCCTCTGGCTTCACCTTTTCTCGTCACGCTTTAACATGGGTGAGACAAGCTCCC
GGAAAGGGACTGGAGTGGGTGTCCGCCATCGACAACGCCGGCACCACCTACTACGC
CAGCTGGGCCAAGAGCAGATTCACCATCTCTCGTGACAACGCCAAGAACTCTTTATA
TTTACAGATGAACTCTTTAAGGGCCGAGGACACCGCCGTGTACTACTGCGCTCGTGT
GTTCTACGACATCAACTCCGGCTACTATTTAGACGGCATGGATTTATGGGGACCCGG
TACACTGGTCACAGTGAGCTCTGGAGGCGGAGGTAGCGGAGGCGGAGGAAGCAGC
GGTGGAGGCAGCCAGTTTGTGCTGACACAGTCCCCTTCCGCTTCCGCCTCTTTAGGA
GCCTCCGTGAAGCTGACTTGTACTTTAAGCAGCGCCCACAAAACCTACACCATCGAC
TGGTACCAGCAGCAGCCCGAGAAGGGCCCACGTTATTTAATGCAAGTTAAGTCCGA
CGGCTCCTACACCAAGGGCACCGGCGTGCCCGATAGATTCAGCGGCTCCAGCAGCG
GCGCCGATAGGTATTTAACCATCTCCTCTTTACAGAGCGAGGACGAGGCCGACTACT
ACTGTGGCGCCGACGACAACGGCGGCTACGTGTTTGGAGGCGGCACCCAGCTGACC
GTGCTGGCTAGCGGTGGCGGAGGTTCTGGAGGTGGAGGTTCCTCCGGAATCTACATC
TGGGCGCCCTTGGCCGGGACTTGTGGGGTCCTTCTCCTGTCACTGGTTATCACCCTTT
ACTGCAAACGGGGCAGAAAGAAACTCCTGTATATATTCAAACAACCATTTATGAGA
CCAGTACAAACTACTCAAGAGGAAGATGGCTGTAGCTGCCGATTTCCAGAAGAAGA
AGAAGGAGGATGTGAACTGAGAGTGAAGTTCAGCAGGAGCGCAGACGCCCCCGCGT
ACCAGCAGGGCCAGAACCAGCTCTATAACGAGCTCAATCTAGGACGAAGAGAGGA
GTACGATGTTTTGGACAAGAGACGTGGCCGGGACCCTGAGATGGGGGGAAAGCCGA
GAAGGAAGAACCCTCAGGAAGGCCTGTACAATGAACTGCAGAAAGATAAGATGGC
```

-continued

GGAGGCCTACAGTGAGATTGGGATGAAAGGCGAGCGCCGGAGGGGCAAGGGGCAC

GATGGCCTTTACCAGGGTCTCAGTACAGCCACCAAGGACACCTACGACGCCCTTCAC

ATGCAGGCCCTGCCCCCTCGCTAAGTCGACAATCAACCTCTGGATTACAAAATTTGT

GAAAGATTGACTGGTATTCTTAACTATGTTGCTCCTTTTACGCTATGTGGATACGCTG

CTTTAATGCCTTTGTATCATGCTATTGCTTCCCGTATGGCTTTCATTTTCTCCTCCTTG

TATAAATCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATTGCCACC

ACCTGTCAGCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGCACTGACA

ATTCCGTGGTGTTGTCGGGGAAGCTGACGTCCTTTCCTTGGCTGCTCGCCTGTGTTGC

CACCTGGATTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGTCTTCGCCTT

CGCCCTCAGACGAGTCGGATCTCCCTTTGGGCCGCCTCCCCGCCTGGAATTCGAGCT

CGGTACCTTTAAGACCAATGACTTACAAGGCAGCTGTAGATCTTAGCCACTTTTTAA

AAGAAAAGGGGGGACTGGAAGGGCTAATTCACTCCCAACGAAGACAAGATCTGCTT

TTTGCTTGTACTGGGTCTCTCTGGTTAGACCAGATCTGAGCCTGGGAGCTCTCTGGCT

AACTAGGGAACCCACTGCTTAAGCCTCAATAAAGCTTGCCTTGAGTGCTTCAAGTAG

TGTGTGCCCGTCTGTTGTGTGACTCTGGTAACTAGAGATCCCTCAGACCCTTTTAGTC

AGTGTGGAAAATCTCTAGCAGTAGTAGTTCATGTCATCTTATTATTCAGTATTTATAA

CTTGCAAAGAAATGAATATCAGAGAGTGAGAGGAACTTGTTTATTGCAGCTTATAAT

GGTTACAAATAAAGCAATAGCATCACAAATTTCACAAATAAAGCATTTTTTTCACTG

CATTCTAGTTGTGGTTTGTCCAAACTCATCAATGTATCTTATCATGTCTGGCTCTAGC

TATCCCGCCCCTAACTCCGCCCAGTTCCGCCCATTCTCCGCCCCATGGCTGACTAATT

TTTTTTATTTATGCAGAGGCCGAGGCCGCCTCGGCCTCTGAGCTATTCCAGAAGTAG

TGAGGAGGCTTTTTTGGAGGCCTAGCTAGGGACGTACCCAATTCGCCCTATAGTGAG

TCGTATTACGCGCGCTCACTGGCCGTCGTTTTACAACGTCGTGACTGGGAAAACCCT

GGCGTTACCCAACTTAATCGCCTTGCAGCACATCCCCCTTTCGCCAGCTGGCGTAAT

AGCGAAGAGGCCCGCACCGATCGCCCTTCCCAACAGTTGCGCAGCCTGAATGGCGA

ATGGGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTTTA

GGGTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGGAG

TCCACGTTCTTTAATAGTGGACTCTTGTTCCAAACTGGAACAACACTCAACCCTATCT

CGGTCTATTCTTTTGATTTATAAGGGATTTTGCCGATTTCGGCCTATTGGTTAAAAAA

TGAGCTGATTTAACAAAAATTTAACGCGAATTTTAACAAAATATTAACGCTTACAAT

TTAGGTGGCACTTTTCGGGGAAATGTGCGCGGAACCCCTATTTGTTTATTTTTCTAAA

TACATTCAAATATGTATCCGCTCATGAGACAATAACCCTGATAAATGCTTCAATAAT

ATTGAAAAAGGAAGAGTATGAGTATTCAACATTTCCGTGTCGCCCTTATTCCCTTTTT

TGCGGCATTTTGCCTTCCTGTTTTTGCTCACCCAGAAACGCTGGTGAAAGTAAAAGA

TGCTGAAGATCAGTTGG pTRPE-C14-gs-BBz (plasmid for CAR14)
(SEQ ID NO: 112)
GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

-continued

```
GAGAGAAAAAGCACCGTGCATGCCGATTGGTGGAAGTAAGGTGGTACGATCGTGCC

TTATTAGGAAGGCAACAGACGGGTCTGACATGGATTGGACGAACCACTGAATTGCC

GCATTGCAGAGATATTGTATTTAAGTGCCTAGCTCGATACATAAACGGGTCTCTCTG

GTTAGACCAGATCTGAGCCTGGGAGCTCTCTGGCTAACTAGGGAACCCACTGCTTAA

GCCTCAATAAAGCTTGCCTTGAGTGCTTCAAGTAGTGTGTGCCCGTCTGTTGTGTGA

CTCTGGTAACTAGAGATCCCTCAGACCCTTTTAGTCAGTGTGGAAAATCTCTAGCAG

TGGCGCCCGAACAGGGACTTGAAAGCGAAAGGGAAACCAGAGGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCGCTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGATTAGACTGTAGCCC

AGGAATATGGCAGCTAGATTGTACACATTTAGAAGGAAAAGTTATCTTGGTAGCAG

TTCATGTAGCCAGTGGATATATAGAAGCAGAAGTAATTCCAGCAGAGACAGGGCAA

GAAACAGCATACTTCCTCTTAAAATTAGCAGGAAGATGGCCAGTAAAAACAGTACA

TACAGACAATGGCAGCAATTTCACCAGTACTACAGTTAAGGCCGCCTGTTGGTGGGC

GGGGATCAAGCAGGAATTTGGCATTCCCTACAATCCCCAAAGTCAAGGAGTAATAG

AATCTATGAATAAAGAATTAAAGAAAATTATAGGACAGGTAAGAGATCAGGCTGAA

CATCTTAAGACAGCAGTACAAATGGCAGTATTCATCCACAATTTTAAAAGAAAAGG

GGGGATTGGGGGGTACAGTGCAGGGGAAAGAATAGTAGACATAATAGCAACAGAC

ATACAAACTAAAGAATTACAAAAACAAATTACAAAAATTCAAAATTTTCGGGTTTAT

TACAGGGACAGCAGAGATCCAGTTTGGCTGCATACGCGTCGTGAGGCTCCGGTGCC
```

-continued

```
CGTCAGTGGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAG

TAGTCGCCGTGAACGTTCTTTTTCGCAACGGGTTTGCCGCCAGAACACAGGTAAGTG

CCGTGTGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTGGAAG

TGGGTGGGAGAGTTCGAGGCCTTGCGCTTAAGGAGCCCCTTCGCCTCGTGCTTGAGT

TGAGGCCTGGCCTGGGCGCTGGGGCCGCCGCGTGCGAATCTGGTGGCACCTTCGCG

CCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGC

GGGTGAGTCACCCACACAAAGGAAAAGGGCCTTTCCGTCCTCAGCCGTCGCTTCATG

TGACTCCACTGAGTACCGGGCGCCGTCCAGGCACCTCGATTAGTTCTCGTGCTTTTG

GAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGA

ATTTGCCCTTTTTGAGTTTGGATCTTGGTTCATTCTCAAGCCTCAGACAGTGGTTCAA

AGTTTTTTTCTTCCATTTCAGGTGTCGTGAGCTAGAGCCACCATGGAGTTTGGGCTGA

GCTGGCTTTTTCTTGTGGCTATTTTAAAAGGTGTCCAGTGCGGATCCCAAGTTCAGCT

GCAAGAAAGCGGACCCGGTTTAGTGAAACCCTCCGAGACTTTATCTTTAACATGCGC

CGTGAGCGGCTACAGCATCTCTCGTCATGCTTTAACTTGGATTCGTCAGCCTCCCGG

AAAGGGTTTAGAGTGGATCGGCGCCATCGACAACGCCGGCACCACCTATTACGCCA

GCTGGGCCAAGTCTCGTGTGACCATCAGCGTGGACACCAGCAAGAACCAGTTCTCTT

TAAAGCTGTCCAGCGTGACCGCTGCCGACACAGCCGTGTACTACTGCGCTCGTGTGT

TCTACGACATCAACAGCGGCTACTATTTAGACGGAATGGATCTGTGGGGCCCCGGA

ACTTTAGTGACAGTCAGCAGCGGAGGCGGAGGAAGCGGAGGAGGAGGAAGCTCCG

GAGGCGGTTCTCAATTCGTGCTGACACAGAGCCCTAGCGCCTCTGCCTCTTTAGGAG

CCTCCGTGAAGCTGACTTGTACTTTAAGCAGCGCCCACAAGACCTACACCATCGACT

GGTACCAGCAGCAGCCCGAGAAGGGCCCTAGATATTTAATGCAAGTTAAGAGCGAC

GGCAGCTACACCAAAGGCACTGGTGTGCCCGATCGTTTTAGCGGCAGCAGCAGCGG

CGCCGATAGGTATTTAACCATCAGCTCTTTACAGAGCGAGGACGAGGCCGACTACTA

CTGTGGCGCCGACGACAACGGCGGCTACGTGTTTGGCGGCGGCACACAGCTGACCG

TTTTAGCTAGCGGTGGCGGAGGTTCTGGAGGTGGAGGTTCCTCCGGAATCTACATCT

GGGCGCCCTTGGCCGGGACTTGTGGGGTCCTTCTCCTGTCACTGGTTATCACCCTTTA

CTGCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA
```

-continued

```
CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGAGA

AGGAAGAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGGCACGA

TGGCCTTTACCAGGGTCTCAGTACAGCCACCAAGGACACCTACGACGCCCTTCACAT

GCAGGCCCTGCCCCCTCGCTAAGTCGACAATCAACCTCTGGATTACAAAATTTGTGA

AAGATTGACTGGTATTCTTAACTATGTTGCTCCTTTTACGCTATGTGGATACGCTGCT

TTAATGCCTTTGTATCATGCTATTGCTTCCCGTATGGCTTTCATTTTCTCCTCCTTGTA

TAAATCCTGGTTGCTGTCTCTTTATGAGGAGTTGTGGCCCGTTGTCAGGCAACGTGG

CGTGGTGTGCACTGTGTTTGCTGACGCAACCCCCACTGGTTGGGGCATTGCCACCAC

CTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAAT

TCCGTGGTGTTGTCGGGGAAGCTGACGTCCTTTCCTTGGCTGCTCGCCTGTGTTGCCA

CCTGGATTCTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTGGAATTCGAGCTCG

GTACCTTTAAGACCAATGACTTACAAGGCAGCTGTAGATCTTAGCCACTTTTTAAAA

GAAAAGGGGGACTGGAAGGGCTAATTCACTCCCAACGAAGACAAGATCTGCTTTT

TGCTTGTACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTCAAGTAGT

GTGTGCCCGTCTGTTGTGTGACTCTGGTAACTAGAGATCCCTCAGACCCTTTTAGTCA

GTGTGGAAAATCTCTAGCAGTAGTAGTTCATGTCATCTTATTATTCAGTATTTATAAC

TTGCAAAGAAATGAATATCAGAGAGTGAGAGGAACTTGTTTATTGCAGCTTATAATG

GTTACAAATAAAGCAATAGCATCACAAATTTCACAAATAAAGCATTTTTTTCACTGC

ATTCTAGTTGTGGTTTGTCCAAACTCATCAATGTATCTTATCATGTCTGGCTCTAGCT

ATCCCGCCCCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAGAAGTAGT

GAGGAGGCTTTTTTGGAGGCCTAGCTAGGGACGTACCCAATTCGCCCTATAGTGAGT

CGTATTACGCGCGCTCACTGGCCGTCGTTTTACAACGTCGTGACTGGGAAAACCCTG

GCGTTACCCAACTTAATCGCCTTGCAGCACATCCCCCTTTCGCCAGCTGGCGTAATA

GCGAAGAGGCCCGCACCGATCGCCCTTCCCAACAGTTGCGCAGCCTGAATGGCGAA

TGGGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTTCC

TTTCTCGCCACGTTCGCCGGCTTTCCCCGTCAAGCTCTAAATCGGGGGCTCCCTTTAG

GGTTCCGATTTAGTGCTTTACGGCACCTCGACCCCAAAAAACTTGATTAGGGTGATG

GTTCACGTAGTGGGCCATCGCCCTGATAGACGGTTTTTCGCCCTTTGACGTTGGAGT

CCACGTTCTTTAATAGTGGACTCTTGTTCCAAACTGGAACAACACTCAACCCTATCTC

GGTCTATTCTTTTGATTTATAAGGGATTTTGCCGATTTCGGCCTATTGGTTAAAAAAT

GAGCTGATTTAACAAAAATTTAACGCGAATTTTAACAAAATATTAACGCTTACAATT

TAGGTGGCACTTTTCGGGGAAATGTGCGCGGAACCCCTATTTGTTTATTTTTCTAAAT

ACATTCAAATATGTATCCGCTCATGAGACAATAACCCTGATAAATGCTTCAATAATA
```

-continued

TTGAAAAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAAAGAT

GCTGAAGATCAGTTGG pTRPE-C25-gs-BBz (plasmid for CAR25)

(SEQ ID NO: 113)

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

-continued

```
GAGAGAAAAAGCACCGTGCATGCCGATTGGTGGAAGTAAGGTGGTACGATCGTGCC
TTATTAGGAAGGCAACAGACGGGTCTGACATGGATTGGACGAACCACTGAATTGCC
GCATTGCAGAGATATTGTATTTAAGTGCCTAGCTCGATACATAAACGGGTCTCTCTG
GTTAGACCAGATCTGAGCCTGGGAGCTCTCTGGCTAACTAGGGAACCCACTGCTTAA
GCCTCAATAAAGCTTGCCTTGAGTGCTTCAAGTAGTGTGTGCCCGTCTGTTGTGTGA
CTCTGGTAACTAGAGATCCCTCAGACCCTTTTAGTCAGTGTGGAAAATCTCTAGCAG
TGGCGCCCGAACAGGGACTTGAAAGCGAAAGGGAAACCAGAGGAGCTCTCTCGAC
GCAGGACTCGGCTTGCTGAAGCGCGCACGGCAAGAGGCGAGGGGCGGCGACTGGT
GAGTACGCCAAAAATTTTGACTAGCGGAGGCTAGAAGGAGAGAGATGGGTGCGAG
AGCGTCAGTATTAAGCGGGGGAGAATTAGATCGCGATGGGAAAAAATTCGGTTAAG
GCCAGGGGAAAGAAAAAATATAAATTAAAACATATAGTATGGGCAAGCAGGGAG
CTAGAACGATTCGCAGTTAATCCTGGCCTGTTAGAAACATCAGAAGGCTGTAGACA
AATACTGGGACAGCTACAACCATCCCTTCAGACAGGATCAGAAGAACTTAGATCAT
TATATAATACAGTAGCAACCCTCTATTGTGTGCATCAAAGGATAGAGATAAAAGAC
ACCAAGGAAGCTTTAGACAAGATAGAGGAAGAGCAAAACAAAAGTAAGACCACCG
CACAGCAAGCGGCCGCTGATCTTCAGACCTGGAGGAGGAGATATGAGGGACAATTG
GAGAAGTGAATTATATAAATATAAAGTAGTAAAAATTGAACCATTAGGAGTAGCAC
CCACCAAGGCAAAGAGAAGAGTGGTGCAGAGAGAAAAAAGAGCAGTGGGAATAGG
AGCTTTGTTCCTTGGGTTCTTGGGAGCAGCAGGAAGCACTATGGGCGCAGCGTCAAT
GACGCTGACGGTACAGGCCAGACAATTATTGTCTGGTATAGTGCAGCAGCAGAACA
ATTTGCTGAGGGCTATTGAGGCGCAACAGCATCTGTTGCAACTCACAGTCTGGGCA
TCAAGCAGCTCCAGGCAAGAATCCTGGCTGTGGAAAGATACCTAAAGGATCAACAG
CTCCTGGGGATTTGGGGTTGCTCTGGAAAACTCATTTGCACCACTGCTGTGCCTTGG
AATGCTAGTTGGAGTAATAAATCTCTGGAACAGATTTGGAATCACACGACCTGGATG
GAGTGGGACAGAGAAATTAACAATTACACAAGCTTAATACACTCCTTAATTGAAGA
ATCGCAAAACCAGCAAGAAAAGAATGAACAAGAATTATTGGAATTAGATAAATGGG
CAAGTTTGTGGAATTGGTTTAACATAACAAATTGGCTGTGGTATATAAAATTATTCA
TAATGATAGTAGGAGGCTTGGTAGGTTTAAGAATAGTTTTTGCTGTACTTTCTATAGT
GAATAGAGTTAGGCAGGGATATTCACCATTATCGTTTCAGACCCACCTCCCAACCCC
GAGGGGACCCGACAGGCCCGAAGGAATAGAAGAAGAAGGTGGAGAGAGAGACAG
AGACAGATCCATTCGATTAGTGAACGGATCTCGACGGTATCGATTAGACTGTAGCCC
AGGAATATGGCAGCTAGATTGTACACATTTAGAAGGAAAAGTTATCTTGGTAGCAG
TTCATGTAGCCAGTGGATATATAGAAGCAGAAGTAATTCCAGCAGAGACAGGGCAA
GAAACAGCATACTTCCTCTTAAAATTAGCAGGAAGATGGCCAGTAAAAACAGTACA
TACAGACAATGGCAGCAATTTCACCAGTACTACAGTTAAGGCCGCCTGTTGGTGGGC
GGGGATCAAGCAGGAATTTGGCATTCCCTACAATCCCCAAAGTCAAGGAGTAATAG
AATCTATGAATAAAGAATTAAAGAAAATTATAGGACAGGTAAGAGATCAGGCTGAA
CATCTTAAGACAGCAGTACAAATGGCAGTATTCATCCACAATTTTAAAAGAAAAGG
GGGGATTGGGGGGTACAGTGCAGGGGAAAGAATAGTAGACATAATAGCAACAGAC
ATACAAACTAAAGAATTACAAAAACAAATTACAAAAATTCAAAATTTTCGGGTTTAT
TACAGGGACAGCAGAGATCCAGTTTGGCTGCATACGCGTCGTGAGGCTCCGGTGCC
```

-continued

```
CGTCAGTGGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAG

TAGTCGCCGTGAACGTTCTTTTTCGCAACGGGTTTGCCGCCAGAACACAGGTAAGTG

CCGTGTGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTGGAAG

TGGGTGGGAGAGTTCGAGGCCTTGCGCTTAAGGAGCCCCTTCGCCTCGTGCTTGAGT

TGAGGCCTGGCCTGGGCGCTGGGGCCGCCGCGTGCGAATCTGGTGGCACCTTCGCG

CCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGC

GGGTGAGTCACCCACACAAAGGAAAAGGGCCTTTCCGTCCTCAGCCGTCGCTTCATG

TGACTCCACTGAGTACCGGGCGCCGTCCAGGCACCTCGATTAGTTCTCGTGCTTTTG

GAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGA

ATTTGCCCTTTTTGAGTTTGGATCTTGGTTCATTCTCAAGCCTCAGACAGTGGTTCAA

AGTTTTTTTCTTCCATTTCAGGTGTCGTGAGCTAGAGCCACCATGGAGTTTGGGCTGA

GCTGGCTTTTTCTTGTGGCTATTTTAAAAGGTGTCCAGTGCGGATCCCAAGTTCAGCT

GCAAGAAAGCGGACCCGGTTTAGTGAAACCCTCCGAGACTTTATCTTTAACATGCGC

CGTGAGCGGCTACAGCATCTCTCGTCATGCTTTAACTTGGATTCGTCAGCCTCCCGG

AAAGGGTTTAGAGTGGATCGGCGCCATCGACAACGCCGGCACCACCTATTACGCCA

GCTGGGCCAAGTCTCGTGTGACCATCAGCGTGGACACCAGCAAGAACCAGTTCTCTT

TAAAGCTGTCCAGCGTGACCGCTGCCGACACAGCCGTGTACTACTGCGCTCGTGTGT

TCTACGACATCAACAGCGGCTACTATTTAGACGGAATGGATCTGTGGGGCCCCGGA

ACTTTAGTGACAGTCAGCAGCGGAGGCGGAGGAAGCGGAGGAGGAGGAAGCTCCG

GAGGCGGTTCTCAACTGGTGCTGACACAGAGCCCTAGCGCCTCTGCCTCTTTAGGAG

CCTCCGTGAAGCTGACTTGTACTTTAAGCAGCGCCCACAAGACCTACACCATCGACT

GGTACCAGCAGCAGCCCGAGAAGGGCCCTAGATATTTAATGCAAGTTAAGAGCGAC

GGCAGCTACACCAAAGGCACTGGTGTGCCCGATCGTTTTAGCGGCAGCAGCAGCGG

CGCCGATAGGTATTTAACCATCAGCTCTTTACAGAGCGAGGACGAGGCCGACTACTA

CTGTGGCGCCGACGACAACGGCGGCTACGTGTTTGGCGGCGGCACACAGCTGACCG

TTTTAGCTAGCGGTGGCGGAGGTTCTGGAGGTGGAGGTTCCTCCGGAATCTACATCT

GGGCGCCCTTGGCCGGGACTTGTGGGGTCCTTCTCCTGTCACTGGTTATCACCCTTTA

CTGCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA
```

-continued

```
CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGAGA

AGGAAGAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGGCACGA

TGGCCTTTACCAGGGTCTCAGTACAGCCACCAAGGACACCTACGACGCCCTTCACAT

GCAGGCCCTGCCCCCTCGCTAAGTCGACAATCAACCTCTGGATTACAAAATTTGTGA

AAGATTGACTGGTATTCTTAACTATGTTGCTCCTTTTACGCTATGTGGATACGCTGCT

TTAATGCCTTTGTATCATGCTATTGCTTCCCGTATGGCTTTCATTTTCTCCTCCTTGTA

TAAATCCTGGTTGCTGTCTCTTTATGAGGAGTTGTGGCCCGTTGTCAGGCAACGTGG

CGTGGTGTGCACTGTGTTTGCTGACGCAACCCCCACTGGTTGGGGCATTGCCACCAC

CTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAAT

TCCGTGGTGTTGTCGGGGAAGCTGACGTCCTTTCCTTGGCTGCTCGCCTGTGTTGCCA

CCTGGATTCTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTGGAATTCGAGCTCG

GTACCTTTAAGACCAATGACTTACAAGGCAGCTGTAGATCTTAGCCACTTTTTAAAA

GAAAAGGGGGACTGGAAGGGCTAATTCACTCCCAACGAAGACAAGATCTGCTTTT

TGCTTGTACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTCAAGTAGT

GTGTGCCCGTCTGTTGTGTGACTCTGGTAACTAGAGATCCCTCAGACCCTTTTAGTCA

GTGTGGAAAATCTCTAGCAGTAGTAGTTCATGTCATCTTATTATTCAGTATTTATAAC

TTGCAAAGAAATGAATATCAGAGAGTGAGAGGAACTTGTTTATTGCAGCTTATAATG

GTTACAAATAAAGCAATAGCATCACAAATTTCACAAATAAAGCATTTTTTTCACTGC

ATTCTAGTTGTGGTTTGTCCAAACTCATCAATGTATCTTATCATGTCTGGCTCTAGCT

ATCCCGCCCCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAGAAGTAGT

GAGGAGGCTTTTTTGGAGGCCTAGCTAGGGACGTACCCAATTCGCCCTATAGTGAGT

CGTATTACGCGCGCTCACTGGCCGTCGTTTTACAACGTCGTGACTGGGAAAACCCTG

GCGTTACCCAACTTAATCGCCTTGCAGCACATCCCCCTTTCGCCAGCTGGCGTAATA

GCGAAGAGGCCCGCACCGATCGCCCTTCCCAACAGTTGCGCAGCCTGAATGGCGAA

TGGGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTTCC

TTTCTCGCCACGTTCGCCGGCTTTCCCCGTCAAGCTCTAAATCGGGGGCTCCCTTTAG

GGTTCCGATTTAGTGCTTTACGGCACCTCGACCCCAAAAAACTTGATTAGGGTGATG

GTTCACGTAGTGGGCCATCGCCCTGATAGACGGTTTTTCGCCCTTTGACGTTGGAGT

CCACGTTCTTTAATAGTGGACTCTTGTTCCAAACTGGAACAACACTCAACCCTATCTC

GGTCTATTCTTTTGATTTATAAGGGATTTTGCCGATTTCGGCCTATTGGTTAAAAAAT

GAGCTGATTTAACAAAAATTTAACGCGAATTTTAACAAAATATTAACGCTTACAATT

TAGGTGGCACTTTTCGGGGAAATGTGCGCGGAACCCCTATTTGTTTATTTTTCTAAAT

ACATTCAAATATGTATCCGCTCATGAGACAATAACCCTGATAAATGCTTCAATAATA
```

TTGAAAAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAAAGAT

GCTGAAGATCAGTTGG pTRPE-C29-gs-BBz (plasmid for CAR29)

(SEQ ID NO: 114)

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

-continued

```
GAGAGAAAAAGCACCGTGCATGCCGATTGGTGGAAGTAAGGTGGTACGATCGTGCC

TTATTAGGAAGGCAACAGACGGGTCTGACATGGATTGGACGAACCACTGAATTGCC

GCATTGCAGAGATATTGTATTTAAGTGCCTAGCTCGATACATAAACGGGTCTCTCTG

GTTAGACCAGATCTGAGCCTGGGAGCTCTCTGGCTAACTAGGGAACCCACTGCTTAA

GCCTCAATAAAGCTTGCCTTGAGTGCTTCAAGTAGTGTGTGCCCGTCTGTTGTGTGA

CTCTGGTAACTAGAGATCCCTCAGACCCTTTTAGTCAGTGTGGAAAATCTCTAGCAG

TGGCGCCCGAACAGGGACTTGAAAGCGAAAGGGAAACCAGAGGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAACAAAAGTAAGACCACCG

CACAGCAAGCGGCCGCTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGATTAGACTGTAGCCC

AGGAATATGGCAGCTAGATTGTACACATTTAGAAGGAAAAGTTATCTTGGTAGCAG

TTCATGTAGCCAGTGGATATATAGAAGCAGAAGTAATTCCAGCAGAGACAGGGCAA

GAAACAGCATACTTCCTCTTAAAATTAGCAGGAAGATGGCCAGTAAAAACAGTACA

TACAGACAATGGCAGCAATTTCACCAGTACTACAGTTAAGGCCGCCTGTTGGTGGGC

GGGGATCAAGCAGGAATTTGGCATTCCCTACAATCCCCAAAGTCAAGGAGTAATAG

AATCTATGAATAAAGAATTAAAGAAAATTATAGGACAGGTAAGAGATCAGGCTGAA

CATCTTAAGACAGCAGTACAAATGGCAGTATTCATCCACAATTTTAAAAGAAAAGG

GGGGATTGGGGGGTACAGTGCAGGGGAAAGAATAGTAGACATAATAGCAACAGAC

ATACAAACTAAAGAATTACAAAAACAAATTACAAAAATTCAAAATTTTCGGGTTTAT

TACAGGGACAGCAGAGATCCAGTTTGGCTGCATACGCGTCGTGAGGCTCCGGTGCC
```

-continued

```
CGTCAGTGGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAG

TAGTCGCCGTGAACGTTCTTTTTCGCAACGGGTTTGCCGCCAGAACACAGGTAAGTG

CCGTGTGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTGGAAG

TGGGTGGGAGAGTTCGAGGCCTTGCGCTTAAGGAGCCCCTTCGCCTCGTGCTTGAGT

TGAGGCCTGGCCTGGGCGCTGGGGCCGCCGCGTGCGAATCTGGTGGCACCTTCGCG

CCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGC

GGGTGAGTCACCCACACAAAGGAAAAGGGCCTTTCCGTCCTCAGCCGTCGCTTCATG

TGACTCCACTGAGTACCGGGCGCCGTCCAGGCACCTCGATTAGTTCTCGTGCTTTTG

GAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGA

ATTTGCCCTTTTTGAGTTTGGATCTTGGTTCATTCTCAAGCCTCAGACAGTGGTTCAA

AGTTTTTTTCTTCCATTTCAGGTGTCGTGAGCTAGAGCCACCATGGAGTTTGGGCTGA

GCTGGCTTTTTCTTGTGGCTATTTTAAAAGGTGTCCAGTGCGGATCCGAGGTGCAGC

TGGTGGAGTCTGGAGGAGGACTGGTGCAACCCGGTGGCTCTTTAAGACTGAGCTGC

GCCGCCTCTGGCTTCACCTTTTCTCGTCACGCTTTAACATGGGTGAGACAAGCTCCC

GGAAAGGGACTGGAGTGGGTGTCCGCCATCGACAACGCCGGCACCACCTACTACGC

CAGCTGGGCCAAGAGCAGATTCACCATCTCTCGTGACAACGCCAAGAACTCTTTATA

TTTACAGATGAACTCTTTAAGGGCCGAGGACACCGCCGTGTACTACTGCGCTCGTGT

GTTCTACGACATCAACTCCGGCTACTATTTAGACGGCATGGATTTATGGGGACCCGG

TACACTGGTCACAGTGAGCTCTGGAGGCGGAGGTAGCGGAGGCGGAGGAAGCAGC

GGTGGAGGCAGCCAGCTGGTGCTGACACAGTCCCCTTCCGCTTCCGCCTCTTTAGGA

GCCTCCGTGAAGCTGACTTGTACTTTAAGCAGCGCCCACAAAACCTACACCATCGAC

TGGTACCAGCAGCAGCCCGAGAAGGGCCCACGTTATTTAATGCAAGTTAAGTCCGA

CGGCTCCTACACCAAGGGCACCGGCGTGCCCGATAGATTCAGCGGCTCCAGCAGCG

GCGCCGATAGGTATTTAACCATCTCCTCTTTACAGAGCGAGGACGAGGCCGACTACT

ACTGTGGCGCCGACGACAACGGCGGCTACGTGTTTGGAGGCGGCACCCAGCTGACC

GTGCTGGCTAGCGGTGGCGGAGGTTCTGGAGGTGGAGGTTCCTCCGGAATCTACATC

TGGGCGCCCTTGGCCGGGACTTGTGGGGTCCTTCTCCTGTCACTGGTTATCACCCTTT

ACTGCAAACGGGGCAGAAAGAAACTCCTGTATATATTCAAACAACCATTTATGAGA

CCAGTACAAACTACTCAAGAGGAAGATGGCTGTAGCTGCCGATTTCCAGAAGAAGA

AGAAGGAGGATGTGAACTGAGAGTGAAGTTCAGCAGGAGCGCAGACGCCCCCGCGT
```

-continued

```
ACCAGCAGGGCCAGAACCAGCTCTATAACGAGCTCAATCTAGGACGAAGAGAGGA

GTACGATGTTTTGGACAAGAGACGTGGCCGGGACCCTGAGATGGGGGGAAAGCCGA

GAAGGAAGAACCCTCAGGAAGGCCTGTACAATGAACTGCAGAAAGATAAGATGGC

GGAGGCCTACAGTGAGATTGGGATGAAAGGCGAGCGCCGGAGGGGCAAGGGCAC

GATGGCCTTTACCAGGGTCTCAGTACAGCCACCAAGGACACCTACGACGCCCTTCAC

ATGCAGGCCCTGCCCCCTCGCTAAGTCGACAATCAACCTCTGGATTACAAAATTTGT

GAAAGATTGACTGGTATTCTTAACTATGTTGCTCCTTTTACGCTATGTGGATACGCTG

CTTTAATGCCTTTGTATCATGCTATTGCTTCCCGTATGGCTTTCATTTTCTCCTCCTTG

TATAAATCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATTGCCACC

ACCTGTCAGCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGCACTGACA

ATTCCGTGGTGTTGTCGGGAAGCTGACGTCCTTTCCTTGGCTGCTCGCCTGTGTTGC

CACCTGGATTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGTCTTCGCCTT

CGCCCTCAGACGAGTCGGATCTCCCTTTGGGCCGCCTCCCCGCCTGGAATTCGAGCT

CGGTACCTTTAAGACCAATGACTTACAAGGCAGCTGTAGATCTTAGCCACTTTTTAA

AAGAAAAGGGGGGACTGGAAGGGCTAATTCACTCCCAACGAAGACAAGATCTGCTT

TTTGCTTGTACTGGGTCTCTCTGGTTAGACCAGATCTGAGCCTGGGAGCTCTCTGGCT

AACTAGGGAACCCACTGCTTAAGCCTCAATAAAGCTTGCCTTGAGTGCTTCAAGTAG

TGTGTGCCCGTCTGTTGTGTGACTCTGGTAACTAGAGATCCCTCAGACCCTTTTAGTC

AGTGTGGAAAATCTCTAGCAGTAGTAGTTCATGTCATCTTATTATTCAGTATTTATAA

CTTGCAAAGAAATGAATATCAGAGAGTGAGAGGAACTTGTTTATTGCAGCTTATAAT

GGTTACAAATAAAGCAATAGCATCACAAATTTCACAAATAAAGCATTTTTTTCACTG

CATTCTAGTTGTGGTTTGTCCAAACTCATCAATGTATCTTATCATGTCTGGCTCTAGC

TATCCCGCCCCTAACTCCGCCCAGTTCCGCCCATTCTCCGCCCCATGGCTGACTAATT

TTTTTTATTTATGCAGAGGCCGAGGCCGCCTCGGCCTCTGAGCTATTCCAGAAGTAG

TGAGGAGGCTTTTTTGGAGGCCTAGCTAGGGACGTACCCAATTCGCCCTATAGTGAG

TCGTATTACGCGCGCTCACTGGCCGTCGTTTTACAACGTCGTGACTGGGAAAACCCT

GGCGTTACCCAACTTAATCGCCTTGCAGCACATCCCCCTTTCGCCAGCTGGCGTAAT

AGCGAAGAGGCCCGCACCGATCGCCCTTCCCAACAGTTGCGCAGCCTGAATGGCGA

ATGGGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTTTA

GGGTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGGAG

TCCACGTTCTTTAATAGTGGACTCTTGTTCCAAACTGGAACAACACTCAACCCTATCT

CGGTCTATTCTTTTGATTTATAAGGGATTTTGCCGATTTCGGCCTATTGGTTAAAAA

TGAGCTGATTTAACAAAAATTTAACGCGAATTTTAACAAAATATTAACGCTTACAAT

TTAGGTGGCACTTTCGGGGAAATGTGCGCGGAACCCCTATTTGTTTATTTTTCTAAA

TACATTCAAATATGTATCCGCTCATGAGACAATAACCCTGATAAATGCTTCAATAAT
```

-continued

ATTGAAAAAGGAAGAGTATGAGTATTCAACATTTCCGTGTCGCCCTTATTCCCTTTTT

TGCGGCATTTTGCCTTCCTGTTTTTGCTCACCCAGAAACGCTGGTGAAAGTAAAAGA

TGCTGAAGATCAGTTGG

Antigen Sequences

GFRα1

(SEQ ID NO: 115)
ATGTTCCTGGCCACCCTGTACTTCGCCCTGCCTCTGCTGGACCTGCTGCTGAGCGCCG

AAGTGAGCGGAGGAGACAGACTGGACTGCGTGAAGGCCAGCGACCAATGTCTGAA

GGAGCAATCCTGCTCCACCAAGTACAGGACACTCAGGCAGTGCGTGGCCGGAAAGG

AAACCAACTTCAGCCTGGCCAGCGGCCTCGAAGCTAAGGACGAATGCAGGAGCGCC

ATGGAGGCCCTGAAACAGAAGAGCCTGTACAACTGCAGGTGCAAGAGGGGCATGA

AGAAGGAGAAAAACTGCCTGAGGATCTACTGGAGCATGTATCAGAGCCTCCAGGGC

AACGATCTGCTGGAGGACAGCCCCTACGAGCCTGTCAACAGCAGGCTGTCCGATAT

CTTCAGGGTGGTGCCTTTCATTAGCGACGTGTTCCAGCAGGTGGAGCACATCCCCAA

AGGCAACAATTGTCTGGACGCTGCCAAAGCTTGCAACCTCGATGACATCTGTAAGA

AATACAGGAGCGCCTACATCACCCCCTGCACCACATCCGTGAGCAATGACGTGTGT

AACAGGAGGAAGTGCCACAAAGCTCTGAGGCAGTTCTTCGACAAGGTGCCTGCCAA

GCACAGCTACGGAATGCTCTTTTGCAGCTGCAGAGACATCGCCTGTACCGAGAGGA

GGAGACAAACCATCGTGCCCGTGTGCTCCTATGAAGAGAGGGAGAAACCCAACTGC

CTGAATCTGCAGGACAGCTGCAAGACCAACTACATCTGCAGGAGCAGGCTGGCCGA

CTTCTTCACCAATTGTCAGCCCGAATCCAGATCCGTGAGCTCCTGCCTGAAAGAGAA

TTATGCCGACTGCCTGCTGGCTTACAGCGGACTGATCGGCACAGTCATGACACCCAA

CTACATCGACAGCTCCTCCCTGTCCGTGGCCCCTTGGTGCGATTGCTCCAACTCCGG

CAACGACCTGGAGGAGTGTCTGAAGTTCCTGAACTTCTTCAAGGACAATACCTGCCT

CAAGAACGCCATCCAGGCTTTCGGAAACGGCAGCGACGTGACCGTGTGGCAGCCCG

CCTTTCCCGTGCAGACCACCACAGCTACCACAACCACCGCCCTGAGGGTGAAGAAT

AAGCCTCTGGGCCCCGCCGGCAGCGAGAATGAGATCCCCACACACGTGCTGCCTCC

TTGTGCCAATCTCCAGGCCCAGAAGCTGAAGTCCAACGTGAGCGGCAATACCCACC

TCTGCATCTCCAATGGCAACTACGAGAAGGAGGGACTGGGAGCCAGCAGCCACATT

ACCACCAAATCCATGGCTGCCCCTCCCAGCTGTGGACTGAGCCCTCTCCTCGTGCTG

GTGGTCACCGCCCTGTCCACACTGCTGTCCCTCACCGAGACCAGCTGA

GFRα2

(SEQ ID NO: 116)
ATGATCCTCGCCAACGTGTTCTGCCTGTTCTTTTTCCTGGACGAGACCCTGAGAAGCC

TGGCTAGCCCCTCCAGCCTCCAGGGACCTGAACTGCACGGCTGGAGGCCCCCTGTGG

ATTGCGTGAGAGCCAACGAGCTGTGCGCCGCCGAGAGCAACTGTTCCAGCAGATAC

AGGACCCTCAGACAGTGCCTGGCCGGCAGAGACAGAAACACCATGCTGGCCAACAA

GGAGTGTCAGGCCGCCCTGGAAGTGCTGCAAGAGTCCCCTCTGTACGATTGTAGGTG

CAAGAGGGGCATGAAGAAGGAACTGCAGTGCCTGCAGATCTATTGGAGCATCCATC

TGGGCCTCACCGAGGGCGAAGAATTTTATGAGGCCAGCCCCTACGAGCCCGTGACC

TCCAGACTCAGCGACATCTTCAGGCTCGCTTCCATCTTCAGCGGCACAGGCGCCGAT

-continued

CCTGTGGTGAGCGCCAAGAGCAACCATTGCCTGGACGCTGCCAAGGCCTGCAACCT

CAACGACAACTGCAAGAAGCTCAGGAGCTCCTATATCAGCATTTGCAACAGGGAGA

TTTCCCCCACCGAGAGGTGTAACAGGAGAAAGTGCCACAAGGCCCTGAGACAGTTC

TTCGACAGAGTGCCTTCCGAGTACACCTACAGGATGCTCTTCTGCAGCTGCCAGGAC

CAAGCCTGCGCTGAGAGAAGGAGGCAGACCATCCTGCCCTCCTGCAGCTACGAAGA

CAAGGAGAAGCCTAACTGCCTGGATCTCAGGGGCGTCTGCAGAACCGACCACCTCT

GTAGGTCCAGACTGGCCGACTTCCACGCCAATTGCAGGGCCAGCTACCAAACCGTG

ACCAGCTGCCCCGCCGACAACTATCAGGCCTGCCTGGGCAGCTACGCCGGCATGATT

GGCTTCGACATGACCCCCAATTACGTTGATAGCTCCCCCACAGGCATCGTGGTGAGC

CCTTGGTGCAGCTGCAGGGGCAGCGGCAACATGGAGGAAGAGTGCGAGAAGTTCCT

GAGGGACTTCACCGAGAATCCCTGCCTGAGAAACGCCATCCAGGCCTTCGGCAACG

GCACAGACGTGAACGTGTCCCCCAAAGGCCCCAGCTTTCAGGCCACCCAAGCTCCC

AGGGTCGAGAAAACCCCTTCCCTGCCCGACGACCTGAGCGATTCCACATCCCTCGGC

ACCTCCGTGATCACCACCTGCACATCCGTGCAGGAACAGGGCCTGAAGGCCAATAA

CTCCAAGGAGCTGAGCATGTGCTTCACAGAGCTGACCACCAACATTATCCCCGGCA

GCAACAAGGTGATCAAGCCCAATTCCGGACCTAGCAGAGCCAGACCCAGCGCCGCT

CTGACAGTGCTGTCCGTGCTGATGCTGAAACTGGCCCTGTGA

GFRα3

(SEQ ID NO: 117)
ATGGTGAGGCCTCTGAATCCCAGACCCCTGCCTCCCGTGGTGCTGATGCTGCTGCTG

CTGCTCCCTCCCTCCCCTCTGCCCCTGGCCGCTGGAGATCCTCTGCCCACAGAGAGC

AGACTCATGAACAGCTGCCTCCAGGCCAGGAGAAAGTGCCAGGCCGACCCTACCTG

TTCCGCCGCCTACCACCACCTGGACTCCTGCACCAGCAGCATCAGCACCCCTCTGCC

CAGCGAAGAACCCTCCGTCCCCGCTGATTGCCTGGAAGCCGCCCAGCAGCTGAGAA

ATAGCAGCCTGATCGGCTGCATGTGCCACAGAAGGATGAAGAACCAGGTGGCCTGC

CTGGATATTTACTGGACCGTCCACAGGGCCAGAAGCCTGGGAAATTACGAACTGGA

CGTGTCCCCCTACGAGGACACAGTGACAAGCAAGCCCTGGAAGATGAACCTCAGCA

AGCTGAACATGCTCAAGCCCGACAGCGACCTGTGCCTCAAATTCGCCATGCTGTGCA

CCCTGAACGACAAGTGCGACAGGCTGAGGAAAGCCTACGAGAAGCCTGTAGCGGC

CCCCATTGCCAGAGGCACGTGTGCCTGAGACAGCTGCTGACCTTCTTCGAGAAGGCC

GCTGAGCCTCACGCCCAAGGACTGCTCCTGTGCCCTTGCGCCCCCAATGATAGGGGC

TGCGGCGAGAGGAGAAGAAACACCATCGCTCCCAACTGCGCCCTGCCCCCTGTGGC

CCCTAATTGCCTCGAGCTGAGAAGACTGTGCTTCTCCGACCCTCTGTGCAGGAGCAG

ACTGGTGGATTTCCAGACCCACTGTCACCCCATGGACATCCTCGGAACCTGCGCCAC

CGAGCAGAGCAGGTGTCTCAGAGCCTACCTGGGCCTGATCGGCACCGCCATGACCC

CCAATTTTGTGAGCAACGTGAACACCTCCGTGGCCCTGTCCTGTACCTGCAGGGGAA

GCGGCAACCTCCAGGAGGAGTGCGAGATGCTCGAGGGCTTCTTCTCCCACAATCCCT

GCCTGACCGAGGCCATCGCCGCCAAGATGAGGTTCCACAGCCAGCTGTTCTCCCAG

GATTGGCCCCACCCCACCTTCGCTGTGATGGCCCACCAGAACGAAAACCCCGCTGTG

AGACCCCAGCCTTGGGTGCCCTCCCTGTTCAGCTGCACCCTGCCTCTCATCCTGCTGC

TGAGCCTGTGGTGA

-continued

GFRα4 isoform a
(SEQ ID NO: 118)
NRCVDAAEACTADARCQRLRSEYVAQCLGRAAQGGCPRARCRRALRRFFARGPPALT

HALLFCPCAGPACAERRRQTFVPSCAFSGPGPAPPSCLEPLNFCERSRVCRPRLLAFQVSC

TPAPSAPDGCLLDQGARCLRAYAGLVGTAVTPNYVDNVSARVAPWCDCGASGNRRED

CEAFRGLFTRNRCLDGAIQAFASGWPPVLLDQLNPQGDPEHSLLQVSIEGRMDPKSCDK

THTCPPCPAPEAEGAPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKATPPVL

DSDGSFFLYSKLTVDKSRWQQGNVFSCSVMHEALHNHYTQKSLSLSPGKHHHHHH

GFRα4 isoform b
(SEQ ID NO: 119)
NRCVDAAEACTADARCQRLRSEYVAQCLGRAAQGGCPRARCRRALRRFFARGPPALT

HALLFCPCAGPACAERRRQTFVPSCAFSGPGPAPPSCLEPLNFCERSRVCRCARAAAGP

WRGWGRGLSPAHRPPAAQASPPGLSGLVHPSAQRPRRLPAGPGRPLPARLRGPRGVPA

GTAVTPNYVDNVSARVAPWCDCGASGNRREDCEAFRGLFTRNRCLDGAIQAFASGWPP

VLLDQLNPQGDPEHSLLQVGGGENLYFQGGGGGAGGGGDKTHTCPPCPAPELLGGPSV

FLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSR

WQQGNVFSCSVMHEALHNHYTQKSLSLSPGK

TABLE 1

Nomenclature for heavy chain/light chain composition
of humanized rabbit P4-10 antibodies

| |
| --- |
| 0. 410HC.410LC |
| 1. H1.L3 |
| 2. H1.L3m1 |
| 3. H1m.L3 |
| 4. H1m1.L3m1 |
| 5. H2.L2 |
| 6. H2.L2m1 |
| 7. H2m1.L2 |
| 8. H2m1.L2m1 |
| 9. H2.L1 |
| 10. H2.L1m1 |
| 11. H2m1.L1 |
| 12. H2m1.L1m1 |
| 13. H1.L1 |
| 14. H1.L1m1 |
| 15. H1m1.L1 |
| 16. H1m1.L1m1 |
| 17. H1.L3m2 |
| 18. H1.L3m3 |
| 19. H2.L2m2 |
| 20. H2.L2m3 |
| 21. H2.L1m2 |
| 22. H1.L1m2 |
| 23. H1.L2m1 |
| 24. H2.L3m1 |
| 25. H1.L1m3 |
| 26. H1.L1m4 |
| 27. H1.L3m4 |
| 28. H1.L3m5 |
| 29. H2.L1m3 |

TABLE 2

Summary of binding results to GFRα4a/GFRα4b
for humanized P4-10 antibodies

| | H1 GFRα4a/ GFRα4b | H1m1 GFRα4a/ GFRα4b | H2 GFRα4a/ GFRα4b | H2m1 GFRα4a/ GFRα4b |
| --- | --- | --- | --- | --- |
| L1 | −/NT | −/NT | −/NT | −/NT |
| L1m2 | −/− | | −/− | |
| L1m4 | −/− | | | |
| L1m3 | +/+ | | +/+ | |
| L1m1 | +/+ | +/+ | +/+ | +/+ |
| L2 | | | −/NT | −/NT |
| L2m3 | | | −/− | |
| L2m2 | | | −/− | |
| L2m1 | w/+ | | +/+ | +/+ |
| L3 | −/NT | −/NT | | |
| L3m3 | −/− | | | |
| L3m5 | −/− | | | |
| L3m4 | −/− | | | |
| L3m2 | w/+ | | | |
| L3m1 | +/+ | +/+ | +/+ | |

Key:
"−" no binding
"+" binding
W weak binding
NT not tested

TABLE 3

Heavy chain/light chain % amino acid identity to human VH and VL germline genes for humanized scFv 10, 14, 25 and 29.

| | % Human | |
| --- | --- | --- |
| | Heavy chain | Light chain |
| 14. H1.L1m1 | 85 | 84 |
| 25. H1.L1m3 | 85 | 85 |
| 10. H2.L1m1 | 85 | 84 |
| 29. H2.L1m3 | 85 | 85 |

Embodiments of the Disclosure

In some aspects, the invention provides an isolated binding polypeptide comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds a glial cell derived neurotrophic factor (GDNF) family receptor alpha-4 (GFRα4). In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region comprising an amino acid sequence having at least 95-99% identity to the amino acid sequence of any of the heavy chain variable regions set forth in SEQ ID NOs: 7-10. In some embodiments, the binding polypeptide comprises a heavy chain variable region comprising at least 1, 2, or 3 modifications but not more than 20 modifications of the amino acid sequence of any of the heavy chain variable regions set forth in SEQ ID NOs: 7-10. In further embodiments, the binding polypeptide comprises a heavy chain variable region comprising an amino acid sequence of any of the heavy chain variable regions set forth in SEQ ID NOs: 7-10. In yet further embodiments, the binding polypeptide comprises a heavy chain variable region consisting of an amino acid sequence of any of the heavy chain variable regions set forth in SEQ ID NOs: 7-10.

In some embodiments, the binding polypeptide comprises a light chain variable region comprising an amino acid sequence having at least 95-99% identity to the amino acid sequence of any of the light chain variable regions set forth in SEQ ID NOs: 28-42. In some embodiments, the binding polypeptide comprises a light chain variable region comprising at least 1, 2, or 3 modifications but not more than 20 modifications of the amino acid sequence of any of the light chain variable regions set forth in SEQ ID NOs: 28-42. In further embodiments, the binding polypeptide comprises a light chain variable region comprising an amino acid sequence of any of the light chain variable regions set forth in SEQ ID NOs: 28-42. In yet further embodiments, the binding polypeptide comprises a light chain variable region consisting of an amino acid sequence of any of the light chain variable regions set forth in SEQ ID NOs: 28-42.

Provided is an isolated binding polypeptide comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

In some aspects, the invention provides a single-chain variable fragment (scFv) comprising: a heavy chain variable region that comprises three heavy chain complementarity determining regions (HCDRs), wherein HCDR1 comprises the amino acid sequence RHALT (SEQ ID NO:162), HCDR2 comprises the amino acid sequence AIDNAGTTYYASWAKS (SEQ ID NO:163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides a single-chain variable fragment (scFv) comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

In some aspects, the invention provides a single chain variable fragment comprising any one of the amino acid sequences set forth in SEQ ID NOs: 74-102. Also provided is a is a single chain variable fragment consisting of any one of the amino acid sequences set forth in SEQ ID NOs: 74-102.

In some aspects, the invention provides an isolated nucleic acid encoding the binding polypeptide or scFv of any preceding embodiment.

In some aspects, the invention provides an isolated nucleic acid encoding a binding polypeptide comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region encoded by a nucleotide sequence having at least 95-99% identity to the nucleotide sequence of any of the heavy chain variable regions set forth in SEQ ID NOs: 2-5. In further embodiments, the binding polypeptide comprises a heavy chain variable region encoded by a nucleotide sequence comprising any of the heavy chain variable region sequences provided in SEQ ID NOs: 2-5. In yet further embodiments, the binding polypeptide comprises a heavy chain variable region encoded by a nucleotide sequence consisting of any of the heavy chain variable region sequences provided in SEQ ID NOs: 2-5.

In some embodiments, the binding polypeptide comprises a light chain variable region encoded by a nucleotide sequence having at least 95-99% identity to the nucleotide sequence of any of the light chain variable regions provided in SEQ ID NOs: 12-26. In further embodiments, the binding polypeptide comprises a light chain variable region encoded by a nucleotide sequence comprising any of the light chain variable region sequences provided in SEQ ID NOs: 12-26. In yet further embodiments, the binding polypeptide comprises a light chain variable region encoded by a nucleotide sequence consisting of any of the light chain variable region sequences provided in SEQ ID NOs: 12-26.

In some aspects, the invention provides an isolated nucleic acid encoding a binding polypeptide comprising:

a heavy chain variable region encoded by any of the nucleotide sequences set forth in SEQ ID NO: 2-5; and a light chain variable region encoded by any of the nucleotide sequences set forth in SEQ ID NO: 12-26.

In some aspects, the invention provides an isolated nucleic acid encoding a single-chain variable fragment (scFv) comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides an isolated nucleic acid encoding a single-chain variable fragment (scFv) comprising: a heavy chain variable region comprising any of the nucleotide sequences set forth in SEQ ID NO: 2-5; and a light chain variable region comprising any of the nucleotide sequences set forth in SEQ ID NO: 12-26. Also provided is an isolated nucleic acid encoding a single-chain variable fragment (scFv) comprising any one of the nucleotide sequences set forth in SEQ ID NOs: 43-72. Also provided is an isolated nucleic acid encoding a single-chain variable fragment (scFv) consisting of any one of the nucleotide sequences set forth in SEQ ID NOs: 43-72.

In some aspects, the invention provides a vector comprising the isolated nucleic acid of any one of the preceding embodiments. In further embodiments, the vector is an expression vector. In yet further embodiments, the vector is selected from the group consisting of a DNA vector, an RNA vector, a plasmid, a lentiviral vector, an adenoviral vector, an adeno-associated viral vector, and a retroviral vector.

In some aspects, the invention provides a host cell comprising the vector of any one of the preceding embodiments. In further embodiments, the host cell is of eukaryotic or prokaryotic origin. In some embodiments, the host cell is of mammalian origin. In some embodiments, the host cell is of bacterial origin.

In some aspects, the invention provides a pharmaceutical composition comprising the binding polypeptide or scFv of any one of the preceding embodiments. Also provided is a pharmaceutical composition comprising the antibody or an antigen-binding fragment of any one of the preceding embodiments.

In some aspects, the invention provides a chimeric chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody.

In some embodiments, the antibody or antigen-binding fragment is a humanized antibody or a fragment thereof. In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42. In some embodiments, the antigen binding domain comprises a light chain variable region comprising at least 1, 2, or 3 modifications but not more than 20 modifications of the amino acid sequence of any of the light chain variable regions set forth in SEQ ID NOs: 28-42. In further embodiments, the antigen binding domain comprises a light chain variable region comprising an amino acid sequence of any of the light chain variable regions set forth in SEQ ID NOs: 28-42. In yet further embodiments, the antigen binding domain comprises a light chain variable region consisting of an amino acid sequence of any of the light chain variable regions set forth in SEQ ID NOs: 28-42.

In some aspects, the invention provides a chimeric antigen receptor (CAR) comprising an antigen binding domain, a transmembrane domain, and an intracellular domain, wherein the antigen binding domain comprises: a heavy chain variable region comprising any of the amino acid sequences set forth in SEQ ID NO: 7-10; and a light chain variable region comprising any of the amino acid sequences set forth in SEQ ID NO: 28-42.

In some aspects, the invention provides a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CDS, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcyRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

In some aspects, the invention provides a chimeric antigen receptor (CAR) comprising: an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

In some aspects, the invention provides a chimeric antigen receptor (CAR) comprising: an antigen binding domain comprising: a heavy chain variable region comprising any of the amino acid sequences set forth in SEQ ID NO: 7-10; and a light chain variable region comprising any of the amino acid sequences set forth in SEQ ID NO: 28-42; a CD8 transmembrane domain; a 4-1BB costimulatory domain; and a CD3ζ intracellular signaling domain.

In some aspects, the invention provides a chimeric antigen receptor (CAR) comprising any one of the amino acid sequences set forth in SEQ ID NOs: 107-110. Also provided is a chimeric antigen receptor (CAR) consisting of any one of the amino acid sequences set forth in SEQ ID NOs: 107-110.

In some aspects, the invention provides a nucleic acid encoding for the CAR of any one of the preceding embodiments.

In some aspects, the invention provides a nucleic acid encoding a chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region encoded by a nucleotide sequence having at least 95-99% identity to the nucleotide sequence of any of the heavy chain variable regions set forth in SEQ ID NOs: 2-5. In some embodiments, the antigen binding domain comprises a heavy chain variable region encoded by a nucleotide sequence comprising any of the heavy chain variable region sequences set forth in SEQ ID NOs: 2-5. In further embodiments, the antigen binding domain comprises a heavy chain variable region encoded by a nucleotide sequence consisting of any of the heavy chain variable region sequences set forth in SEQ ID NOs: 2-5.

In some embodiments, the antigen binding domain comprises a light chain variable region encoded by a nucleotide sequence having at least 95-99% identity to the nucleotide sequence of any of the light chain variable regions set forth in SEQ ID NOs: 12-26. In some embodiments, the antigen binding domain comprises a light chain variable region encoded by a nucleotide sequence comprising any of the light chain variable region sequences set forth in SEQ ID NOs: 12-26. In further embodiments, the antigen binding domain comprises a light chain variable region encoded by a nucleotide sequence consisting of any of the light chain variable region sequences set forth in SEQ ID NOs: 12-26.

In some aspects, the invention provides a nucleic acid encoding a chimeric antigen receptor (CAR) comprising an antigen binding domain, a transmembrane domain, and an intracellular domain, wherein the antigen binding domain comprises: a heavy chain variable region encoded by any of the nucleotide sequences set forth in SEQ ID NO: 2-5; and a light chain variable region encoded by any of the nucleotide sequences set forth in SEQ ID NO: 12-26.

In some aspects, the invention provides a nucleic acid encoding a chimeric antigen receptor (CAR) comprising an antigen binding domain, a transmembrane domain, and an intracellular signaling domain, wherein the antigen binding domain is encoded by any one of the nucleotide sequences set forth in SEQ ID NOs: 103-106.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CDS, ICAM-1, LFA-1, Lck, TNFR-I, TNFI-II, Fas, CD30, CD40, ICOS, NKG2C, and B7-H3 (CD276), or a variant thereof. In some embodiments, the costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcyRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

In some aspects, the invention provides a nucleic acid encoding a chimeric antigen receptor (CAR) comprising: an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGT-TYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3 intracellular signaling domain.

Provided is a nucleic acid encoding a chimeric antigen receptor (CAR) comprising: an antigen binding domain comprising: a heavy chain variable region encoded by any of the nucleotide sequences set forth in SEQ ID NO: 2-5; and a light chain variable region encoded by any of the nucleotide sequences set forth in SEQ ID NO: 12-26; a CD8 transmembrane domain; a 4-1BB costimulatory domain; and a CD3ζ intracellular signaling domain.

In some aspects, the invention provides a nucleic acid encoding a chimeric antigen receptor (CAR) comprising any one of the nucleotide sequences set forth in SEQ ID NOs: 111-114.

In some aspects, the invention provides a nucleic acid encoding a chimeric antigen receptor (CAR) consisting of any one of the nucleotide sequences set forth in SEQ ID NOs: 111-114.

In some aspects, the invention provides a vector comprising the nucleic acid of any one of the preceding embodiments. In some embodiments, the vector is an expression vector. In some embodiments, the vector is selected from the group consisting of a DNA vector, an RNA vector, a plasmid, a lentiviral vector, an adenoviral vector, an adeno-associated viral vector, and a retroviral vector. In some embodiments, the vector further comprises an EF-1 a promoter. In some embodiments, the vector further comprises a woodchuck hepatitis virus posttranscriptional regulatory element (WPRE). In further embodiments, the vector further comprises a rev response element (RRE). In further embodiments, the vector further comprises a cPPT sequence. In yet further embodiments, the vector is a self-inactivating vector.

In some aspects, the invention provides a cell comprising the CAR of any one of the preceding embodiments, the nucleic acid of any one of the preceding embodiments, or the vector of any one of the preceding embodiments. In some embodiments, the cell is selected from the group consisting of a T cell, a natural killer (NK) cell, a cytotoxic T lymphocyte (CTL), and a regulatory T cell.

In some aspects, the invention provides the CAR of any one of the preceding embodiments, the nucleic acid of any one of the preceding embodiments, the vector of any one of the preceding embodiments, or the cell of any one of the preceding embodiments, for use in the treatment of a disease associated with expression of a thyroid cell antigen.

In some aspects, the invention provides a modified immune cell or precursor cell thereof, comprising a chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42.

In some aspects, the invention provides the cell of any one of the preceding embodiments, wherein the antigen binding domain comprises a light chain variable region comprising at least 1, 2, or 3 modifications but not more than 20 modifications of the amino acid sequence of any of the light chain variable regions set forth in SEQ ID NOs: 28-42. Provided is the cell of any one of the preceding embodiments, wherein the antigen binding domain comprises a light chain variable region comprising an amino acid sequence of any of the light chain variable regions set forth in SEQ ID NOs: 28-42. In some embodiments, the antigen binding domain comprises a light chain variable region consisting of an amino acid sequence of any of the light chain variable regions set forth in SEQ ID NOs: 28-42.

In some aspects, the invention provides a modified immune cell or precursor cell thereof, comprising a chimeric antigen receptor (CAR) comprising an antigen binding domain, a transmembrane domain, and an intracellular domain, wherein the antigen binding domain comprises: a heavy chain variable region comprising any of the amino acid sequences set forth in SEQ ID NO: 7-10; and a light chain variable region comprising any of the amino acid sequences set forth in SEQ ID NO: 28-42.

Also provided is a modified immune cell or precursor cell thereof, comprising a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102. In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CDS, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

In some aspects, the invention provides a modified immune cell or precursor cell thereof, comprising a chimeric antigen receptor (CAR) comprising: an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO:164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3 intracellular signaling domain.

In some aspects, the invention provides a modified immune cell or precursor cell thereof, comprising chimeric antigen receptor (CAR) comprising an antigen binding domain comprising: a heavy chain variable region comprising any of the amino acid sequences set forth in SEQ ID NO: 7-10; a light chain variable region comprising any of the amino acid sequences set forth in SEQ ID NO: 28-42; a CD8 transmembrane domain; a 4-1BB costimulatory domain; and a CD3 intracellular signaling domain.

In some aspects, the invention provides a modified immune cell or precursor cell thereof, comprising a chimeric antigen receptor (CAR) comprising any one of the amino acid sequences set forth in SEQ ID NOs: 107-110.

In some aspects, the invention provides a modified immune cell or precursor cell thereof, comprising a chimeric antigen receptor (CAR) consisting of any one of the amino acid sequences set forth in SEQ ID NOs: 107-110.

In some embodiments, the modified cell is a modified immune cell. In some embodiments, the modified cell is a modified T cell. In some embodiments, the modified cell is an autologous cell. In further embodiments, the modified cell is an autologous cell obtained from a human subject.

In some aspects, the invention provides a pharmaceutical composition comprising a therapeutically effective amount of the modified cell of any one of the preceding embodiments.

In some aspects, the invention provides a method of treating a disease in a subject in need thereof, comprising administering to the subject an effective amount of the cell of any one of the preceding embodiments, or the pharmaceutical composition of any one of the preceding embodiments. In some embodiments, the disease is associated with expression of a thyroid cell antigen. In further embodiments, the disease is associated with expression of GFRα4. In yet further embodiments, the disease is a cancer. In yet further embodiments, the cancer is medullary thyroid carcinoma (MTC) or a metastasis resulting from MTC.

In some aspects, the invention provides a method of treating a disease associated with expression of a thyroid cell antigen in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides a method of treating a GFRα4-associated disease in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides a method of treating medullary thyroid cancer (MTC) in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore specifically point out the preferred embodiments of the present invention and are not to be construed as limiting in any way the remainder of the disclosure.

Example 1: In Silico Design of Humanized Versions of Rabbit P4-10 Antibody

Rabbit and human antibodies comprise heterodimers of heavy chains and light chains. In both humans and rabbits, the heavy chain variable region is encoded by the rearrangement of 3 germline genes designated $V_H$, D and $J_H$. In the human repertoire, there are approximately 70 $V_H$ gene segments, approximately 25 D gene segments, and 7 $J_H$ segments. During B cell development in the bone marrow, a given B cell selects one $V_H$ gene segment, one D segment, and one $J_H$ segment and splices them together to form a single gene that encodes the entire heavy chain variable region. With respect to FRs and CDRs, the $V_H$ gene segment contributes FR1-CDR1-FR2-CDR2-FR3, the D gene contributes the bulk of CDR3, and the $J_H$ gene contributes the bulk of FR4. During the splicing process, nucleotides can be added or removed at the junctions between the $V_H$ and D gene segments and between the D and $J_H$ gene segments that can result in increases or decreases in the number of amino acid residues in the CDR3, or shift the reading frame of the CDR3 entirely, creating yet additional diversity.

Light chain variable regions are also encoded by rearranged genes, though there are no light chain D gene segments, just $V_L$'s and $J_L$'s. In humans and rabbits, there are 2 classes of light chains-kappa and lambda-and thus their genomes comprise 2 distinct sets of light chain germline genes. A given B cell expresses either a kappa or lambda light chain paired with the heavy chain whose gene was rearranged as described above. During B cell development in humans, a kappa light gene is created through the selection and splicing together of 1 of approximately 30 Vkappa gene segments and 1 of 5 Jkappa gene segments. A lambda light chain gene is created through the selection and splicing together of 1 of approximately 30 Vlambda gene segments and 1 of 7 Jlambda gene segments. The rabbit anti-GFRα4 antibody P4-10 which humanization is described herein comprises a lambda light chain.

The amino acid sequences for the heavy and light chain variable regions of the rabbit antibody P4-10 are shown in FIG. 1. One approach for humanizing rabbit P4-10 would be to retain the 6 rabbit antigen-contacting CDR sequences but replace the bulk of the heavy and light chain variable regions with framework sequences chosen from human germline genes that are closest in identity to the original rabbit framework residues. In order to accomplish this, it is first necessary to identify framework and CDR regions in rabbit antibody P4-10. Using two different conventions used in the art for identifying CDR regions—Kabat and IMGT nomenclatures—the 4 FRs (plain text, dashed underlines) and 3 CDRs (bold text and solid underlines) are shown for the P4-10 heavy chain (FIG. 1A) and P4-10 light chain (FIG. 1B). The internet tool IgBlast (www.ncbi.nlm.nih.gov/igblast/) was used to identify CDR regions using either Kabat or IMGT nomenclatures.

The process of humanizing rabbit P4-10 utilized several approaches for identifying prospective human heavy and light chain germline sequences to combine with rabbit CDRs. Each construct would be designed in silico, synthesized as a single-chain Fv (scFv) antibody gene fragment, expressed in *E. coli*, and tested for binding to the GFRα4 antigen.

In order to select human VH and VL germline genes based on amino acid identity to rabbit P4-10 VH and VL, a search was performed using an internet tool that analyzed the P4-10 heavy and light chain amino acid sequences and identified the closest human heavy and light chain germline VH or Vλ based on amino acid sequence identity to the rabbit antibody. Once identified, potential humanized versions of P4-10 could be designed in silico by replacing the 2 human heavy chain CDRs and 2 human light chain CDRs with their P4-10 rabbit counterparts. Human heavy and light chain CDR3 and FR4 regions would then be appended after the VH or Vλ to complete the variable region sequences.

Figures 2A, 2B:
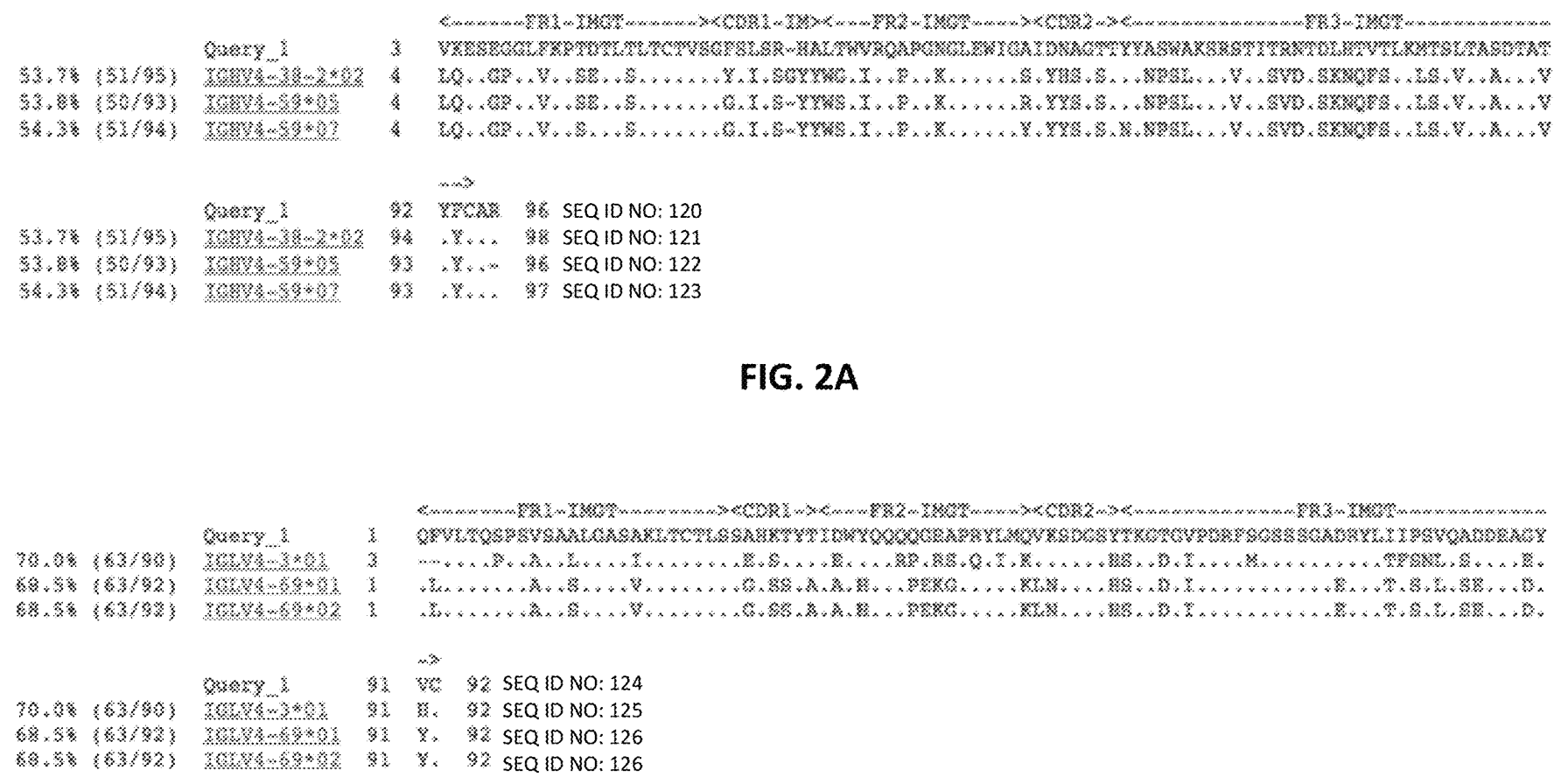

Using IgBlast (www.ncbi.nlm.nih.gov/igblast/), a search of rabbit P4-10 VH identified the closest human VH germline genes based on amino acid sequence identity. FIG. 2A shows the 3 top candidates all with amino acid identities of ~54%. IGHV4-38-2*02 was chosen over IGHV4-59*05 and *07 because the former has only 2 human polymorphisms and the latter has 10 (imgt.org/IMGTrepertoire/LocusGenes/#F). It was reasoned that increased polymorphisms could lead to increased immunogenicity since the version of IGHV4-59 we might choose could be different than the polymorphic variant(s) present in a given patient.

A search of rabbit P4-10 VL identified human Vλ IGLV4-3*01 as a closest match (FIG. 2B). Further analysis of this germline gene revealed that it has a stop codon in its CDR3 (imgt.org/genedb/fasta?outputFormat=fastaAGaps&selectGenes=IGLV4-3&selectSpecies=Homo%20sapiens) as shown in FIG. 3B (bottom line, stop codon indicated by an asterisk) suggesting that antibodies attempting to use this germline gene would not be present in vivo. Because of this, without wishing to be bound by theory, it was hypothesized that a humanized antibody based on the human light chain Vλ gene IGLV4-3*01 might be immunogenic. Therefore, the second closest human Vλ germline gene, IGLV4-69*01 was selected.

In order to select human VH and VL germline genes based on pairing frequency, additional human variable region germline genes were selected as possible structural frameworks on which to build humanized versions of rabbit P4-10 by considering pairing frequencies observed in vivo of human heavy and light chains based on germline gene of origin. Use of such pairs might produce antibody variable regions that were more stable. For example, the human light chain Vλ IGLV4-69*01 identified above is most commonly found paired with a heavy chain encoded by VH germline gene IGHV3-48*03 (DeKosky et al. (2016) *Proc Natl Acad Sci* 113:E2636-E2645). Therefore, germline gene IGHV3-48*03 was added to germline gene IGHV4-38-2*02 as a potential candidate on which to graft the rabbit heavy chain CDRs. An alignment of rabbit P4-10 VH with each of these human germline genes is shown in FIG. 3A with their % homologies to the original rabbit sequence indicated. Since these are VH germline gene segments, CDR3 and FR4 regions are not part of this analysis and not shown in the figure. Similarly, for selection of additional human Vλ genes, a review of the literature revealed that human VH germline gene IGHV4-38-2 is seen commonly paired with light chain Vλ germline gene IGLV2-14*01, and human heavy chain VH germline gene IGHV3-48*03 is commonly paired with human light chain Vλ germline gene IGLV1-44*01 (DeKosky et al. (2016) *Proc Natl Acad Sci.* 113: E2636-E2645). An alignment of rabbit P4-10 light chain VL region is shown with each of these human germline genes in FIG. 3B. Unlike VH germline genes, VL germline genes include most of the light chain CDR3 (light chains do not use D gene segments as do heavy chains). Like heavy chains, FR4 is not part of this analysis and not shown in the figure.

Repertoires of humanized rabbit P4-10 VH and VL were then created using human germline genes, CDR substitution, and back mutation to rabbit amino acid residues. To create humanized versions of rabbit P4-10 heavy and light chain variable regions, the rabbit CDRs could be substituted into the human germline genes, however, it was unpredictable as to whether the resultant collection of heavy and light chains when paired together in different combinations would retain binding to antigen. As can be seen in FIG. 3, the rabbit and human CDRs do not precisely line up within the sequences of VH or VL, the corresponding rabbit/human CDRs are of different lengths, and even the precise identification of rabbit CDRs varies depending on whether one uses Kabat or IMGT definitions for CDR. Furthermore, the importance of retaining additional rabbit amino acids that flank the P4-10 rabbit CDRs is not obvious nor is the potential importance of retaining certain rabbit framework region amino acids that may contribute to antigen binding as described in the literature. Even without these considerations, it can be seen that the overall lengths of the P4-10 heavy and light chains are not the same as their closest matching human counterparts (gaps indicated with dashes in FIG. 3) so that it is not clear that the human frameworks even in the most ideal alignments would position the rabbit CDRs appropriately in space to retain affinity for the GFRα4 antigen. To address these potentially confounding issues, collections of humanized versions of rabbit P4-10 were designed that started with straightforward CDR substitutions into a human germline gene and then continued by "back mutating" to rabbit amino acid residues to decrease the degree of "humanness" and potential disruption to the ability to bind to antigen. Overall, this comprised an iterative process by which variable region sequences were designed in silico, expressed as scFv, and tested for binding to antigen as described in the examples below. For example, FIG. 4 shows the creation of heavy chains H1 and H2 derived from substitution of rabbit CDR1 and CDR2 into human germline VH genes IGHV-38-2*02 and IGHV3-48*03, respectively. These idealized humanized versions of rabbit P4-10 VH brought the degree of identity match between rabbit and human from 54% to 85% for IGHV4-38-2*02 and 51% to 85% for IGHV3-48*03 (img-t.org/3Dstructure-DB/cgi/DomainGapAlign.cgi). Less human versions of H1 and H2 were then designed by substituting certain amino acid residues back to their rabbit counterparts from the original P4-10 antibody. This resulted in the design of H1m3, H1m2, and H1m1 that show sequence identities to P4-10 heavy chain of decreasing percentage as shown (back-mutated amino acids shown in white lettering with dark background). The positions and priority of which amino acid residues to "back mutate" were based in part on the significance of certain rabbit heavy chain amino acid residue positions described in the literature, notably the identification of non-CDR antigen-contacting loops in FR3 of both rabbit heavy and light chains (Zhang and Ho (2017) *MABS*, 9:419-429).

Similarly, for the light chain, FIG. 5 illustrates the design of light chains L1, L2, and L3 from direct substitution of CDR1, CDR2, and CDR3 from rabbit P4-10 into human Vλ germline genes along with sets of rabbit back-mutated versions.

Example 2: Expression of Humanized Rabbit P4-10 Variants as scFv and Testing for Binding to Antigen In order to test whether in silico-designed humanized VH and Vλ retained binding to GFRα4, an initial cohort of VH/Vλ pairs were created that (1) took into account the germline derivation of those heavy and light chains that pair most frequently in vivo and (2) paired the most human and least human heavy and light chains as a starting point. This resulted in the creation of 16 scFvs numbered 1 through 16 as listed in Table 1. To express these 16 scFvs along with the original rabbit P4-10 as a positive control (numbered "0" in Table 1), the nucleotide sequence for each scFv was synthesized in the order Vλ-VH where the gene block was flanked by SfiI restriction enzyme sites for cloning into the pComb3X phagemid vector, and the light and heavy chain variable regions were separated by a nucleic acid sequence encoding the linker "GGSSRSSSSGGGGSGGGG" (SEQ ID NO: 169) (Andris-Widhoff, et al. (2001) Phage Display: A Laboratory Manual, Chapter 9, Cold Spring Harbor Press). For gene block synthesis of each scFv (Genewiz, South Plainfield, N.J.), rabbit P4-10 heavy chain CDR3 and FR4 (FIG. 1A) were appended to the amino acid sequences for each VH in FIG. 4. For gene block synthesis of the light chains, rabbit P4-10 light chain FR4 was appended to the amino acid sequences for each Vλ in FIG. 5. The only change to light chain FR4 was substitution of the terminal threonine (T, FIG. 1B) by leucine (L), an amino acid residue that can be found in that position in both rabbit and human lambda light chain FR4 regions (IMGT Repertoire, www.imgt.org). For gene block synthesis of all scFv, human codon usage was used.

After restriction digestion and agarose gel purification of scFv gene blocks, Vλ-VH constructs were ligated into SfiI-digested pComb3X as described (Andris-Widhoff, Steinberger, Fuller, Rader, and Barbas in Phage Display: A Laboratory Manual, Chapter 9, Cold Spring Harbor Press, 2001). Ligated DNA was electroporated into the ER2738 strain of *E. coli*, and transformed bacterial colonies were grown in culture and rescued with VCSM13 helper phage to create phage particles expressing recombinant scFv linked to the pIII M13 coat protein (Rader, Steinberger, and Barbas in Phage Display: A Laboratory Manual, Chapter 10, Cold Spring Harbor Press, 2001).

To screen phage-displayed scFvs for binding to the two isoforms of GFRα4, isoform "a" (GFRα4a) and isoform "b" (GFRα4b), phage ELISAs were performed where the binding of scFv to antigen-coated plates was detected with a horseradish peroxidase-conjugated anti-M13 monoclonal antibody (Steinberger, Rader, and Barbas in Phage Display: A Laboratory Manual, Chapter 11, Cold Spring Harbor Press, 2001). To perform these ELISAs, the GFRα4a isoform comprising a portion of GFRα4a (Asn24-Ser245, UniProt accession #Q9GZZ7-2) was used, followed by a Factor Xa cleavage site/linker, a portion of optimized IgG1 Fc domain (Pro100-Lys330), and 6 His residues for purification. The GFRα4b isoform comprised a portion of GFRα4b (Asn24-Val274, UniProt #Q9GZZ7-1), followed by a TEV cleavage site linker, and a portion of human IgG1 Fc domain (Asp104-Lys330).

Figure 7:
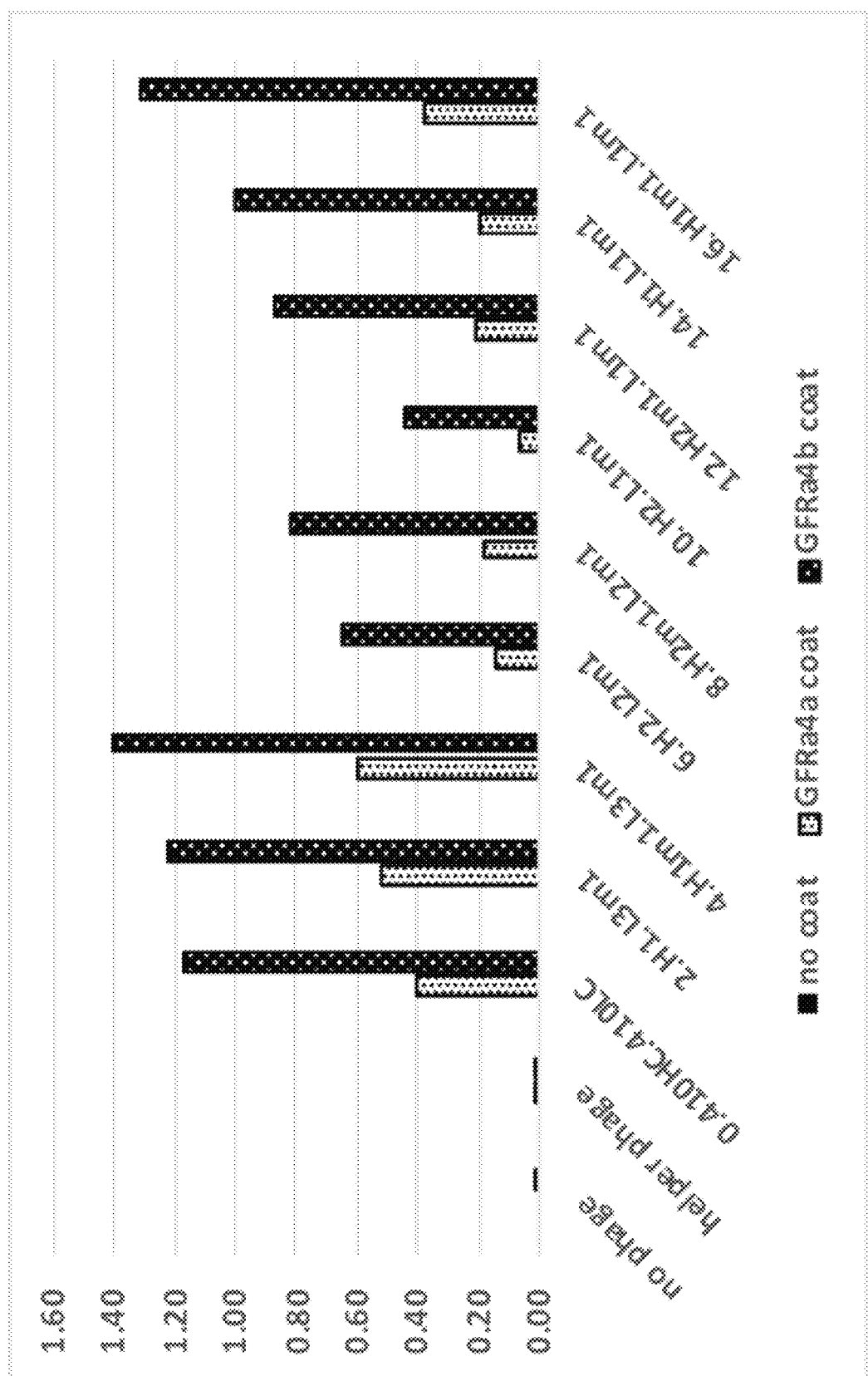
FIG. 7 is a bar graph showing the binding of humanized scFv 1 through 16 to immobilized GFRα4 isoform a (GFR4α4a) and isoform b (GFR4α4b) as measured by ELISA.

FIG. 6 shows the results of a phage ELISA performed with immobilized GFRα4a and humanized scFvs 1 through 16 using VCSM13 helper phage and the original rabbit P4-10 scFv as negative and positive controls, respectively. The results demonstrate that both the most and least humanized heavy chains (H1, H1m1, H2, H2m1) confer binding to antigen but only when paired with the least humanized version of light chain (L1m1, L2m1, L3m1). Binding of the positive scFvs from this experiment were also screened for binding to GFRα4b (FIG. 7). The results demonstrated that those scFvs that were positive against GFRα4a were also positive against GFRα4b. As observed in previous ELISAs of this type with the original rabbit P4-10 expressed as an antibody fragment on phage, reactivity always appears greater against the GFRα4b isoform.

From this point on, additional scFvs were constructed using the most human of the in silico designed heavy chains, H1 and H2, but with various light chain sequences illustrated in FIG. 5 in an iterative fashion. Since only the least human of the initial set of tested light chains conferred binding when compared with most human, a second set of scFvs was constructed that paired H1 and H2 with light chains that were intermediate in amino acid sequence between those two extremes (scFvs 17-22, Table 1; FIG. 5). In addition, 2 heavy/light chain combinations were constructed that had not been tested in the first experiment by pairing H1 and H2 with L2m1 and L3m1, respectively (scFvs 23-24, Table 1; FIG. 5). As above, gene blocks were synthesized, ligated into the pComb3X vector, and scFvs were expressed on phage and screened by ELISA.

Figure 8:
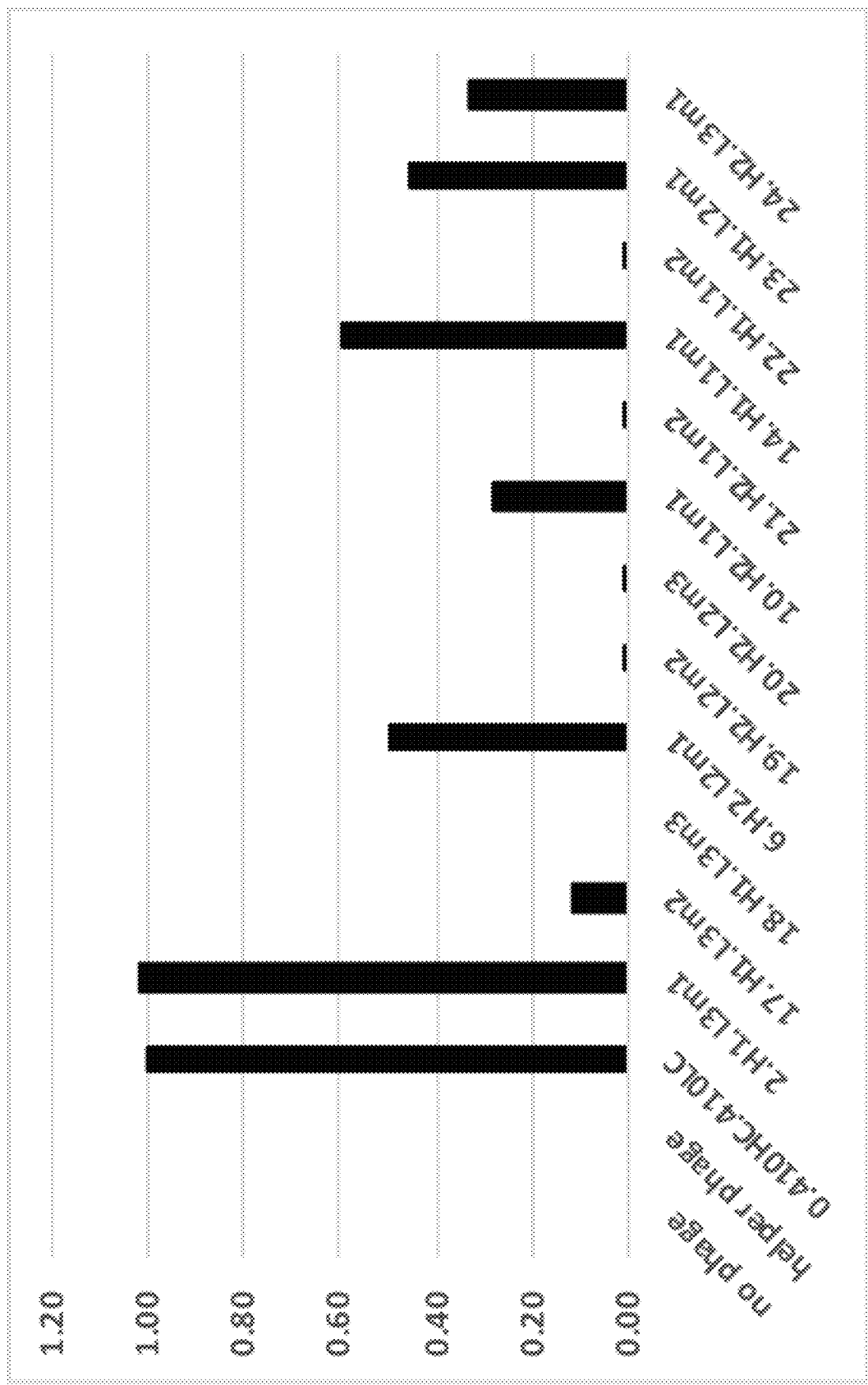
FIG. 8 is a bar graph illustrating the binding of humanized scFv 17 through 24 and select previously tested positive clones to immobilized GFRα4 isoform b (GFR4α4b) as measured by ELISA.
Figure 9:
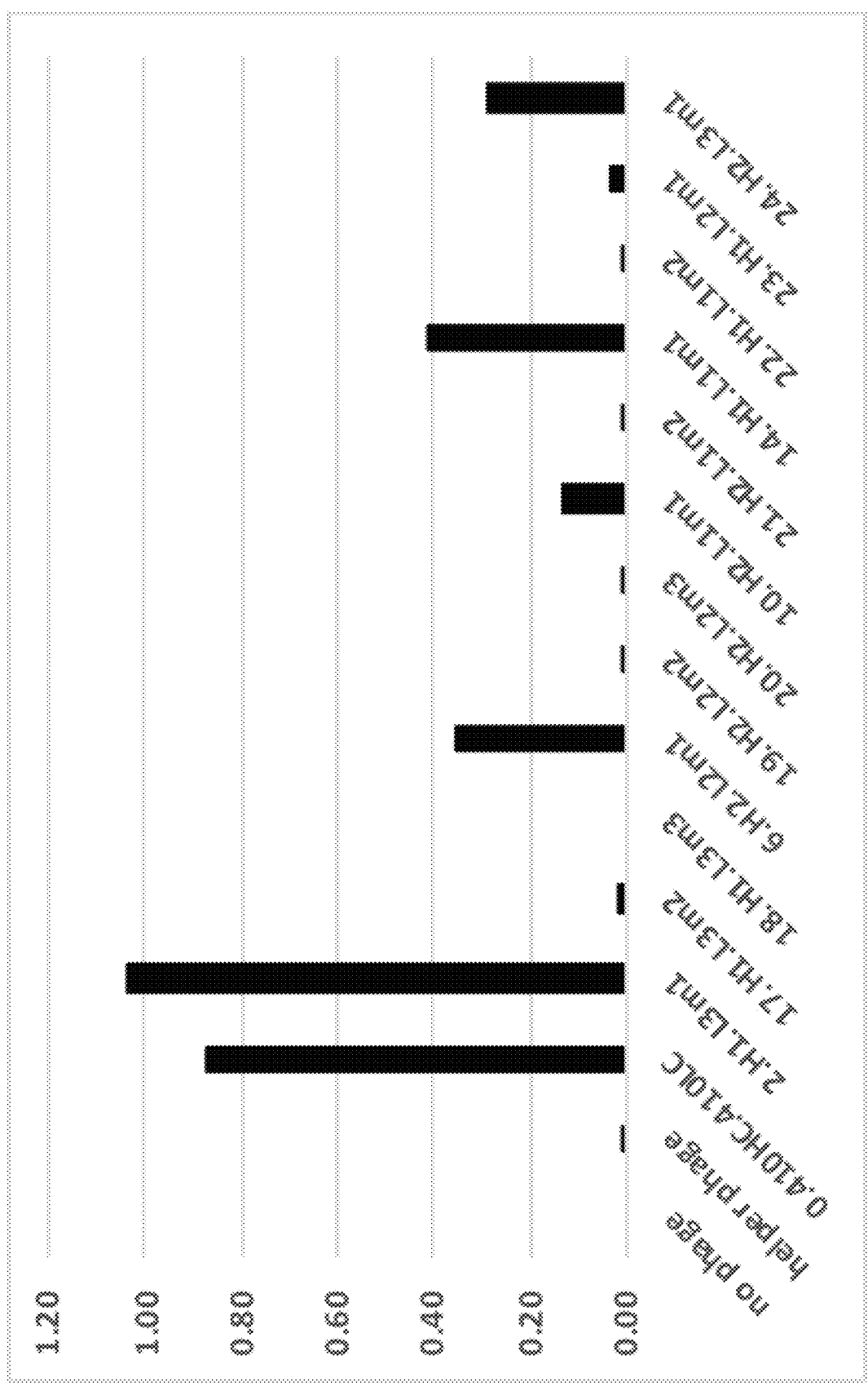
FIG. 9 is a bar graph showing the binding of humanized scFv 17 through 24 and select previously tested positive clones to immobilized GFRα4 isoform a (GFR4α4a) as measured by ELISA.
Figure 10:
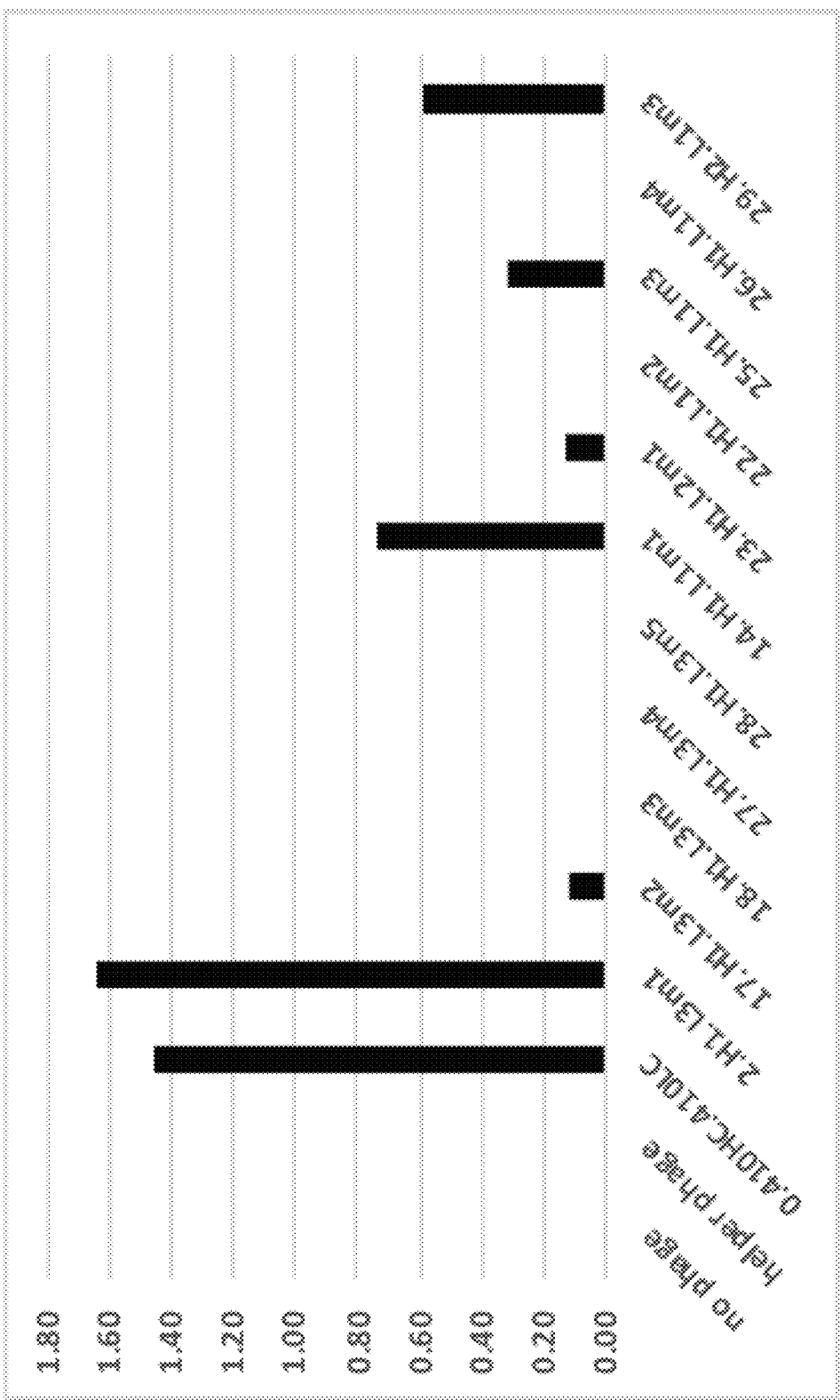
FIG. 10 is a bar graph showing binding of humanized scFvs 25 through 29 and select previously tested positive clones to immobilized GFRα4 isoform b (GFR4α4b) as measured by ELISA.
Figure 11:
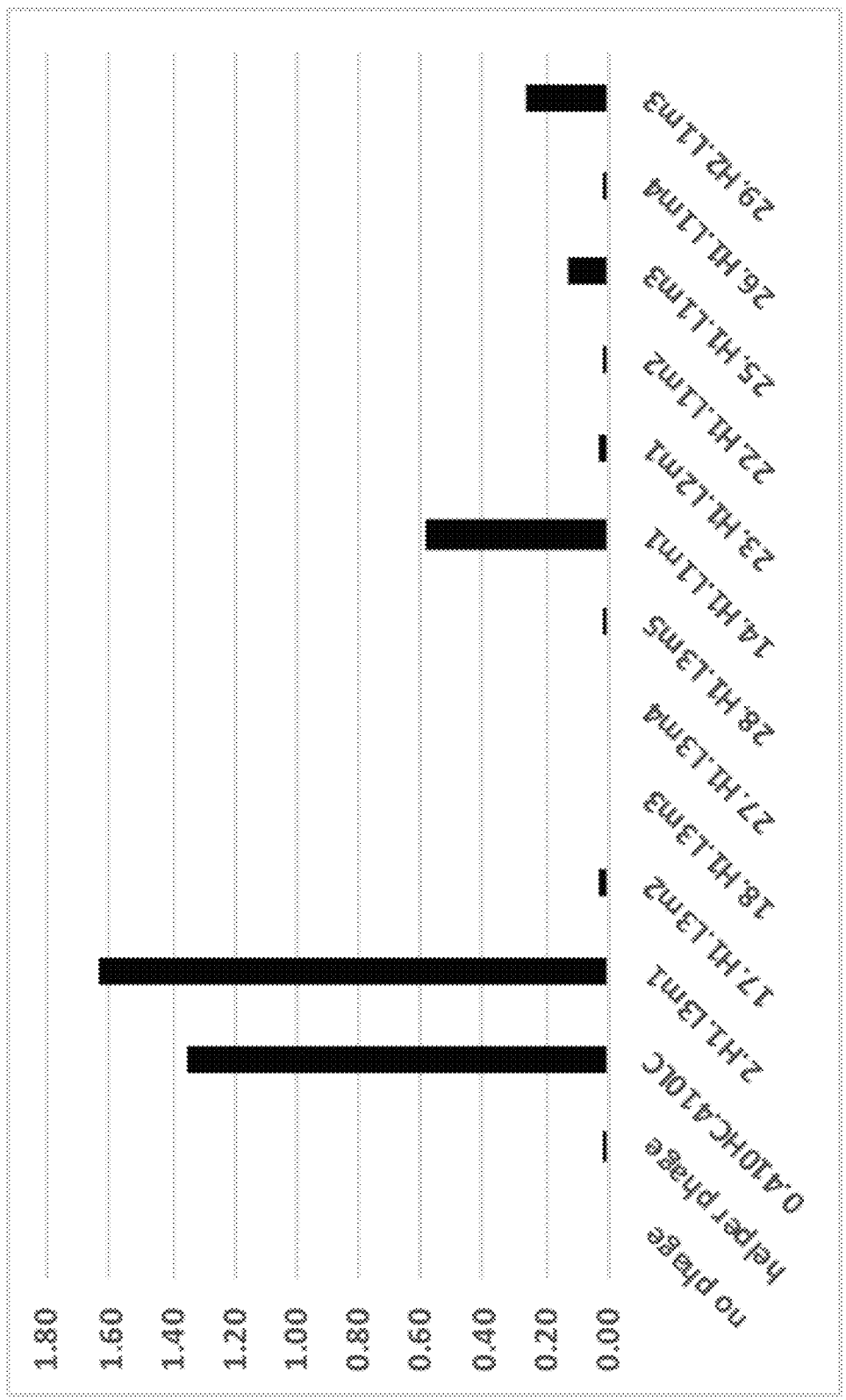
FIG. 11 is a bar graph showing the binding of humanized scFvs 25 though 29 and select previously tested positive clones to immobilized GFRα4 isoform a (GFR4α4a) by ELISA.

FIGS. 8 and 9 show the ELISA results for this second cohort of scFvs run in parallel with previous positives tested against GFRα4b and GFRα4a, respectively. Of the new scFvs, only the combination of the previously-positive light chain L3m1 now in combination with H2 (scFv 24) was clearly positive against both isoforms of GFRα4. ScFvs 17 and 23 were positive against GFRα4b but marginally positive against GFRα4a. Attempts to improve the percent human amino acid identity of scFv 17's light chain L3m2 by testing scFv 27 (H1/L1m4), and scFv 28 (H1/L1m5) were unsuccessful (FIGS. 10 and 11). Similarly, pairing H1 with L1m4 (scFv 26), a more humanized L1m1 (scFv 14) was unsuccessful. However, pairing H1 and H2 with L1m3, a light chain more human than L1m1 but less than L1m4, created scFvs 25 and 29 that screened positive against GFRα4a and GFRα4b. The binding results for all 29 humanized scFv variants of rabbit P4-10 are summarized in Table 2.

In order to determine which variants to pursue for further development into chimeric antigen receptor T-cells, reference was made to reports of the World Health Organization (WHO) International Nonproprietary Name (INN) Expert Group that helped define requirements for non-human derived antibodies to be considered "humanized". According to guidelines, comparison of a candidate antibody to human sequences should be done through the International Immunogenetics Information System® (IMGT®) Domain-GapAlign tool (www.imgt.org). This tool interrogates the IMGT® database of antibody germline variable region genes where the alignment score is made only against germline sequence variable region exons, thus omitting part of CDR3 and the J region from the analysis. As well as being "closer to human than to other species", the top "hit" should be human and the identity to human sequences must be ≥85%, otherwise the antibody would be designated as "chimeric" not "humanized".

Based on the antigen binding results summarized in Table 2, scFvs 10, 14, 25 and 29 were analyzed using the above approach. As illustrated in FIG. 12, heavy chain H1 (forming the heavy chain in scFvs 14 and 25) was found to be "closer to human than to other species" with identity to human sequences ≥85%. Similar results were found for heavy chain H2 (FIG. 13), the heavy chain used in scFvs 10 and 29. For light chain L1m3 (used in scFvs 25 and 29), the top hit was human with amino acid identity ≥85% (FIG. 14). For light chain L1m1 (used in scFvs 10 and 14), the first hit was rabbit; the second hit was human with an amino acid identity to human sequences of 84%, just below the 85% convention.

Figures 16A, 16B:
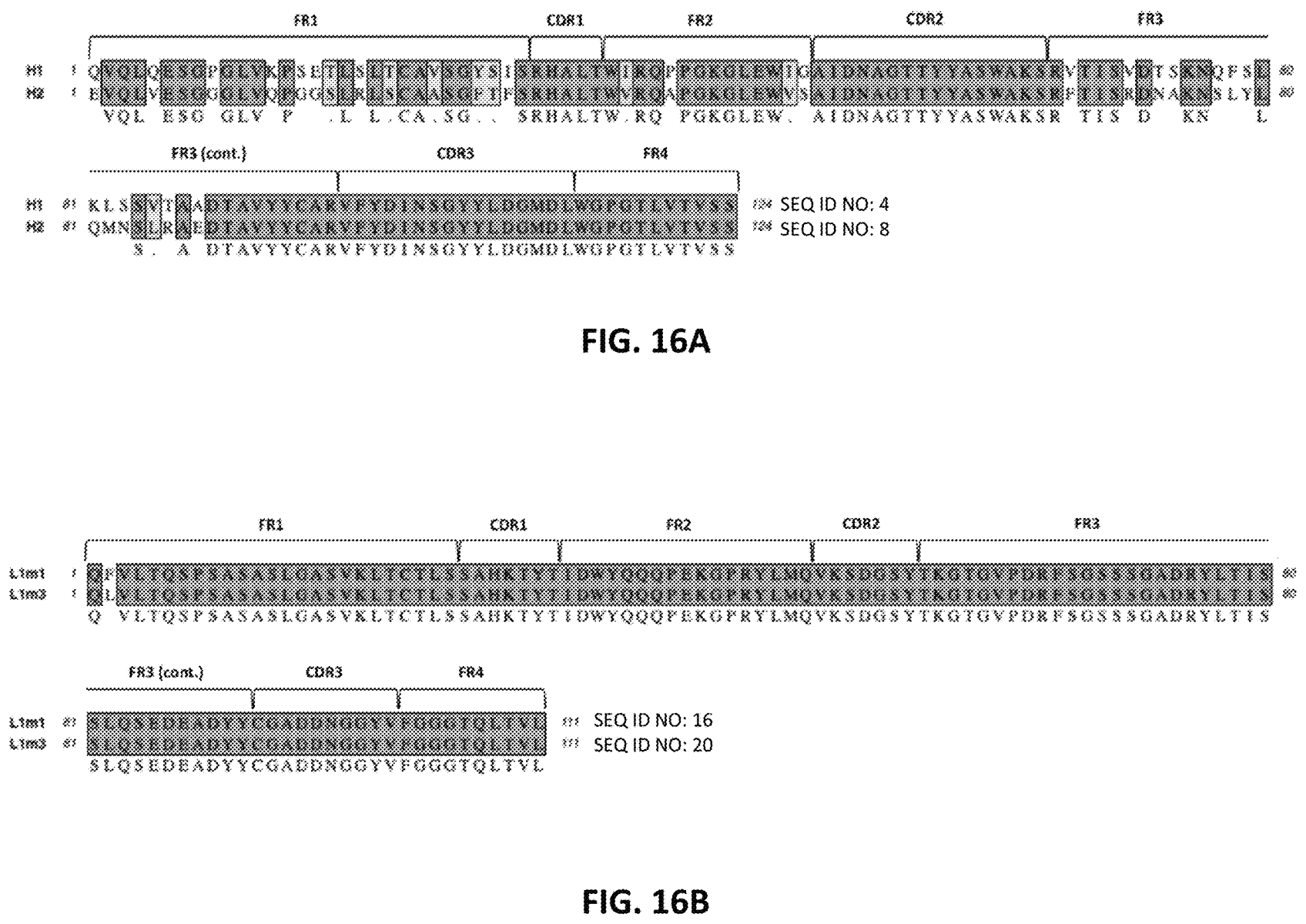

Table 3 summarizes the heavy chain/light chain compositions of scFvs 10, 14, 25 and 29 with their respective homologies to human sequences. Amino acid alignments (with CDR3 and FR4 regions appended) of heavy chains H1 with H2 and light chains L1m1 with L1m3 are shown in FIGS. 16A and 16B, respectively. Heavy chains H1 and H2 are significantly different from each other by virtue of homology to very distinct human germline genes derived from different human VH germline gene families (VH3 and VH4, FIG. 3) and sharing only ~75% sequence homology with each other. Light chains L1m1 and L1m3 are identical to each other except for a single amino acid change at position 2 in FR1 (99% sequence homology, FIG. 5). The additional "human" amino acid at position 2 (a leucine for a phenylalanine) increases the homology to human sequences from 84% to 85%.

Example 3: Design of CAR-T scFv Constructs

Figure 18:
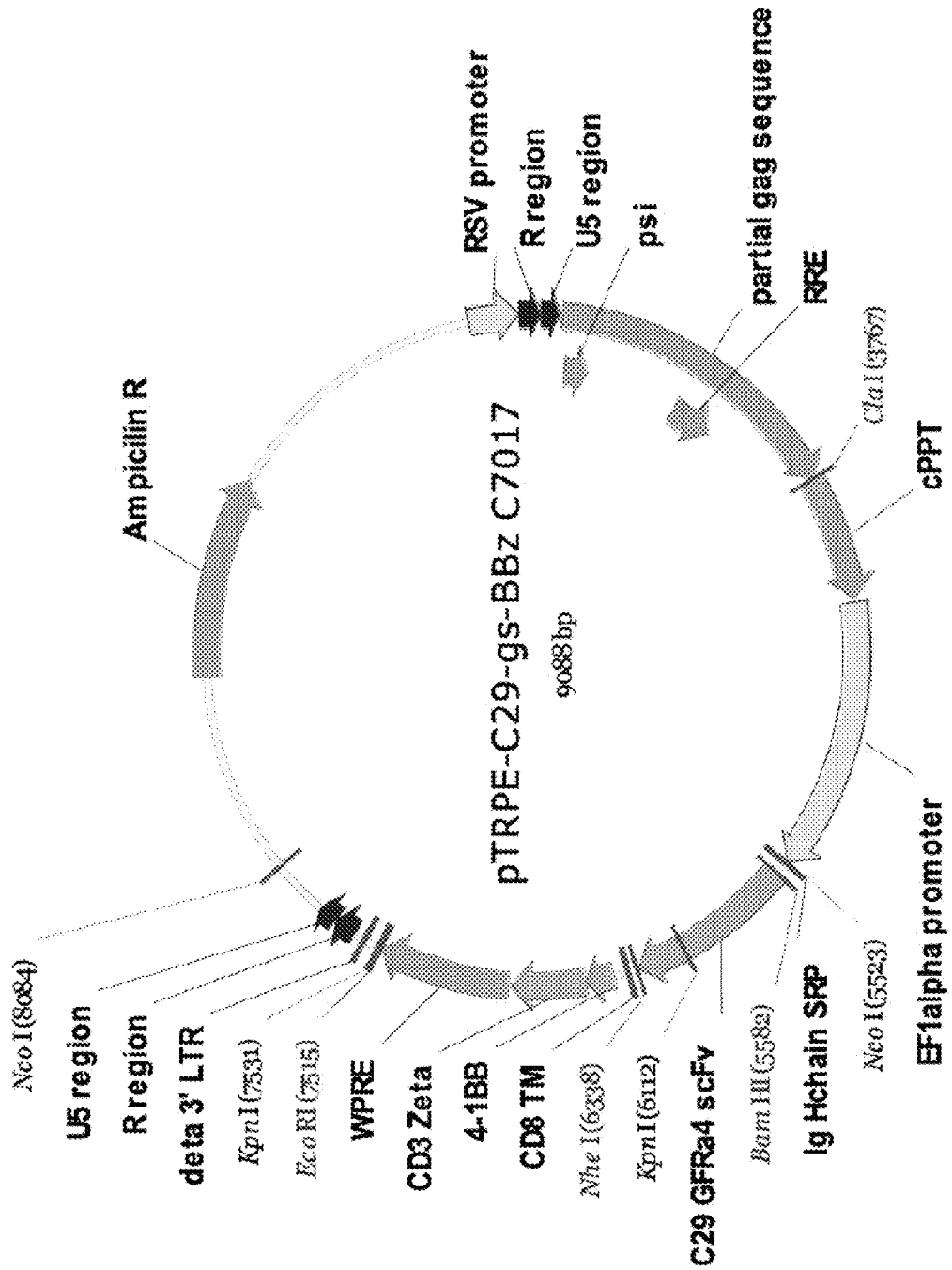
FIG. 18 is an illustration showing the map of the plasmid vector containing CAR29.

Constructs for scFv humanized antibodies 10, 14, 25, and 29 for CAR-T were designed in the orientation VH-linker-VL with the linker comprising nucleotides to encode a 15-amino acid glycine/serine rich peptide and with 5' and 3' BamHl and NheI restriction sites, respectively (FIG. 17). Constructs were synthesized, restriction digested with BamH1 and NheI, agarose gel purified, and ligated into the corresponding restriction sites of plasmid vectors that provide a 10-amino acid glycine/serine (GS)-rich linker (GGGGSGGGGS) (SEQ ID NO: 168) at the carboxy terminus of the scFv, followed by the transmembrane domain of human CD8, a 4-1BB domain, and CD3zeta domain sequentially (FIG. 18 shown for the plasmid containing scFv 29). The resulting vectors for scFvs 10, 14, 25, and 29 encode CARs termed CAR-10, CAR-14, CAR-25, and CAR-29, respectively.

Example 4: Production of Lentivirus and Transduction of Human T Cells

To generate lentiviral supernatants, LentiX-293T cells were seeded on Day 0 and transfected using Lipofectamine 2000 on Day 1 as described (Milone et al. (2009) *Molecular Therapy.*, 17: 1453-1464). For each construct, the plasmids used were pVSV-G (VSV glycoprotein expression plasmid), pRSV.REV (Rev expression plasmid), pMDLg/p-1.RRE (Gag/Pol expression plasmid), and the CAR transfer vectors (pTRPE) described above. Lentiviral supernatants were filtered through 0.45 μm pore size filters and concentrated by centrifugation at 12,000×g at 4° C. for 12-18 hours.

Figure 19A:
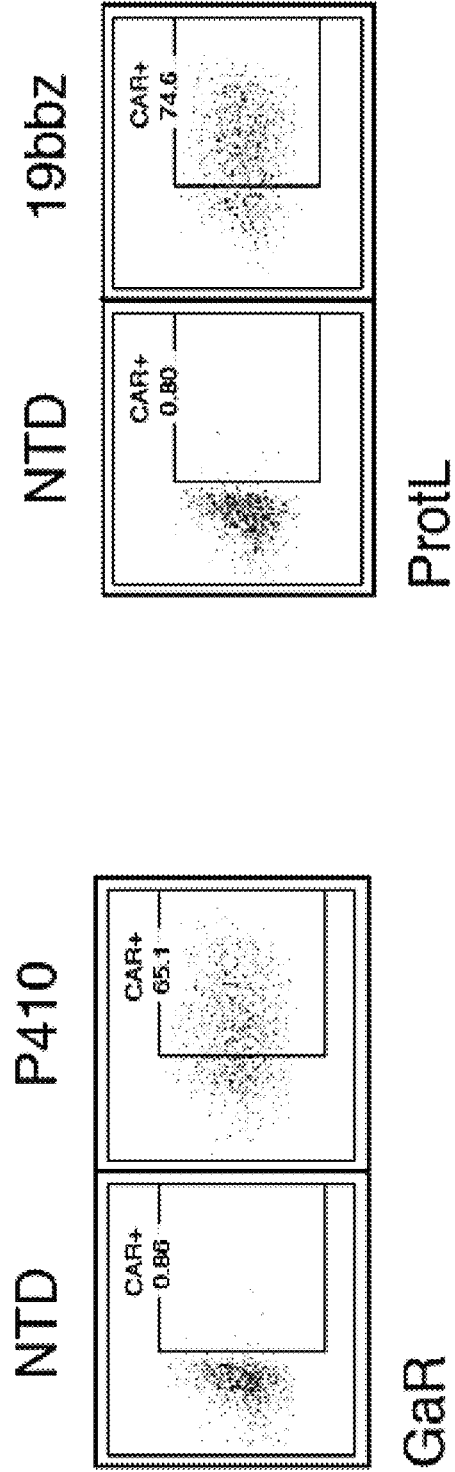
FIGS. 19A-19C are a series of plots showing expression of cell-surface CARs. Original rabbit P4-10 GFRα4-directed and murine 19bbz CD19-directed CARs were detected with goat anti-rabbit antibody (FIG. 19A, left panel) or Protein L (FIG. 19A, right panel). Humanized GFRα4-directed CARs 10, 14, 25, 29 were detected with rabbit anti-human antibody (FIG. 19B), and GFRα4-directed P4-10, 10, 14, 25, 29 CARs and CD19-directed CAR detected with Fc-conjugated soluble GFRα4b or CD19 antigen (FIG. 19C, upper and lower rows, respectively).
Figure 19B:
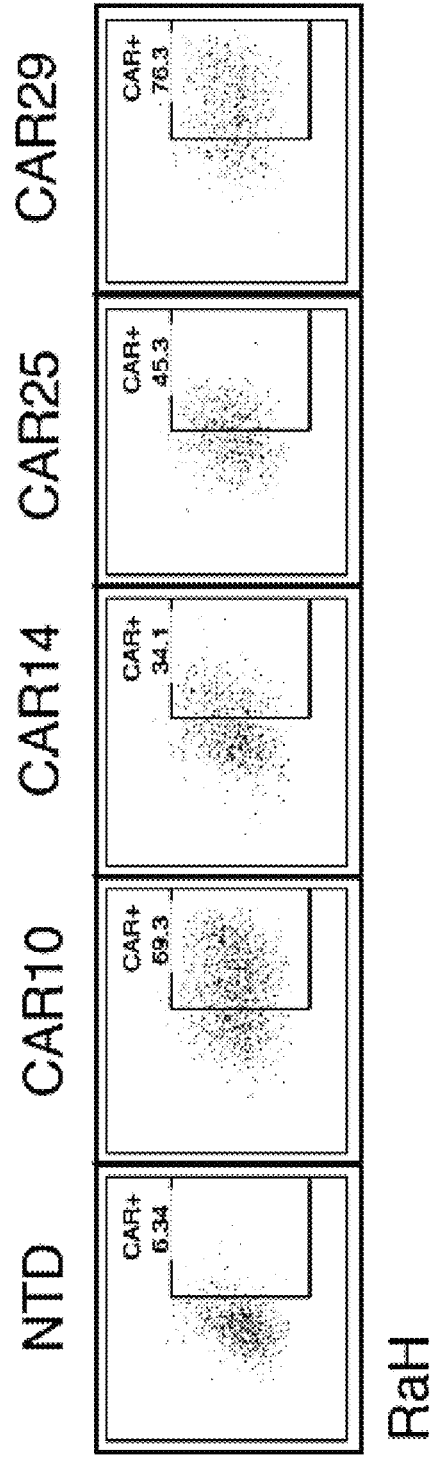
Figure 19C:
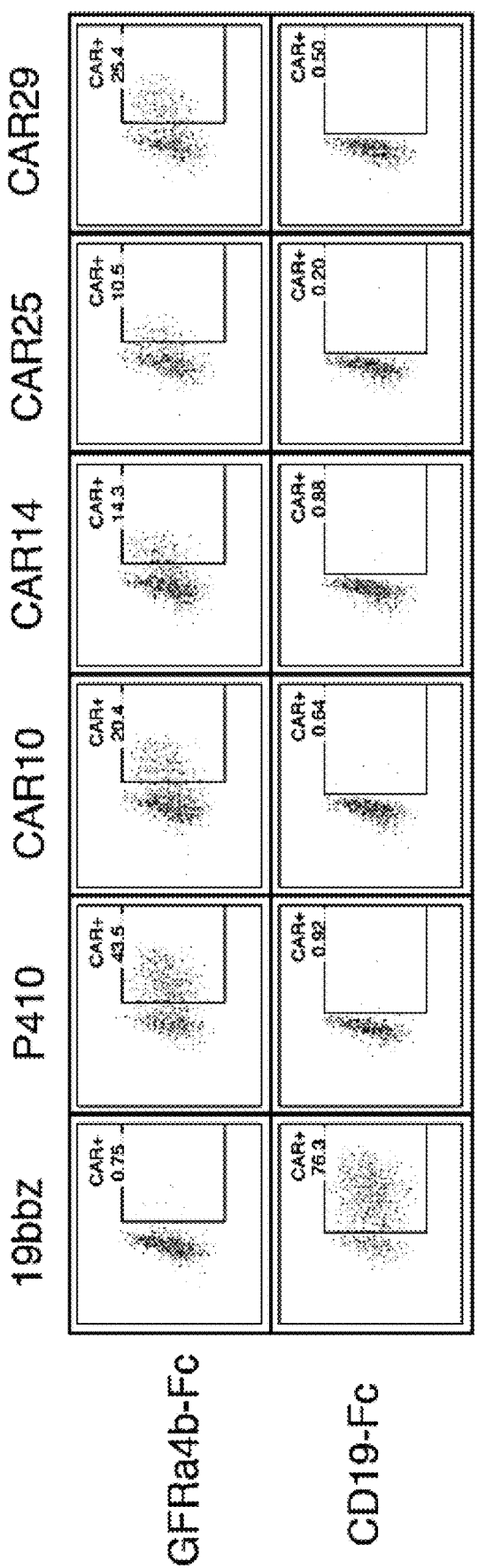

To create CAR-T expressing cells, human T cells from healthy donors were activated with anti-CD3 and anti-CD28 coated paramagnetic beads (DYNABEADS® Human T-Activator CD3/CD28, Life Technologies). One day following activation, cells were transduced with lentiviral vectors encoding GFRα4-directed CARs (original rabbit P4-10 and humanized versions), a CD19-directed control CAR (FMC63(cd8)bbz), or were left non-transduced (NTD). Cells were expanded and on day 7, cells were evaluated for cell-surface expression of the CARs by flow cytometry (FACSCalibur, BD Biosciences, Franklin Lakes, N.J.). Fluorescently-labeled goat anti-rabbit antibodies detected CAR P4-10, the original rabbit GFRα4-directed CAR, and fluorescently-labeled Protein L detected the murine CD19-directed CAR (FIG. 19A, "P410" and "19bbz", respectively). Fluorescently-labeled rabbit anti-human antibodies ("RaH") detected CARs 10, 14, 25, and 29 (FIG. 19B). Expression of cell-surface CARs were also detected by staining with antigen using recombinant human Fc-fusions of GFRα4 or CD19 antigen followed by detection of bound antigen with fluorescently-labeled anti-human Fc-specific antibodies (FIG. 19C). Appropriately, CD19-Fc only bound to CD19-directed CARs while GFRα4-Fc bound to both rabbit P4-10 and humanized P4-10 CARs but not the CD19-directed CAR.

Example 5: In Vitro Killing of GFRα4-Expressing Cells by Humanized P4-10 CAR-T Cells Cytotoxicity of target cells by GFRα4-directed CAR-T cells was evaluated using a 51Cr release-assay. Target cells comprised either Nalm6 cells (a CD19-expressing B-cell precursor leukemia cell line (ATCC® CRL-3273™)), Nalm6 cells expressing the GFRα4 isoform a (GFRα4a) or isoform b (GFRα4b), or TT cells (a human medullary thyroid cancer cell line (ATCC® CRL-1803™)). Nalm6 cells expressing GFRα4 proteins were produced by transduction with lentiviral vectors encoding human GFRα4a-T2A-GFP or human GFRα4b-T2A-GFP (Milone et al. (2009) *Molecular Therapy.,* 17: 1453-1464). Cells were stained with P4-10 antibody followed by AlexaFluor 647-conjugated donkey anti-rabbit antibody and FACS sorted to >98% purity. P4-10 antibody comprised a full-length rabbit IgG containing the P4-10 rabbit variable regions and was a gift of Novartis Pharmaceuticals.

Figure 20:
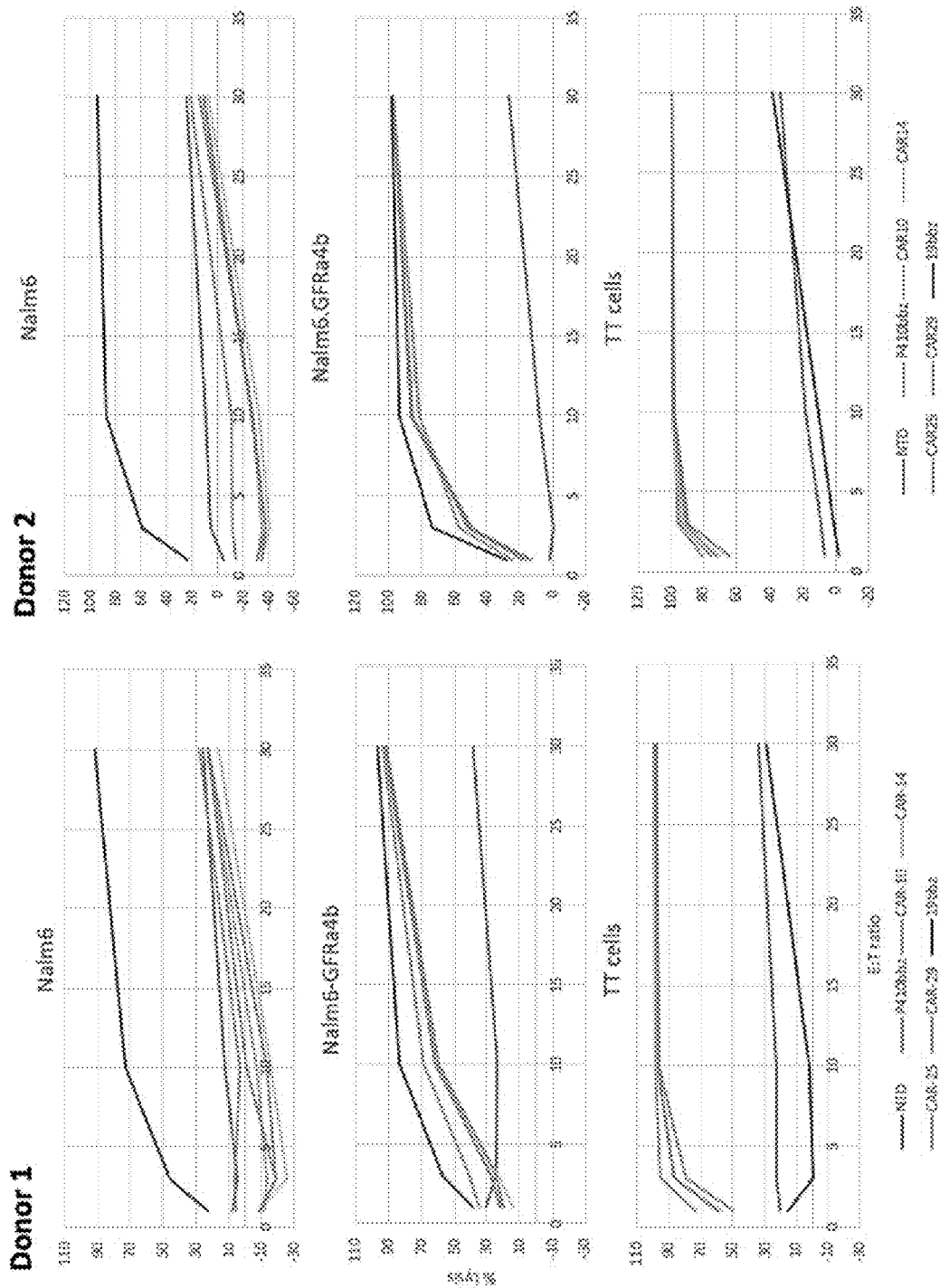
FIG. 20 is a series of graphs showing in vitro killing of GFRα4-expressing cells by GFRα4-directed CAR-T cells. T cells from 2 human donors (left and right panels) were transduced with lentiviral vectors that encoded CARs directed to CD19 (19bbz) or GFRα4 (P410bbz, CAR-10, CAR-14, CAR-25, CAR-29) and incubated with CD19-expressing Nalm6 cells (top row), CD19- and GFRα4 isoform b-expressing Nalm6 cells (middle row), or GFRα4-expressing TT medullary thyroid cancer cells (bottom row). (NTD, non-transduced T cells). T cells from 2 donors (left and right panels) were transduced with lentiviral vectors that encoded CARs directed to CD19 (19bbz) or GFRα4 (P410bbz, CAR-10, CAR-14, CAR-25, CAR-29) and incubated with CD19-expressing Nalm6 cells (top row), CD19- and GFRα4 isoform b-expressing Nalm6 cells (middle row), or GFRα4-expressing TT medullary thyroid cancer cells (bottom row). (NTD, non-transduced T cells).
Figure 21:
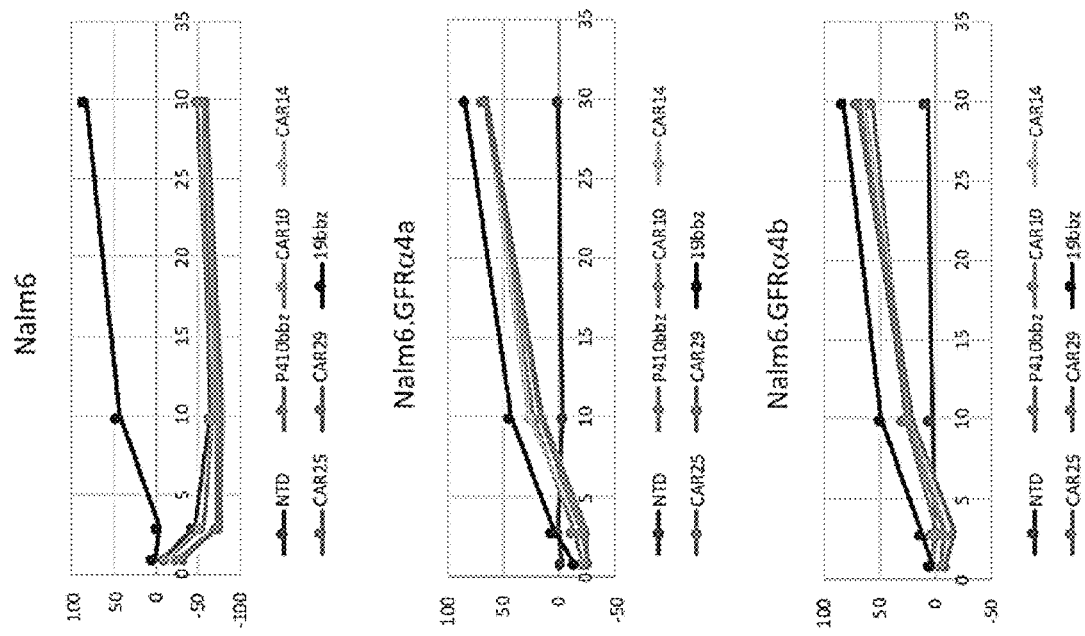
FIG. 21 is a series of graphs showing in vitro killing of GFRα4a and GFRα4b isoform-expressing Nalm 6 cells. Human T cells transduced with lentiviral vectors that encoded CARs directed to CD19 (19bbz) or GFRα4 (P410bbz, CAR-10, CAR-14, CAR-25, CAR-29) were incubated with CD19-expressing Nalm6 cells (top row), CD19- and GFRα4 isoform a-expressing Nalm6 cells (middle row), and CD19- and GFRα4 isoform b-expressing Nalm6 cells (bottom row). (NTD, non-transduced T cells).
Figure 22:
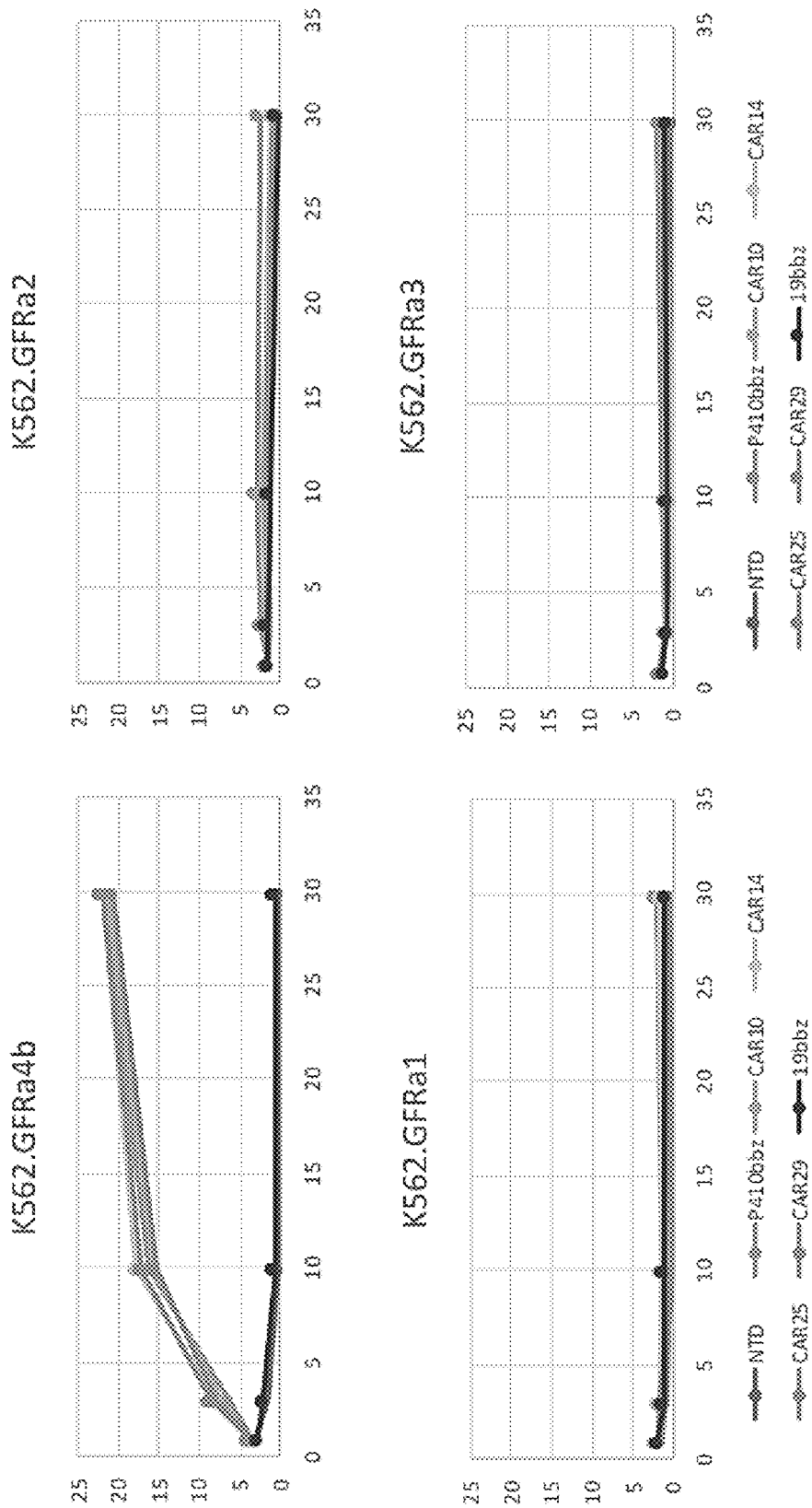
FIG. 22 is a series of graphs illustrating the lack of in vitro killing of Nalm 6 cells expressing non-GFRα4 members of the glial cell-derived neurotrophic factor (GDNF) receptor family. Human T cells transduced with lentiviral vectors that encoded CARs directed to CD19 (19bbz) or GFRα4 (P410bbz, CAR-10, CAR-14, CAR-25, CAR-29) were incubated with CD19-expressing Nalm6 cells co-expressing GFRα1, GFRα2, GFRα3, or GFRα4b as indicated. (NTD, non-transduced T cells).
Figure 23:
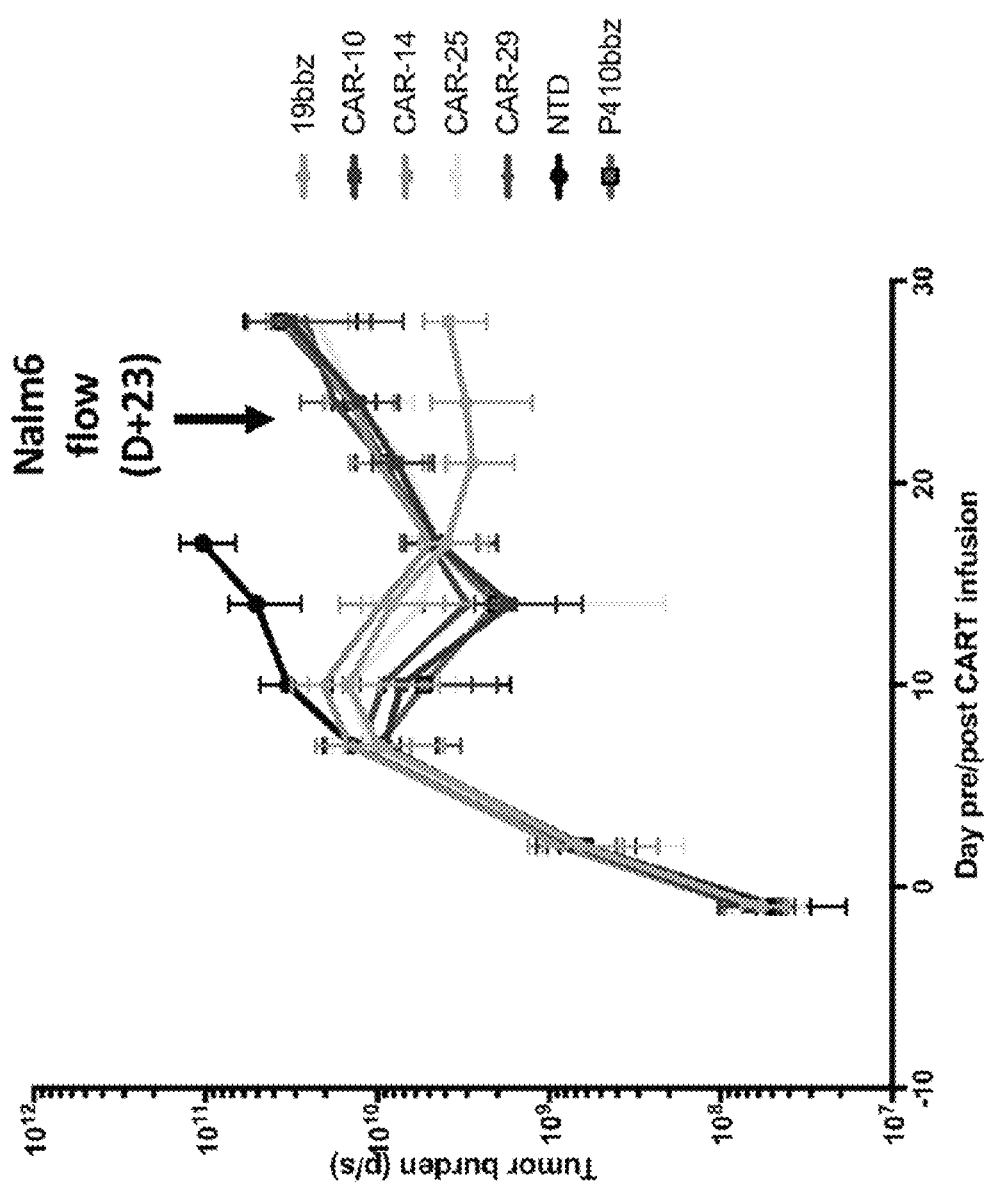
FIG. 23 is a graph demonstrating the in vivo killing of GFRα4-expressing cells by GFRα4-directed CAR-T cells in a mouse model. On Day −4, $5 \times 10^6$ Nalm6 cells engineered to express click-beetle green luciferase and human GFRα4b were injected intravenously into NOD-SCID-Y−/− (NSG) mice. On Day 0, $5 \times 10^6$ non-transduced human T cells (NTD, n=6 mice), or human T cells transduced with CARs 19bbz (n=9 mice), P410 (n=9 mice), CAR-10 (n=9 mice), CAR-14 (n=9 mice), CAR-25 (n=9 mice), or CAR-29 (n=9) were injected intravenously. Bioluminescence photons/second (p/s) was measured twice weekly over a 28-day period. Values for each group at each time point represent means +/− one standard deviation. Mice were bled on Day 23 and Nalm6 cells in the blood were analyzed for antigen expression by flow cytometry.

To perform the in vitro killing assay, target cells were labeled with 51Cr (sodium dichromate salt), washed, and co-cultured with effector CAR T cells at effector:target ratios of 30:1, 10:1, and 3:1. Ten thousand target cells were co-cultured with the appropriate number of effector T cells in each well. Supernatants were collected after overnight co-culture and placed into 96-well Lumaplates (Perkin Elmer, Inc., Walthan Mass.). The amount of 51Cr released from the labeled target cells was measured on a liquid scintillation counter (MicroBeta Trilux, Perkin Elmer). Target cells incubated in medium alone or with 1% SDS were used to determine spontaneous (S) or maximum (M) 51Cr release. Percentage of specific lysis was calculated as follow: [(cpm experimental release–cpm S release)/(cpm M release–cpm S release)]×100. As shown in FIG. 20 for CAR-T cells made from 2 different healthy human donors (left and right panels), Nalm6 cells expressing only endogenous CD19 are only killed by a CD19-directed CAR-T ("19bbz", row A) whereas Nalm6 cells expressing both CD19 and GFRα4b were killed by both CD19-directed and GFRα4-directed CAR-T cells (row B). Conversely, TT cells were only killed by GFRα4-directed CAR-T cells (row C). FIG. 21 shows that the humanized GFRα4-directed CAR-Ts also recognize and kill Nalm6 cells expressing GFRα4 isoform a. GFRα4 is a member of a related group of 4 glial cell-derived neurotrophic factor (GDNF) receptors including those designated GFRα1, GFRα2, and GFRα3. Because non-GFRα4 GDNF receptor proteins are found in non-thyroid tissues including the central nervous system, lack of reactivity of humanized GFRα4-directed CAR-Ts to GFRα1-, GFRα2-, and GFRα3-expressing cells was confirmed. Target cells expressing human GFRα1, GFRα2, GFRα3 and GFRα4 were created by transducing K562 cells (ATCC® CCL-243™) with lentiviral vectors encoding a respective GFRα sequence followed by a T2A sequence derived from *Thosea asigna* virus followed by GFP. Expression of GFRα4 on the surface of K562 cells was confirmed as described above for GFRα4-expressing Nalm6 cells. Expression of GFRα1, GFRα2, and GFRα3 on the surface of K562 cells was confirmed using commercially-available murine monoclonal antibodies specific to the respective GFRα isoform (R&D Systems, Minneapolis, Minn.). As shown in FIG. 22, cells expressing non-GFRα4 GDNF receptors are not killed by any of the GFRα4-directed CAR-T cells.

Figures 24A, 24B:
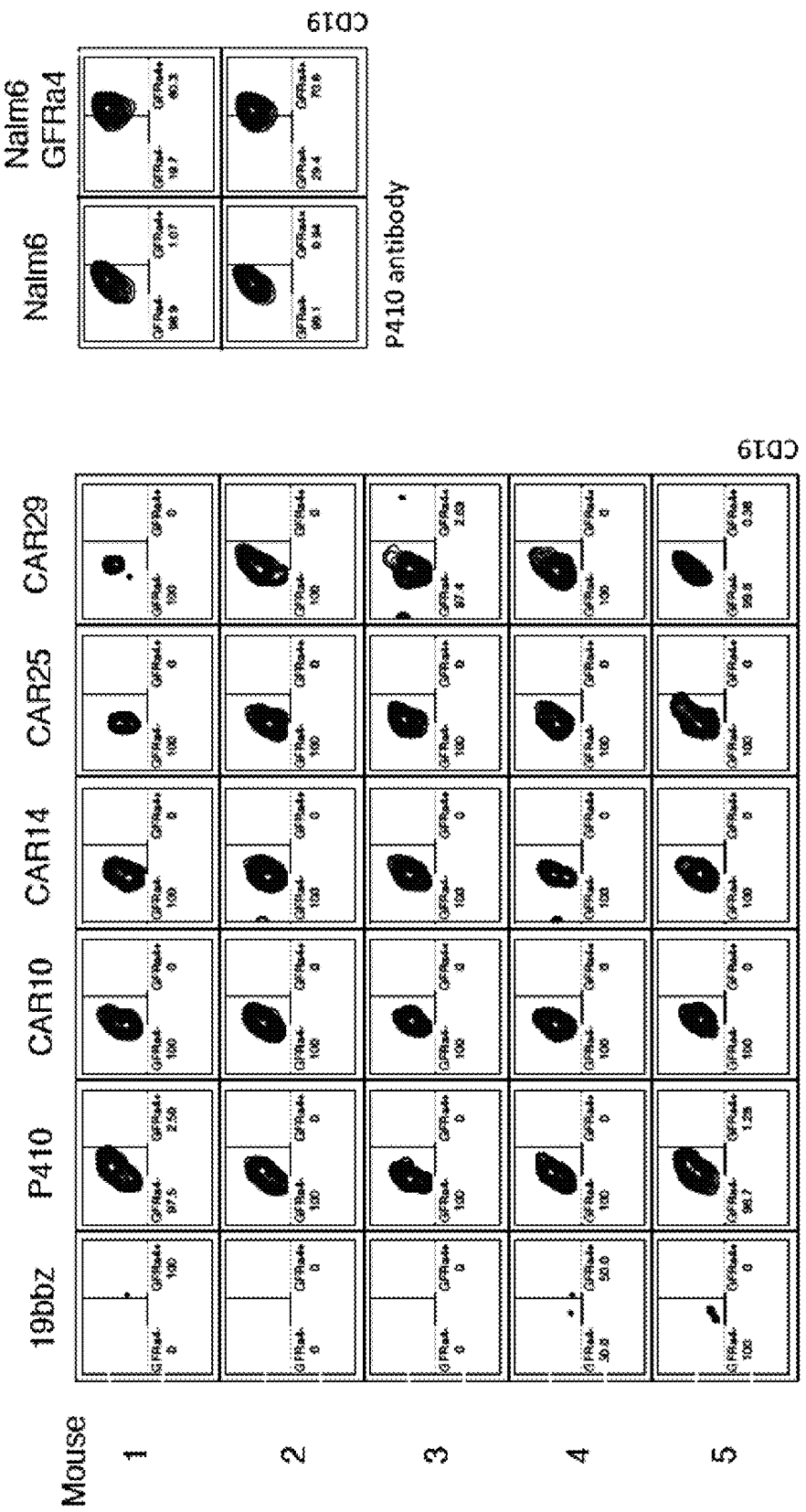
FIGS. 24A-24B are a series of graphs showing Nalm6 cell phenotype after in vivo killing of GFRα4-expressing targets.

Example 6: In Vivo Killing of GFRα4-Expressing Cells by Humanized P4-10 CAR-T cells On Day −4, 5×10⁶ Nalm6 cells engineered to express click-beetle green luciferase (Ghassemi et al. Cancer Immunol Res 6:1100-1109, 2018) and human GFRα4b were injected intravenously into NOD-SCID-Y-/- (NSG) mice. On Day 0, 5×10⁶ non-transduced human T cells (NTD, n=6 mice), or human T cells transduced with CARs 19bbz (n=9 mice), P4-10 (n=9 mice), CAR10 (n=9 mice), CAR14 (n=9 mice), CAR25 (n=9 mice), or CAR29 (n=9) were injected intravenously. Bioluminescence was measured twice weekly over a 28-day period. As shown in FIG. 22, Nalm6 cells began to shrink in size beginning around Day 9 in mice infused with CD19-directed and all GFRα4-directed CAR-T cells until about Day 18 when tumors in mice treated with GFRα4-directed CAR-T cells began to re-expand. On Day 23, mice were bled and Nalm6 cells in blood were stained with anti-CD19 and P4-10 antibodies to assess expression of CD19 and GFRα4b in residual Nalm6 cells post treatment with CAR-Ts (FIG. 24, panel A, 5 representative mice from each group). Also stained with anti-CD19 and P4-10 antibodies are control samples of wild-type Nalm6 cells and Nalm6-GFRα4 target cells spiked into mouse blood (FIG. 24B in duplicate). These data show that the majority of Nalm6 cells initially injected into the mice were positive for both CD19 and GFRα4 and, following their killing by GFRα4-directed CAR-T cells, Nalm6 cells that subsequently grew out around Day 18 were GFRα4-negative.

Figure 25:
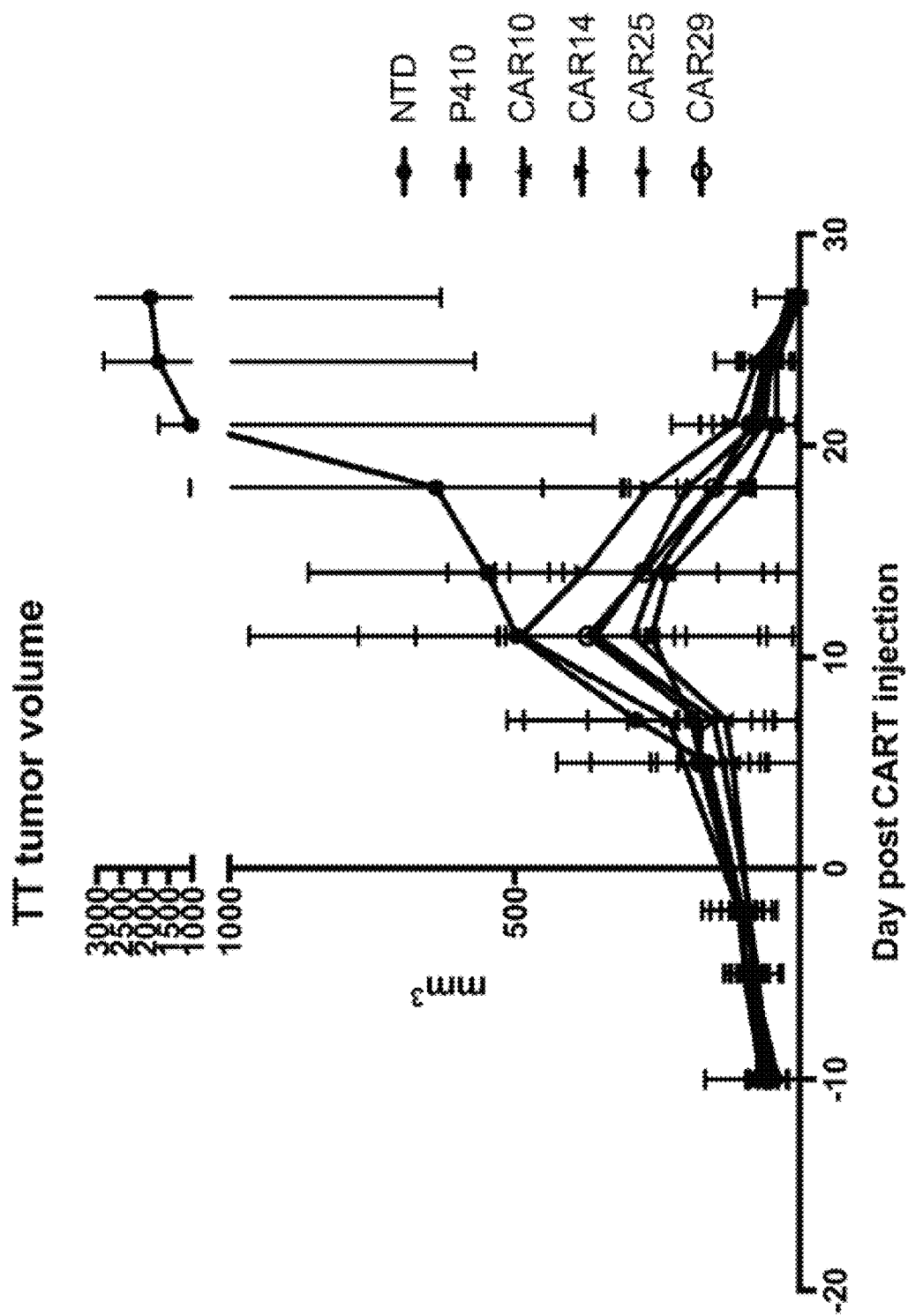
FIG. 25 is a graph illustrating the in vivo killing of TT medullary thyroid cancer cells in a mouse model. TT tumor volumes measured over time in NSG mice treated with $5 \times 10^6$ P4-10 (n=8 mice), CAR10 (n=8 mice), CAR14 (n=7 mice), CAR25 (n=7 mice), and CAR29 (n=8 mice) CAR+ T cells or an equivalent number of non-transduced cells (NTD, n=7 mice) 10 days after subcutaneous implantation of $5 \times 10^6$ wild-type TT cells. Curves plots means of tumor volumes in mm3+/− one standard deviation for each experimental group.
Figure 26:
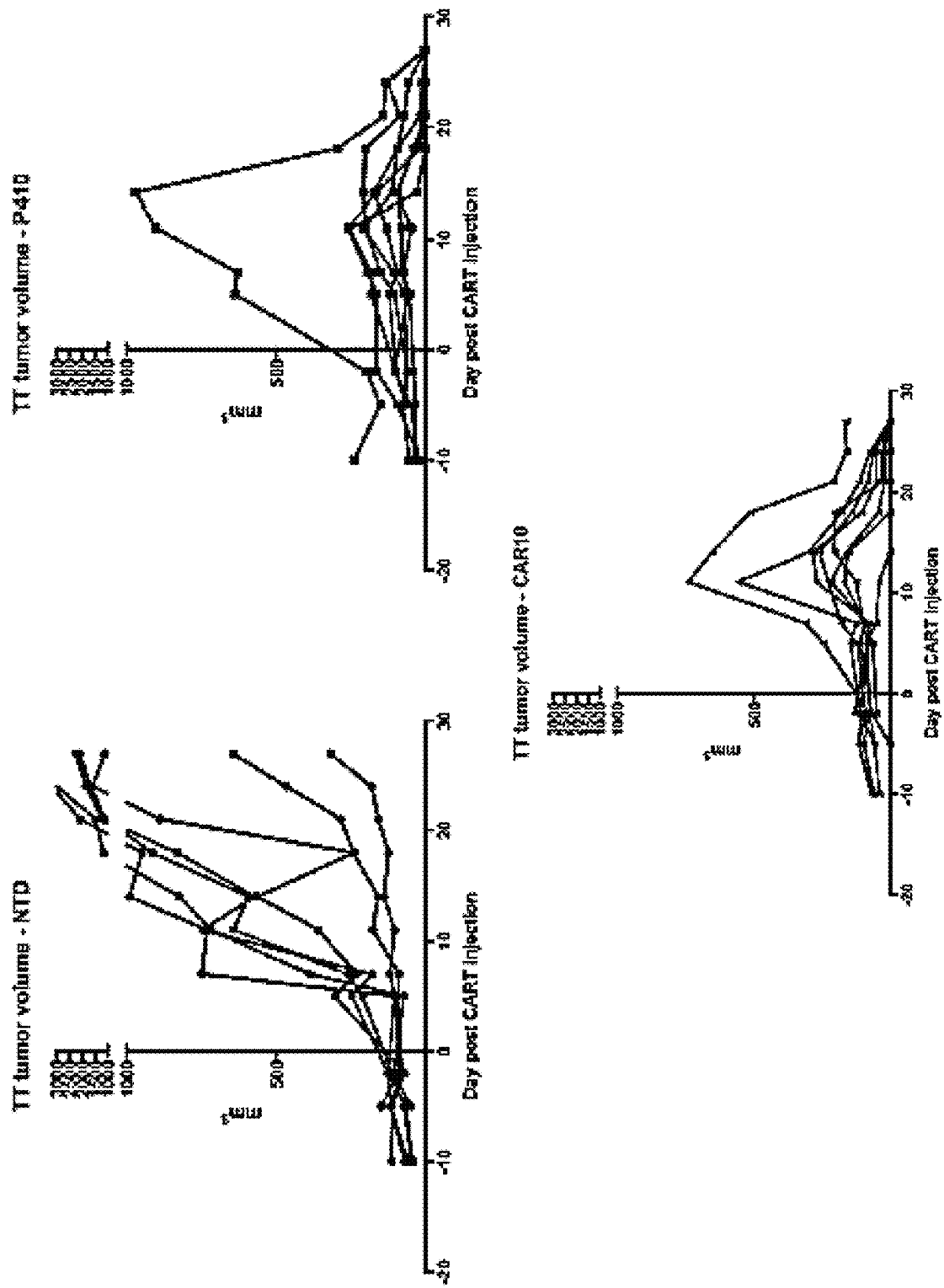
FIG. 26 is a series of graphs demonstrating in vivo killing of TT medullary thyroid cancer cells in individual mice from each experimental group. Data is from the experiment shown in FIG. 25 where curves show tumor volumes over time for individual mice in each CAR− T treatment group.
Figure 27:
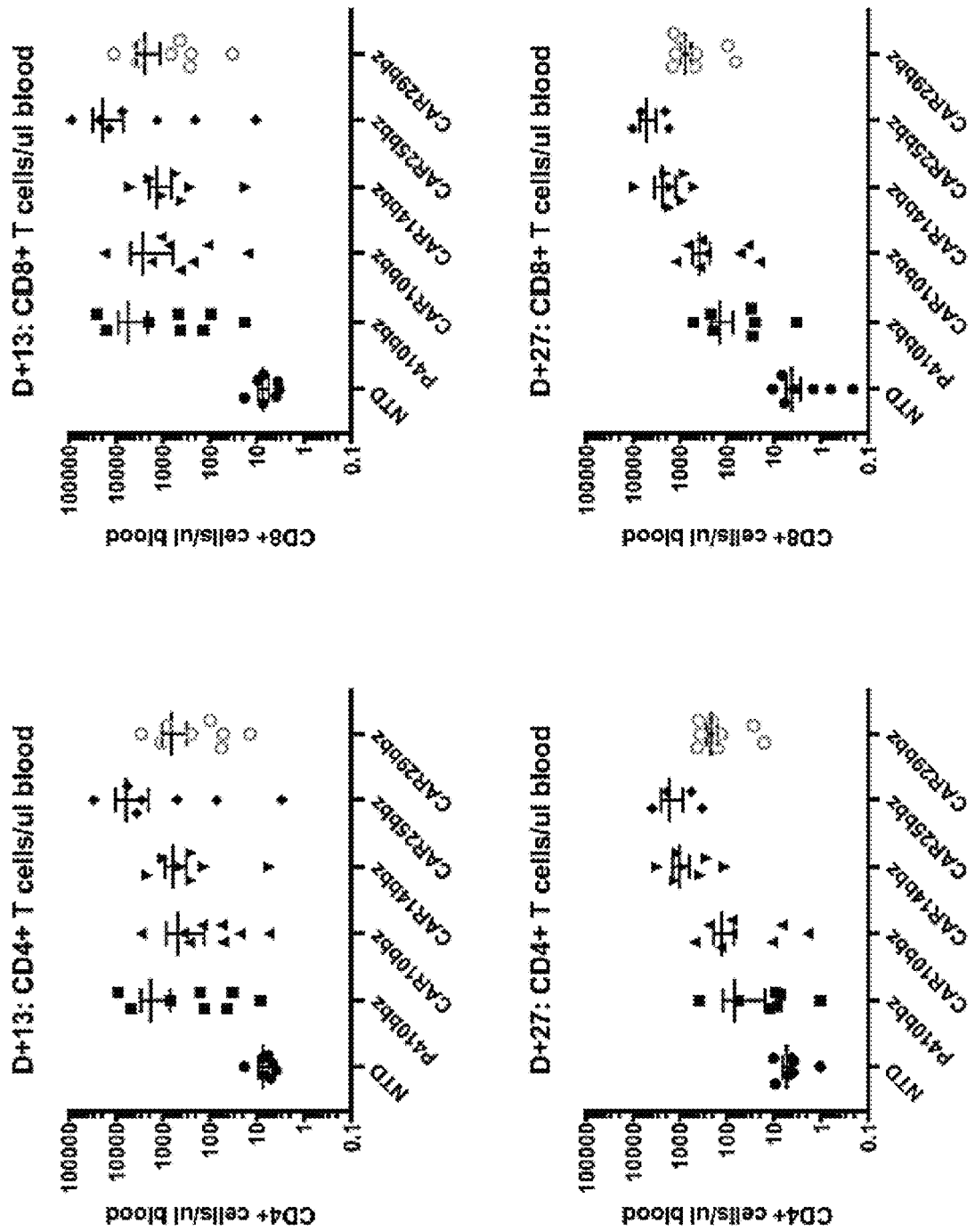
FIG. 27 is a series of graphs showing the measurement of GFRα4-directed CAR− T cell levels in mice challenged with TT medullary thyroid cancer cells. In the experiment shown in FIGS. 25 and 26, blood samples were collected from mice on Day 13 (top row) and Day 27 (bottom row), and human CD3+CD4+ T cells (left column) and CD3+CD8+ T cells (right column) were enumerated by flow cytometry. Values for individual mice are shown and error bars represent SEM. Using a Kriskal-Wallis ANOVA test with Dunn's multiple comparisons test and an alpha value of 0.05, all CAR groups were significantly different from the non-transduced (NTD) control group except for NTD vs. CAR10bbz on Day 13 CD3+CD4+ T cells, NTD vs. P410bbz and NTD vs. CAR10bbz on Day 27 CD3+CD4+ T cells, and NTD vs. P410bbz and NTD vs. CAR10bbz on Day27 CD3+CD8+ T cells.

Example 7: In Vivo Killing of TT Medullary Cancer Cell Line by Humanized P4-10 CAR-T Cells NSG mice were implanted subcutaneously with 5×10⁶ TT cells. When tumors reached approximately 100 mm³ 10 days later ("Day 0"), 5×10⁶ P4-10 (n=8 mice), CAR10 (n=8 mice), CAR14 (n=7 mice), CAR25 (n=7 mice), and CAR29 (n=8 mice) CAR+ T cells or an equivalent number of non-transduced cells (NTD, n=7 mice) were injected via the tail vein. Tumors size was measured over time in two dimensions by caliper measurement, and tumor volume was estimated using the formula: (D1×D1×D2)/2, where D1 is the smaller dimension. As shown in FIG. 25 where the mean tumor volumes are charted for all mice in each treatment group, all GFRα4-expressing CAR− T cells resulted in tumor eradication. Data for individual mice in each group are shown in FIG. 26. To assess levels of circulating CAR− T cells in mice, blood samples were collected on Day 13 and Day 27, and CD3+CD4+ T cells and CD3+CD8+ T cells were enumerated by flow cytometry (FIG. 27). These data show the presence of adoptively transferred T cells in all groups with higher levels seen in CAR groups compared to the NTD group, likely due to antigen stimulated proliferation.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments 5 and variations of this invention may be devised by others skilled in the art without departing from the true spirit and scope of the invention. The appended claims are intended to be construed to include all such embodiments and equivalent variations.

What is claimed is:

1. An isolated binding polypeptide comprising:
   (a) a heavy chain variable region that comprises an amino acid sequence having at least 95-99% identity to the amino acid sequence of any of the heavy chain variable regions set forth in SEQ ID NOs: 7-10; or
   (b) a light chain variable region that comprises an amino acid sequence having at least 95-99% identity to the amino acid sequence of any of the light chain variable regions set forth in SEQ ID NOs: 28-42.

2. The isolated binding polypeptide of claim 1, wherein the binding polypeptide comprises an antibody or an antigen-binding fragment thereof that binds a glial cell derived neurotrophic factor (GDNF) family receptor alpha-4a (GFRa4a) or GFRa4b; and
   (a) the antibody or an antigen-binding fragment thereof comprises a heavy chain variable region comprising the amino acid sequence of SEQ ID NO: 7 and a light chain variable region comprising the amino acid sequence of SEQ ID NOS: 29, 31, 34, 38, or 39;
   (b) the antibody or an antigen-binding fragment thereof comprises a heavy chain variable region comprising the amino acid sequence of SEQ ID NO: 8 and a light chain variable region comprising the amino acid sequence of SEQ ID NOS: 29 or 38;
   (c) the antibody or an antigen-binding fragment thereof comprises a heavy the antibody or an antigen-binding fragment thereof comprises a heavy chain variable region comprising the amino acid sequence of SEQ ID NO: 9 and a light chain variable region comprising the amino acid sequence of SEQ ID NOS: 29, 31, 34, or 38;
   (d) the antibody or an antigen-binding fragment thereof comprises a heavy chain variable region comprising the amino acid sequence of SEQ ID NO: 10 and a light chain variable region comprising the amino acid sequence of SEQ ID NOS: 29 or 34; or
   (e) the antibody or an antigen-binding fragment thereof comprises an amino acid sequence selected from the group consisting of SEQ ID NOs: 75, 77, 79, 81, 83, 85, 87, 89, 90, 96-98, or 102.

3. The isolated binding polypeptide of claim 2, wherein:
   (a) the antigen-binding fragment is selected from the group consisting of a Fab, a single-chain variable fragment (scFv), or a single-domain antibody; or
   (b) the antibody is a full-length antibody.

4. The isolated binding polypeptide of claim 1, wherein the binding polypeptide:
   (a) comprises a heavy chain variable region comprising an amino acid sequence of any of the heavy chain variable regions set forth in SEQ ID NOs: 7-10;
   (b) comprises a heavy chain variable region consisting of an amino acid sequence of any of the heavy chain variable regions set forth in SEQ ID NOs: 7-10;
   (c) comprises a light chain variable region comprising an amino acid sequence of any of the light chain variable regions set forth in SEQ ID NOs: 28-42; or (d) comprises a light chain variable region consisting of an amino acid sequence of any of the light chain variable regions set forth in SEQ ID NOs: 28-42.

5. A pharmaceutical composition comprising the isolated binding polypeptide of claim 1.

6. A single-chain variable fragment (scFv) comprising:
(a) a heavy chain variable region comprising the amino acid sequence of any of the heavy chain variable regions set forth in SEQ ID NOs: 7-10;
(b) a light chain variable region comprising the amino acid sequence of any of the light chain variable regions set forth in SEQ ID NOs: 28-42; or
(c) any one of the amino acid sequences set forth in SEQ ID NOs: 74-102.

7. An isolated nucleic acid encoding a binding polypeptide comprising:
(a) a heavy chain variable region encoded by a nucleotide sequence having at least 95-99% identity to the nucleotide sequence of any of the heavy chain variable regions set forth in SEQ ID NOs: 2-5; or
(b) a light chain variable region encoded by a nucleotide sequence having at least 95-99% identity to the nucleotide sequence of any of the light chain variable regions provided in SEQ ID NOs: 12-26.

8. The isolated nucleic acid of claim 7, wherein
the binding polypeptide comprises an antibody or an antigen-binding fragment thereof that binds GFRa4a and GFRa4b; and
(a) the antibody or an antigen-binding fragment thereof comprises a heavy chain variable region comprising the amino acid sequence of SEQ ID NO: 7 and a light chain variable region comprising the amino acid sequence of SEQ ID NOs: 29, 31, 34, 38, or 39;
(b) the antibody or an antigen-binding fragment thereof comprises a heavy chain variable region comprising the amino acid sequence of SEQ ID NO: 8 and a light chain variable region comprising the amino acid sequence of SEQ ID NOs: 29 or 38;
(c) the antibody or an antigen-binding fragment thereof comprises a heavy chain variable region comprising the amino acid sequence of SEQ ID NO: 9 and a light chain variable region comprising the amino acid sequence of SEQ ID NOs: 29, 31, 34, or 38;
(d) the antibody or an antigen-binding fragment thereof comprises a heavy chain variable region comprising the amino acid sequence of SEQ ID NO: 10 and a light chain variable region comprising the amino acid sequence of SEQ ID NOs: 29 or 34; or
(e) the antibody or an antigen-binding fragment thereof comprises an amino acid sequence selected from the group consisting of SEQ ID NOs: 75, 77, 79, 81, 83, 85, 87, 89, 90, 96-98, or 102.

9. The isolated nucleic acid of claim 8, wherein:
(a) the antigen-binding fragment is selected from the group consisting of a Fab, a single-chain variable fragment (scFv), or a single-domain antibody; or
(b) the antibody is a full-length antibody.

10. The isolated nucleic acid of claim 7, wherein:
(a) the binding polypeptide comprises a heavy chain variable region encoded by a nucleotide sequence comprising any of the heavy chain variable region sequences provided in SEQ ID NOs: 2-5;
(b) the binding polypeptide comprises a heavy chain variable region encoded by a nucleotide sequence consisting of any of the heavy chain variable region sequences provided in SEQ ID NOs: 2-5;
(c) the binding polypeptide comprises a light chain variable region encoded by a nucleotide sequence comprising any of the light chain variable region sequences provided in SEQ ID NOs: 12-26; or
(d) the binding polypeptide comprises a light chain variable region the binding polypeptide comprises a light chain variable region encoded by a nucleotide sequence consisting of any of the light chain variable region sequences provided in SEQ ID NOs: 12-26.

11. A vector comprising the isolated nucleic acid of claim 7.

12. The vector of claim 11, wherein the vector is:
(a) an expression vector; or
(b) selected from the group consisting of a DNA vector, an RNA vector, a plasmid, a lentiviral vector, an adenoviral vector, an adeno-associated viral vector, and a retroviral vector.

13. A host cell comprising the vector of claim 11, wherein the host cell is of:
(a) eukaryotic or prokaryotic origin;
(b) mammalian origin; or
(c) bacterial origin.

14. An isolated nucleic acid encoding a single-chain variable fragment (scFv) comprising:
(a) a heavy chain variable region comprising any of the nucleotide sequences set forth in SEQ ID NO: 2-5; and a light chain variable region comprising any of the nucleotide sequences set forth in SEQ ID NO: 12-26; or
(b) any one of the nucleotide sequences set forth in SEQ ID NOs: 43-72.

15. A chimeric antigen receptor (CAR) comprising an antigen binding domain, a transmembrane domain, and an intracellular domain, wherein the antigen binding domain comprises an antibody or an antigen-binding fragment thereof that binds GFRa4a and GFRa4b, wherein:
(a) the antibody or an antigen-binding fragment thereof comprises a heavy chain variable region comprising the amino acid sequence of SEQ ID NO: 7 and a light chain variable region comprising the amino acid sequence of SEQ ID NOs: 29, 31, 34, 38, or 39;
(b) the antibody or an antigen-binding fragment thereof comprises a heavy chain the antibody or an antigen-binding fragment thereof comprises a heavy chain variable region comprising the amino acid sequence of SEQ ID NO: 8 and a light chain variable region comprising the amino acid sequence of SEQ ID NOs: 29 or 38;
(c) the antibody or an antigen-binding fragment thereof comprises a heavy chain variable region comprising the amino acid sequence of SEQ ID NO: 9 and a light chain variable region comprising the amino acid sequence of SEQ ID NOs: 29, 31, 34, or 38;
(d) the antibody or an antigen-binding fragment thereof comprises a heavy chain variable region comprising the amino acid sequence of SEQ ID NO: 10 and a light chain variable region comprising the amino acid sequence of SEQ ID NO: 29 or 34; or
(e) the antibody or an antigen-binding fragment thereof comprises an amino acid sequence selected from the group consisting of SEQ ID NOs: 75, 77, 79, 81, 83, 85, 87, 89, 90, 96-98, or 102.

16. The CAR of claim 15, wherein:
(a) the antigen-binding fragment is selected from the group consisting of a Fab, a single-chain variable fragment (scFv), or a single-domain antibody; or
(b) the antibody is a full-length antibody.

17. The CAR of claim 15, wherein:
(a) the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD9, CD16, CD22, CD33, CD37, CD64, CD80, CD86, OX40 (CD134), 4-1BB (CD137), and CD154;
(b) the transmembrane domain comprises a transmembrane domain of CD8;
(c) the CAR further comprises a hinge domain, and wherein the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof;
(d) the CAR further comprises an artificial hinge domain comprising a glycine/serine (GS)-rich linker or the amino acid sequence of GGGGSGGGGS (SEQ ID NO: 168); or
(e) the intracellular domain comprises a costimulatory signaling domain and an intracellular signaling domain.

18. The CAR of claim 17, wherein:
(a) the costimulatory signaling domain comprises a costimulatory domain of a protein selected from the group consisting of proteins in the TNFR superfamily, CD28, OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof, or
(b) the costimulatory signaling domain comprises a costimulatory domain of 4-1BB; or
(c) the intracellular signaling domain comprises an intracellular domain selected from the group consisting of cytoplasmic signaling domains of FcyRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof, or
(d) the intracellular signaling domain comprises an intracellular domain of CD3ζ.

19. A modified immune cell or precursor cell thereof, comprising the CAR of claim 15.

20. The modified immune cell or precursor cell thereof of claim 19, wherein:
(a) the cell is selected from the group consisting of a T cell, a natural killer (NK) cell, a cytotoxic T lymphocyte (CTL), and a regulatory T cell;
(b) the modified cell is a modified immune cell;
(c) the modified cell is a modified T cell;
(d) the modified cell is an autologous cell; or
(e) the modified cell is an autologous cell obtained from a human subject.

21. A pharmaceutical composition comprising a therapeutically effective amount of the modified cell of claim 19.

22. A method of treating a disease in a subject in need thereof, comprising administering to the subject an effective amount of a modified immune cell or precursor cell thereof comprising the CAR of claim 15, wherein:
(a) the disease is associated with expression of a thyroid cell antigen;
(b) the disease is associated with expression of GFRα4;
(c) the disease is a cancer;
(d) the disease is a medullary thyroid carcinoma (MTC); or
(e) the disease is a metastasis resulting from a MTC.

23. A chimeric antigen receptor (CAR):
(a) comprising any one of the amino acid sequences set forth in SEQ ID NOs: 107-110; or
(b) consisting of any one of the amino acid sequences set forth in SEQ ID NOs: 107-110.

24. A nucleic acid encoding a chimeric antigen receptor (CAR) comprising an antigen binding domain, a transmembrane domain, and an intracellular domain, wherein the antigen binding domain comprises an antibody or an antigen-binding fragment thereof that binds GFRa4a and GFRa4b and:
(a) the antibody or an antigen-binding fragment thereof comprises a nucleic acid encoding a heavy chain variable region comprising the nucleic acid sequence of SEQ ID NO: 2 and a light chain variable region comprising the nucleic acid sequence of SEQ ID NOs: 13, 15, 18, 22, or 23;
(b) the antibody or an antigen-binding fragment thereof comprises a nucleic acid (b) encoding a heavy chain variable region comprising the nucleic acid sequence of SEQ ID NO: 3 and a light chain variable region comprising the nucleic acid sequence of SEQ ID NOs: 13 or 22;
(c) the antibody or an antigen-binding fragment thereof comprises a nucleic acid encoding a heavy chain variable region comprising the nucleic acid sequence of SEQ ID NO: 4 and a light chain variable region comprising the nucleic acid sequence of SEQ ID NO: 13, 15, 18, or 22;
(d) the antibody or an antigen-binding fragment thereof comprises a nucleic acid encoding a heavy chain variable region comprising the nucleic acid sequence of SEQ ID NO: 5 and a light chain variable region comprising the nucleic acid sequence of SEQ ID NO: 13 or 18; or
(e) the antibody or an antigen-binding fragment thereof comprises an amino acid sequence selected from the group consisting of SEQ ID NOs: 45, 47, 49, 51, 53, 55, 57, 59, 60, 66-68, or 72.

25. The nucleic acid of claim 24, wherein:
the antigen binding domain is encoded by any one of the nucleotide sequences set forth in SEQ ID NOs: 103-106.

26. The nucleic acid of claim 24, wherein:
(a) the transmembrane domain is selected from the group consisting of an artificial hydrophobic sequence, and a transmembrane domain of a type I transmembrane protein, an alpha, beta, or zeta chain of a T cell receptor, CD28, CD3epsilon, CD45, CD4, CD5, CD9, CD16, CD22, CD33, CD37, CD64, CD80, CD86, OX40 (CD134), 4-1BB (CD137), and CD154;
(b) the transmembrane domain comprises a transmembrane domain of CD8;
(c) the CAR further comprises a hinge domain, wherein the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof, wherein the artificial hinge domain is a glycine/serine (GS)-rich linker comprising GGGGSGGGGS (SEQ ID NO: 168; or
(d) the intracellular domain comprises a costimulatory signaling domain and an intracellular signaling domain.

27. The nucleic acid of claim 26, wherein:
(a) the costimulatory signaling domain comprises a costimulatory domain of a protein selected from the group consisting of proteins in the TNFR superfamily, CD28, OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof; and
(b) the costimulatory signaling domain comprises a costimulatory domain of 4-1BB;
(c) the intracellular signaling domain comprises an intracellular domain selected from the group consisting of cytoplasmic signaling domains of FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof, or
(d) the intracellular signaling domain comprises an intracellular domain of CD3ζ.

28. A vector comprising the nucleic acid of claim 24, wherein the vector:
(a) is an expression vector;
(b) is selected from the group consisting of a DNA vector, an RNA vector, a plasmid, a lentiviral vector, an adenoviral vector, an adeno-associated viral vector, and a retroviral vector;
(c) further comprises an EF-1 a promoter;
(d) further comprises a woodchuck hepatitis virus post-transcriptional regulatory element (WPRE);
(e) further comprises a rev response element (RRE);
(f) further comprises a cPPT sequence; or
(g) is a self-inactivating vector.

29. A nucleic acid encoding a chimeric antigen receptor (CAR):
(a) comprising any one of the nucleotide sequences set forth in SEQ ID NOs: 111-114; or
(b) consisting of any one of the nucleotide sequences set forth in SEQ ID NOs: 111-114.

* * * * *